(12) United States Patent
Geuijen et al.

(10) Patent No.: US 11,685,786 B2
(45) Date of Patent: Jun. 27, 2023

(54) BINDING MOLECULES THAT BIND CD137 AND PD-L1

(71) Applicant: MERUS N.V., Utrecht (NL)

(72) Inventors: Cecilia Anna Wilhelmina Geuijen, Utrecht (NL); Mark Throsby, Utrecht (NL); Cornelis Adriaan De Kruif, Utrecht (NL); Rinse Klooster, Utrecht (NL); Paulus Johannes Tacken, Utrecht (NL); Ton Logtenberg, Utrecht (NL)

(73) Assignee: MERUS N.V., Utrecht (NL)

( * ) Notice: Subject to any disclaimer, the term of this patent is extended or adjusted under 35 U.S.C. 154(b) by 872 days.

(21) Appl. No.: 16/335,971

(22) PCT Filed: Sep. 22, 2017

(86) PCT No.: PCT/NL2017/050634
§ 371 (c)(1),
(2) Date: May 11, 2020

(87) PCT Pub. No.: WO2018/056821
PCT Pub. Date: Mar. 29, 2018

(65) Prior Publication Data
US 2020/0017595 A1  Jan. 16, 2020

(30) Foreign Application Priority Data
Sep. 23, 2016 (EP) .................... 16190499

(51) Int. Cl.
*C07K 16/28* (2006.01)
*A61K 39/00* (2006.01)

(52) U.S. Cl.
CPC ...... *C07K 16/2878* (2013.01); *C07K 16/2827* (2013.01); *A61K 2039/505* (2013.01);
(Continued)

(58) Field of Classification Search
None
See application file for complete search history.

(56) References Cited

U.S. PATENT DOCUMENTS 8,337,850 B2  12/2012 Ahrens et al.
9,248,181 B2   2/2016 De Kruif et al.
(Continued)

FOREIGN PATENT DOCUMENTS

EP  3130606 A1  2/2017
EP  3778648 A1  2/2021
(Continued)

OTHER PUBLICATIONS

Dondelinger et al., Understanding the significance and implications of antibody numbering and antigen-binding surface/residue definitions, Front. Immunol. 9:2278, , doi.org/10.3389/fimmu.2018. 02278, Oct. 16, 2018.*

(Continued)

*Primary Examiner* — Claire Kaufman
(74) *Attorney, Agent, or Firm* — Sterne, Kessler, Goldstein & Fox P.L.L.C.; Paul A. Calvo

(57) ABSTRACT

The invention provides means and methods of stimulating activity of a member of the TNF receptor superfamily on a cell. The invention also provides binding molecules such as antibodies that comprises at least two antigen binding sites, wherein a first antigen binding site can bind an extracellular part of CD137 and a second antigen binding site can bind an extracellular part of PD-L1.

10 Claims, 56 Drawing Sheets

Specification includes a Sequence Listing.

(52) U.S. Cl.
CPC ...... *C07K 2317/24* (2013.01); *C07K 2317/31* (2013.01); *C07K 2317/35* (2013.01); *C07K 2317/522* (2013.01); *C07K 2317/524* (2013.01); *C07K 2317/526* (2013.01); *C07K 2317/53* (2013.01); *C07K 2317/55* (2013.01); *C07K 2317/732* (2013.01); *C07K 2317/734* (2013.01); *C07K 2317/75* (2013.01); *C07K 2317/76* (2013.01); *C07K 2317/92* (2013.01)

(56) References Cited

U.S. PATENT DOCUMENTS

| | | |
|---|---|---|
| 9,358,286 B2 | 6/2016 | De Kruif et al. |
| 2003/0078385 A1 | 4/2003 | Arathoon et al. |
| 2013/0336971 A9 | 12/2013 | De Kruif et al. |
| 2015/0190506 A1 | 7/2015 | Cheung et al. |
| 2015/0307620 A1 | 10/2015 | Vella et al. |
| 2022/0041702 A1 | 2/2022 | Liu et al. |

FOREIGN PATENT DOCUMENTS

| | | | |
|---|---|---|---|
| TW | 201946655 A | 12/2019 | |
| WO | WO 01/14424 A2 | 3/2001 | |
| WO | WO 01/56603 A1 | 8/2001 | |
| WO | WO 2004/009618 A2 | 1/2004 | |
| WO | WO 2005/035584 A1 | 4/2005 | |
| WO | WO-2006091209 A2 * | 8/2006 | .............. A61P 35/00 |
| WO | WO 2008/027236 A2 | 3/2008 | |
| WO | WO 2009/126920 A2 | 10/2009 | |
| WO | WO 2009/157771 A2 | 12/2009 | |
| WO | WO 2010/077634 A1 | 7/2010 | |
| WO | WO 2010/108127 A1 | 9/2010 | |
| WO | WO 2013/157953 A1 | 10/2013 | |
| WO | WO 2013/157954 A1 | 10/2013 | |
| WO | WO 2017/060144 A1 | 4/2014 | |
| WO | WO 2014/116846 A2 | 7/2014 | |
| WO | WO-2014163684 A1 | 10/2014 | |
| WO | WO 2015/063339 A1 | 5/2015 | |
| WO | WO 2015/095423 A2 | 6/2015 | |
| WO | WO 2015/119923 A1 | 8/2015 | |
| WO | WO 2015/156268 A1 | 10/2015 | |
| WO | WO 2016/110584 A1 | 7/2016 | |
| WO | WO 2016/115274 A1 | 7/2016 | |
| WO | WO-2016111645 A1 | 7/2016 | |
| WO | WO 2016/145085 A2 | 9/2016 | |
| WO | WO 2016/164480 A1 | 10/2016 | |
| WO | WO 2016/185016 A1 | 11/2016 | |
| WO | WO 2016/196228 A1 | 12/2016 | |
| WO | WO 2016/207273 A2 | 12/2016 | |
| WO | WO 2017/055398 A2 | 4/2017 | |
| WO | WO 2017/096179 A1 | 6/2017 | |
| WO | WO 2017/123650 A2 | 7/2017 | |
| WO | WO 2017/123673 A2 | 7/2017 | |
| WO | WO 2017/182672 A1 | 10/2017 | |
| WO | WO 2017/193032 A2 | 11/2017 | |
| WO | WO 2017/205738 A1 | 11/2017 | |
| WO | WO 2018/045110 A1 | 3/2018 | |
| WO | WO-2018056821 A1 | 3/2018 | |

OTHER PUBLICATIONS

Rudinger, J, Peptide Hormones, Ed. Parsons, J.A., (University Park Press:Baltimore) pp. 2-7, 1976.*
Kranz et al., Restricted reassociation of heavy and light chains from hapten-specific monoclonal antibodies, Proc. Natl. Acad. Sci. USA, 78(9):5807-5811, Spet. 1981.*
Nezlin, RS, Biochemistry of Antibodies, Plenum Press:New York, p. 160, 1970.*
MacCallum et al., Antibody-atnigen interactions: Contac analysis and binding site topolography, J. Mol. Miol. 262:732-745, 1996.*
Lamminmaki et al., Crystal structure of a recombinant anti-estradiol Fab fragment in compelxt with 17B-estradiol, J. Biol. Chem. 276 (39):36687-94, 2001.*
Chen et al., Enhancement and destruction of antibody function by somatic mutation: unequal occurrence is controlled by V gene combinatorial associationsEMBO J. 14 (12): 2784-2794, 1995.*
ClinicalTrials.gov, Study NCT02179918(v25), A Study of 4-1 BB Agonist PF-05082566 Plus PD-1 Inhibitor MK-3475 in Patients With Solid Tumors, Retrieved from <URL:https://clinicaltrials.gov/ct2/history/NCT02179918?V_25=View#StudyPageTop>,[Retrived on: May 12, 2022] May 2, 2016.*
Akbay, E. A., et al., "Activation of the PD-1 Pathway Contributes to Immune Escape in EGFR-Driven Lung Tumors," Cancer Discov, 3(12): 1355-1363, American Association for Cancer Research, United States (2013).
Almagro, C., and Fransson, J., "Humanization of antibodies," *Frontiers in Bioscience*, 13:1619-1633, Frontiers in Bioscience, United States (2008).
Arch, R. H., and Thompson, C. B., "4-1BB and Ox40 are members of a tumor necrosis factor (TNF)-nerve growth factor receptor subfamily that bind TNF receptor-associated factors and activate nuclear factor $_k$B," *Mol Cell Biol*, 18(1), 558-65, American Society for Microbiology, United States (1998).
Armour, KL. et al., "Recombinant human IgG molecules lacking Fcgamma receptor I binding and monocyte triggering activities," *Eur J Immunol.*, 29(8): 2613-2624, Wiley-VCH Verlag GmbH, Germany (1999).
Arndt C., et al., "Costimulation Improves the Killing Capability of T Cells Redirected to Tumor Cells Expressing Low Levels of CD33: Description of a Novel Modular Targeting System," *Leukemia*, 28(1): 59-59, Macmillan Publisher Limited, United Kingdom (2014).
Bakker, A.B., et al., "C-Type Lectin-Like Molecule-1: A Novel Myeloid Cell Surface Marker Associated With Acute Myeloid Leukemia," *Cancer Res.*, 64(22): 8443-8450, American Association for Cancer Research, United States (2004).
Bernstein, M. B., et al., "Radiation-induced modulation of costimulatory and coinhibitory T-cell signaling molecules on human prostate carcinoma cells promotes productive antitumor immune interactions," Cancer Biother Radiopharm, 29(4): 153-161, Mary Ann Liebert, United States (2014).
Bertram, E.M., et al., "Role of T cell costimulation in anti-viral immunity," *Seminars in Immunology*, 16(3): 185-196, Elsevier, Netherlands (2004).
Boland, J. M., et al., "Tumor B7-H1 and B7-H3 Expression in Squamous Cell Carcinoma of the Lung," *Clin Lung Cancer* 14(2): 157-163, Elsevier Inc., Netherlands (2013).
Brandt, C.S., et al., "The B7 family member B7-H6 is a tumor cell ligand for the activating natural killer cell receptor NKp30 in humans," *J Exp Med.*, 206(7): 1495-1503, The Rockefeller University Press, Unite States (2009).
Chen, C.H., et al., "Dendritic-cell-associated C-type lectin 2 (DCAL-2) alters dendritic-cell maturation and cytokine production," *Blood*, 107(4): 1459-1467, The American Society of Hematology, United States (2006).
Compaan, D.M., and Hymowitz, S.G. The Crystal Structure of the Costimulatory OX40-OX40L Complex, *Structure*, 14(8): 1321-1330, Elsevier Ltd., Netherlands (2006).
Davidson, E. and Doranz, B.J., "A high-throughput shotgun mutagenesis approach to mapping B-cell antibody epitope.," *Immunology* 143, 13-20. (2014).
De Haard, H.J., et al., "A Large Non-Immunized Human Fab Fragment Phage Library That Permits Rapid Isolation and Kinetic Analysis of High Affinity Antibodies," *J Biol Chem.*, 274(26): 18218-18230, The American Society for Biochemistry and Molecular Biology, Inc., United States (1999).
Dong, H., et al., "Tumor-associated B7-H1 promotes T-cell apoptosis: a potential mechanism of immune evasion," *Nat Med* 8: 793-800, Springer Nature Limited, Germany (2002).
Fisher, T.S., et al., "Targeting of 4-1BB by monoclonal antibody PF-05082566 enhances T-cell function and promotes anti-tumor activity," *Cancer Immunology Immunotherapy*, 61: 1721-1733, Springer Nature Limited, Germany (2012).
Ghosh, R., et al., "Trastuzumab Has Preferential Activity Against Breast Cancers Driven By HER2 Homodimer," *Cancer Research*, 71(5): 1871-1882, American Association for Cancer Research, United States (2011).

(56) References Cited

OTHER PUBLICATIONS

Gunasekaran, K., et al., "Enhancing Antibody Fc Heterodimer Formation Through Electrostatic Steering Effects: Applications to Bispecific Molecules and Monovalent IgG,", *J Biol Chem.*, 285(25): 19637-19646, The American Society for Biochemistry and Molecular Biology, Inc., United States (2010).
Han, Y., et al., KLRL1, a novel killer cell lectinlike receptor, inhibits natural killer cell cytotoxicity, *Blood*, 104(9): 2858-2866, The American Society of Hematology (2004).
Hinner, M. J., et al., "Costimulatory T cell engagement via a novel bispecific anti-CD137 / anti-Her2 protein," *Journal for Immunotherpay of Cancer*, 3(2):P187, BioMed Central Ltd, London, UK (2015).
Hinner, M. J., et al., "Costimulatory T cell engagement via a novel bispecific anti-CD137/anti-Her2 protein based on Anticalin® technology," Pieris Pharmaceuticals, CRI 2015, New York September 18th.
Idusogie, E.E., et al., "Mapping of the C1q binding site on rituxan, a chimeric antibody with a human IgG1 Fc," *J Immunol.*, 164(8): 4178-4184, The American Association of Immunologists, United States (2000).
International Search Report and Written Opinion for International Application No. PCT/NL2017/050634, European Patent Office, Netherlands, dated Feb. 19, 2018, 37 pages.
Janakiram, M., et al., "Expression, Clinical Significance, and Receptor Identification of the Newest B7 Family Member HHLA2 Protein," *Clin Cancer Res.*, 21(10), 2359-2366, American Association for Cancer Research (2015).
Jaron-Mendelson, M., et al., "Dimerization of Nkp46 Receptor Is Essential for Nkp46-Mediated Lysis: Characterization of the Dimerization Site by Epitope Mapping," *Journal of Immunology*, 188: 6165-6174, The American Association of Immunologists, United States (2012).
Koide, A., et al., "The Fibronectin Type Iii Domain as a Scaffold for Novel Binding Proteins," *J Mol Biol.*, 284(4): 1141-1151, Elsevier, Netherlands (1998).
Kraan, J. et al., "Endothelial CD276 (B7-H3) expression is increased in human malignancies and distinguishes between normal and tumour-derived circulating endothelial cells," *Br J Cancer*, 111(1):149-156, Cancer Research UK, United Kingdom (2014).
Labrijn, A.F. et al., "Therapeutic Igg4 Antibodies Engage In Fab-Arm Exchange With Endogenous Human Igg4 In Vivo," *Nat Biotechnol.*, 27(8), 767-771 (2009).
Lu, D., et al. "Abstract 572: A novel anti-PDL1 × anti-VEGFR1 bispecific antibody for enhanced antitumor immunity," Proceedings: AACR 107th Annual Meeting 2016; Apr. 16-20, 2016; New Orleans, LA, available at https://cancerres.aacrjournals.org/content/76/14_Supplement/572.
Makkouk, A., et al., "Rationale for anti-CD137 cancer immunotherapy," *Eur J Cancer*, 54: 112-119, Elsevier, Netherlands (2016).
Marks, J.D. et al., "By-passing immunization. Human antibodies from V-gene libraries displayed on phage," *J Mol Biol.*, 222(3): 581-597, Elsevier Ltd., Netherlands (1991).
Marshall, A.S. et al., "Identification and characterization of a novel human myeloid inhibitory C-type lectin-like receptor (MICL) that is predominantly expressed on granulocytes and monocytes," *J Biol Chem.*, 279(15): 14792-14802, The American Society of Biochemistry and Molecular Biology, Inc., United States (2004).
McNamara, J.O. et al., "Multivalent 4-1BB binding aptamers costimulate CD8+ T cells and inhibit tumor growth in mice," *J Clin Invest.*, 118(1): 376-386, American Society for Clinical Investigation (2008).
Melero, I. et al., "Clinical development of immunostimulatory monoclonal antibodies and opportunities for combination," *Clin Cancer Res.*, 19(5): 997-1008, American Association for Cancer Research, United States (2013).
Melero, I et al., "Agonist antibodies to TNFR molecules that costimulate T and NK cells," *Clin Cancer Res.*, 19(5): 1044-1053, (2013).
Merchant, A.M. et al., "An efficient route to human bispecific IgG," *Nat Biotechnol.*, 16(7): 677-681, Springer Nature Limited, Germany (1998).

Michel, J., et al., "A soluble form of CD137 (ILA/4-1BB), a member of the TNF receptor family, is released by activated lymphocytes and is detectable in sera of patients with rheumatoid arthritis," *European Journal of Immunology*, 28(1): 290-295, Wiley-VCH Verlag GmbH, Germany (1998).
Morrison, S.L., "Two heads are better than one," *Nat Biotechnol.*, 25(11): 1233-1234, Springer Nature Limited, Germany (2007).
Moshaver, B. et al., "Identification of a small subpopulation of candidate leukemia-initiating cells in the side population of patients with acute myeloid leukemia," *Stem Cells*, 26(12): 3059-3067, AlphaMed Press, United States (2008).
Nissim, A. et al., "Antibody fragments from a 'single pot' phage display library as immunochemical reagents," *The EMBO J.*, 13(3): 692-698, Oxford University Press, England (1994).
Pollok, K. E., et al., "Inducible T cell antigen 4-IBB. Analysis of expression and function," *Journal of Immunology*, 150(3): 771-781, American Association of Immunologists, United States (1993).
Pulko, V. et al., "B7-H1 expressed by activated CD8 T cells is essential for their survival," *J Immunol.*, 187(11): 5606-5614, The American Association of Immunologists, Inc., United States (2011).
Reyes-Moreno, C., et al., "CD40/CD40 homodimers are required for CD40-induced phosphatidylinositol 3-kinase-dependent expression of B7.2 by human B lymphocytes," *The Journal of Biological Chemistry*, 279(9): 7799-7806, The American Society for Biochemistry and Molecular Biology, Inc., United States (2004).
Ross, J.S., et al., "A High Frequency of Activating Extracellular Domain ERBB2 (HER.2) Mutation in Micropapillary Urothelial Carcinoma," *Clin Cancer Res*, 20(1): 68-75, American Association for Cancer Research, United States (2013).
Sanmamed, M.F., et al., "Nivolumab and 20H4.9 Enhance Antitumor Activity of Human T Lymphocytes Engrafted in Rag2$^{-/-}$IL2 Rγ$^{null}$ Immunodeficient Mice," *Cancer Research*, 75(17): 3466-78, American Association for Cancer Research, United States, 2015.
Schaefer, G., et al., "A Two-In-One Antibody Against HER3 and EGFR Has Superior Inhibitory Activity Compared With Monospecific Antibodies," *Cancer Cell*, 20(4): 472-486, Elsevier Inc., Netherlands (2011).
Schwarz, H., "Biological activities of reverse signal transduction through C137 ligand," *Journal of Leukocyte Biology*, 77(3): 281-286, Society for Leukocyte Biology, United States (2005).
Shao, Z., et al., "Admission levels of soluble CD 137 are increased in patients with acute pancreatitis and are associated with subsequent complications," *Experimental and Molecular Pathology*, 92(1): 1-6, Elsevier, Netherlands (2012).
Shao, Z., and Schwarz, H., "CD 137 ligand, a member of the tumor necrosis factor family, regulates immune responses via reverse signal transduction.," *Journal of Leukocyte Biology*, 89(1): 21-29, Society for Leukocyte Biology, United States (2011).
Sharma, P., et al., "Primary, Adaptive, and Acquired Resistance to Cancer Immunotherapy," *Cell*, 168(4): 707-723, Elsevier B.V., Netherlands (2017).
Simon, H. U. "Evidence for a pro-apoptotic function of CD137 in granulocytes," *Swiss Medical Weekly*, 131(31-32): 455-458. EMH Swiss Medical Publishers, Switzerland (2001).
Sharpe, A.H., and Freeman, G., "The B7-CD28 Superfamily," *The Journal of Immunology*, 2: 116-126, American Association of Immunologists, United States (2002).
Shields, R.L., et al., "High resolution mapping of the binding site on human IgG1 for Fc gamma RI, Fc gamma RII, Fc gamma RIII, and FcRn and design of IgG1 variants with improved binding to the Fc gamma R," *J Biol Chem.*, 276(9): 6591-6604, The American Society for Biochemistry and Molecular Biology, Inc., United States (2001).
Sznol, M., and Chen, L., "Antagonist antibodies to PD-1 and B7-H1 (PD-L1) in the treatment of advanced human cancer," *Clin Cancer Res*, 19(5): 1021-1034, American Association for Cancer Research, United States (2013).
Thompson, R. H., et al., "Costimulatory molecule B7-H1 in primary and metastatic clear cell renal cell carcinoma," *Cancer*, 104(10): 2084-2091, American Cancer Society (2005).
Tumeh, P. C., et al., "PD-1 blockade induces responses by inhibiting adaptive immune resistance," *Nature*, 515(7528): 568-571, Springer Nature Limited, Germany (2014).

(56) References Cited

OTHER PUBLICATIONS

Van Rhenen, A., et al., "The novel AML stem cell associated antigen CLL-1 aids in discrimination between normal and leukemic stem cells," *Blood*, 110(7); 2659-2666, The American Society of Hematology, United States (2007).

Velcheti, V., et al., "Programmed death ligand-1 expression in non-small cell lung cancer," *Lab Invest*, 94(1): 107-116, USCAP, Inc., United States (2014).

Vereb, G., et al., "Dynamic, yet structured: The cell membrane three decades after the Singer-Nicolson model," *Proc Natl Acad Sci USA*, 100(14): 8053-8058, National Academy of Sciences, United States (2003).

Vezys, V., et al., "4-1BB Signaling Synergizes with Programmed Death Ligand 1 Blockade to Augment CD8 T Cell Responses during Chronic Viral Infection," *Journal of Immunology*, 187: 634-1642, The American Association of Immunologist, Inc., United States (2011).

Vinay, D. S., and Kwon, B. S., "4-1BB signaling beyond T cells," Cellular & Molecular Immunology, 8(4):281-284, Springer Nature Limited, Germany (2011).

Wu, C., et al., "Simultaneous targeting of multiple disease mediators by a dual-variable-domain immunoglobulin," *Nat Biotechnol.*, 25(11): 1290-1297, Nature Publishing Group, United Kingdom (2007).

Wolf B., et al., "A whole blood in vitro cytokine release assay with aqueous monoclonal antibody presentation for the prediction of therapeutic protein induced cytokine release syndrome in humans," *Cytokine*, 60(3): 828-831, Elsevier, Netherlands (2012).

Wölfl, M., and Greenberg, P.D., "Antigen-specific activation and cytokine-facilitated expansion of naive, human CD8+ T cells," *Nature Protocols* 9(4): 950-966, Springer Nature Switzerland AG, Switzerland (2014).

Won, E. Y., et al., "The structure of the trimer of human 4-1BB ligand is unique among members of the tumor necrosis factor superfamily," *Journal of Biological Chemistry*, 285(12): 9202-9210, The American Society for Biochemistry and Molecular Biology, Inc., United States (2010).

Xu, L. et al., "Stimulation of B7-H3 (CD276) directs the differentiation of human marrow stromal cells to osteoblasts," *Immunobiology*, 216(12): 1311-1317, Elsevier, Netherlands (2011).

Yarden, Y., and Pines, G., "The ERBB network: at last, cancer therapy meets systems biology," *Nature Reviews*, 12(8):553-563, Macmillan Publishers Limited, United Kingdom (2012).

Yi, L., et al., "Human and mouse CD137 have predominantly different binding CRDs to their respective ligands," *PLoS ONE*, 9(1): e86337, 10 pages, Public Library of Science, United States (2014).

Zhang, F., et al., "Structural basis of a novel PD-L1 nanobody for immune checkpoint blockade," *Cell Discovery*, 3(17004), 12 pages, Springer Nature Limited, Germany (2017).

Zhao, Y., et al., "Targeting 4-1BB (CD137) to enhance CD8 T cell responses with poxviruses and viral antigens," *Frontiers in Immunology* 3(332),12 pages, Frontiers Media SA, Switzerland (2012).

Zhou, G., et al., "Antibodies Against Immune Checkpoint Molecules Restore Functions of Tumor-infiltrating T cells in Hepatocellular Carcinomas," *Gastroenterology*, 153(4): P1107-1119, Elsevier, Netherlands (2017).

Kondo, A., et al., Interferon-? And tumor necrosis factor-a induce an immunoinhibitory molecule, B7-H1, via nuclear factor-?B activation in blasts in myelodysplastic syndromes. *Blood*, 116 (7): 1124-1131, The American Society of Hematology, United States (2010).

Dickopf, S., et al., "Format and geometries matter: Structure-based design defines the functionality of bispecific antibodies," Computational and Structural Biotechnology Journal 18:1221-1227, Elsevier, Netherlands (2020).

Geuijen, C., et al., "A human CD137×PD-L1 bispecific antibody promotes anti-tumor immunity via context-dependent T cell costimulation and checkpoint blockade," Nat Commun 12(1):4445, Nature Publishing Group, United Kingdom (Jul. 2021).

\* cited by examiner

DIQMTQSPSSLSASVGDRVTITCRASQSISSYLNWYQQKPGKAPKLLIYAASSLQSGVPSRFSGSGSGTDFTLTISSLQPEDFATYYCQQSYSTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 101)

Figure 1B

```
gacatccagatgacccagtctccatcctccctgtctgcatctgtaggagacagagtcacc
 D   I   Q   M   T   Q   S   P   S   S   L   S   A   S   V   G   D   R   V   T
atcacttgccgggcaagtcagagcattagcagctacttaaattggtatcagcagaaacca
 I   T   C   R   A   S   Q   S   I   S   S   Y   L   N   W   Y   Q   Q   K   P
gggaaagcccctaagctcctgatctatgctgcatccagtttgcaaagtggggtcccatca
 G   K   A   P   K   L   L   I   Y   A   A   S   S   L   Q   S   G   V   P   S
aggttcagtggcagtggatctgggacagatttcactctcaccatcagcagtctgcaacct
 R   F   S   G   S   G   S   G   T   D   F   T   L   T   I   S   S   L   Q   P
gaagattttgcaacttactactgtcaacagagttacagtaccccctccaacgttcggccaa
 E   D   F   A   T   Y   Y   C   Q   Q   S   Y   S   T   P   P   T   F   G   Q
gggaccaaggtggagatcaaa (SEQ ID NO: 102)
 G   T   K   V   E   I   K  (SEQ ID NO: 103)
```

Figure 1C

```
cgaactgtggctgcaccatctgtcttcatcttcccgccatctgatgagcagttgaaatct
 R   T   V   A   A   P   S   V   F   I   F   P   P   S   D   E   Q   L   K   S
ggaactgcctctgttgtgtgcctgctgaataacttctatcccagagaggccaaagtacag
 G   T   A   S   V   V   C   L   L   N   N   F   Y   P   R   E   A   K   V   Q
tggaaggtggataacgccctccaatcgggtaactcccaggagagtgtcacagagcaggac
 W   K   V   D   N   A   L   Q   S   G   N   S   Q   E   S   V   T   E   Q   D
agcaaggacagcacctacagcctcagcagcaccctgacgctgagcaaagcagactacgag
 S   K   D   S   T   Y   S   L   S   S   T   L   T   L   S   K   A   D   Y   E
aaacacaaagtctacgcctgcgaagtcacccatcagggcctgagctcgcccgtcacaaag
 K   H   K   V   Y   A   C   E   V   T   H   Q   G   L   S   S   P   V   T   K
agcttcaacaggggagagtgttag (SEQ ID NO: 104)
 S   F   N   R   G   C   -  (SEQ ID NO: 105)
```

Figure 1D

DIQMTQSPSSLSASVGDRVTITCRASQSISSYLNWYQQKPGKAPKLLIYAASSLQSGVPSRFSGSGSG
TDFTLTISSLQPEDFATYYCQQSYSTPPITFGQGTRLEIK (SEQ ID NO: 106)

Figure 1E

DIQMTQSPSSLSASVGDRVTITCRASQSISSYLNWYQQKPGKAPKLLIYAASSLQSGVPSRFSGSGSG
TDFTLTISSLQPEDFATYYCQQSYSTP (SEQ ID NO: 107)

Figure 2

Figure 2A
VH: dependent on the MF (target): Figure 3.

Figure 2B
CH1:

```
gctagcaccaagggcccatcggtcttccccctggcaccctcctccaagagcacctctggg
 A  S  T  K  G  P  S  V  F  P  L  A  P  S  S  K  S  T  S  G
ggcacagcggccctgggctgcctggtcaaggactacttccccgaaccggtgacggtgtcg
 G  T  A  A  L  G  C  L  V  K  D  Y  F  P  E  P  V  T  V  S
tggaactcaggcgccctgaccagcggcgtgcacaccttcccggctgtcctacagtcctca
 W  N  S  G  A  L  T  S  G  V  H  T  F  P  A  V  L  Q  S  S
ggactctactccctcagcagcgtcgtgaccgtgccctccagcagcttgggcacccagacc
 G  L  Y  S  L  S  S  V  V  T  V  P  S  S  S  L  G  T  Q  T
tacatctgcaacgtgaatcacaagcccagcaacaccaaggtggacaagagagtt  (SEQ ID NO: 108)
 Y  I  C  N  V  N  H  K  P  S  N  T  K  V  D  K  R  V    (SEQ ID NO: 109)
```

Figure 2C

Hinge:

gagcccaaatcttgtgacaaaactcacacatgcccaccgtgccca (SEQ ID NO: 110)

E P K S C D K T H T C P P C P (SEQ ID NO: 111)

gcacctgaactcctggggggaccgtcagtcttcctcttccccccaaaacccaaggacacc

A P E L L G G P S V F L F P P K P K D T ctcatgatctcccggacccctgaggtcacatgcgtggtggtggacgtgagccacgaagac

L M I S R T P E V T C V V V D V S H E D cctgaggtcaagttcaactggtacgtggacggcgtggaggtgcataatgccaagacaaag

P E V K F N W Y V D G V E V H N A K T K ccgcgggaggagcagtacaacagcacgtaccgtgtggtcagcgtcctcaccgtcctgcac

P R E E Q Y N S T Y R V V S V L T V L H caggactggctgaatggcaaggagtacaagtgcaaggtctccaacaaagccctcccagcc

Q D W L N G K E Y K C K V S N K A L P A cccatcgagaaaaccatctccaaagccaaa (SEQ ID NO: 112)

P I E K T I S K A K (SEQ ID NO: 113)

Figure 2E

CH2 containing L235G and G236R silencing substitutions:

gcacctgaactcggcaggggaccgtcagtcttcctcttccccccaaaacccaaggacacc

A P E L G R G P S V F L F P P K P K D T ctcatgatctcccggacccctgaggtcacatgcgtggtggtggacgtgagccacgaagac

L M I S R T P E V T C V V V D V S H E D cctgaggtcaagttcaactggtacgtggacggcgtggaggtgcataatgccaagacaaag

P E V K F N W Y V D G V E V H N A K T K ccgcgggaggagcagtacaacagcacgtaccgtgtggtcagcgtcctcaccgtcctgcac

P R E E Q Y N S T Y R V V S V L T V L H caggactggctgaatggcaaggagtacaagtgcaaggtctccaacaaagccctcccagcc

Q D W L N G K E Y K C K V S N K A L P A cccatcgagaaaaccatctccaaagccaaa (SEQ ID NO: 114)

P I E K T I S K A K (SEQ ID NO: 115)

Figure 2F

CH3: KK of DEKK

```
gggcagccccgagaaccacaggtgtacaccaagccccatcccgggaggagatgaccaag
  G  Q  P  R  E  P  Q  V  Y  T  K  P  P  S  R  E  E  M  T  K
aaccaggtcagcctgaagtgcctggtcaaaggcttctatcccagcgacatcgccgtggag
  N  Q  V  S  L  K  C  L  V  K  G  F  Y  P  S  D  I  A  V  E
tgggagagcaatgggcagccggagaacaactacaagaccacgcctcccgtgctggactcc
  W  E  S  N  G  Q  P  E  N  N  Y  K  T  T  P  P  V  L  D  S
gacggctccttcttcctctatagcaagctcaccgtggacaagagcaggtggcagcagggg
  D  G  S  F  F  L  Y  S  K  L  T  V  D  K  S  R  W  Q  Q  G
aacgtcttctcatgctccgtgatgcatgaggctctgcacaaccactacacgcagaagagc
  N  V  F  S  C  S  V  M  H  E  A  L  H  N  H  Y  T  Q  K  S
ctctccctgtctccgggttga  (SEQ ID NO: 116)
  L  S  L  S  P  G  -   (SEQ ID NO: 117)
```

Figure 2G

CH3: DE of DEKK

```
gggcagccccgagaaccacaggtgtacaccgacccccatcccgggaggagatgaccaag
  G  Q  P  R  E  P  Q  V  Y  T  D  P  P  S  R  E  E  M  T  K
aaccaggtcagcctgacctgcgaggtcaaaggcttctatcccagcgacatcgccgtggag
  N  Q  V  S  L  T  C  E  V  K  G  F  Y  P  S  D  I  A  V  E
tgggagagcaatgggcagccggagaacaactacaagaccacgcctcccgtgctggactcc
  W  E  S  N  G  Q  P  E  N  N  Y  K  T  T  P  P  V  L  D  S
gacggctccttcttcctctatagcaagctcaccgtggacaagagcaggtggcagcagggg
  D  G  S  F  F  L  Y  S  K  L  T  V  D  K  S  R  W  Q  Q  G
aacgtcttctcatgctccgtgatgcatgaggctctgcacaaccactacacgcagaagagc
  N  V  F  S  C  S  V  M  H  E  A  L  H  N  H  Y  T  Q  K  S
ctctccctgtctccgggttga  (SEQ ID NO: 118)
  L  S  L  S  P  G  -   (SEQ ID NO: 119)
```

MF6737
EVQLVQSGAEVKKPGESLKISCKVSGYSFT<u>NYWIG</u>WVRQMPGKGLEWMG<u>IIYPGDSD
TRYSPSFQG</u>QVTISADKSISTAYLQWHTLKASDTAMYYCAR<u>HQGYSFSGSHIDDY</u>WG
QGTLVTVSS (SEQ ID NO: 120)

MF6744
EVQLVQSGAEVKKPGESLKISCKGSGYSFT<u>SYWIG</u>WVRQMPGKGLEWMG<u>IIFPDDSD
TRYSPSFQG</u>QVTISADKSISTAYLQWSSLKPSDTAMYYCVR<u>LGGYSGYAEDFVDF</u>WGQ
GTLVTVSS (SEQ ID NO: 121)

MF6749
EVQLVQSGAEVRKPGESLKISCKGSGYSFT<u>TYWIG</u>WVRQMPGKGLEWMG<u>IIYPGDSD
TRYSPSFQG</u>QVTISADKSISTVYLQWSSLKASDTAMYYCAR<u>HAGFIITSQNIDDY</u>WGQ
GTLVTVSS (SEQ ID NO: 122)

MF6754
QVQLVQSGAEVKKPGASVKVSCKVSGYTL<u>SELSIH</u>WVRQAPGKGVEWMG<u>GFYPEDV
EPIYARKFQG</u>RVTMTEDTSTDTAYMELNSLRSEDTAVYYCAA<u>EGFDNYGSGIRGNWF
DP</u>WGQGTLVTVSS (SEQ ID NO: 123)

MF6763
EVQLVQSGAEVKKPGASVKVSCKVSGYTL<u>TELSMH</u>WVRQSPGKGLEWMG<u>SFYPEDG
ETIYAQKFQG</u>RITMTEDTSADTAYMELSSLRSEDTAVYYCAT<u>EGVGVIRGNWFDP</u>WG
QGTLVTVSS (SEQ ID NO: 124)

MF6783
QVQLVQSGSELKKPGASVKVSCKASGYTFT<u>NFAMN</u>WVRRAPGQGLEWMG<u>WINTNT
GNPTYAQGFTG</u>RFVFSLDTSVNTAYLQISSLKAEDTAVYYCAR<u>DWGVIGGHYMDV</u>WG
KGTTVTVSS (SEQ ID NO: 125)

Figure 3A (continued)

MF6785
EVQLVQSGAEVKKPGASVKVSCKVSGYTLTKLSMHWVRQAPGKGLEWMGGFEPED
GETINAQKFQGRVTMTEDTSTDTAYMELSSLRSEDTAVYYCATDLRLGASYYYSYMD
YWGRGTMVTVSS (SEQ ID NO: 126)

MF6788
EVQLVQSGSELKKPGASVKVSCKASGYTFTNFAMNWVRQAPGQGLEWMGWINTNT
GNPTYAQDFTGRFVFSLDTSGNTAYLQISSLKAEDTAVYYCARDWGLVAIGYFDYWG
QGTLVTVSS (SEQ ID NO: 127)

MF6795
EVQLVQSGAEVKKPGESLKISCKGSGYSFTSYWIGWVRQMPGKGLEWMGHYPDDSD
TRYSPSFQGQVTISADKSSSTAYLQWSSLKASDTAMYYCASFYTGIVGATGAFDVWGQ
GTTVTVSS (SEQ ID NO: 128)

MF6797
QITLKESGPTLVKPTQTLTLTCTFSGFSLSTTGVGVNWIRQPPGEALEWLALIYWNDD
TYYSPSLKSRLTITKDTSKNQVVLTMTNMDPVDTATYYCAHEGIIGFLGGNWFDPWG
QGTLVTVSS (SEQ ID NO: 129)

MF6798
QVQLVQSGSELKKPGASVKVSCRASGYTFTNFAMTWVRQAPGQGPEYMGWINTNTG
NPTYAQGFTGRFVFSLDTSVNTAYLQISSLKAEDTAVYYCARDWASVMVRGDLDYWG
QGTLVTVSS (SEQ ID NO: 130)

MF6805
QVQLVQSGSELKKPGASVKVSCKASGYTFTTYAMNWVRQAPGQGLEWMGWIHTNT
GNPTYAQGFTGRFVFSLDTSVSTAYLQISSLQAEDTAVYYCVRTEYSYGYVFYYWGQG
TLVTVSS (SEQ ID NO: 131)

MF6808
QVQLVQSGAEVKKPGSSVKVSCKASGGTFSSDAISWVRQAPGQGLEWMGGMIPILGT
ANYAQKFQGRVTITADRSTSTAYMELSSLRSEDTAVYYCVRGATYYYGSGTYYSINWF
DPWGQGTLVTVSS (SEQ ID NO: 132)

QITLKESGPTLVKPTQTLTLSCTFSGFSLSTSGMSVGWIRQPPGKALEWLALIYWNDD
KYFSPSLKSRLTITKDTSKNQVVLTLTNMDPVDTATYYCAHTLWGSDDVFDVWGQGT
MVTVSS (SEQ ID NO: 133)

MF6832

EVQLVESGGGLVQPGGSLRLSCAASGFTFSSYAMSWVRQAPGKGLEWVSAISGSGGS
TYYADSVKGRFTISRDNSKNTLYLQMNSLRAEDTAVYYCARGWNAFWFDYWGQGTL
VTVSS (SEQ ID NO: 134)

MF6847

QVQLVQSGAEVKKPGASVKVSCKASGYTFTSYGISWVRQAPGQGLEWMGWISAYNG
NTNYAQKLQGRVTMTTDTSTSTAYMELRSLRSDDTAVYYCARDSGYDSAYLAFDYW
GQGTLVTVSS (SEQ ID NO: 135)

MF6848

QVQLVQSGAEVKKPGASVKVSCKASGYTFTSYGISWVRQAPGQGLEWMGWISAYNG
NTNYAQKLQGRVTMTTDTSTSTAYMELRSLRSDDTAVYYCARDWSGWGSPYAFDYW
GQGTLVTVSS (SEQ ID NO: 136)

MF6856

EVQLLESGGGLVQPGGSLRLSCAASGFTFSSYAMSWVRQAPGKGLEWVSAISGSGGS
TYYADSVKGRFTISRDNSKNTLYLQMNSLRAEDTAVYYCARDWSGSWDYGSSAFDY
WGQGTLVTVSS (SEQ ID NO: 137)

MF6860

EVQLVQSGAEVKKPGESLKISCKGSGYSFTSYWIGWVRQMPGKGLEWMGIIYPGDSD
TRYSPSFQGQVTISADKSISTAYLQWSSLKASDTAVYYCAKGLLWGKTDYYSGFDYW
GQGTLVTVSS (SEQ ID NO: 138)

MF6861

QVQLVQSGAEVKKPGASVKVSCKASGYTFTSYGISWVRQAPGQGLEWMGWISAYNG
NTNYAQKLQGRVTMTTDTSTSTAYMELRSLRSDDTAVYYCARDSDGYGPKAFDYWG
QGTLVTVSS (SEQ ID NO: 139)

QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCARGRGWRNYFQWWGF
DYWGQGTLVTVSS  (SEQ ID NO: 140)

MF6870

EVQLLESGGGLVQPGGSLRLSCAASGFTFSSYAMSWVRQAPGKGLEWVSAISGSGGS
TYYADSVKGRFTISRDNSKNTLYLQMNSLRAEDTAVYYCAKGSGHRFYQYRSGFDYW
GQGTLVTVSS  (SEQ ID NO: 141)

MF6873

QVQLVQSGAEVKKPGASVKVSCKASGYTFTSYGISWVRQAPGQGLEWMGWISAYNG
NTNYAQKLQGRVTMTTDTSTSTAYMELRSLRSDDTAVYYCAKDRWSWYQGRGFGFD
YWGQGTLVTVSS  (SEQ ID NO: 142)

MF6875

EVQLLESGGGLVQPGGSLRLSCAASGFTFSSYAMSWVRQAPGKGLEWVSAISGSGGS
TYYADSVKGRFTISRDNSKNTLYLQMNSLRAEDTAVYYCAKGRWWFTYDGFDYWGQ
GTLVTVSS  (SEQ ID NO: 143)

EVQLVQSGAEVKKPGSSVKVSCKASGDTFNTYSITWVRQAPGQGLEWMGSIVPIFGTI
NNAQKFQGRVTITADKSANTAYMELSSLRSEDTAVYYCARDNTMVRGVDYYYMDVW
GKGTMVTVSS  (SEQ ID NO: 144)

MF5361

QVQLVQSGSELKKPGASVKVSCKASGYTFTSYSLNWVRQAPGQGLEWMGWINTNTG
NPTYAQGFTGRFVFSLDSSVTTAYLQISSLKAEDTAVYYCTRDHDFRRGRSLDVWGK
GTTVTVSS  (SEQ ID NO: 145)

Figure 3B (continued)

MF5377
EVQLVQSGAEVKKPGSSVKVSCKASGGIFSTYAISWVRQAPGQGLEWMGGIIPIFDTPNYAQKFQGRVTITADKSTSTAYMDLSSLRSEDTAVYYCAKNVRGYSAYDLDYWGQGTLVTVSS (SEQ ID NO: 146)

MF5382
EVQLVQSGAEVKNPGSSVKVSCKATGGTFNTYGTNWVRQAPGQGLEWMGGIIPIFGTANYAQKFQGRVTITADKSTTTAYMEVSSLRSEDTAVYYCARGGADMGTLDYWGQGTLVTVSS (SEQ ID NO: 147)

MF5424
EVQLVQSGAEVMRPGSSVKVSCKASGGIFNTYTIHWVRQAPGQGLEWMGGIIPIFDTPNFAQKFQGRLTITADKSTNTAYMELTSLRSEDTAVYYCAREGCNHGVCYPYWGQGTLVTVSS (SEQ ID NO: 148)

MF5426
QVQLVQSGAEVKKPGSSVKVSCKASGDTFRSYGITWVRQAPGQGLEWMGGIIPIFGTTNYAQKFQGRVTITADKSTSTVYMELSSLRSEDTAVYYCARRRGYSNPHWLDPWGQGTLVTVSS (SEQ ID NO: 149)

MF5439
QVQLVQSGAEVKKPGSSVKVSCKASGGTFSTYGILWVRQAPGQGLEWMGGIIPIFGTANYAQKFQGRVTITADISTSTAYMELSSLRSEDTAVYYCARGGGNYYEFVYWGQGTLVTVSS (SEQ ID NO: 150)

MF5442
EVQLVQSGAEVKKPGSSVRVSCKASGGTFNTYAINWVRQAPGQGLEWVGRIIPIFDTANYAQKFQGRVTISADKSTTTAYMELSSLRSEDTAVFYCAKDETGYSSSNFQHWGQGTLVTVSS (SEQ ID NO: 151)

MF5553
QVQLVQSGSELKKPGASVKVSCKASGYTFTNYAINWVRQAPGQGLEWMGWINPNTGNPTYAQGFTGRFVFSLDTSVSTAYLQISSLKAEDTAVYYCARDRKYVTNWVFAEDFQHWGQGTLVTVSS (SEQ ID NO: 152)

QVQLVQSGAEVKRPGSSVKVSCKASGGTFNTYSITWVRQAPGQGLEWMGGIIPVFGT
SKYAQKFQDRVTITADKSTNTAYMELSSLRSEDTAVYYCARDPSFSSSSGWFDPWGQ
GTLVTVSS (SEQ ID NO: 153)

MF5561

QVQLVQSGAEVKKPGSSVKVSCKASGGTFNTYAINWVRQAPGQGLEWMGGIIPIFDT
ANYAQRFQGRVTITADKSTSTAYMELSSLRSEDTAVYFCAKDQTGYSSTLFDYWGQG
TLVTVSS (SEQ ID NO: 154)

MF5576

QVQLVQSGSELKKPGASVKVSCKASGYTFTSHAMNWVRQAPGQGLEWMGWINPNT
GNPTYAQGFTGRFVFSLDTSVSTAYLQISSLKAEDTAVYYCAIDRGYMSNWVFAEYFP
HWGQGTLVTVSS (SEQ ID NO: 155)

MF5594

EVQLVQSGAEVKKPGSSVKVSCKASGGTFSTYAISWVRQAPGQGLEWMGWIIPIFDT
GNYAQKIQGRVTITADKSTSTAYMELTSLRSEDTAVYYCARHDYTNTVDAFDIWGQG
TMVTVSS (SEQ ID NO: 156)

MF5708

QVQLVQSGAEVKKPGSSVKVSCKASGDTFRSYGITWVRQAPGQGLEWMGGIIPVFGT
TNYAQKFQGRVTITADKSTSTVFMELNSLRSEDTAVYYCARRGYSNPHWLDPWGQ
GTLVTVSS (SEQ ID NO: 157)

QVQLVQSGAEVKKPGESLRISCKGSGYSFSNYWIGWVRQMPGKGLEWMGIIYPGDSE
TRYSPSFQGQFTISADKSISTAYLQWSSLRASDTAMYYCATGWDFWGQGTLVTVSS
(SEQ ID NO: 158)

MF6630

EVQLVQSGAEVKKPGASVKVSCKASGYTPFTSYYMHWVRQAPGQGLEWMGIINPSGG
STNYAQKFQGRVTMTRDTSTSTVYMELSSLRSEDTAVYYCARGGTMVRGVIDDWFDP
WGQGTLVTVSS
(SEQ ID NO: 159)

Figure 3C (continued)

MF6637
QVQLVQSGAEVKKPGSSVKVSCKASGGTFS<u>DYPIS</u>WVRQAPGQGFEWMG<u>GIIPIFDTS
NIEQKFQG</u>RVTLTADKSTSTVYMELSGLRSEDTAIYYCAR<u>VGGLRQAWYFDL</u>WGRGT
LVTVSS (SEQ ID NO: 160)

MF6643
QVQLVQSGSELKKPGASVKVSCKASGYTFT<u>SYPMN</u>WVRQAPGQGLEWLG<u>WINTNTG
TPTYAHDFTG</u>RFVFSLDTSVSTAYLQISSLKSEDTAVYYCAR<u>GGWELLPNYFQQ</u>WGQ
GTLVTVSS (SEQ ID NO: 161)

MF6645
QVQLQESGPGLVKPSETLSLTCSVSGGSIS<u>NRYWS</u>WIRQSPGKGLEWIG<u>YIYYSGNTN
YNPSLKS</u>RVTISVDTSKNQFSLKVNSVTAADTAVYYCAS<u>SPPYYMDV</u>WGKGTTVTVSS
(SEQ ID NO: 162)

MF6646
EVQLVESGGGLVKPGGSLRLSCAASGFTFS<u>NAYMT</u>WVRQAPGGGLEWVG<u>RIRSKTD
GGTTDYAAPVKG</u>RFTISRDDSKNTLYLQMNSLKTEDTAIFYCTT<u>GFDWYFTL</u>WGRGT
LVTVSS (SEQ ID NO: 163)

MF6648
EVQLVESGGGLVKPGGSLRLSCAASGFTFS<u>NAWMS</u>WVRQVPGKGLEWVG<u>RIKSKTD
GGTTDYAVAVKG</u>RFTISRDDSKNTLYLQMNSLKTEDTAVFYCTT<u>GWGYSGYGPEGFD
IWGQG</u>TTVTVSS (SEQ ID NO: 164)

MF6655
QVQLVQSGAEVKKPGSSVKVSCKASGGTFS<u>NYAIS</u>WVRQAPGQGLEWMG<u>GIIPIFDT
ANSAQNFQG</u>RLTITADTSTSTAYMELSSLRSEDTAVYYCAR<u>IGGTGTTDWYFDL</u>WGR
GTLVTVSS (SEQ ID NO: 165)

MF6658
QVQLVQSGAEVKKPGSSVKVSCKASGGTFS<u>NYAIS</u>WVRQAPGQGLEWLG<u>GIIPIFGTS
NSAQNFLG</u>RVTITADKSTSTVYMELSSLRSEDTAIYYCAR<u>VGGYTSSSWFFDL</u>WGRGT
LVTVSS (SEQ ID NO: 166)

EVQLVQSGAEVKKPGSSVKVSCKASGGTFS<u>SYAIS</u>WVRQAPGQGLEWMG<u>GIIPIFDTA
NYVPKFQG</u>RVTITADKSTSTAYMELSSLRSEDTAVYYCAR<u>VDGGNSDWYFDL</u>WGRGT
LVTVSS   (SEQ ID NO: 167)

MF6675

QVQLVQSGAEVKKPGSSVKVSCKASGGTFS<u>SYPIS</u>WVRQAPGEGLEWMG<u>GIIPIFETA
NFAQKFQG</u>RVTITADKSTNTVYMELSRLRSEDTAVYYCVR<u>VDGRSSGGNWHFDL</u>WG
RGTLVTVSS   (SEQ ID NO: 168)

MF6686

EVQLVQSGAEVKKPGSSVKVSCKASGGTFS<u>YYTIT</u>WVRQAPGQGFEWMG<u>GIIPIFGTP
SYAQKFQG</u>RVTITADKYTNTAYMELSSLRSEDTAVYYCAR<u>DPYYFDSNGYPPEDD</u>WG
QGTLVTVSS  (SEQ ID NO: 169)

MF6690

QVQLVQSGSELKKPGASVKVSCKASGYTFT<u>RYAMN</u>WVRQAPGQGLEWMG<u>WINTITG
NPTYAQGFTGR</u>FVFSLDTSVSTAYLQISSLKAEDTAVYFCAR<u>GWDFFDS</u>WGQGTLVT
VSS   (SEQ ID NO: 170)

MF6692

QVQLVQSGAEVKKPGSSVKVSCKASGDTDS<u>SNAVS</u>WVRQAPGQGFEWMG<u>GIIPIFGT
ANYAQKFQG</u>RVTITADKSTSTVNMELRSLRSEDTAVYYCAR<u>VGGLGTTPHWYFDL</u>W
GRGTLVTVSS   (SEQ ID NO: 171)

MF6700

QVQLVQSGAEVKKPGSSVKVSCKTSGDTFS<u>TNAIS</u>WVRQAPGQGLEWMG<u>GIVPILDT
VNYAQNFLG</u>RVTITADRATRTAYMELTNLRSEDTAVYYCAI<u>PSYNWNRLYYYYMDV</u>W
GKGTTVTVSS  (SEQ ID NO: 172)

MF6706

QITLKESGPTLVRPTQTLTLTCTFSGFSLS<u>TSAVGVD</u>WIRQPPGKALEWLA<u>LIYWSDD
KRYSPSLKSR</u>LTITKDTSKNQVVLTMTNMDPVDTATYYCAR<u>SQPNLDFWSGYHFDY</u>
WGQGTLVTVSS   (SEQ ID NO: 173)

Figure 3C (continued)

MF6714
EVQLVQSGAEVKKSGSSVKVSCEASGGSFNSYTITWMRQAPGQGLEWMGGHPIFGT
ASYAQKFQGRVTITADRSTNTAYMELSSLRSEDTAVYYCARDPFFYDRSGYPPFDYW
GQGTLVTVSS (SEQ ID NO: 174)

MF6721
EVQLVESGGGLVKPGGSLRLSCAASGFTFSNAWMSWVRQAPGKGLEWVGRIKSKTD
GGTTDYAAPVKGRFTISRDDSKNTLYLQMNSLKTEDTAVYYCTKGWGSGWGQGTLV
TVSS (SEQ ID NO: 175)

MF6722
QVQLVQSGAGVKEPGSSVKVSCKTSGDTFSSYAISWLRQAPGQGLEWMGGHPIFDTA
NSDQKFQDRVTITADRSTNTVYMELSSLRSDDTAVYYCARVGGYGNNYNFDYWGQG
TLVTVSS (SEQ ID NO: 176)

MF6724
EVQLVESGGGLVKPGGSLRLSCAASGFTFSDDWMSWVRQAPGKGLEWVGRIKGKTD
GGTTDYASPVKGRFTISRDDSKNTLYLHLNSLKTEDTAVYYCTTDPSGSYFYHYYMD
YWGKGTLVTVSS (SEQ ID NO: 177)

MF6728
QITLKESGPTLVKPTQTLTLTCTFSGFSLSTSAVGVGWIRQPPGKSLEWLAVIYWSDD
KRYSPSLKSRLTITKDTSKNQVVLRMTNMDPVDTATYYCAHRRPNYDSWSGYYEDY
WGQGTLVTVSS (SEQ ID NO: 178)

MF6729
QVQLVQSGSELKKPGASVKVSCKASGYTFTSHVMNWVRQAPGHGLEWMGWIDTNT
GNPTYAQDFTGRFVFSLDSSVSTAYLQISSLKTEDTAVYYCARGGWGLLREYFLQWG
QGTLVTVSS (SEQ ID NO: 179)

MF6826
EVQLVESGGGVVQPGRSLRLSCAASGFIFSSYGMHWVRQAPGKGLEWVAVISFDGTN
EYYVDSVKGRFTISRDNSKNTLYLQMSSLKAEDTAVYYCATHTGHYSGFDYWGQGTL
VTVSS (SEQ ID NO: 180)

Figure 3C (continued)

MF6940
QVQLVQSGAEVKKPGSSVKVSCKASGGTFS<u>DYPIS</u>WVRQAPGQGFEWMG<u>GIIPIFDTS
NIEQKFQG</u>RVTLTADKSTSTVYMELSGLRSEDTAIYYCAR<u>VDGTGISNWYFDL</u>WGRG
TLVTVSS (SEQ ID NO: 181)

MF6942
EVQLVQSGAEVKKPGSSVKVSCKASGGTFS<u>SYAMN</u>WVRQAPGQGLEWMG<u>WINTNT
GNPTYAQGFTG</u>RFVFSLDTSVSTAYLQISGLKAEDTAVYFCTR<u>GYSSIWHGENFQY</u>W
GQGTLVTVSS (SEQ ID NO: 182)

MF6943
QVQLVQSGSELKKPGASVKVSCKASGYTFT<u>GYAIN</u>WVRQAPGQGLEWMG<u>WINTNTG
NPTYAQDFTG</u>RFVFSVDTSVSTAYLQISSLKAEDTAVYYCARD<u>MDNWNYEGYYVMD
VW</u>GKGTTVTVSS (SEQ ID NO: 183)

MF6944
EVQLVQSGAEVKKPGSSVKVSCRASGGTFS<u>NYAIS</u>WVRQAPGQRLEWMG<u>GIIPIFDTA
NSAQTFQD</u>RVTITADTSTSTVYMELSSLKSEDTAVYYCAR<u>VEGWGSQWYFDL</u>WGRGT
LVTVSS (SEQ ID NO: 184)

MF6947
QVQLVQSGAEVKKPGSSVKVSCKASGGTFN<u>NYPIS</u>WVRQAPGQGLEWMG<u>THPIFDTS
SSAQQFQG</u>RVTITADESTNTVSMELSSLRSEDTAIYYCAR<u>VEGTDSNWGWDF</u>WGQGT
LVTVSS (SEQ ID NO: 185)

MF6949
QVQLVQSGSELKKPGASVKVSCKASGYTFT<u>SYAVN</u>WVRQAPGQGLEWMG<u>WINTDTG
NPTYAQGFTG</u>RFVFSLDTSVNTAYLQINSLKPEDTAVYYCAR<u>DDGTGTGDYVWGRYR
YTLDF</u>WGQGTLVTVSS (SEQ ID NO: 186)

MF7331
QVQLVQSGAEVKKPGASVKVSCKASGYTFT<u>SYGIS</u>WVRQAPGQGLEWMG<u>WISAYNG
NTNYAQKLQG</u>RVTMTTDTSTSTAYMELRSLRSDDTAVYYCAR<u>DGYKLYAADGFDY</u>W
GQGTLVTVSS (SEQ ID NO: 187)

Figure 3C (continued)

MF7332
QVQLVQSGAEVKKPGASVKVSCKASGYTFTSYGISWVRQAPGQGLEWMGWISAYNG
NTNYAQKLQGRVTMTTDTSTSTAYMELRSLRSDDTAVYYCARDMDSYPFYRGFDYW
GQGTLVTVSS (SEQ ID NO: 188)

MF7334
QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCAKDDNTMWYSRPYAFD
YWGQGTLVTVSS (SEQ ID NO: 189)

MF7341
QVQLVQSGAEVKKPGASVKVSCKASGYTFTSYGISWVRQAPGQGLEWMGWISVYNG
NTNYAQKLQGRVTMTTDTSTSTAYMELRSLRSDDTAVYYCARDSPYWSLPGGFDYW
GQGTLVTVSS (SEQ ID NO: 190)

MF7345
QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCARDQRWWYMDPGAGF
DYWGQGTLVTVSS (SEQ ID NO: 191)

MF7350
QVQLVQSGAEVKKPGASVKVSCKASGYTFTSYGISWVRQAPGQGLEWMGWISAYNG
NTNYAQKLQGRVTMTTDTSTSTAYMELRSLRSDDTAVYYCAKDYSYSGTGSSSAFDY
WGQGTLVTVSS (SEQ ID NO: 192)

MF7351
QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCARDYLHGSYYRGSAFDY
WGQGTLVTVSS (SEQ ID NO: 193)

MF7352
QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCAKDSWHGQYYYGKGFD
YWGQGTLVTVSS (SEQ ID NO: 194)

Figure 3C (continued)

MF7353
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAR<u>DGLGWDPGYGFDY</u>W
GQGTLVTVSS (SEQ ID NO: 195)

MF7356
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAR<u>DNYQGMYYFGTGFD
Y</u>WGQGTLVTVSS (SEQ ID NO: 196)

MF7358
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAK<u>DNHYYSPPTYWGFD
Y</u>WGQGTLVTVSS (SEQ ID NO: 197)

MF7365
EVQLLESGGGLVQPGGSLRLSCAASGFTFS<u>SYAMS</u>WVRQAPGKGLEWVS<u>AISGSGGS
TYYADSVKG</u>RFTISRDNSKNTLYLQMNSLRAEDTAVYYCAK<u>GGQSQYHSYPFGFDY</u>W
GQGTLVTVSS (SEQ ID NO: 198)

MF7366
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAR<u>DWWQGHWYRSGGF
DY</u>WGQGTLVTVSS (SEQ ID NO: 199)

MF7371
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAR<u>GQMDYYDDWYSAFD
Y</u>WGQGTLVTVSS (SEQ ID NO: 200)

MF7372
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAR<u>DYYQGSHYFGPAFDY</u>
WGQGTLVTVSS (SEQ ID NO: 201)

Figure 3C (continued)

MF7374
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAR<u>GDDNRMYSNPKGFD
Y</u>WGQGTLVTVSS  (SEQ ID NO: 202)

MF7378
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAR<u>DNTQGNYYRSRGFD
Y</u>WGQGTLVTVSS  (SEQ ID NO: 203)

MF7382
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAR<u>DGLQGSNYHLGGFD
Y</u>WGQGTLVTVSS  (SEQ ID NO: 204)

MF7383
EVQLLESGGGLVQPGGSLRLSCAASGFTFS<u>SYAMS</u>WVRQAPGKGLEWVS<u>AISGSGGS
TYYADSVKG</u>RFTISRDNSKNTLYLQMNSLRAEDTAVYYCAK<u>GYDMYGGWGAWGFDY</u>
WGQGTLVTVSS  (SEQ ID NO: 205)

MF7394
QVQLVQSGAEVKKPGASVKVSCKASGYTFT<u>SYGIS</u>WVRQAPGQGLEWMG<u>WISAYNG
NTNYAQKLQG</u>RVTMTTDTSTSTAYMELRSLRSDDTAVYYCAR<u>DYPAWAYSAFDY</u>WG
QGTLVTVSS (SEQ ID NO: 206)

MF7395
QVQLVESGGGVVQPGRSLRLSCAASGFTFS<u>SYGMH</u>WVRQAPGKGLEWVA<u>VISYDGS
NKYYADSVKG</u>RFTISRDNSKNTLYLQMNSLRAEDTAVYYCAK<u>DYWYYLSDAFDY</u>WG
QGTLVTVSS (SEQ ID NO: 207)

MF7397
EVQLLESGGGLVQPGGSLRLSCAASGFTFS<u>SYAMS</u>WVRQAPGKGLEWVS<u>AISGSGGS
TYYADSVKG</u>RFTISRDNSKNTLYLQMNSLRAEDTAVYYCAR<u>DHWGSFYGDFDY</u>WGQ
GTLVTVSS  (SEQ ID NO: 208)

Figure 3D

MF5554
QVQLVQSGSELKKPGASVKVSCKASGYTFTSHAMNWVRQAPGQGLEWMGWINPNT
GNPTYAQGFTGRFVFSLDTSVSTAYLQISSLKAEDTAVYYCARDRKYVTNWVFAEDF
QHWGQGTLVTVSS  (SEQ ID NO: 209)

MF5576
QVQLVQSGSELKKPGASVKVSCKASGYTFTSHAMNWVRQAPGQGLEWMGWINPNT
GNPTYAQGFTGRFVFSLDTSVSTAYLQISSLKAEDTAVYYCAIDRGYMSNWVFAEYFP
HWGQGTLVTVSS  (SEQ ID NO: 210)

MF5578
QVQLVQSGSELKKPGASVKVSCKASGYTFTSYAMNWVRQAPGQGLEWMGWINTNT
GNPTYAQGFTGRFVFSLDTSVSTAYLQISSLKAEDTAVYYCATDRGYISSWVFAEDFQ
HWGQGTLVTVSS  (SEQ ID NO: 211)

MF7702
QVQLVQSGSELKKPGASVKVSCKASGYTFTNYAINWVRQAPGQGLEWMGWINPNTG
NPTYAQGFTGRFVFSLDTSVSTAYLQISSLKAEDTAVYYCARDRKYVTNWVFAEDFQ
HWGRGTLVT  (SEQ ID NO: 212)

MF9375
QVQLVQSGSELKKPGASVKVSCTASGYTFTSYAMNWVRQAPGQRLEWMACVNPNTG
SPTYAQGSTGRFVVSLDTSVSTAYLQISSLKAEDTAVYYCARDRKYVTNWVFAEDFQH
WGHGTLVTVSS (SEQ ID NO: 213)

MF9376
QVQLVQSGSELKKPGASVKVSCKASGYTFTNYAMNWVRQAPGQGLEWMGWMNPN
TGNPTYAQGSTGRFVVSLDTSVSTAYLQISSLKAEDTAVYYCARDRKYVTNWVFAEDF
QHWGRGTLVTVSS  (SEQ ID NO: 214)

EVQLVETGAEVKKPGASVKVSCKASDYIFTKYDINWVRQAPGQGLEWMGWMSANTGNTGYAQKFQGRVTMTRDTS
INTAYMELSSLTSGDTAVYFCARSSLFKTETAPYYHFALDVWGQGTTVTVSS (SEQ ID NO: 215)

Figure 31
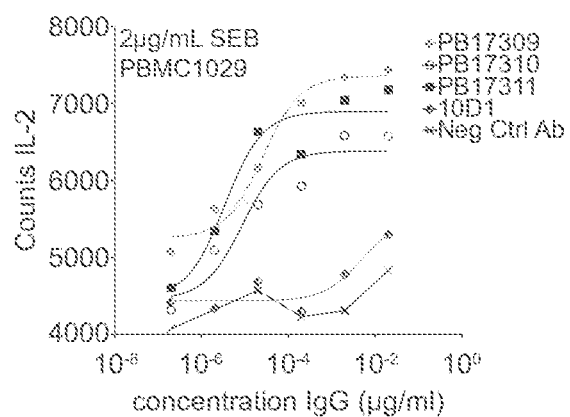
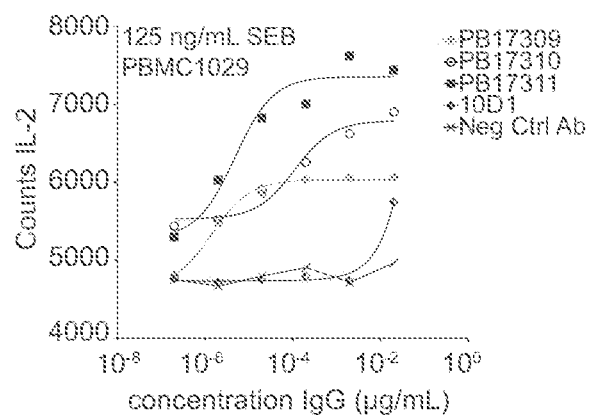
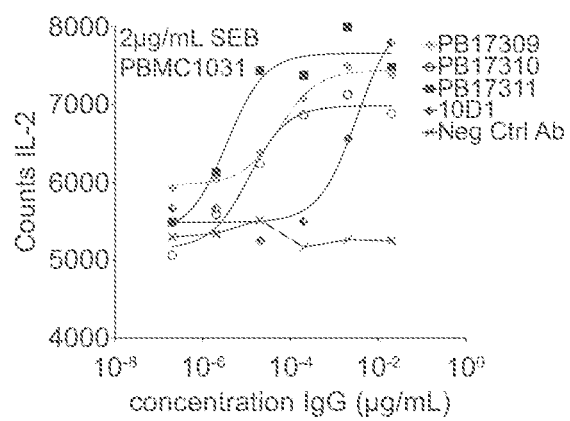
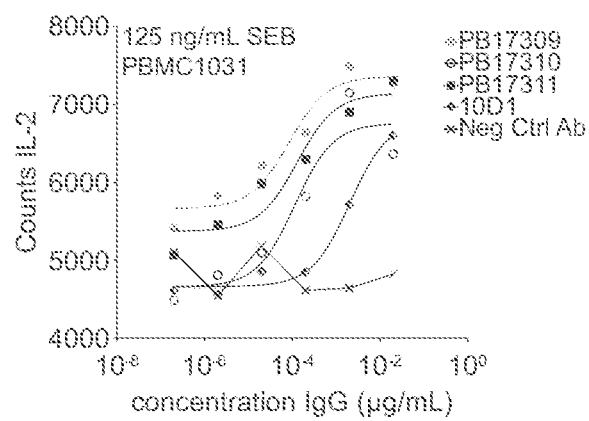
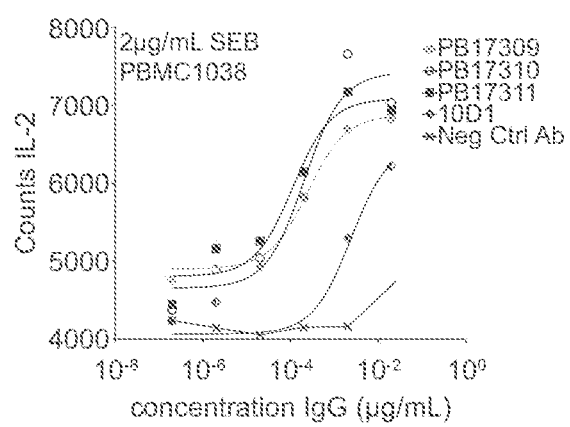
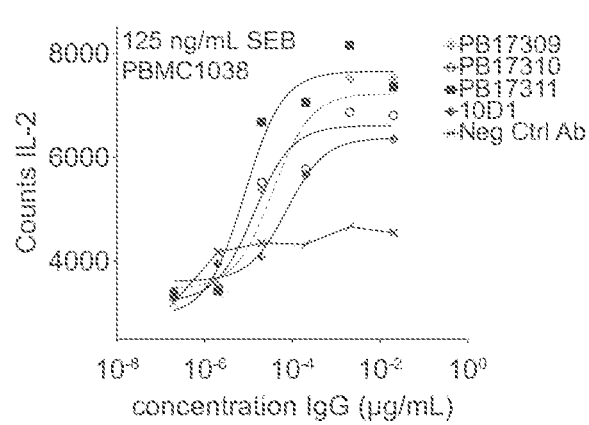

+ M2 macrophages

Figure 39
FIG. 39A
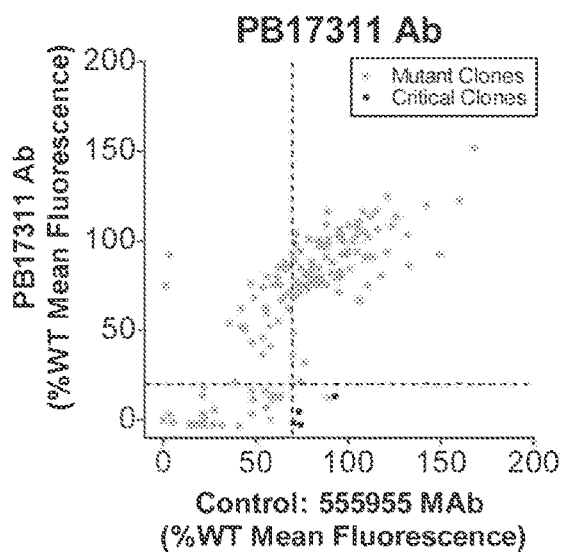
FIG. 39B
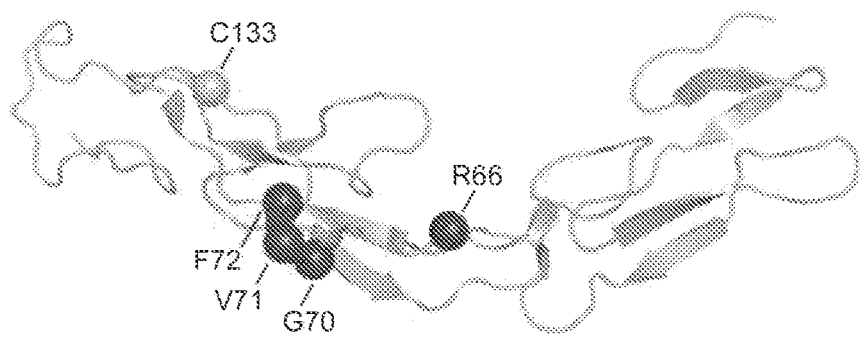
FIG. 39C

Figure 42

```
  1 MGNSCYNIVA TLLLVLNFER TRSLQDPCSN CPAGTFCDNN RNQICSPCPP
 51 NSFSSAGGQR TCDICRQCKG MFRTRKECSS TSNAECDCTP GFHCLGAGCS
101 MCEQDCKQGQ ELTKKGCKDC CFGTFNDQKR GICRPWTNCS LDGKSVLVNG
151 TKERDVVCGP SPADLSPGAS SVTPPAPARE PGHSPQIISF FLALTSTALL
201 FLLFFLTLRF SVVKRGRKKL LYIFKQPFMR PVQTTQEEDG CSCRFPEEEE
251 GGCEL   (SEQ ID NO: 216)
```

EVQLVQSGAEVKKPGSSMKVSCKASGGTFS<u>SYVIS</u>WVRQAPGQGLEWMG<u>MIIPVFDT
SSYEKKFQG</u>RITIADKSTSTVYLELSSLRSEDAAVYYCAR<u>GTVEATLLFDF</u>WGQGTLV
TVSS  (SEQ ID NO: 217)

BINDING MOLECULES THAT BIND CD137 AND PD-L1

CROSS-REFERENCE TO RELATED APPLICATIONS

This application is a U.S. national stage filing of International Application No. PCT/NL2017/050634, filed Sep. 22, 2017; which claims priority to EP Application No. 16190499.0, filed Sep. 23, 2016. The entire contents of International Application No. PCT/NL2017/050634 are hereby incorporated herein by reference.

REFERENCE TO A SEQUENCE LISTING SUBMITTED ELECTRONICALLY

This application includes a Sequence Listing submitted electronically (name: "4096_0250001_Seqlisting_ST25.txt"; size: 241,020 bytes; and created on: Dec. 27, 2022), which is hereby incorporated by reference in its entirety.

The invention relates to the field of binding molecules. In particular it relates to the field of therapeutic binding molecules for the treatment of diseases involving aberrant cells. More in particular it relates to binding molecules that bind an extracellular part of two or more different membrane associated proteins and thereby modulates a biological activity expressed by a cell.

Cancer is still a major cause of morbidity and death in the world, in spite of the many advances that have been made in the treatment of the disease and the increased knowledge of the molecular events that lead to cancer. It is the second leading cause of death worldwide. According to the World Health Organization, cancer was responsible for 8.8 million deaths in 2015. Globally, nearly 1 in 6 deaths is due to cancer. Colorectal cancer (CRC), for instance, is the third most common cancer worldwide. In 2008, 1.23 million people were diagnosed with the disease. It is the second most common cancer in Europe, with around 447,000 new cases diagnosed in 2012 (13% of the total). Colorectal cancer is the fourth most common cause of cancer death, estimated to be responsible for 608,000 (EU 148,000) deaths per annum. While some new treatments have been advanced in CRC many have failed clinical testing; metastatic CRC is still largely incurable.

Traditionally, most cancer drug discovery has focused on agents that block essential cell functions and kill dividing cells. However, in cases of advanced cancer, no matter how aggressively applied, even to the point where patients suffer life-threatening side-effects from the treatment, chemotherapy rarely results in a complete cure. In most cases, the tumors in the patients stop growing or temporarily shrink (referred to as remission) only to start proliferating again, some times more rapidly (referred to as relapse), and become increasingly more difficult to treat. More recently the focus of cancer drug development has moved away from broadly cytotoxic chemotherapy to targeted cytostatic therapies with less toxicity. Treatment of advanced cancer has been validated clinically in leukemia and some other cancers. However, in a majority of carcinomas, targeted approaches are still proving not effective enough to completely abolish cancer in the majority of the patients. Melanoma is another example of a cancer that occurs very frequently. When detection is not early enough the cancer is likely to metastasize at which stage it is very hard to treat. Immune-intervention treatments have been shown to be effective to at least some of the patients with metastasized melanoma. Non-small cell lung cancer is a cancer type that is rarely discovered at an early enough stage for surgery. Also these types of cancers have been successfully treatment with immune-intervention treatments.

Targeting of cancers has been achieved using a variety of different methods including for instance small molecules directed towards signaling proteins on which the cancer depends for survival and/or growth; vaccines with tumor specific proteins; cell therapies with immune cells that actively kill tumor cells and antibodies that target cytotoxic molecules to the tumor; interfere with signaling and/or that (re)direct the immune system of the host to the tumor cells. Monoclonal antibodies blocking CTLA-4 or PD-1 axis have been shown to induce durable clinical responses in a subset of melanoma, NSCLC, renal cell carcinoma and urothelial carcinoma patients.

The present invention provides novel means and methods for (re)directing immune system components. The invention also relates to means and methods for modulating a biological activity expressed by cells.

SUMMARY OF THE INVENTION

The invention provides a method of stimulating activity of a member of the TNF receptor superfamily on a cell comprising providing a first and a second cell of which the first cell has said member on the cell membrane and said second cell has a second membrane protein on the cell membrane, the method comprising contacting said cells with a binding molecule that comprises two antigen binding sites, wherein a first antigen binding site can bind an extracellular part of said member (first membrane protein) and a second antigen binding site can bind an extracellular part of said second membrane protein, thereby stimulating activity of said member on said first cell. In some embodiments, said method is an in vitro method. In some embodiments said member of the TNF receptor superfamily is CD137 or OX40, preferably CD137. In some embodiments said second membrane protein is not a member of the TNF receptor superfamily. In some embodiments said second membrane protein is a member of the B7 family. In some embodiments, said second membrane protein is PD-L1.

In a preferred embodiment the method further comprises providing a further binding molecule (second binding molecule) comprising an antigen binding site that can bind an extracellular part of said member of the TNF receptor superfamily and an antigen binding site that can bind an extracellular part of said second membrane protein, wherein said first and second binding molecule bind:
  different epitopes on said first membrane protein;
  different epitopes on said second membrane protein; or
  different epitopes on said first membrane protein and different epitopes on said second membrane protein;
  the method further comprising incubating said first cell and second cell with said first and second binding molecule, thereby stimulating or enhancing activation of said member of the TNF receptor superfamily on said first cell.

The invention also provides a binding molecule that comprises an antigen binding site that can bind an extracellular part of a member of the TNF receptor superfamily (first membrane protein) and an antigen binding site that can bind an extracellular part of a second membrane protein. The TNF receptor superfamily member is preferably CD137 or OX40, preferably CD137. In some embodiments said second membrane protein is not a member of the TNF receptor superfamily. Said second membrane protein is preferably a member of the B7 family. In some embodiments, said second membrane protein is PD-L1.

The invention further provides a composition or kit of parts comprising one or more binding molecules that comprises an antigen binding site that can bind an extracellular part of a member of the TNF receptor superfamily (first membrane protein) and an antigen binding site that can bind an extracellular part of a second membrane protein. In a preferred embodiment the invention provides a composition or kit of parts comprising two or more of such binding molecules; wherein at least two of said binding molecules can bind:
- different epitopes on said first membrane protein;
- different epitopes on said second membrane protein; or
- different epitopes on said first membrane protein and different epitopes on said second membrane protein. It is preferred that at least two of the binding molecules bind the same epitope on said first membrane protein and bind different epitopes on said second membrane protein.

The invention further provides a method of stimulating activity of CD137 or OX40 on a cell, the method comprising providing a first cell and a second cell, wherein said first cell has CD137 or OX40 on the cell membrane and said second cell has a second membrane protein on the cell membrane and contacting said first cell and second cell with a binding molecule (first binding molecule) that comprises an antigen binding site that can bind to an extracellular part of said CD137 or OX40 (first membrane protein); and an antigen binding site that can bind to an extracellular part of a second membrane protein; the method further comprising incubating said first cell and said second cell with said first binding molecule, thereby stimulating activity of said CD137 or OX40 on said first cell. In some embodiments said second membrane protein is not a member of the TNF receptor superfamily. In some embodiments, said method is an in vitro method.

In a preferred embodiment the method further comprises providing a further binding molecule (second binding molecule) comprising an antigen binding site that can bind an extracellular part of said first membrane protein; and an antigen binding site that can bind an extracellular part of said second membrane protein, wherein said first and second binding molecule bind:
- different epitopes on said first membrane protein;
- different epitopes on said second membrane protein; or
- different epitopes on said first membrane protein; and different epitopes on said second membrane protein;
the method further comprising incubating said first cell and said second cell with said first and second binding molecule, thereby stimulating activity of CD137 or OX40 on said first cell.

In some embodiments a binding molecule according to the invention comprises an antigen binding site that can bind an extracellular part of a member of the TNF receptor superfamily and an antigen binding site that can bind a member of the B7 family. In some embodiments the antigen binding sites of said binding molecule according to the invention consist of one antigen binding site that can bind an extracellular part of a member of the TNF receptor superfamily and one antigen binding site that can bind a member of the B7 family. In some embodiments said binding molecule according to the invention comprises an antigen binding site that can bind CD137 and an antigen binding site that can bind a member of the B7 family. In some embodiments the antigen binding sites of said binding molecule according to the invention consist of one antigen binding site that can bind an extracellular part of CD137 and one antigen binding site that can bind a member of the B7 family. In some embodiments said binding molecule according to the invention comprises an antigen binding site that can bind CD137 and an antigen binding site that can bind PD-L1. In some embodiments the antigen binding sites of said binding molecule according to the invention consist of one antigen binding site that can bind CD137 and one antigen binding site that can bind PD-L1. In some embodiments said binding molecule according to the invention has no more than two antigen binding sites.

A binding molecule as described herein is preferably an antibody.

The invention further provides a method of stimulating activity of a member of the TNF receptor superfamily on a cell comprising providing a first cell and a second cell, wherein said first cell has said member on the cell membrane (first membrane protein) and said second cell has a second membrane protein on the cell membrane, the method comprising contacting said cells with an antibody according to the present invention that comprises at least two variable domains, wherein one variable domain comprises a first antigen binding site that can bind an extracellular part of said first membrane protein and another variable domain comprises a second antigen binding site that can bind an extracellular part of said second membrane protein, thereby stimulating activity of said member on said first cell. In some embodiments, said method is an in vitro method.

The invention further provides an antibody or a functional part, derivative and/or analogue thereof that comprises
- a variable domain that can bind to an extracellular part of a member of the TNF receptor superfamily (first membrane protein); and
- a variable domain that can bind to an extracellular part of a second membrane protein. The first membrane protein is preferably CD137 or OX40, preferably CD137. In some embodiments said second membrane protein is not a member of the TNF receptor superfamily.

The binding molecule is preferably a bispecific antibody. The invention further provides a method of stimulating activity of a member of the TNF receptor superfamily on a cell comprising providing a first cell and a second cell, wherein said first cell has said member on the cell membrane (first membrane protein) and said second cell has a second membrane protein on the cell membrane, the method comprising contacting said cells with a bispecific antibody that comprises two variable domains, wherein one variable domain comprises a first antigen binding site that can bind an extracellular part of said first membrane protein and another variable domain comprises a second antigen binding site that can bind an extracellular part of said second membrane protein, thereby stimulating activity of said member on said first cell. In some embodiments, said method is an in vitro method. Also provided is a bispecific antibody that comprises a variable domain with an antigen binding site that can bind an extracellular part of a member of the TNF receptor superfamily (first membrane protein) and a variable domain with an antigen binding site that can bind an extracellular part of a second membrane protein. The first membrane protein is preferably CD137 or OX40, preferably CD137. The second membrane protein is preferably not a member of the TNF receptor superfamily.

In some embodiments an antibody according to the invention comprises a variable domain that comprises an antigen binding site that can bind an extracellular part of a member of the TNF receptor superfamily and an antigen binding site that can bind a member of the B7 family. In some embodiments the antigen binding sites of said antibody according to the invention consist of one antigen binding site that can bind an extracellular part of a member of the TNF receptor superfamily and one antigen binding site that can bind a member of the B7 family. In some embodiments said antibody according to the invention comprises an antigen binding site that can bind an extracellular part of CD137 and an antigen binding site that can bind a member of the B7 family. In some embodiments the antigen binding sites of said antibody according to the invention consist of one antigen binding site that can bind an extracellular part of CD137 and one antigen binding site that can bind a member of the B7 family. In some embodiments said antibody according to the invention comprises an antigen binding site that can bind CD137 and an antigen binding site that can bind PD-L1. In some embodiments the antigen binding sites of said antibody according to the invention consist of one antigen binding site that can bind CD137 and one antigen binding site that can bind PD-L1. In some embodiments said antibody according to the invention has no more than two antigen binding sites.

Further provided is a pharmaceutical composition that comprises one or more binding molecules preferably antibodies or variants thereof of the invention.

Also provided is a nucleic acid molecule or a collection of nucleic acid molecules that codes for a heavy chain(s) or a heavy chain variable region(s) of an antibody of the invention or a variant thereof.

Also provided is a nucleic acid molecule or collection of nucleic acid molecules that codes for an antibody of the invention.

An antibody of the invention preferably comprises a heavy chain variable region comprising an amino acid sequence of an MF as depicted in FIG. 3. In a preferred embodiment the antibody further comprises a light chain variable region that comprises an amino acid sequence of a light chain variable region depicted in FIG. 1. In a preferred embodiment the light chain comprises an amino acid sequence as depicted in FIG. 1A. In a preferred embodiment the heavy chain comprises a constant region of an IgG1 antibody, preferably a human IgG1 antibody. In a preferred embodiment the CH2 region of said IgG1 constant region is engineered to reduce ADCC and/or CDC activity of the antibody. In a preferred embodiment the CH2 region comprises a sequence as depicted in FIG. 2E. In a preferred embodiment the CH3-region of the antibody is engineered to facilitate heterodimerization of the heavy chains. In a preferred embodiment one heavy chain comprises a sequence as depicted in FIG. 2F and another heavy chain comprises a sequence as depicted in FIG. 2G.

Also provided is a cell comprising one or more nucleic acid molecules that alone or together code for an antibody or a variant thereof of the invention. Also provided are methods of producing an antibody or a variant thereof of the invention using a cell as described, preferably together with the harvesting of the antibody or variant thereof from a culture of the cells.

Further provided is a cell system that comprises an antibody or variant thereof of the invention.

Also provided is a method for the treatment of an individual that has a disease involving aberrant cells such as cancer or has a chronic infection with a virus or parasite, the method comprising administering a binding molecule, preferably an antibody or a variant thereof of the invention to the individual in need thereof.

The invention further provides a binding molecule, preferably an antibody or variant thereof of the invention; preferably a bispecific antibody or variant thereof of the invention, for use in the treatment of an individual that has disease involving aberrant cells such as cancer, or a chronic infection with a virus or parasite.

In a preferred embodiment the parasite is an intracellular parasite.

Further provided is a method of stimulating an immune response in an individual against an aberrant cell in said individual, the method comprising providing (administering to) said individual with a binding molecule, preferably an antibody or a variant thereof, preferably a bispecific antibody or a variant thereof of the invention. The aberrant cell is preferably a cancer cell, a virus-infected cell, a parasite or a parasite infected cell. In a preferred embodiment the cell is a cancer cell or a neoplastic cell.

DETAILED DESCRIPTION OF THE INVENTION

The tumor necrosis factor receptor superfamily (TNFRSF) is a group of receptors. They are typically characterized by the ability to bind tumor necrosis factors (TNFs) via an extracellular cysteine-rich domain. With the exception of nerve growth factor (NGF), all TNFs are homologous to the archetypal TNF-alpha. In their active form, the majority of TNF receptors form trimeric complexes in the plasma membrane. Accordingly, most TNF receptors contain transmembrane domains (TMDs) and are located on the cell membrane. However, some can be cleaved into soluble forms (e.g. TNFR1), and some lack a TMD entirely (e.g. DcR3). An antibody of the invention that binds to a member of the TNF receptor superfamily binds to a membrane bound member of the superfamily. Members that exist only in forms that are not associated with the cell membrane are not within the scope of the present invention.

TNF receptors are involved in signaling to the inside of the cell upon binding of the ligand of the receptor. Some receptors require specific adaptor protein such as TRADD, TRAF, RIP and FADD for downstream signaling. In the context of the present invention various members of the TNF superfamily are preferred. These include Tumor necrosis factor receptor 1; Tumor necrosis factor receptor 2; Lymphotoxin beta receptor; OX40; CD40; Fas receptor; CD27; CD30; CD137; Death receptor 3; Death receptor 4; Death receptor 5; Death receptor 6; RANK; TROY; BAFF receptor; B-cell maturation antigen (BCMA) and a trans-membrane activator and calcium-modulating cyclophilin ligand-interacting protein (TACI).

Tumor necrosis factor receptor 1 is one of the major receptors for the tumor necrosis factor-alpha. The receptor has a large number of alternative names some of which are Tumor Necrosis Factor Receptor Superfamily Member 1A; TNFRSF1A; TNF-R1; TNF-RI; TNFR-I; TNFR1; TNFAR; P60; P55; Tumor Necrosis Factor Receptor 1A Isoform Beta; Tumor Necrosis Factor Binding Protein 1; Tumor Necrosis Factor Receptor Type 1; Tumor Necrosis Factor Receptor Type I; Tumor Necrosis Factor-Alpha Receptor; Tumor Necrosis Factor Receptor 1; CD120a Antigen; TNFR1-D2; TNF-R-I; TNF-R55; CD120a; TNFR55; TNFR60; TNF-R; P55-R; Tbp1; FPF; and MS5. External Ids for Tumor necrosis factor receptor 1 are HGNC: 11916; Entrez Gene: 7132; Ensembl: ENSG00000067182; OMIM: 191190 and UniProtKB: P19438.

Tumor necrosis factor receptor 2 is a membrane receptor that binds tumor necrosis factor-alpha (TNFα). The receptor has a large number of alternative names some of which are: Tumor Necrosis Factor Receptor Superfamily Member 1B;

TNFRSF1B; Tumor Necrosis Factor Receptor Type II; Tumor Necrosis Factor Receptor 2; P80 TNF-Alpha Receptor; TNF-RII; TNF-R2; TNFR2; TNFBR; P75; Tumor Necrosis Factor Binding Protein 2; Tumor Necrosis Factor Beta Receptor; P75 TNF Receptor; CD120b Antigen; Etanercept; TNF-R-II; TNF-R75; P75TNFR; TNFR-II; CD120b; TNFR1B; TNFR80; TBPII. External Ids for Tumor necrosis factor receptor 2 are: HGNC: 11917; Entrez Gene: 7133; Ensembl: ENSG00000028137; OMIM: 191191; and UniProtKB: P20333.

Lymphotoxin beta receptor is expressed on the surface of most cell types, including cells of epithelial and myeloid lineages, but typically not on normal T and B lymphocytes. The protein binds the lymphotoxin membrane form (a complex of lymphotoxin-alpha and lymphotoxin-beta). The encoded protein and its ligand play a role in the development and organization of lymphoid tissue and transformed cells. Activation of the protein can in instances trigger apoptosis. The protein is known under a large number of aliases among which there are: LTBR; Tumor Necrosis Factor Receptor 2-Related Protein; Tumor Necrosis Factor Receptor Type III; Tumor Necrosis Factor C Receptor; D12S370; TNFRSF3; TNFCR; TNFR3; Lymphotoxin Beta Receptor (TNFR Superfamily, Member 3); Lymphotoxin B Receptor; LT-BETA-R; TNF-R-III; TNFR2-RP; TNF-RIII; TNFR-III; TNFR-RP; and CD18. External Ids for Lymphotoxin beta receptor are HGNC: 6718; Entrez Gene: 4055; Ensembl: ENSG00000111321; OMIM: 600979 and UniProtKB: P36941.

OX40 is not constitutively expressed on resting naïve T cells, unlike CD28, OX40 is a secondary co-stimulatory immune checkpoint molecule, expressed after 24 to 72 hours following activation; its ligand, OX40L, is also not expressed on resting antigen presenting cells, but is following their activation. Expression of OX40 is dependent on activation of the T cell. Without CD28, expression of OX40 is typically delayed and present at lower levels. The protein is known under a large number of aliases among which there are: TNFRSF4; Tumor Necrosis Factor Receptor Superfamily Member 4; TAX Transcriptionally-Activated Glycoprotein 1 Receptor; OX40L Receptor; ACT35 Antigen; CD134 Antigen; TXGP1L; Tax-Transcriptionally Activated Glycoprotein 1 Receptor; Lymphoid Activation Antigene ACT35; OX40 Cell Surface Antigen; ATC35 Antigen; OX40 Antigen; ACT35; CD134; and IMD16. External Ids for OX40 are HGNC: 11918; Entrez Gene: 7293; Ensembl: ENSG00000186827; OMIM: 600315 and UniProtKB: P43489.

CD40 is a costimulatory protein found on antigen presenting cells and is involved in their activation. The binding of CD154 (CD40L) on T-helper cells to CD40 activates antigen presenting cells and induces intracellular signaling by CD40 and a variety of downstream effects. The protein is known under a number of different aliases among which there are: CD40 Molecule; CD40 Molecule TNF Receptor Superfamily Member 5; CD40L Receptor; TNFRSF5; CDW40; Bp50; Tumor Necrosis Factor Receptor Superfamily, Member 5; B Cell Surface Antigen CD40; B-Cell Surface Antigen CD40; B Cell-Associated Molecule; CD40 Antigen; and P50. External Ids for CD40 are HGNC: 11919; Entrez Gene: 958; Ensembl: ENSG00000101017; OMIM: 109535; and UniProtKB: P25942.

Fas receptor is a death receptor on the surface of cells that leads to programmed cell death (apoptosis). It forms part of one of the more prominent apoptosis pathways. It is known under a number of alternatives such as: Fas Cell Surface Death Receptor; Tumor Necrosis Factor Receptor Superfamily, Member 6; Apoptosis-Mediating Surface Antigen FAS; TNF Receptor Superfamily Member 6; FASLG Receptor; CD95 Antigen; TNFRSF6; APT1; FAS1; APO-1 Cell Surface Antigen; Apoptosis Antigen 1; Apo-1 Antigen; Fas AMA; ALPS1A; APO-1; FAS™; and CD95. External Ids for FAS are HGNC: 11920; Entrez Gene: 355; Ensembl: ENSG00000026103; OMIM: 134637; and UniProtKB: P25445.

CD27 is thought to be important for generation and long-term maintenance of T cell immunity. It binds to ligand CD70, and plays a role in regulating B-cell activation and immunoglobulin synthesis. CD27 transduces signals that lead to the activation of NF-κB and MAPK8/JNK. CD27-binding protein (SIVA), a proapoptotic protein, can bind to this receptor and is thought to play a role in the apoptosis induced by this receptor. Alternative names for this protein are among others: CD27 Molecule; Tumor Necrosis Factor Receptor Superfamily, Member 7; T-Cell Activation Antigen CD27; CD27L Receptor; TNFRSF7; T14; T Cell Activation Antigen S152; CD27 Antigen; s152. LPFS2; S152 and Tp55. External Ids for CD27 are: HGNC: 11922; Entrez Gene: 939; Ensembl: ENSG00000139193; OMIM: 186711; and UniProtKB: P26842.

CD30 is expressed by activated T and B cells. TRAF2 and TRAF5 are thought to interact with this receptor, and mediate the signal transduction that leads to the activation of NF-kappaB. It is a positive regulator of apoptosis, and also has been shown to limit the proliferative potential of autoreactive CD8 effector T cells and protect the body against autoimmunity. It is known under a number of different names such as: TNFRSF8; Tumor Necrosis Factor Receptor Superfamily Member 8; Lymphocyte Activation Antigen CD30; CD30L Receptor; Ki-1 Antigen; D1S166E; CD30; Cytokine Receptor CD30; CD30 Antigen; and Ki-1. External Ids for CD30 are: HGNC: 11923; Entrez Gene: 943; Ensembl: ENSG00000120949; OMIM: 153243; and UniProtKB: P28908.

CD137 can be expressed by activated T-cells. It is also found on other cells such as dendritic cells, natural killer cells, granulocytes and cells of the blood vessel wall at sites of inflammation. The protein is known for its costimulatory activity for activation of T-cells. CD137 is known under a number of different names such as: TNFRSF9; TNF Receptor Superfamily Member 9; Tumor Necrosis Factor Receptor Superfamily Member 9; T-Cell Antigen 4-1BB Homolog; 4-1BB Ligand Receptor; T-Cell Antigen ILA; CD137 Antigen; CDw137; ILA; Interleukin-Activated Receptor, Homolog Of Mouse Ly63; Induced By Lymphocyte Activation (ILA); Homolog Of Mouse 4-1BB; Receptor Protein 4-1BB; T Cell Antigen ILA; and 4-1BB. External Ids for CD137 are HGNC: 11924; Entrez Gene: 3604; Ensembl: ENSG00000049249; OMIM: 602250; and UniProtKB: Q07011. CD137 is an inducible receptor most commonly upregulated on activated CD8+ T cells. CD137 signaling enhances T cell function by activating NF-κB [Arch et al, 1998]. Other cell immune cell types including CD4+ T cells, monocytes, B cells, dendritic cell (DC) subpopulations and granulocytes and NK cells can express CD137 at various levels [Shao et al, 2011]. In monocytes, CD137 is inducible by activation with lipopolysaccharide (LPS) and IL-1p. In B lymphocytes, CD137 expression is induced by antibodies against cell-surface immunoglobulin and by transformation with EBV. In DCs, CD137 ligation induces their maturation through upregulation of B7 co-stimulatory molecules (CD80 and CD86), in addition to enhancing their production of inflammatory cytokines (IL-6 and IL-12) and their survival [Makkouk et al, 2015]. The natural function of CD137 ligation on neutrophils is the increment of phagocytosis of bacterial and parasitic infections. In addition ligation of CD137 blocks the anti-apoptosis signals mediated by the IL-3/IL-5/GM-CSF receptors in neutrophils and eosinophils in vitro, thereby preventing granulocyte accumulation [Simon, 2001; Vinay et al, 2011]. In non-lymphoid cells such as chondrocytes, endothelial cells and tumor cells CD137 expression is driven by cytokine stimulation such as IL-1P for chondrocytes, the inflammatory cytokines TNFalpha/IFNγ/IL-1β for endothelial cells and IFNγ for tumor cells. The ligand that stimulates CD137 (CD137L) is expressed on activated antigen presenting cells. CD137 exists in the membrane as monomers and dimers [Pollok et al, 1993].

Death receptor 3 is expressed by activated and antigen-experienced T lymphocytes. The receptor is also expressed by FoxP3 positive regulatory T lymphocytes. The ligand for the receptor is TL1A (TNFSF15), which is upregulated in antigen presenting cells and some endothelial cells following Toll-Like Receptor or Fc receptor activation. Various alternatively spliced transcript variants that code for distinct isoforms have been reported, most of which are potentially secreted molecules. The receptor is thought to be involved in controlling lymphocyte proliferation induced by T-cell activation. Activation is thought to be dependent on previous engagement of the T cell receptor. Binding of the ligand increases the sensitivity of T cells to endogenous IL-2 via the IL-2 receptor and enhances T cell proliferation. In vivo activation is likely specific to those T cells that are encountering cognate antigen. At rest, and for individuals without underlying autoimmunity, the majority of T cells that regularly encounter cognate antigen are FoxP3+ regulatory T cells. Stimulation of death receptor 3 in the absence of any other exogenous signals stimulates profound and specific proliferation of FoxP3+ regulatory (CD4 positive) T cells. Therapeutic agonists of death receptor 3 can be used to stimulate Treg expansion, which can reduce inflammation in experimental models of asthma, allogeneic solid organ transplantation and ocular keratitis. On the other hand costimulation of the receptor together with an autoantigen or with a vaccine antigen can lead to exacerbation of immunopathology or enhanced vaccine-stimulated immunity, respectively. Receptor stimulation is specific to T cell mediated immunity, which can be used to enhance or dampen inflammation depending on the temporal context and quality of foreign versus self-antigen availability. Stimulation of TNFRSF25 in humans may lead to similar, but more controllable, effects as costimulatory blockade targeting molecules such as CTLA-4 and PD-1. Death receptor 3 is also known under a number of other names such as TNFRSF25; Tumor Necrosis Factor Receptor Superfamily Member 25; Tumor Necrosis Factor Receptor Superfamily, Member 12 (Translocating Chain-Association Membrane Protein); Lymphocyte-Associated Receptor Of Death; Apoptosis-Mediating Receptor TRAMP; Apoptosis-Mediating Receptor DR3; Apoptosis-Inducing Receptor AIR; Protein WSL-1; TNFRSF12; APO-3; DDR3; LARD; DR3; Apoptosis Inducing Receptor; Death Receptor Beta; Protein WSL; WSL-LR; TRAMP; WSL-1; APO3; WSL1; TR3; and WSL. External Ids for death receptor 3 are HGNC: 11910; Entrez Gene: 8718; Ensembl: ENSG00000215788; OMIM: 603366; and UniProtKB: Q93038.

Death receptor 4 is a cell surface receptor of the TNF-receptor superfamily that binds TRAIL and thought to transduce a cell death signal and induce cell apoptosis. It is known under a number of names such as: TNFRSF10A; Tumor Necrosis Factor Receptor Superfamily Member 10a; TNF-Related Apoptosis-Inducing Ligand Receptor 1; Death Receptor 4; TRAIL Receptor 1; TRAIL-R1; TRAILR1; APO2; DR4; Tumor Necrosis Factor Receptor Superfamily Member 10a Variant 2; Cytotoxic TRAIL Receptor; CD261 Antigen; TRAILR-I and CD261. External Ids for Death receptor 4 are HGNC: 11904; Entrez Gene: 8797; Ensembl: ENSG00000104689; OMIM: 603611; and UniProtKB: 000220

Death receptor 5 is a cell surface receptor of the TNF-receptor superfamily that binds TRAIL and mediates apoptosis. The receptor can be activated by tumor necrosis factor-related apoptosis inducing ligand (TNFSF10/TRAIL/APO-2L), and transduces apoptosis signal. The receptor is known under a number of different names among which there are: TNFRSF10B; Tumor Necrosis Factor Receptor Superfamily Member 10b; TNF-Related Apoptosis-Inducing Ligand Receptor 2; Death Receptor 5; TRAIL-R2; TRAILR2; KILLER; TRICK2; ZTNFR9; DR5; P53-Regulated DNA Damage-Inducible Cell Death Receptor(Killer); Tumor Necrosis Factor Receptor-Like Protein ZTNFR9; Death Domain Containing Receptor For TRAIL/Apo-2L; Apoptosis Inducing Protein TRICK2A/2B; Apoptosis Inducing Receptor TRAIL-R2; TNF Receptor Superfamily Member 10b; Cytotoxic TRAIL Receptor-2; Fas-Like Protein; TRAIL Receptor 2; CD262 Antigen; KILLER/DR5; TRICK2A; TRICK2B; TRICKB; and CD262. External Ids for Death receptor 5 are: HGNC: 11905; Entrez Gene: 8795; Ensembl: ENSG00000120889; OMIM: 603612; and UniProtKB: 014763.

Death receptor 6 can induce cell apoptosis upon activation. Knockout studies in mice suggest that the receptor plays a role in T helper cell activation, and may be involved in inflammation and immune regulation. The receptor is also thought to be involved in neurodegeneration in the brain that causes Alzheimer's disease as well as signal transduction in stress response and cellular survival. Over-expression induces apoptosis of the expressing cell. APP (amyloid precursor protein) is the natural ligand of the receptor and is first cleaved into AB and N-APP. N-APP is the fragment that interacts with DR6 to trigger axonal degradation in Alzheimer's patients. Death receptor 6 is also known under a number of other names such as TNFRSF21; Tumor Necrosis Factor Receptor Superfamily Member 21; DR6; TNFR-Related Death Receptor 6; CD358 Antigen; BM-018; and CD358. External Ids for death receptor 6 are HGNC: 13469; Entrez Gene: 27242; Ensembl: ENSG00000146072; OMIM: 605732; UniProtKB: 075509.

RANK is a receptor for RANK-Ligand (RANKL) and part of the RANK/RANKL/OPG signaling pathway that regulates osteoclast differentiation and activation. It is associated with bone remodeling and repair, immune cell function, lymph node development, thermal regulation, and mammary gland development. Osteoprotegerin (OPG) is a decoy receptor for RANK, and regulates the stimulation of the RANK signaling pathway by competing for RANKL. The cytoplasmic domain of RANK transmits signals to downstream targets such as NF-κB and JNK. RANK is expressed in skeletal muscle, thymus, liver, colon, small intestine, adrenal gland, osteoclast, mammary gland epithelial cells, prostate, vascular cell, and pancreas. Often activation of NF-κB is mediated by RANKL, but over-expression of RANK alone is can also activate the NF-κB pathway. RANK is known under a number of different names such as: TNFRSF11A; Tumor Necrosis Factor Receptor Superfamily Member 11a NFKB Activator; Loss Of Heterozygosity, 18, Chromosomal Region 1; Osteoclast Differentiation Factor Receptor; Receptor Activator Of NF-KB; Paget Disease Of Bone 2; ODFR; Tumor Necrosis Factor Receptor Superfamily, Member 11a, Activator Of NFKB; Tumor Necrosis Factor Receptor Superfamily Member 11a, NFKB Activator; Receptor Activator Of Nuclear Factor-Kappa B; CD265 Antigen; LOH18CR1; TRANCER; CD265; OPTB7; OSTS; PDB2; FEO and OFE. External Ids for RANK are: HGNC: 11908; Entrez Gene: 8792; Ensembl: ENSG00000141655; OMIM: 603499 and UniProtKB: Q9Y6Q6.

The BAFF receptor is a membrane protein of the TNF receptor superfamily which recognizes BAFF. B-cell activating factor (BAFF) enhances B-cell survival in vitro and is a regulator of the peripheral B-cell population. The BAFF receptor is a receptor for BAFF and is a type III transmembrane protein containing a single extracellular phenylalanine-rich domain. It is thought that this receptor is the principal receptor required for BAFF-mediated mature B-cell survival. BAFF is also bound by the TNF receptors B-cell maturation antigen (BCMA) and a trans-membrane activator and calcium-modulating cyclophilin ligand-interacting protein (TACI). The BAFF-receptor is known under a number of different names such as TNFRSF13C; Tumor Necrosis Factor Receptor Superfamily Member 13C; B-Cell-Activating Factor Receptor; BLyS Receptor 3; BAFF-R; BAFFR; B Cell-Activating Factor Receptor; CD268 Antigen; Prolixin; BROMIX; CD268; CVID4; and BR3. External Ids for the BAFF-receptor are HGNC: 17755; Entrez Gene: 115650; Ensembl: ENSG00000159958; OMIM: 606269; and UniProtKB: Q96RJ3.

B-cell maturation antigen (BCMA) is a cell surface receptor of the TNF receptor superfamily which recognizes B-cell activating factor (BAFF). The receptor is preferentially expressed in mature B lymphocytes, and is thought to be important for B cell development and autoimmune response. The receptor has been shown to specifically bind to the tumor necrosis factor (ligand) superfamily, member 13b (TNFSF13B/TALL-1/BAFF), and to lead to NF-kappaB and MAPK8/JNK activation. B-cell maturation antigen is also known under a number of aliases such as TNFRSF17; Tumor Necrosis Factor Receptor Superfamily Member 17; B-Cell Maturation Protein; BCM; B-Cell Maturation Factor; CD269 Antigen; TNFRSF13A; and CD269. External Ids for BCMA are HGNC: 11913; Entrez Gene: 608; Ensembl: ENSG00000048462; OMIM: 109545; and UniProtKB: Q02223.

Trans-membrane activator and calcium-modulating cyclophilin ligand-interacting protein (TACI). The protein encoded by this gene is a lymphocyte-specific member of the tumor necrosis factor (TNF) receptor superfamily. It interacts with calcium-modulator and cyclophilin ligand (CAML). The protein can also bind BAFF and APRIL (TNSF13 or CD256). TACI induces activation of the transcription factors NFAT, AP1, and NF-kappa-B and plays a role in humoral immunity by interacting with a TNF ligand. Mice deficient for TACI have increased splenic B cells and serum Igs, which was suggested to mean a potential negative regulatory role for TACI in B cell survival. However, a simpler explanation might be that the lack of TACI allows more circulating BAFF to become available, which can bind to BR3 and increase B cell numbers. Diseases associated with TACI include immunodeficiency, common variable, 2 and immunoglobulin a deficiency 2. The gene coding for TACI is located within the Smith-Magenis syndrome region on chromosome 17. TACI is also known under number of other names such as TNFRSF13B, Tumor Necrosis Factor Receptor Superfamily Member 13B; Transmembrane Activator And CAML Interactor; Tumor Necrosis Factor Receptor 13B; CD267 Antigen; TNFRSF14B; CD267; CVID2; IGAD2; CVID; and RYZN 3. External Ids for TACI are HGNC: 18153; Entrez Gene: 23495; Ensembl: ENSG00000240505; OMIM: 604907; and UniProtKB: 014836.

TROY is expressed during embryonic development. It has been shown activate JNK signaling pathway when overexpressed in cells. Activation of the receptor can induce apoptosis. The receptor is believed to play a role in embryonic development. Alternatively spliced transcript variants encoding distinct isoforms have been described. TROY is also known under a number of other names such as TNFRSF19; Tumor Necrosis Factor Receptor Superfamily Member 19; Toxicity And JNK Inducer; TRADE; TAJ; and TAJ-Alpha. External Ids for TROY are HGNC: 11915; Entrez Gene: 55504; Ensembl: ENSG00000127863; OMIM: 606122; and UniProtKB: Q9NS68.

The B7 family comprises a number of structurally related, cell-surface proteins, which bind to receptors on lymphocytes that regulate immune responses. Activation of lymphocytes is initiated by engagement of cell-surface, antigen-specific T-cell receptors or B-cell receptors. Additional signals delivered simultaneously by B7 ligands further determine the immune response of these cells. These so-called 'costimulatory' or 'coinhibitory' signals are delivered by B7 family members through the CD28 family of receptors on lymphocytes. Binding of B7-family members with costimulatory receptors augments immune responses, and binding with coinhibitory receptors attenuates immune responses. Presently the following members are believed to be part of this family: B7.1 (CD80), B7.2 (CD86), inducible costimulator ligand (ICOS-L), programmed death-1 ligand (PD-L1), programmed death-2 ligand (PD-L2), B7-H3 (CD276), B7-H4, B7-H5, B7-H6 and B7-H7. B7 family members are expressed in lymphoid and non-lymphoid tissues. Effects of members on regulating immune responses are shown in the development of immunodeficiency and autoimmune diseases in mice with mutations in B7-family genes. Manipulation of the signals delivered by B7 ligands has shown potential in the treatment of autoimmunity, inflammatory diseases and cancer.

A binding molecule or antibody or variant thereof according to the invention that binds an extracellular part of a member of the TNF receptor superfamily and an extracellular part of a member of the B7 family provides the advantage that a desired immune response can be particularly well promoted, since B7 family members deliver 'costimulatory' or 'coinhibitory' signals to lymphocytes, thereby augmenting or attenuating an immune response. Hence, by targeting a member of the B7 family it is possible to enhance stimulatory signals and/or to counteract inhibitory signals, thereby inducing or enhancing a desired immune response, for instance against aberrant cells.

CD80 is a protein found on activated B cells and monocytes that provides a costimulatory signal necessary for T cell activation and survival. It is the ligand for two different proteins on the T cell surface: CD28 and CTLA-4. When bound to CD28 it is associated with co-stimulation whereas binding to CTLA4 is associated with attenuation of an immune response. CD80 works in tandem with CD86 to activate T cells. CD80 is reported to also bind PD-L1. CD80 is known under a number of other names such as CD80 Molecule; CD80 Antigen; CD28 Antigen Ligand 1; B7-1 Antigen; B-Lymphocyte Activation Antigen B7; CTLA-4 Counter-Receptor B7.1; Activation B7-1 Antigen; CD28LG1; CD28LG; LAB7; BB1; B7; Costimulatory Factor CD80; CD80 Antigen; and B7-1. External Ids for CD80 are HGNC: 1700; Entrez Gene: 941; Ensembl: ENSG00000121594; OMIM: 112203; and UniProtKB: P33681.

CD86 is a protein expressed on antigen-presenting cells. It can provide costimulatory signals for T cell activation and survival. It is the ligand for two different proteins on the T cell surface: CD28 and CTLA-4. When bound to CD28 it is associated with co-stimulation whereas binding to CTLA4 is associated with attenuation of an immune response. CD86 works in tandem with CD80 to activate T cells. It is known under a number of different names such as CD86 Molecule; CD86 Antigen; CD28 Antigen Ligand 2; B7-2 Antigen; CTLA-4 Counter-Receptor B7.2; CD28LG2; FUN-1; BU63; B70; B-Lymphocyte Activation Antigen B7-2; B-Lymphocyte Antigen B7-2; Activation B7-2 Antigen; CD86 Antigen; LAB72; and B7-2. External Ids for CD86 are HGNC: 1705; Entrez Gene: 942; Ensembl: ENSG00000114013; OMIM: 601020; and UniProtKB: P42081.

Inducible T-Cell Co-Stimulator Ligand (ICOSL or CD275) is constitutively expressed by APCs as well as a number of non-hematologic tissues. Expression can be down-regulated with ongoing inflammation. ICOSL is presently known to interact with ICOS, CD28 and CTLA-4 in humans. ICOSL/CD28 interaction appears to co-stimulate human T cells' primary responses to allogeneic antigens and memory recall responses. ICOSL/CTLA-4 is thought to result coinhibitory signals. ICOSL is also known as ICOSLG; B7-Related Protein 1; B7 Homolog 2; B7-Like Protein G150; B7 Homologue 2; B7RP-1; B7-H2; B7RP1; B7H2; Transmembrane Protein B7-H2 ICOS Ligand; CD275 Antigen; KIAA0653; ICOS-L; LICOS; and GL50. External Ids for ICOSL are HGNC: 17087; Entrez Gene: 23308; Ensembl: ENSG00000160223; OMIM: 605717; and UniProtKB: O75144.

PD-L1 is a type 1 transmembrane protein that plays a role in suppressing an immune response during particular events such as pregnancy, tissue allografts, autoimmune disease and other disease states such as hepatitis. PD-L1 is expressed in various types of cancers, especially in NSCLC (Boland et al., 2013; Velcheti et al., 2014), melanoma, renal cell carcinoma, gastric cancer, hepatocellular as well as various leukemias and multiple myeloma (Bernstein et al., 2014; Thompson et al., 2005). PD-L1 is present in the cytoplasm and plasma membrane of cancer cells, but not all cancers or all cells within a tumor express PD-L1 (Dong et al., 2002). Multiple tumor microenvironment cells contribute to immune suppression by upregulating PD-L1 expression. This effect is called "adaptive immune resistance", because the tumor protects itself by inducing PD-L1 in response to IFN-γ produced by activated T cells (Sharma et al., 2017). PD-L1 can also be regulated by oncogenes, this mechanism is known as inherent immune resistance (Akbay et al., 2013). Within the tumor microenvironment, PD-L1 is also expressed on myeloid cells and activated T cells (Tumeh et al., 2014). The expression of PD-L1 is induced by multiple proinflammatory molecules, including types I and II IFN-γ, TNF-α, LPS, GM-CSF and VEGF, as well as the cytokines IL-10 and IL-4, with IFN-γ being the most potent inducer (Kondo et al., 2010; Sznol and Chen, 2013).

The binding of PD-L1 to PD-1 or B7.1 (CD80) transmits an inhibitory signal which reduces the proliferation of the PD-1 expressing T cells. PD-1 is thought to be able to control the accumulation of foreign antigen specific T cells through apoptosis. PD-L1 is expressed by a variety of cancer cells and the expression thereof is thought to be at least in part responsible for a dampening of an immune response against the cancer cell. PD-L1 is a member of the B7-family of protein and is known under a variety of other names such as CD274 Molecule; CD274 Antigen; B7 Homolog 1; PDCD1 Ligand 1; PDCD1LG1; PDCD1L1; B7H1; PDL1; Programmed Cell Death 1 Ligand 1; Programmed Death Ligand 1; B7-H1; and B7-H. External Ids for CD274 are HGNC: 17635; Entrez Gene: 29126; Ensembl: ENSG00000120217; OMIM: 605402; UniProtKB: Q9NZQ7.

PD-L2 is a second ligand for PD-1. Engagement of PD-1 by PD-L2 inhibits T cell receptor (TCR)-mediated proliferation and cytokine production by CD4+ T cells. At low antigen concentrations, PD-L2/PD-1 binding inhibits B7-CD28 signals. At high antigen concentrations, PD-L2/PD-1 binding reduces cytokine production. PD-L expression is up-regulated on antigen-presenting cells by interferon gamma treatment. It is expressed in some normal tissues and a variety of tumors. PD-L1 and PD-L2 are thought to have overlapping functions and regulate T cell responses. The protein is known under a number of other names such as Programmed Cell Death 1 Ligand 2; B7 Dendritic Cell Molecule; Programmed Death Ligand 2; Butyrophilin B7-DC; PDCD1 Ligand 2; PD-1 Ligand 2; PDCD1L2; B7-DC; CD273; B7DC; PDL2; PD-1-Ligand 2; CD273 Antigen; BA574F11.2; and Btdc. External Ids for PD-L2 are HGNC: 18731; Entrez Gene: 80380; Ensembl: ENSG00000197646; OMIM: 605723; and UniProtKB: Q9BQ51.

B7-H3 (CD276) expression is increased in various malignancies and can distinguish between normal and tumor-derived circulating endothelial cells (Kraan et al British Journal of Cancer (2014) 111, 149-156). Stimulation of the receptor directs the differentiation of human marrow stromal cells to osteoblasts (Xu et al 2011; Immunobiology 216 (2011) 1311-1317). The protein contains 4 Ig-like domains in humans whereas the mouse protein appears to have 2 of such domains. The protein is thought to be the first identified ligand for the triggering receptor expressed on myeloid cells (TREM)-like transcript 2 (TLT-2 or TREMML2). The latter protein binds B7-H3 (4Ig-B7-H3) and costimulates activation of CD8 T-cells (Hofmeyer et al 2009 PNAS 105; 10277-10278). CD276 is broadly expressed. It acts as a T cell costimulator. CD276 is also known under a number of other names such as CD276 Molecule; Costimulatory Molecule; CD276 Antigen; B7 Homolog 3; 4Ig-B7-H3; B7-H3; B7H3; and B7RP-2. External Ids for CD276 are HGNC: 19137; Entrez Gene: 80381; Ensembl: ENSG00000103855; OMIM: 605715; and UniProtKB: Q5ZPR3.

B7-H4 (VTCN1) mRNA appears to be broadly expressed but only few cells actively express the protein on the membrane. B7-H4 expression and binding to activated T cells inhibits T-cell effector function via cell cycle arrest, decreased proliferation, and reduced IL-2 production. B7-H4 is up-regulated on the surface of cancer cells and immunosuppressive tumor-associated macrophages (TAMs) in a variety of human cancers. Signaling through B7-H4 pathway leads to the inhibition of TCR-mediated CD4+ and CD8+ T cell proliferation, cell-cycle progression, and IL-2 production. B7-H4 is also known under a number of other names such as V-Set Domain Containing T Cell Activation Inhibitor 1; Immune Costimulatory Protein B7-H4; T-Cell Costimulatory Molecule B7x; B7 Superfamily Member 1; B7 Homolog 4; B7h.5; B7H4; T Cell Costimulatory Molecule B7x; B7 Family Member, H4; Protein B7S1; PRO1291; VCTN1; B7S1; B7X; and H4 2. External Ids for B7-H4 are HGNC: 28873; Entrez Gene: 79679; Ensembl: ENSG00000134258; OMIM: 608162 and UniProtKB: Q7Z7D3.

B7-H5 (VISTA) is a 55-65 kDa member of the B7 family. It is a transmembrane molecule expressed in bone, on embryonic stem cells (ESCs), and on tumor cell surfaces. On tumor cells, the protein both promotes MT1-MMP expression and activity and serves as a substrate for MT1-MMP. This increases the potential for cell motility. The protein is known under a number of other names such as Chromosome 10 Open Reading Frame 54; V-Set Domain-Containing Immunoregulatory Receptor; V-Domain Ig Suppressor Of T Cell Activation; Stress-Induced Secreted Protein-1; Sisp-1; SISP1; Stress Induced Secreted Protein 1; Platelet Receptor GI24; Platelet Receptor Gi24; Death Domain1alpha; DD1alpha; B7H5; and GI24. External IDs for the protein are: HGNC: 30085; Entrez Gene: 64115; Ensembl: ENSG00000107738; OMIM: 615608; and UniProtKB: Q9H7M9.

B7-H6 belongs to the B7 family (see MIM 605402) and is selectively expressed on tumor cells. Binding of B7-H6 with NKp30 (NCR3; MIM 611550) results in natural killer (NK) cell activation and cytotoxicity (Brandt et al., 2009 J Exp Med. 2009 Jul. 6; 206(7):1495-503). Natural killer (NK) cells are lymphocytes of the innate immune system that participate in the elimination of tumors. B7-H6 is a tumor cell surface molecule that binds NKp30, a human receptor which triggers antitumor NK cell cytotoxicity and cytokine secretion. Other names for B7-H6 are NCR3LG1; Natural Killer Cell Cytotoxicity Receptor 3 Ligand 1; B7 Homolog 6; B7H6; Putative Ig-Like Domain-Containing Protein DKFZp686O24166/DKFZp686I21167; and DKFZp686O24166. External Ids for B7-H6 are HGNC: 42400; Entrez Gene: 374383; Ensembl: ENSG00000188211; OMIM: 613714; and UniProtKB: Q68D85.

B7-H7 (HHLA2) protein was detected in trophoblastic cells of the placenta and the epithelium of gut, kidney, gallbladder, and breast, but not in most other organs. HHLA2 protein is widely expressed in human cancers from the breast, lung, thyroid, melanoma, pancreas, ovary, liver, bladder, colon, prostate, kidney, and esophagus. High HHLA2 expression is associated with regional lymph node metastasis and stage (Janakiram et al. Clin Cancer Res; 21(10): 2359-66; May 15, 2015). TMIGD2 is identified as one of the receptors for HHLA2. B7-H7 is known under a number of different names such as HERV-H LTR-Associating 2; Human Endogenous Retrovirus-H Long Terminal Repeat-Associating Protein 2; B7H7 and B7y. External Ids for B7-H7 are HGNC: 4905; Entrez Gene: 11148; Ensembl: ENSG00000114455; OMIM: 604371 and UniProtKB: Q9UM44.

Programmed Cell Death 1 protein (PD-1) is a cell surface receptor that belongs to the CD28 family of receptors and is expressed on T cells and pro-B cells. PD-1 is presently known to bind two ligands, PD-L1 and PD-L2. PD-1, functioning as an immune checkpoint, plays an important role in down regulating the immune system by inhibiting the activation of T-cells, which in turn reduces autoimmunity and promotes self-tolerance. The inhibitory effect of PD-1 is thought to be accomplished through a dual mechanism of promoting apoptosis (programmed cell death) in antigen specific T-cells in lymph nodes while simultaneously reducing apoptosis in regulatory T cells (suppressor T cells). PD-1 is also known under a number of different aliases such as PDCD1; Programmed Cell Death 1; Systemic Lupus Erythematosus Susceptibility 2; Protein PD-1; HPD-1; PD1; Programmed Cell Death 1 Protein; CD279 Antigen; CD279; HPD-L; HSLE1; SLEB2; and PD-1. External Ids for PD-1 are HGNC: 8760; Entrez Gene: 5133; Ensembl: ENSG00000188389; OMIM: 600244; and UniProtKB: Q15116. New classes of drugs that block the activity of PD-1, the PD-1 inhibitors, activate the immune system to attack tumors and are therefore used with success to treat some types of cancer.

CLEC12A is also referred to as C-Type Lectin Domain Family 12, Member A; C-Type Lectin Protein CLL-1; MICL; Dendritic Cell-Associated Lectin 2; C-Type Lectin Superfamily; Myeloid Inhibitory C-Type Lectin-Like Receptor; C-Type Lectin-Like Molecule-1; CLL-1; DCAL2; CLL1; C-Type Lectin-Like Molecule 1; DCAL-2; Killer cell lectin like receptor subfamily L, member 1 (KLRL1); CD371 (Bakker A. et al. Cancer Res. 2004, 64, p 8843 50; GenBank™ access. no: AY547296; Zhang W. et al. GenBank™ access. no: AF247788; A.S. Marshall, et al. J Biol Chem 2004, 279, p 14792-802; GenBank™ access. no: AY498550; Y. Han et al. Blood 2004, 104, p 2858 66; H. Floyd, et al. GenBank™ access. no: AY426759; C. H. Chen, et al. Blood 2006, 107, p 1459 67). Ids: HGNC: 31713; Entrez Gene: 160364; Ensembl: ENSG00000172322; OMIM: 612088; UniProtKB: Q5QGZ9. CLEC12A is an antigen that is expressed on leukemic blast cells and on leukemic stem cells in acute myeloid leukemia (AML), including the CD34 negative or CD34 low expressing leukemic stem cells (side population) (A. B. Bakker et al. Cancer Res 2004, 64, p 8443 50; Van Rhenen et al. 2007 Blood 110:2659; Moshaver et al. 2008 Stem Cells 26:3059). Expression of CLEC12A is otherwise thought to be restricted to the hematopoietic lineage, particularly to myeloid cells in peripheral blood and bone marrow, i.e., granulocytes, monocytes and dendritic cell precursors. More importantly, CLEC12A is absent on hematopoietic stem cells. This expression profile makes CLEC12A a particularly favorable target in AML. The full length form of CLEC12A comprises 275 amino acid residues, including an additional intracellular stretch of 10 amino acids which is absent in most other isoforms, and shows the strictly myeloid expression profile (surface expression and mRNA level). The term 'CLEC12A or functional equivalent thereof' means all (such as splice and mutation) variants that are referenced above and isoforms thereof that retain the strict myeloid expression profile (both at surface expression level and mRNA level) as described in Bakker et al. Cancer Res 2004, 64, p 8443-50 and Marshall 2004—J Biol Chem 279(15), p 14792-802. A CLEC12A binding antibody of the invention binds human CLEC12A. Where herein reference is made to CLEC12A, the reference is to human CLEC12A, unless specifically stated otherwise.

'ErbB1' or 'EGFR' is a member of a family of four receptor tyrosine kinases (RTKs), named Her- or cErbB-1, -2, -3 and -4. The EGFR has an extracellular domain (ECD) that is composed of four sub-domains, two of which are involved in ligand binding and one of which is involved in homo-dimerisation and hetero-dimerisation. The reference numbers used in this section refer to the numbering of the references in the list headed "References cited in the specification". EGFR integrates extracellular signals from a variety of ligands to yield diverse intracellular responses. The major signal transduction pathway activated by EGFR is composed of the Ras-mitogen-activated protein kinase (MAPK) mitogenic signalling cascade. Activation of this pathway is initiated by the recruitment of Grb2 to tyrosine phosphorylated EGFR. This leads to activation of Ras through the Grb2-bound Ras-guanine nucleotide exchange factor Son of Sevenless (SOS). In addition, the PI3-kinase-Akt signal transduction pathway is also activated by EGFR, although this activation is much stronger in case there is co-expression of Her3. The EGFR is implicated in several human epithelial malignancies, notably cancers of the breast, bladder, non-small cell lung cancer lung, colon, ovarian head and neck and brain. Activating mutations in the gene have been found, as well as over-expression of the receptor and of its ligands, giving rise to autocrine activation loops. This RTK has therefore been extensively used as target for cancer therapy. Both small-molecule inhibitors targeting the RTK and monoclonal antibodies (mAbs) directed to the extracellular ligand-binding domains have been developed and have shown hitherto several clinical successes, albeit mostly for a select group of patients. A database accession number for the human EGFR protein and the gene encoding it is (GenBank NM_005228.3). The accession number is primarily given to provide a further method of identification of EGFR protein as a target, the actual sequence of the EGFR protein bound by an antibody may vary, for instance because of a mutation in the encoding gene such as those occurring in some cancers or the like. Where reference herein is made to EGFR, the reference refers to human EGFR unless otherwise stated. The antigen-binding site that binds EGFR, binds EGFR and a variety of variants thereof such as those expressed on some EGFR positive tumors.

'ErbB-2' or 'HER2' as used herein refers to the protein that in humans is encoded by the ERBB-2 gene. Alternative names for the gene or protein include CD340; HER-2; HER-2/neu; MLN 19; NEU; NGL; TKR1. The ERBB-2 gene is frequently called HER2 (from human epidermal growth factor receptor 2). Where reference is made herein to ErbB-2, the reference refers to human ErbB-2. An antibody comprising an antigen-binding site that binds ErbB-2, binds human ErbB-2. The ErbB-2 antigen-binding site may, due to sequence and tertiary structure similarity between human and other mammalian orthologs, also bind such an ortholog but not necessarily so. Database accession numbers for the human ErbB-2 protein and the gene encoding it are (NP_001005862.1, NP_004439.2 NC_000017.10 NT_010783.15 NC_018928.2). The accession numbers are primarily given to provide a further method of identification of ErbB-2 as a target, the actual sequence of the ErbB-2 protein bound the antibody may vary, for instance because of a mutation in the encoding gene such as those occurring in some cancers or the like. The ErbB-2 antigen binding site binds ErbB-2 and a variety of variants thereof, such as those expressed by some ErbB-2 positive tumor cells.

'ErbB-3' or 'HER3' as used herein refers to the protein that in humans is encoded by the ERBB-3 gene. Alternative names for the gene or protein are HER3; LCCS2; MDA-BF-1; c-ErbB-3; c-erbb-3; erbB-3-S; p180-Erbb-3; p45-sErbb-3; and p85-sErbb-3. Where reference is made herein to ErbB-3, the reference refers to human ErbB-3. An antibody comprising an antigen-binding site that binds ErbB-3, binds human ErbB-3. The ErbB-3 antigen-binding site, may, due to sequence and tertiary structure similarity between human and other mammalian orthologs, also bind such an ortholog but not necessarily so. Database accession numbers for the human ErbB-3 protein and the gene encoding it are (NP_001005915.1 NP_001973.2, NC_000012.11 NC_018923.2 NT_029419.12). The accession numbers are primarily given to provide a further method of identification of ErbB-3 as a target, the actual sequence of the ErbB-3 protein bound by an antibody may vary, for instance because of a mutation in the encoding gene such as those occurring in some cancers or the like. The ErbB-3 antigen binding site binds ErbB-3 and a variety of variants thereof, such as those expressed by some ErbB-2 positive tumor cells.

LGR4 is Leucine-Rich Repeat Containing G-Protein-Coupled Receptor 4 Alternative names for the gene or protein are; GPR48; G Protein-Coupled Receptor 48; BNMD17; Leucine-Rich Repeat-Containing G-Protein-Coupled Receptor 4; Leucine-Rich Repeat-Containing G-Protein Coupled Receptor 4; G-Protein Coupled Receptor 48;

A protein or antibody of the invention that binds LGR4, binds human LGR4. The LGR4 binding protein or antibody of the invention may, due to sequence and tertiary structure similarity between human and other mammalian orthologs, also bind such an ortholog but not necessarily so. Database accession numbers for the human LGR4 protein and the gene encoding it are (NC_000011.10; NC_018922.2; NT_009237.19; NP_060960.2). The accession numbers are primarily given to provide a further method of identification of LGR4 as a target, the actual sequence of the LGR4 protein bound may vary, for instance because of a mutation in the encoding gene such as those occurring in some cancers or the like. The LGR4 antigen binding site binds LGR4 and a variety of variants thereof, such as those expressed by some LGR4 positive tumor cells.

LGR5 is Leucine-Rich Repeat Containing G Protein-Coupled Receptor 5 Alternative names for the gene or protein are Leucine-Rich Repeat Containing G Protein-Coupled Receptor 5; Leucine-Rich Repeat-Containing G Protein-Coupled Receptor 5; G-Protein Coupled Receptor HG38; G-Protein Coupled Receptor 49; G-Protein Coupled Receptor 67; GPR67; GPR49; Orphan G Protein-Coupled Receptor HG38; G Protein-Coupled Receptor 49; GPR49; HG38 and FEX.

A protein or antibody of the invention that binds LGR5, binds human LGR5. The LGR5 binding protein or antibody of the invention may, due to sequence and tertiary structure similarity between human and other mammalian ortho-logues, also bind such an orthologue but not necessarily so. Database accession numbers for the human LGR5 protein and the gene encoding it are (NC_000012.12; NT_029419.13; NC_018923.2; NP_001264155.1; NP_001264156.1; NP_003658.1). The accession numbers are primarily given to provide a further method of identification of LGR5 as a target, the actual sequence of the LGR5 protein bound may vary, for instance because of a mutation in the encoding gene such as those occurring in some cancers or the like. The LGR5 antigen binding site binds LGR5 and a variety of variants thereof, such as those expressed by some LGR5 positive tumor cells.

ZNRF3 is Zinc And Ring Finger 3. Alternative names for the gene or protein are Zinc And Ring Finger 3; Zinc/RING Finger Protein 3; RING Finger Protein 203; KIAA1133; RNF203; Novel C3HC4 Type Zinc Finger (Ring Finger); E3 Ubiquitin-Protein Ligase ZNRF3; CTA-292E10.6; EC 6.3.2; and BK747E2.3 3.

A protein or antibody of the invention that binds ZNRF3, binds human ZNRF3. The ZNRF3 binding protein or antibody of the invention may, due to sequence and tertiary structure similarity between human and other mammalian orthologues, also bind such an orthologue but not necessarily so. Database accession numbers for the human ZNRF3 protein and the gene encoding it are (NC 000022.11; NT_011520.13; NC_018933.2; NP_001193927.1; NP_115549.2). The accession numbers are primarily given to provide a further method of identification of ZNRF3 as a target, the actual sequence of the ZNRF3 protein bound may vary, for instance because of a mutation in the encoding gene such as those occurring in some cancers or the like. The ZNRF3 antigen binding site binds ZNRF3 and a variety of variants thereof, such as those expressed by some ZNRF3 positive tumor cells RNF43 is Ring Finger Protein 43. Alternative names for the gene or protein are Ring Finger Protein 43; RNF124; E3 Ubiquitin-Protein Ligase RNF43; RING Finger Protein 43; EC 6.3.2; URCC.

A protein or antibody of the invention that binds RNF43, binds human RNF43. The RNF43 binding protein or antibody of the invention may, due to sequence and tertiary structure similarity between human and other mammalian orthologues, also bind such an orthologue but not necessarily so. Database accession numbers for the human RNF43 protein and the gene encoding it are (NC_000017.11; NT_010783.16; NC_018928.2; NP_001292473.1; NP_001292474.1; NP_060233.3). The accession numbers are primarily given to provide a further method of identification of RNF43 as a target, the actual sequence of the RNF43 protein bound may vary, for instance because of a mutation in the encoding gene such as those occurring in some cancers or the like. The RNF43 antigen binding site binds RNF43 and a variety of variants thereof, such as those expressed by some RNF43 positive tumor cells.

Reference to sequence identifiers is done to identify which protein is targeted. A binding molecule such as an antibody of the invention also recognizes at least some variants thereof such as allelic variants, splice variants and mutant variants thereof as long as the epitope recognized by the respective variable domain of the antibody has not been affected. Some of the alternative names may or may not have also been used to refer to other proteins. The names are given for reference purposes only. A binding molecule such as an antibody of the invention binds to the protein as expressed on cells. It can also bind to variants of the protein as long as the epitope to which the binding molecule binds is available. Thus splicing variants or mutant proteins (if any) will also be bound as long as the epitope is available. The fact that the binding molecule binds to the indicated protein means that it can bind to protein as a property and does not imply that the binding molecule is actually bound to the target, although it can be. It also does not mean that the antibody does not bind to other proteins. Such cross-reactivity is at present not known for a binding molecule such as an antibody of the present invention; however, it is not expressly excluded that such cross-reactivity may exist.

The invention discloses a binding molecule that binds an extracellular part of a member of the TNF receptor superfamily (first membrane protein) and an extracellular part of a second membrane protein. Said second membrane protein is preferably not a member of the TNF receptor superfamily. Such a binding molecule is further also referred to as "a binding molecule of the invention". The binding molecule is preferably a binding protein. In a preferred embodiment the binding molecule is an antibody or a variant thereof, preferably a bispecific antibody or a variant thereof. Also provided are compositions and kits of parts comprising two or more binding molecules as described herein.

A binding molecule of the invention is preferably an antibody (or variant thereof as described elsewhere in the application), an antibody mimetic, a polypeptide, an aptamer or a combination thereof. These proteins or aptamers typically bind to one target. The binding molecule of the invention binds to two or more targets. The binding molecule preferably binds two targets. A variant of an antibody or bispecific antibody maintains this aspect. Binding proteins or aptamers have binding sites (antigen binding sites) with which targets are bound. The binding protein or aptamer preferably comprises two or more domains that preferably have a binding site for the target (antigen), preferably one binding site per domain. Such domains are preferably antibody variable domains or variants thereof. Antibody variable domains have been the subject of a lot of research. Many variants are made that resemble variable domains or parts thereof that retain the binding specificity of a normal variable domain. Non-limiting examples of such variants are described elsewhere herein.

It is to be understood that any combination of these antibodies, antibody mimetics, polypeptides and aptamers can be linked together by methods known in the art. For example, in some embodiments the binding molecule of the invention is a conjugate or a fusion protein. For antibodies the technology of making multi-specific antibodies has progressed to also include bispecific antibodies that have the same overall structure as a normal mono-specific antibody but wherein the two arms of the antibody each bind a different target.

An antibody mimetic is a polypeptide that, like antibodies, can specifically bind an antigen, but that is not structurally related to antibodies. Antibody mimetics are usually artificial peptides or proteins with a molar mass of about 3 to 20 kDa. Common advantages over antibodies are better solubility, tissue penetration, stability towards heat and enzymes, and comparatively low production costs. Non-limiting examples of antibody mimetics are affibody molecules (typically based on the Z domain of Protein A); affilins (typically based on Gamma-B crystalline or Ubiquitin); affimers (typically based on Cystatin); affitins (typically based on Sac7d from *Sulfolobus acidocaldarius*); alphabodies (typically based on Triple helix coiled coil); anticalins (typically based on Lipocalins); avimers (typically based on A domains of various membrane receptors); DARPins (typically based on ankyrin repeat motif); fynomers (typically based on SH3 domain of Fyn 7); kunitz domain peptides (typically based on Kunitz domains of various protease inhibitors); and monobodies (typically based on type III domain of fibronectin).

Monobodies are synthetic binding proteins that are constructed using a fibronectin type III domain (FN3) as a molecular scaffold. Monobodies are simple and robust alternative to antibodies for creating target-binding proteins. The term "monobody" was coined in 1998 by the Koide group who published the first paper demonstrating the monobody concept using the tenth FN3 domain of human fibronectin.

Monobodies and other antibody mimetics are typically generated from combinatorial libraries in which portions of the scaffold are diversified using molecular display and directed evolution technologies such as phage display, mRNA display and yeast surface display. A large number of antibody mimetics have high affinity and high specificity to their respective targets.

Aptamers are oligonucleotide or peptide molecules that bind to a specific target molecule. Aptamers are usually created by selecting them from a large random sequence pool, but natural aptamers also exist in riboswitches. Aptamers can be used for both basic research and clinical purposes as macromolecules.

As used herein, the term "conjugate" refers to two or more molecules that have been covalently joined, optionally by a linking region. For example, in some embodiments, a conjugate is a first protein or non-protein moiety joined to a second protein or non-protein moiety by a linking region. For example, in some embodiments of a binding molecule of the invention it comprises or consists of two or more antibodies that have been covalently joined. A conjugate is not limited to a first and second moiety but in some embodiments may also have a third, fourth or more moieties joined by further linking regions. As described elsewhere in this application, examples of protein moieties include, but are not limited to: a polypeptide, a peptidomimetic or an antibody (or antibody part, derivative, or analogue, as described elsewhere in the application). Examples of non-protein moieties include, but are not limited to aptamers. Numerous types of linker can be used, and the linker will be selected to be appropriate according to the molecule types in the conjugate and on the desired properties of the linker (length, flexibility, resistance to protease activity and other similar characteristics). Such linkers may comprise nucleotides, polypeptides, or a suitable synthetic material. For example, a linker may be a flexible peptide linker. In certain embodiments, the linker may be a cleavable linker, allowing the parts of the conjugate to be separated from each other. In other embodiments, a peptide linker might be a helical linker. Various examples and kits for linking proteins and other molecules are known in the art. As used herein, the term "fusion protein" refers to a protein that comprises two or more polypeptides or proteins that have been joined at the DNA level by recombination and are expressed together as a single polypeptide. A fusion protein may also comprise a peptide linking region also encoded by the DNA and expressed together with the fusion protein. A peptide linker that is part of a fusion protein may be designed to have particular characteristics such as flexibility, hydrophilicity, protease-resistance, cleavability etc. All these properties can be designed within the DNA sequence and methods for designing linkers are well known in the art. For example, antibodies can be linked together by methods well-known in the art, and as described herein, to form bispecific or multi-targeting antibodies. Furthermore, bispecific antibodies can be constructed by various methods known in the art, for example, by using technology such as Biclonics® (see for instance WO 2013/157954). A bispecific monoclonal antibody (BsMAb, BsAb) typically comprises binding domains of two different monoclonal antibodies and consequently binds to two different epitopes. Biclonics® molecules, but also other full length IgG bispecific antibodies have two different antigen binding specificities encoded by two different variable regions of a full length IgG molecule of a Fab of a scFv. Biclonics® can be produced by co-transfection of individual cells with genetic constructs encoding two different common light chain (cLC) antibodies as detailed elsewhere herein. CH3 engineering ensures efficient hetero-dimerization and formation of essentially pure bispecific antibodies.

A binding molecule of the invention is preferably an antibody or variant thereof. A binding molecule of the invention is preferably a bispecific antibody or a variant thereof.

Antibodies typically bind their target via the so-called antigen binding site. An unmodified antigen-binding site is typically formed by and present in the variable domain of the antibody. The variable domain contains said antigen-binding site. A variable domain that binds an antigen is a variable domain comprising an antigen-binding site that binds the antigen.

In one embodiment an antibody variable domain comprises a heavy chain variable region (VH) and a light chain variable region (VL). The antigen-binding site can be present in the combined VH/VL variable domain, or in only the VH region or only the VL region. When the antigen-binding site is present in one of the two regions of the variable domain, the counterpart variable region can contribute to the folding and/or stability of the binding variable region, but does not significantly contribute to the binding of the antigen itself.

As used herein, antigen-binding refers to the typical binding capacity of an antibody to its antigen. Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity determining regions (CDR) of the antibody and the specific three-dimensional structure of both the antigen and the variable domain allowing these two structures to bind together with precision (an interaction similar to a lock and key), as opposed to random, non-specific sticking of proteins. As an antibody typically recognizes part of an antigen called the epitope of an antigen, and as such epitope may be present in other compounds as well, antibodies according to the present invention may recognize other proteins as well, if such other compounds contain the same epitope. Hence, the term "binding" does not exclude binding of the antibodies to another protein or protein(s) that contain the same epitope. Such other protein(s) is preferably not a human protein.

A protein of the invention such as an antibody typically does not bind to other proteins than the specified target protein on the membrane of cells in a post-natal, preferably adult human.

The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Preferably the affinity of the separate arms of the antibodies according to the invention is in the nanomolar range. Antibodies such as the bispecific antibodies of the present invention typically comprise the constant domains (Fc part) of a natural antibody, which may be engineered as described elsewhere herein, for instance to reduce ADCC and/or CDC activity. An antibody of the invention is typically a bispecific full length antibody, preferably of the human IgG subclass.

The terms 'variable domain', 'VH/VL pair', 'VH/VL' are used herein interchangeably. A variable domain is composed of the variable region of a heavy chain and a variable region of a light chain. The variable region of a heavy chain is typically formed by a rearranged VDJ region. A variable region of a light chain is typically formed by a rearranged VJ region. The VDJ/VJ regions can now also be artificially produced using for instance the large body of sequence information that is available of functional antibodies.

In some embodiments a binding molecule or antibody or variant according to the invention comprises an antigen binding site that can bind an extracellular part of a member of the TNF receptor superfamily and an antigen binding site that can bind a member of the B7 family. In some embodiments a binding molecule or antibody or variant according to the invention comprises an antigen binding site that can bind an extracellular part of CD137 and an antigen binding site that can bind a member of the B7 family. In some embodiments a binding molecule or antibody or variant according to the invention comprises an antigen binding site that can bind CD137 and an antigen binding site that can bind PD-L1.

In some embodiments, a binding molecule or antibody or variant according to the invention has no more than two antigen binding sites. This means that the antigen binding part of such binding molecule or antibody or variant consists of two antigen binding sites, without the presence of additional antigen binding sites. Each of the two antigen binding sites preferably contains an immunoglobulin VH/VL pair. Preferably, the antigen binding part of a binding molecule or antibody or variant of the invention consists of one immunoglobulin variable domain that can bind an extracellular part of a member of the TNF receptor superfamily and one immunoglobulin variable domain that can bind a second membrane protein. Certain preferred embodiments are immunoglobulins having an IgG format, providing the advantage that the half-lives of bivalent binding molecules/antibodies/variants according to the invention are typically longer as compared to multivalent compounds. Moreover, the immunogenicity of bivalent binding molecules according to the invention is typically lower as compared to multivalent compounds. Molecules/antibodies/variants according to these embodiments preferably maintain the structure of natural IgGs and therefore maintain all benefits associated to that structure of natural IgGs.

As used herein, the term "multivalent" embraces three or more specificities, which is for instance present in trivalent and tetravalent binding molecules.

Some embodiments provide a binding molecule or antibody or variant according to the invention wherein the antigen binding sites of said binding molecule or antibody or variant consist of one antigen binding site that can bind an extracellular part of a member of the TNF receptor superfamily and one antigen binding site that can bind a member of the B7 family. In some embodiments the antigen binding sites of said binding molecule or antibody or variant according to the invention consist of one antigen binding site that can bind an extracellular part of CD137 and one antigen binding site that can bind a member of the B7 family. In some embodiments the antigen binding sites of said binding molecule or antibody or variant according to the invention consist of one antigen binding site that can bind CD137 and one antigen binding site that can bind PD-L1.

As used herein, the term "antigen binding site" means a site of a binding molecule or antibody that specifically binds an epitope of an antigen. Such antigen binding site is preferably derived from or shares sequence homology with the variable domain of an antibody, in particular the CDR regions thereof. In some preferred embodiments, said antigen binding site is an immunoglobulin variable domain, formed by an immunoglobulin VH/VL pair. In other embodiments, said antigen binding site is derived from an antibody mimetic, such as for instance from an affibody molecule, affilin, affimer, affitin, alphabody, anticalin, avimer, DARPin, fynomer, kunitz domain peptide or monobody, which are described herein before.

An antibody of the invention is preferably a "full length" antibody. The term 'full length' according to the invention is defined as comprising an essentially complete antibody, without one or more artificially added moieties with a size of larger than 20 amino acid residues, such as for instance additional antigen binding sites or additional activation sites or additional ligands or additional ligand-binding moieties. A full length antibody however does not necessarily have all functions of an intact antibody. For the avoidance of doubt, a full length antibody contains two heavy and two light chains. Each chain contains constant (C) and variable (V) regions, which can be broken down into domains designated CHI, CH2, CH3, VH for the heavy chain, and CL, VL for the light chain. The domains of the heavy chains are preferably present in the order of a natural antibody (VH-CH1-CH2-CH3; meaning that the VH domain is adjacent to the CHI domain, followed by a CH2 domain and subsequently followed by a CH3 domain). The domains of the light chains are also preferably present in the order of a natural antibody (VL-CL; meaning that the VL domain is adjacent to the CL domain). An antibody binds to antigen via the variable domains contained in the Fab fragment portion. The antibody can interact with molecules and cells of the immune system through the constant domains, mostly through the Fc portion. In some embodiments, an antibody of the invention is an IgG, preferably a full length IgG. Full length IgG antibodies are preferred because of their typically favorable half-life and the desire to stay as close to fully autologous (human) molecules for reasons of immunogenicity. In some embodiments, an antibody of the invention is a full length IgG1, a full length IgG2, a full length IgG3 or a full length IgG4 antibody.

Full length antibodies according to the invention encompass antibodies wherein mutations may be present that provide desired characteristics or are just alternatives to the ones in the original chain. Such mutations should not be deletions of substantial portions of any of the regions. However, antibodies wherein one or several amino acid residues are acid inserted, deleted, substituted or a combination thereof, without essentially altering the antigen binding characteristics of the resulting antibody are embraced within the term "full length antibody". For instance, an IgG antibody can have 1-20 amino acid residue insertions, substitutions, deletions or a combination thereof in the constant region.

An antibody or a functional part, derivative and/or analogue thereof of the invention is preferably a bispecific antibody or a functional part, derivative and/or analogue thereof. In a preferred embodiment it is a bispecific IgG antibody with reduced effector function. In a preferred embodiment an antibody of the invention is a bispecific full length antibody. An antibody of the invention is preferably a bispecific full length IgG antibody, preferably mutated in the CH2/lower hinge region to reduce effector function. IgG1 which is mutated in the CH2/lower hinge region to reduce effector function is favored based on its long circulatory half-life in man. In order to prevent any immunogenicity in humans it is preferred that the bispecific antibody according to the invention is a human antibody.

The term 'bispecific' (bs) means that one part of the antibody (as defined above) binds to one epitope on an antigen whereas a second part binds to a different epitope on either the same antigen, or a different antigen. The different epitopes are typically present on different antigens. The different epitopes can, however, also be present on the same antigen. According to the present invention, said first and second antigens are in fact two different proteins. A preferred bispecific antibody is an antibody that comprises parts of two different monoclonal antibodies and consequently can bind to two different epitopes, preferably on two different antigens. Dependent on the expression level, (sub-)cellular localization and stoichiometry of the two antigens recognized by a bispecific antibody, both Fab arms of the antibody may or may not simultaneously bind their epitope. One arm of the bispecific antibody typically contains the variable domain of one antibody and the other arm contains the variable domain of another antibody (i.e. one arm of the bispecific antibody is formed by one heavy chain paired with one light chain whereas the other arm is formed by a different heavy chain paired with a light chain). The heavy chain variable regions of the bispecific antibody of the invention are typically different from each other, whereas the light chain variable regions are preferably the same in the bispecific antibodies of the invention. A bispecific antibody wherein the different heavy chain variable regions are associated with the same or a common, light chain variable region is also referred to as a bispecific antibody with a common light chain variable region (cLcv). It is preferred that the light chain constant region is also the same. Such bispecific antibodies are referred to as having a common light chain (cLc). Further provided is therefore a bispecific antibody according to the invention, wherein both arms comprise a common light chain.

Bispecific antibodies as described herein preferably comprise a common light chain variable domain, preferably a common light chain. The term 'common light chain' according to the invention refers to light chains which may be identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common LC', 'cLC', 'single light chain' with or without the addition of the term 'rearranged' are all used herein interchangeably. The terms 'common light chain variable region', 'common VL', 'common LCv', 'cLCv', 'single VL' with or without the addition of the term 'rearranged' are all used herein interchangeably. It is a preferred aspect of the present invention that a bispecific antibody has a common light chain (variable region) that can combine with at least two, and preferably a plurality of heavy chains (variable regions) of different binding specificity to form antibodies with functional antigen binding domains (WO2004/009618, WO2009/157771). The common light chain (variable region) is preferably a human light chain (variable region). A common light chain (variable region) preferably has a germline sequence. A preferred germline sequence is a light chain variable region that is frequently used in the human repertoire and has good thermodynamic stability, yield and solubility. A preferred germline light chain is O12. A common light chain is preferably the rearranged germline human kappa light chain IgVκ1-39*01/IGJκ1*01 (FIG. 1A). The common light chain variable region is preferably the variable region of the rearranged germline human kappa light chain IgVκ1-39*01/IGJκ1*01. A common light chain preferably comprises a light chain variable region as depicted in FIG. 1, or 1D with 0-5 amino acid insertions, deletions, substitutions, additions or a combination thereof. The common light preferably further comprises a light chain constant region, preferably a kappa light chain constant region. A nucleic acid that encodes the common light chain can be codon optimized for the cell system used to express the common light chain protein. The encoding nucleic acid can deviate from a germ-line nucleic acid sequence.

In a preferred embodiment the light chain comprises a light chain region comprising the amino acid sequence of an O12/IgVκ1-39*01 gene segment as depicted in FIG. 1A with 0-10, preferably 0-5 amino acid insertions, deletions, substitutions, additions or a combination thereof. The phrase "O12 light chain" will be used throughout the specification as short for "a light chain comprising a light chain variable region comprising the amino acid sequence of an O12/IgVκ1-39*01 gene segment as depicted in FIG. 1A with 0-10, preferably 0-5 amino acid insertions, deletions, substitutions, additions or a combination thereof. IgVκ1-39 is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. A preferred amino acid sequence for IgVκ1-39 is given in FIG. 1E. This lists the sequence of the V-region. The V-region can be combined with one of five J-regions. FIGS. 1B and 1D describe two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org).

It is preferred that the O12/IgVκ1-39*01 comprising light chain variable region is a germline sequence. It is further preferred that the IGJκ1*01 or /IGJκ5*01 comprising light chain variable region is a germline sequence. In a preferred embodiment, the IGKV1-39/jk1 or IGKV1-39/jk5 light chain variable regions are germline sequences.

In a preferred embodiment the light chain variable region comprises a germline O12/IgVκ1-39*01. In a preferred embodiment the light chain variable region comprises the kappa light chain IgVκ1-39*01/IGJκ1*01 or IgVκ1-39*01/IGJκ5*01. In a preferred embodiment a IgVκ1-39*01/IGJκ1*01. The light chain variable region preferably comprises a germline kappa light chain IgVκ1-39*01/IGJκ1*01 or germline kappa light chain IgVκ1-39*01/IGJκ5*01, preferably a germline IgVκ1-39*01/IGJκ1*01.

Mature B-cells that produce an antibody with an O12 light chain often produce a light chain that has undergone one or more mutations with respect to the germline sequence, i.e. the normal sequence in non-lymphoid cells of the organism. The process that is responsible for these mutations is often referred to as somatic (hyper)mutation. The resulting light chain is referred to as an affinity matured light chain. Such light chains, when derived from an O12 germline sequence are O12-derived light chains. In this specification, the phrase "O12 light chains" will include O12-derived light chains. The mutations that are introduced by somatic hypermutation can of course also be introduced artificially in the lab. In the lab also other mutations can be introduced without affecting the properties of the light chain in kind, not necessarily in amount. A light chain is at least an O12 light chain if it comprises a sequence as depicted in FIG. 1A, FIG. 1; FIG. 1D or FIG. 1E with 0-10, preferably 0-5 amino acid insertions, deletions, substitutions, additions or a combination thereof. In a preferred embodiment the O12 light chain is a light chain comprising a sequence as depicted in FIG. 1A; 1; 1D or 1E with 0-9, 0-8, 0-7, 0-6, 0-5, 0-4 amino acid insertions, deletions, substitutions, additions or a combination thereof. In a preferred embodiment the O12 light chain is a light chain comprising a sequence as depicted in FIG. 1A, FIG. 1; FIG. 1D or FIG. 1E with 0-5, preferably 0-4, more preferably 0-3 amino acid insertions, deletions, substitutions, additions or a combination thereof. In a preferred embodiment the O12 light chain is a light chain comprising a sequence as depicted in FIG. 1A, FIG. 1; FIG. 1D or FIG. 1E with 0-2, more preferably 0-1, most preferably 0 amino acid insertions, deletions, substitutions, additions or a combination thereof. In a preferred embodiment the O12 light chain is a light chain comprising a sequence as depicted in FIG. 1A or FIG. 1B with the mentioned amino acid insertions, deletions, substitutions, additions or a combination thereof. In a preferred embodiment the light chain comprises the sequence of FIG. 1A. In a preferred embodiment the light chain variable region comprises the sequence of FIG. 1B.

The common light chain (variable region) can be a lambda light chain and this is therefore also provided in the context of the invention, however a kappa light chain is preferred. The constant part of a common light chain of the invention can be a constant region of a kappa or a lambda light chain. It is preferably a constant region of a kappa light chain, preferably wherein said common light chain is a germline light chain, preferably a rearranged germline human kappa light chain comprising the IgVκ1-39 gene segment, most preferably the rearranged germline human kappa light chain IgVκ1-39*01/IGJκ1*01 (FIG. 1). The terms rearranged germline human kappa light chain IgVκ1-39*01/IGJκ1*01, IGKV1-39/IGKJ1, huVκ1-39 light chain or in short huVκ1-39, or simply 1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, additions) are present that do not influence the formation of functional binding regions.

IgVκ1-39 is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. A preferred amino acid sequence for IgVκ1-39 is given in FIG. 1. This lists the sequence of the V-region. The V-region can be combined with one of five J-regions. FIG. 1 describes two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org).

A common light chain variable region is preferably linked to a kappa light chain constant region. In a preferred embodiment the light chain comprises the kappa light chain IgVκ1-39*01/IGJκ1*01 or IgVκ1-39*01/IGJκ5*01. In a preferred embodiment a IgVκ1-39*01/IGJκ1*01.

A cell that produces a common light chain can produce for instance rearranged germline human kappa light chain IgVκ1-39*01/IGJκ1*01 and a light chain comprising the variable region of the mentioned light chain fused to a lambda constant region.

Bispecific antibodies or variants thereof as described herein preferably have one heavy chain variable region/light chain variable region (VH/VL) combination that binds an extracellular part of a member of the TNF receptor superfamily and a second VH/VL combination that binds an extracellular part of a second membrane protein, wherein said second membrane protein is not a member of the TNF receptor superfamily.

Bispecific antibodies or variants thereof as described herein preferably have one heavy chain variable region/light chain variable region (VH/VL) combination that binds an extracellular part of a member of the TNF receptor superfamily and a second VH/VL combination that binds an extracellular part of a member of the B7 family. As described herein, this provides the advantage that a desired immune response can be particularly well promoted, since B7 family members deliver 'costimulatory' or 'coinhibitory' signals to lymphocytes, thereby augmenting or attenuating an immune response. Hence, by targeting a member of the B7 family it is possible to enhance stimulatory signals and/or to counteract inhibitory signals, thereby inducing or enhancing a desired immune response, for instance against aberrant cells.

In a preferred embodiment the VL in said first VH/VL combination is similar to the VL in said second VH/VL combination. In a more preferred embodiment, the VLs in the first and second VH/VL combinations are identical. In a preferred embodiment, the bispecific antibody is a full length antibody which has one heavy/light (H/L) chain combination that binds an extracellular part of a member of the TNF receptor superfamily and one H/L chain combination that binds an extracellular part of a member of the B7 family. In a preferred embodiment the light chain in said first H/L chain combination is similar to the light chain in said second H/L chain combination. In a more preferred embodiment, the light chains in the first and second H/L chain combinations are identical.

Several methods have been published to favor the production of the bispecific antibody or vice versa, the monospecific antibodies. In the present invention it is preferred that the cell favors the production of the bispecific antibody over the production of the respective monospecific antibodies. Such is typically achieved by modifying the constant region of the heavy chains such that they favor heterodimerization (i.e. dimerization with the heavy chain of the other heavy/light chain combination) over homodimerization. In a preferred embodiment the bispecific antibody of the invention comprises two different immunoglobulin heavy chains with compatible heterodimerization domains. Various compatible heterodimerization domains have been described in the art. The compatible heterodimerization domains are preferably compatible immunoglobulin heavy chain CH3 heterodimerization domains. When wildtype CH3 domains are used, co-expression of two different heavy chains (A and B) and a common light chain will result in three different antibody species, AA, AB and BB. AA and BB are designations for the two mono-specific, bivalent antibodies, and AB is a designation for the bispecific antibody. To increase the percentage of the desired bispecific product (AB) CH3 engineering can be employed, or in other words, one can use heavy chains with compatible heterodimerization domains, as defined hereunder. The art describes various ways in which such hetero-dimerization of heavy chains can be achieved. One way is to generate 'knob into hole' bispecific antibodies. See US Patent Application 20030078385 (Arathoon et al.).

The term 'compatible hetero-dimerization domains' as used herein refers to protein domains that are engineered such that engineered domain A' will preferentially form heterodimers with engineered domain B' and vice versa, homodimerization between A'-A' and B'-B' is diminished.

In U.S. Ser. No. 13/866,747 (now issued as U.S. Pat. No. 9,248,181), U.S. Ser. No. 14/081,848 (now issued as U.S. Pat. No. 9,358,286) and PCT/NL2013/050294 (published as WO2013/157954); incorporated herein by reference) methods and means are disclosed for producing bispecific antibodies using compatible heterodimerization domains. These means and methods can also be favorably employed in the present invention. Specifically, a bispecific antibody of the invention preferably comprises mutations to produce essentially only bispecific full length IgG molecules. Preferred mutations are the amino acid substitutions L351K and T366K (EU numbering) in the first CH3 domain (the 'KK-variant' heavy chain) and the amino acid substitutions L351D and L368E in the second domain (the 'DE-variant' heavy chain), or vice versa. It was previously demonstrated in our U.S. Pat. Nos. 9,248,181 and 9,358,286 patents as well as the WO2013/157954 PCT application that the DE-variant and KK-variant preferentially pair to form heterodimers (so-called 'DEKK' bispecific molecules). Homodimerization of DE-variant heavy chains (DEDE homodimers) hardly occurs due to repulsion between the charged residues in the CH3-CH3 interface between identical heavy chains.

Bispecific antibodies can be generated by (transient) transfection of a plasmid or plasmids encoding a light chain and two different heavy chains that are CH3 engineered to ensure efficient hetero-dimerization and formation of the bispecific antibodies. The production of these chains in a single cell leads to the favored formation of bispecific antibodies over the formation of monospecific antibodies. Preferred mutations to produce essentially only bispecific full length IgG1 molecules are amino acid substitutions at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa.

In one embodiment the heavy chain/light chain combination that comprises the variable domain that binds CD137, comprises a DE variant of the heavy chain. In this embodiment the heavy chain/light chain combination that comprises the variable domain that can bind to an antigen other than CD137 comprises a KK variant of the heavy chain. It will be recognized that an embodiment of the invention may also comprise a variable domain that binds CD137, and comprises a KK variant of the heavy chain, as well as other variations known to those of skill in the art used to facilitate heterodimerization with a variable domain that can bind to an antigen other than CD137.

The Fc region mediates effector functions of an antibody, such as complement-dependent cytotoxicity (CDC), antibody-dependent cellular cytotoxicity (ADCC) and antibody-dependent cell phagocytosis (ADCP). Depending on the therapeutic antibody or Fc fusion protein application, it may be desired to either reduce or increase the effector function. Reduced effector functions are preferred in the present invention. Reduced effector function can be desired when an immune response is to be activated, enhanced or stimulated as in some of the embodiments of the invention. Antibodies with reduced effector functions can be used to target cell-surface molecules of immune cells, among others.

Binding of IgG to the FcγRs or C1q was found to require residues located in the hinge region and the CH2 domain. Two regions of the CH2 domain (FIG. 2D) are relevant for FcγRs and C1q binding. Substitutions into human IgG1 of IgG2 residues at positions 233-236 and IgG4 residues at positions 327, 330 and 331 were shown to greatly reduce ADCC and CDC (Armour et al., 1999. Eur J Immunol. 29(8):2613-24; Shields et al., 2001. J Biol Chem. 276(9): 6591-604). Furthermore, Idusogie et al. demonstrated that alanine substitution at different positions, including K322, significantly reduced complement activation (Idusogie et al., 2000. J Immunol. 164(8):4178-84.

Due to their reduced effector functions, IgG4 antibodies represent an IgG subclass for receptor blocking without cell depletion. IgG4 molecules can exchange half-molecules in a dynamic process termed Fab-arm exchange. This phenomenon can occur between therapeutic antibodies and endogenous IgG4. The S228P mutation is an example of a mutation that ensures reduced capacity to Fab-arm exchange. (Labrijn. et al., 2009. Nat Biotechnol. 27(8):767-71.

Antibodies with reduced effector functions are preferably IgG antibodies comprising a modified CH2/lower hinge region, for instance to reduce Fc-receptor interaction or to reduce C1q binding. In some embodiments the antibody of the invention is an IgG antibody with a mutant CH2 and/or lower hinge domain such that interaction of the bispecific IgG antibody to an Fc-gamma receptor is reduced. An antibody comprising a mutant CH2 region is preferably an IgG1 antibody. Such a mutant IgG1 CH2 and/or lower hinge domain preferably comprise an amino substitution at position 235 and/or 236 (EU numbering), preferably an L235G and/or G236R substitution (FIG. 2E).

A variant of an antibody or bispecific antibody as described herein comprises a functional part, derivative and/or analogue of the antibody or bispecific antibody. The variant maintains the binding specificity of the (bispecific) antibody. The functional part, derivative and/or analogue maintains the binding specificity of the (bispecific) antibody. Binding specificity is defined by capacity to bind an extracellular part of a first membrane protein and a second membrane protein as described herein.

A functional part of an antibody, or preferably a functional part of a bispecific antibody as described herein is a part comprising a variable domain that binds an extracellular part of a member of the TNF receptor superfamily and a variable domain that an extracellular part of said second membrane protein. A suitable part is for instance an F(ab')2 fragment as created by digestion of a bispecific antibody with pepsin. Other parts comprising said variable domains are included in the present invention.

A functional derivative of an antibody, or preferably a functional derivative of a bispecific antibody as described herein is a protein comprising a variable domain that binds an extracellular part of a member of the TNF receptor superfamily and a variable domain that binds an extracellular part of said second membrane protein that are linked by a linker. The variable domains may be variable domains as such, or Fab fragments or variable domain like molecules such as single chain Fv fragments comprising a VH and a VL linked together via a linker. Other examples of variable domain like molecules are so-called single domain antibody fragment. A single-domain antibody fragment (sdAb) is an antibody fragment with a single monomeric variable antibody region. Like a whole antibody, it is able to bind selectively to a specific antigen. With a molecular weight of only 12-15 kDa, single-domain antibody fragments are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable regions, one from a light and one from a heavy chain). Single-domain antibodies by themselves are not much smaller than normal antibodies (being typically 90-100 kDa). Single-domain antibody fragments are mostly engineered from heavy-chain antibodies found in camelids; these are called VHH fragments (Nanobodies®). Some fishes also have heavy-chain only antibodies (IgNAR, 'immunoglobulin new antigen receptor'), from which single-domain antibody fragments called VNAR fragments can be obtained. An alternative approach is to split the dimeric variable domains from common immunoglobulin G (IgG) from humans or mice into monomers. Although most research into single-domain antibodies is currently based on heavy chain variable domains, nanobodies derived from light chains have also been shown to bind specifically to target epitopes. Other non-limiting examples of variable domain-like molecules are VHH, Human Domain Antibodies (dAbs) and Unibodies. Preferred functional parts are parts that comprise variable domains comprising a heavy chain variable region and a light chain variable region. Non-limiting examples of such variable domains are F(ab)-fragments and Single chain Fv fragments. Bispecific formats for variable domain(-like) linkage are for instance Human Serum Albumine (HSA) bound to two different scFv; bispecific mini-antibodies comprising two different scFv bound together via a dimerization motifs or self-associating secondary structures such as helix bundles or coiled coils to bring about dimerization of the scFv fragments (Morrison (2007) Nat. Biotechnol 25:1233-34). Examples of suitable HSA linkers and method for coupling scFv to the linker are described in WO2009/126920.

An antibody or functional part, derivative and/or analogue thereof or preferably a bispecific antibody or functional part, derivative and/or analogue thereof of the present invention is preferably used in humans. To this end an antibody or functional part, derivative and/or analogue thereof of the invention is preferably a human or humanized antibody. Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody of the present invention preferably comprises a human heavy chain constant region, preferably comprising a sequence as depicted in FIG. 2; and a human light chain constant region, preferably comprising a sequence as depicted in FIG. 1C. The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from common light chain mice immunized with the respective target as described in WO2009/157771. Various antibodies produced herein are derived from a human antibody variable domain library. As such these variable domains are human. The unique CDR regions may be derived from humans, be synthetic or derived from another organism. The variable region is at least a human variable region when it has, with the exception of the CDR regions, an amino acid sequence that is identical to an amino acid sequence of the variable region of a naturally occurring human antibody. In such embodiments the VH of a variable domain of an antibody that binds a member of the TNF receptor superfamily or membrane associated member of the B7 family, or a light chain in an antibody of the invention, may contain one or more, preferably not more than 10, preferably not more than 5 amino-acid differences with the variable region of a naturally occurring human antibody, not counting possible differences in the amino acid sequence of the CDR regions. Such mutations also occur in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3D-structure of the murine heavy chain variable region; de-immunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

De-immunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

An antibody or bispecific antibody or functional part, derivative and/or analogue thereof according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgG constant regions, i.e. selected from the group consisting of IgG1, IgG2, IgG3 and IgG4. Preferably said constant region is an IgG4 or IgG1 constant region (FIG. 2), more preferably a mutated IgG1 constant region. Some variation in the constant region of IgG1 occurs in nature and/or is allowed without changing the immunological properties of the resulting antibody. Typically between about 1-10 amino acid insertions, deletions, substitutions or a combination thereof are allowed in the constant region. The constant region may be mutated as indicated herein for enabling efficient heterodimerization, for reducing effector function or for other reasons including half-life, stability and the like.

Rational methods have evolved toward minimizing the content of non-human residues in the human context. Various methods are available to successfully graft the antigen-binding property of an antibody onto another antibody. The binding properties of antibodies may rest predominantly in the exact sequence of the CDR3 region, often supported by the sequence of the CDR1 and CDR2 regions in the variable domain combined with the appropriate structure of the variable domain as a whole. Various methods are presently available to graft CDR regions onto a suitable variable domain of another antibody. Some of these methods are reviewed in J.C. Almagrol and J. Fransson (2008) Frontiers in Bioscience 13, 1619-1633, which is included by reference herein.

The light chain variable region of a variable domain comprising a variable heavy chain sequence as depicted in FIG. 3, is preferably a germline light chain of or based on O12, preferably the rearranged germline human kappa light chain IgVκ1-39*01/IGJκ1*01 or a fragment or a functional derivative thereof (nomenclature according to the IMGT database worldwide web at imgt.org). The terms rearranged germline human kappa light chain IgVκ1-39*01/IGJκ1*01, IGKV1-39/IGKJ1, huVκ1-39 light chain or in short huVκ1-

39 are used. The light chain can have 1, 2, 3, 4 or 5 amino acid insertions, deletions, substitutions or combination thereof. The mentioned 1, 2, 3, 4 or 5 amino acid substitutions are preferably conservative amino acid substitutions, the insertions, deletions, substitutions or combination thereof are preferably not in the CDR3 region of the VL chain, preferably not in the CDR1, CDR2 or CDR3 region or FR4 region of the VL chain. A preferred sequence for the common light chain is depicted in FIG. 1.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment of the invention, the ratio is increased by expressing not two different light chains but two essentially identical light chains in the cell. The two essentially identical light chains can be light chains with essentially the same light chain variable regions and different light chain constant regions or, preferably, two essentially identical light chain constant regions. This concept is in the art also referred to as the "common light chain" method. When the essentially identical light chains work together with the two different heavy chains allowing the formation of variable domains with different antigen-binding sites and concomitant different binding properties, the ratio of bispecific antibody to other antibody that is produced by the cell is significantly improved over the expression of two essentially different light chains. The ratio of bispecific antibody that is produced by the cell can be further improved by stimulating the pairing of two different heavy chains with each other over the pairing of two identical heavy chains. The art describes various ways in which such hetero-dimerization of heavy chains can be achieved. A preferred method is described in U.S. provisional application 61/635,935, which has been followed up by US regular application Ser. No. 13/866,747 and PCT application No. PCT/NL2013/050294 (WO 2013/157954 A1), which are incorporated herein by reference. Methods and means are disclosed for producing bispecific antibodies (from a single cell), whereby means are provided that favor the formation of bispecific antibodies over the formation of monospecific antibodies. These methods can also be favorably employed in the present invention. Thus the invention provides a method for producing a bispecific antibody according to the invention (from a single cell), wherein said bispecific antibody comprises two CH3 domains that are capable of forming an interface, said method comprising providing in said cell a) a first nucleic acid molecule encoding a 1st CH3 domain comprising heavy chain, b) a second nucleic acid molecule encoding a 2nd CH3 domain comprising heavy chain, wherein said nucleic acid molecules are provided with means for preferential pairing of said 1st and 2nd CH3 domain comprising heavy chains, said method further comprising the step of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell. The host cell comprises at least one light chain, and preferably a common light chain.

A preferred embodiment provides a method for producing a bispecific antibody according to the invention from a single cell, wherein said bispecific antibody comprises two CH3 domains that are capable of forming an interface, said method comprising providing:

a cell having a) a first nucleic acid molecule encoding a heavy chain comprising an antigen binding site that can bind to an extracellular part of a membrane associated member of the TNF receptor superfamily and that contains a 1st CH3 domain, and b) a second nucleic acid molecule encoding a heavy chain comprising an antigen-binding site that can bind to an extracellular part of a membrane associated second protein and that contains a 2nd CH3 domain, wherein said nucleic acid molecules are provided with means for preferential pairing of said 1st and 2nd CH3 domains, said method further comprising the step of culturing said cell and allowing for expression of the proteins encoded by said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is based on O12, preferably it is the rearranged germline human kappa light chain IgVκ1 39*01/IGJκ1*01, as described above. Means for preferential pairing of said 1st and said 2nd CH3 domain are preferably the corresponding mutations in the CH3 domain of the heavy chain coding regions. The preferred mutations to produce essentially only bispecific antibodies are the amino acid substitutions L351K and T366K (numbering according to EU numbering) in the first CH3 domain and the amino acid substitutions L351D and L368E in the second CH3 domain, or vice versa (FIG. 2). Further provided is therefore a method according to the invention for producing a bispecific antibody, wherein said first CH3 domain comprises the amino acid substitutions L351K and T366K (numbering according to EU numbering) and wherein said second CH3 domain comprises the amino acid substitutions L351D and L368E, said method further comprising the step of culturing said cell and allowing for expression of proteins encoded by said nucleic acid molecules and harvesting said bispecific antibody from the culture. Also provided is a method according to the invention for producing a bispecific antibody, wherein said first CH3 domain comprises the amino acid substitutions L351D and L368E (numbering according to EU numbering) and wherein said second CH3 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 hetero-dimerization domains are preferably IgG1 hetero-dimerization domains. The heavy chain constant regions comprising the CH3 hetero-dimerization domains are preferably IgG1 constant regions.

The member of the TNF receptor superfamily (first membrane protein) is preferably CD137; OX40; CD40 or CD30. In a preferred embodiment the first membrane protein is CD137 or OX40, preferably CD137. A binding molecule of the invention preferably comprises one (antigen) binding site for said first membrane protein. In some embodiments a binding molecule of the invention is monovalent for said first membrane protein. A binding molecule preferably comprises one (antigen) binding site for said second membrane protein. In some embodiments a binding molecule of the invention is monovalent for said second membrane protein. In some embodiments a binding molecule of the invention is monovalent for said first membrane protein and monovalent for said second membrane protein. In some embodiments a binding molecule of the invention is monovalent for a member of the TNF receptor superfamily and monovalent for a member of the B7 family. In some embodiments a binding molecule of the invention is monovalent for CD137 and monovalent for a member of the B7 family. In some embodiments a binding molecule of the invention is monovalent for CD137 and monovalent for PD-L1. Bivalent monoclonal anti CD137 antibodies are known in the art to activate CD137 whereas monovalent CD137 binding molecules of the prior art typically do not activate.

A first membrane protein as described herein is a member of the TNF receptor superfamily which is a cell membrane protein. A protein is said to be a membrane protein on a cell if it has a transmembrane region that is present in the cell membrane of the cell it is on. This is typically the first cell as described herein. The protein can have further transmembrane regions. In such case, all transmembrane regions that are present in a cell membrane are present in the cell membrane of the same cell. The first membrane protein is a cell membrane protein that has an extracellular part when present on the cell membrane. The cell membrane is the membrane of a cell that separates the inside of the cell from the outside of the cell. The first membrane protein is typically on the cell membrane of the first cell as described herein. In the context of a binding molecule of the invention or a method or use of the invention the first membrane protein is typically on the cell membrane of the first cell as described herein. The first membrane protein can be present on said second cell, but it is preferred that the expression of the first membrane protein is negligible on said second cell. Typically the level of said first membrane protein on said second cell is at most 10% compared to the expression of the first membrane protein on the first cell. The second cell preferably does not significantly express said first membrane protein. Expression is at least not significant if the first membrane protein cannot be detected (above background) by means of immune fluorescence in a FACS assay with an antibody specific for said first membrane protein.

The second membrane protein is likewise a cell membrane protein. It has a transmembrane region that is present in the cell membrane of the cell it is on. This is typically the second cell as described herein. The second protein can have further transmembrane regions. In such case, all transmembrane regions that are present in a cell membrane are present in the cell membrane of the same cell. The second membrane protein is a cell membrane protein that has an extracellular part when present on the cell membrane. In the context of a binding molecule of the invention or a method or use of the invention the second membrane protein is typically on the cell membrane of the second cell as described herein. The second membrane protein can be present on said first cell, but it is preferred that the expression of the second membrane protein is negligible on said first cell. Typically the level of said second membrane protein on said first cell is at most 10% compared to the expression of the second membrane protein on the second cell. The first cell preferably does not significantly express said second membrane protein. Expression is at least not significant if the second membrane protein cannot be detected (above background) by means of immune fluorescence in a FACS assay with an antibody specific for said second membrane protein.

According to some embodiments, a binding molecule or a (bispecific) antibody or variant according to the invention has one antigen binding site that can bind an extracellular part of a member of the TNF receptor superfamily, and a second antigen binding site that can bind a second membrane protein that is not a member of the TNF receptor superfamily. This provides the advantage that in cis activation of (immune) cells such as T cells expressing several different members of the TNF receptor superfamily is at least in part avoided, thereby reducing the potential adverse side effects and toxicity due to nonspecific T cell activation. These embodiments of the present invention are in contrast to prior art approaches which relate to binding agents binding to receptors of the TNF superfamily, in particular binding agents binding to at least two different receptors of the TNF superfamily. Such prior art approaches may lead to T cell activation in cis, meaning in the absence of a second target, and may involve the risk of an excessive T cell response, for instance resulting in a cytokine storm. Consequently, such prior art approaches have an increased potential of adverse side effects compared to a binding molecule according to the invention having a first antigen binding site that can bind an extracellular part of a member of the TNF receptor superfamily and a second antigen binding site that can bind a membrane protein that is not a member of the TNF receptor superfamily.

Also provided is an antibody or a functional part, derivative and/or analogue thereof that comprises an antigen binding site that can bind an extracellular part of CD137 or OX40 and an antigen binding site that can bind an extracellular part of a second membrane protein, wherein said second membrane protein is not a member of the TNF receptor superfamily. Also provided is a method of stimulating activity of a member of the TNF receptor superfamily on a cell comprising providing a first cell and a second cell, wherein said first cell has said member of the TNF receptor superfamily on the cell membrane and said second cell has a second membrane protein on the cell membrane, the method comprising contacting said cells with an antibody or a functional part, derivative and/or analogue thereof that comprises two variable domains, wherein one variable domain comprises a first antigen binding site that can bind an extracellular part of said member of the TNF receptor superfamily and another variable domain comprises a second antigen binding site that can bind an extracellular part of said second membrane protein, thereby stimulating activity of said member on said first cell; wherein said second membrane protein is not a member of the TNF receptor superfamily. In some embodiments, said method is an in vitro method.

In some embodiments said antibody or functional part, derivative and/or analogue thereof comprises one antigen binding site that can bind said member of the TNF receptor superfamily and one antigen binding site that can bind said second membrane protein that is not a member of the TNF receptor superfamily. In some embodiments, the antigen binding part of said antibody or functional part, derivative and/or analogue of the invention consists of one immunoglobulin variable domain that can bind an extracellular part of said member of the TNF receptor superfamily and one immunoglobulin variable domain that can bind said second membrane protein that is not a member of the TNF receptor superfamily. Said bispecific antibody is preferably a full length antibody. In some embodiments, said bispecific antibody is a full length IgG, i.e. a full length IgG1, IgG2, IgG3 or IgG4, preferably a full length IgG1 or a full length IgG4.

Further provided is an antibody or a functional part, derivative and/or analogue thereof that comprises an antigen binding site that can bind an extracellular part of CD137 or OX40 and an antigen binding site that can bind an extracellular part of a second membrane protein, wherein said second membrane protein is a member of the B7 family, preferably PD-L1. Also provided is a method of stimulating activity of a member of the TNF receptor superfamily on a cell comprising providing a first cell and a second cell, wherein said first cell has said member of the TNF receptor superfamily on the cell membrane and said second cell has a second membrane protein on the cell membrane, the method comprising contacting said cells with an antibody or a functional part, derivative and/or analogue thereof that comprises two variable domains, wherein one variable domain comprises a first antigen binding site that can bind an extracellular part of said member of the TNF receptor superfamily and another variable domain comprises a second antigen binding site that can bind an extracellular part of said second membrane protein, thereby stimulating activity of said member on said first cell; wherein said second membrane protein is a member of the B7 family, preferably PD-L1. In some embodiments, said method is an in vitro method.

In some embodiments said antibody or functional part, derivative and/or analogue thereof comprises one antigen binding site that can bind said member of the TNF receptor superfamily and one antigen binding site that can bind said second membrane protein that is a member of the B7 family, preferably PD-L1. In some preferred embodiments, the antigen binding part of said antibody or functional part, derivative and/or analogue of the invention consists of one immunoglobulin variable domain that can bind an extracellular part of said member of the TNF receptor superfamily and one immunoglobulin variable domain that can bind said second membrane protein that is a member of the B7 family, preferably PD-L1. Said bispecific antibody is preferably a full length antibody. In some embodiments, said bispecific antibody is a full length IgG, i.e. IgG1, IgG2, IgG3 or IgG4, preferably a full length IgG1 or a full length IgG4.

A variable domain that "blocks" the binding of said first membrane protein to a binding partner thereof interferes with binding of the first membrane protein to said binding partner. Such a variable domain can bind the first membrane protein. Such a blocking variable domain can bind an epitope on said first membrane protein and compete with a binding partner of the first membrane protein for binding to the epitope. Such a blocking variable domain and the binding partner of the first membrane protein can also bind to different epitopes on said first membrane protein. In such cases the blocking activity can for instance be due to diminished binding of the binding partner, and/or displacement of the binding partner when it is already bound to said first membrane protein, and/or a blocking variable domain can prevent binding of a binding partner to the first membrane protein through steric hindrance. All these and other mechanisms can, at least partially, prevent that said binding partner binds to said first membrane protein.

In one embodiment the domain that comprises an antigen binding site that binds the TNF receptor superfamily member blocks the binding of the member to a ligand of the member. TNF receptor superfamily member—ligand interactions have been studied extensively in the art. Generally, members of the TNF receptor superfamily typically are known to have at least one ligand. Examples of known receptor ligand pairs are the TNF receptors tumor necrosis factor receptor 1 and 2 and the ligand TNF-alpha; the receptor OX40 and the ligand OX40L; the receptor CD40 and the ligand CD154; the Fas receptor and the ligand FasL; the CD30 receptor and the ligand CD153; and the receptor CD137 and the ligand CD137L. In some embodiments the variable domain that comprises an antigen binding site that binds the TNF receptor superfamily member does not block the binding of the member to a ligand of the member.

In some embodiments, the domain comprises an antigen binding site that binds the TNF receptor superfamily member and blocks the binding of its TNF receptor superfamily target membrane protein to a binding partner thereof. Said variable domain may be further characterized such that when provided in a monospecific bivalent antibody comprising two of said variable domains, it does not stimulate activity of the TNF-receptor superfamily member on a cell without crosslinking. In some embodiments, the domain that comprises an antigen binding site that binds the TNF receptor superfamily member comprises a variable domain that blocks the binding of CD137 to CD137L, said variable domain being further characterized by the fact that, when provided in a monospecific bivalent antibody comprising two of said variable domains, it does not stimulate activity of CD137 on a cell.

The terms "binding partners; binding pair; receptor ligand pair and the like refers to proteins that can bind to each other and exert an activity as a result of the binding. At least one of the partners or pair is a membrane protein on the cell membrane of a cell. The activity is typically exerted on the cell that has this membrane protein on the cell.

A variable domain that blocks the binding of a specific binding pair of membrane proteins as described herein typically reduces binding of the pair when compared to the binding in the absence of the variable domain. This is preferably measured in an in vitro assay. Typically this is done by incubating the variable domain with the membrane protein that it can bind to and subsequently incubating the mixture with the other member of the pair. The binding of the pair is then compared with the binding of the pair in the absence of the variable domain. A variable domain can completely prevent the binding of the first membrane protein to a binding partner thereof. It can also partially prevent the binding of the binding pair. A variable domain that blocks the binding of a specific binding pair of membrane proteins preferably reduces binding of the pair by at least 50%, preferably at least 60%, preferably at least 70%, preferably at least 80%, and more preferably at least 90% when compared to the binding in the absence of the variable domain. Blocking of binding by a variable domain is defined herein as the blocking obtained using a bivalent monoclonal antibody comprising two of the same of said variable domains. The variable domain of course also blocks the binding when present in an antibody comprising said variable domain and a variable domain that binds a second membrane protein.

Specific variable domains that can bind an extracellular part of CD137 and that at least partially block the binding of CD137 ligand to CD137 are variable domains that comprise the amino acid sequence of the VH of: MF6783; MF6861; MF6795; MF6808; MF6798; MF6754; MF6763; MF6744; MF6785; MF6825; MF6737; MF6749; MF6788; or MF6797.

Specific variable domains that can bind an extracellular part of PD-L1 and that block the binding of PD1 to PD-L1 are variable domains that comprise the amino acid sequence of the VH of MF5554; MF5576; MF5578; MF9375; MF9376; MF7702; MF5359; MF5377; MF5382; MF5424; MF5426; MF5439; MF5442; MF5553; MF5557; MF5561; MF5576; MF5594; or MF5708. The amino acid sequences are depicted in FIG. 3.

The variable domain that binds the member of the TNF receptor superfamily is preferably a variable domain that, when provided in a monospecific bivalent antibody comprising two of said domains, does not stimulate activity of the TNF-receptor superfamily member on a cell. Said variable domain in the context of a bivalent monospecific antibody comprises two of the same of said variable domains and does not stimulate the activity of cells comprising the TNF-receptor superfamily member.

Stimulating activity of a member of the TNF receptor superfamily on a cell is typically measured by measuring a biological activity of the cell. The type of activity depends on which member of the TNF receptor superfamily is analyzed. For OX40 and CD137, for instance, the activation state of an OX40 and/or CD137 positive T-cell can be measured. OX40 and CD137 are so-called co-stimulatory proteins that stimulate the activation of an activated T-cell. Suitable methods for measuring the activation of a T-cell are provided in the example section. One method is measuring IL-2, IFNγ and/or TNFα production by an activated T-cell or composition comprising said T-cell. Other TNF receptors have different biological activities. For instance CD30 is expressed on activated T- and B-cells and is a positive regulator of apoptosis. Stimulation of CD30 can be measured by measuring apoptosis of activated B- or T-cells in response to a binding molecule of the invention. CD40 is a costimulatory protein found on antigen presenting cells such as macrophages and stimulation further stimulates the activation of the antigen presenting cell. Activity of a member of the TNF receptor superfamily is stimulated when the activity measured in the presence of a binding molecule as discussed herein, preferably in the presence of an antibody or functional part, derivative and/or analogue according to the invention, is higher than the activity measured under otherwise identical conditions in the absence of the binding molecule, preferably the antibody or functional part, derivative and/or analogue according to the invention. Stimulating the activity includes induction of an activity and enhancement of an already present activity.

Stimulating activity of CD137 or OX40 is preferably measured by measuring a biological activity of the CD137 or OX40 comprising cell. The biological activity is preferably the activation state of the CD137 or OX40 expressing cell. CD137 and OX40 are co-stimulatory molecules expressed on immune cells, including activated T cells. Stimulation of activity of CD137 or OX40 is preferably measured by determining the level of activation of the immune cells, e.g. of activated T-cells. In an individual the stimulation of activity of CD137 or OX40 is preferably measured by measuring the activation of the immune cells and/or T-cells of the individual. Alternatively, it can also be determined by, where applicable, measuring the tumor response in the individual; the virus load of the individual; or the parasite load of the individual.

The invention also provides a method of engaging and/or activating T-cells comprising providing a system comprising a T-cell and a cell (second cell) to which said T-cell is to be engaged or activated, and providing said system with at least one antibody, preferably at least one bispecific antibody, that comprises a variable domain that can bind a member of the TNF receptor superfamily and a variable domain that can bind to an extracellular part of a second protein and incubating said system under conditions that are permissive for the T-cell to become engaged and/or activated. In some embodiments, said method is an in vitro method. Said TNF receptor superfamily member is preferably CD137 or OX40, most preferably CD137, and said second membrane protein is preferably not a member of the TNF receptor superfamily. Said second membrane protein is preferably a member of the B7 family, most preferably PD-L1. The cell to which said T-cell is to be engaged or activated is preferably an immune cell, (for example antigen presenting cell, or macrophage), a neoplastic cell, a virus infected cell, or an intracellular parasite infected cell. Engaging and/or activating T-cells directs T-cells to a specific target. Activating a T-cell is activating the T-cell receptor of said T-cell. Engaging a T-cell typically is activating a T-cell. Engagement can also direct an already activated T-cell to a target specified by the antibody. Conditions that are permissive for said T-cell to become engaged and/or activated are typically culture conditions but can also be incubation in a non-human animal. The conditions are such that the T-cell is not engaged in the absence of the antibody. If collections of T-cells are measured some of these can be already engaged or activated provided that the collection contains sufficient T-cells that are not engaged or activated.

An antibody of the invention can bring two cells together in close proximity that allows the interactions between the cells mediated by proteins other than the member of the TNF receptor superfamily and the second membrane protein bound by the antibody of the invention. One such interaction is an interaction of a T-cell receptor of one cell and MHC on the other cell.

Said first and second cells are preferably different cells. The different cells can both express said first and second membrane protein. Typically however, the first membrane protein is expressed only on said first cell and said second membrane protein only on said second cell. The biological activity is typically more stimulated if the first cell does not express said second membrane protein; said second cell does not express said first membrane protein; or more preferably a combination thereof. When the TNF receptor superfamily member is OX40; CD137; CD30 or CD40 it is preferred that said first cell is an immune cell, preferably a T cell. In these cases it is preferred that the second cell is an aberrant cell, tumor cell or an immune cell (for example a macrophage or an antigen presenting cell). Aberrant cells are cells that are not normally present in a healthy individual. Non-limiting preferred examples of such cells are cancer cell, virus-infected cells, parasite infected cells or cells induced to express the second membrane protein. A suitable second cell is also an immune cell. Preferred examples of such cells are dendritic cells, macrophages, other cells of the myeloid lineage or B cells. In some cases a cell may express the second membrane protein as a result of suppressive factors released by neighboring cells such as immune cells, fibroblasts or cancer cells. In some embodiments, said second cell is an antigen presenting cell presenting a tumor antigen or a pathogenic antigen, like for instance a viral antigen or a parasite antigen, in the context of a major histocompatibility complex (MHC). Said MHC complex is preferably a human leukocyte antigen (HLA) complex. In this context the antibody of the invention can enhance both the expansion and differentiation of antigen naïve T cells in vitro. Inducing and enhancing novel T cell responses against tumor antigens typically will result in more effective tumor immunity and cancer cell eradication.

CD137 can be expressed by activated T-cells. It is also found on other cells such as dendritic cells, natural killer cells, granulocytes and cells of the blood vessel wall at sites of inflammation. The protein is known for its costimulatory activity for activation of T-cells. The ligand CD137L is expressed on monocytes, macrophages and other cells. Binding of CD137 to CD137 ligand exerts effects in both the receptor and the ligand containing cell. Activation of the ligand or receptor can be achieved in various ways. Common ways are coating onto tissue-culture plates or cross-linking via antibodies (for review see Schwartz, 2004). CD137 expression on both innate and adaptive immune cells, coupled with its ability to potentiate antitumor responses has established it as a therapeutic target to enhance tumor immunity. Various CD137-targeted immunotherapeutics have reached clinical development (for review see Makkouk et al 2016). Activation of the receptor or the ligand appears to require homomeric association in the cellular membrane to exert their effect. Antibodies with two binding sites for CD137 are capable of activating the receptor or ligand. Hence, such antibodies are bivalent for CD137. Molecules that only have one binding site for CD137 were also produced. Such monovalent binding molecules of the prior art could not activate the receptor (McNamara 2008). In contrast, a binding molecule or antibody or variant according to the present invention is able to activate CD137, even when it is monovalent for CD137.

OX40 is a secondary co-stimulatory immune checkpoint molecule expressed on T-cells. OX40 expression is not constitutive, it is typically expressed after 24 to 72 hours following activation; its ligand, OX40L, is also not expressed on resting antigen presenting cells, but is following their activation.

In the present invention it was found that a binding molecule with only one binding site for a TNF receptor superfamily member (first membrane protein) can be activating if the binding molecule also has a binding site for a second membrane protein on another cell (second cell), including when the second membrane protein is not a member of the TNF receptor superfamily member. The second membrane protein can be a ligand for a receptor of the TNF receptor superfamily. However, typically it is not a ligand of the TNF receptor superfamily member that is the first membrane protein. The second membrane protein can be a ligand for a TNF receptor superfamily member that is not the ligand of the first membrane protein.

Stimulation of activity of a member of the TNF receptor superfamily on a cell typically requires the bringing together of two or more receptor complexes. The homotrimeric ligand arrayed on a cell surface membrane typically achieves this by engaging multiple TNF receptor superfamily member complexes on a neighbouring cell. It is thought that the clustering of the TNF receptor superfamily complexes facilitates stimulation of the activity of the cell. This is, for instance, also apparent from artificial receptors that only have a cytoplasmic part of the CD137 receptor. Close proximity of the cytoplasmic parts of various artificial receptors also stimulates the artificial receptor containing cell. Bivalent monospecific antibodies specific of a TNF receptor superfamily member are also capable of mimicking the ligand effect and stimulate the activity. It is thought that the arms of the antibody bring together or cluster the receptors. Such activity is also referred to as cross-linking of the receptors. The activity can on occasion be further stimulated by providing an anti-antibody antibody, this provides further cross-linking of the receptor. Prior art binding molecules that have only one binding site for a TNF-receptor superfamily member are typically not capable of stimulating the activity. Such molecules fail to cluster or cross-link the TNF receptor superfamily members. However, a binding molecule or antibody or variant according to the present invention is capable of stimulating the activity of a TNF-receptor superfamily member, including when it is monovalent for said TNF-receptor superfamily member. Without being bound to any theory, it is believed that a bispecific antibody according to the present invention can also cluster the TNF receptor superfamily receptor complexes, thereby promoting activation of the TNF receptor superfamily member. This holds particularly true when the second membrane protein that is bound by an antibody according to the present invention is a member of the B7 family such as PD-L1.

In one aspect of the present invention the second membrane protein is present on the cell membrane as part of a multimeric protein comprising two or more instances of said second membrane protein. Such multimeric proteins can provide two or more epitopes for the antigen binding site of a binding molecule of the invention. In such a case, bound TNF receptor superfamily member on the other cell will become clustered and stimulate the activity of the TNF receptor containing cell. A binding molecule of the invention can force proximity of TNF receptor superfamily member through binding to another protein on a different cell. A feature also referred to as trans-crosslinking as opposed to cis-crosslinking by binding molecules that bind two or more instances of the TNF receptor superfamily member on the same cell. In some embodiments the second membrane protein is a homodimer or a homotrimer. A homodimer is a protein that is composed of two identical polypeptide units. A homotrimer is a protein that is composed of three identical polypeptide units. Without being bound by any theory it is believed that the epitopes for the antigen binding site of the second membrane protein collectively bind a number of binding molecules. These thereby function as an anchor that forces the close proximity of two or more of the TNF receptor superfamily members. The proximity is sufficiently close to stimulate the activity of the TNF receptor superfamily member on a cell.

In another embodiment the said second membrane protein is a protein that is present in one or more discrete zones on the cell membrane. Cell membranes do not provide a homogenous distribution of all components of the cell membrane. It is presently known that cell membranes have zones wherein one or more components of the cell membrane are more frequently present than other parts of the membrane (for review see Vereb, G., et al. 2003 Proc. Natl. Acad. Sci. 100.14: 8053-8058). Said zone is preferably a cluster of proteins, a domain, a micro-domain or a compartment on the cell membrane, preferably an immunological synapse. Without being bound by any theory it is believed that the non-random distribution facilitates the close proximity of the TNF receptor superfamily member.

In other embodiments stimulation of activity of a TNF receptor superfamily member on a cell is achieved by providing two or more binding molecules that bind the same member of the TNF receptor superfamily (first membrane protein) and the same second membrane protein. Embodiments that involve two or more binding molecules are also referred to as Oligoclonics® embodiments. As for instance shown in FIGS. 15 and 16, Oligoclonics® embodiments can result in T cell activation. General methods for making such Oligoclonics® products are disclosed in WO 2013/157953 and WO2004/009618 and are incorporated here by reference. The term 'Oligoclonics' is a registered trademark, indicated by ®. In an Oligoclonics® embodiment at least two of the binding molecules bind different epitopes on said first membrane protein; different epitopes on said second membrane protein; or different epitopes on said first membrane protein and different epitopes on said second membrane protein. An Oligoclonics® embodiment allows the binding of two or more binding molecules to the same molecule of the first and/or second membrane protein, thereby stimulating activity of a TNF receptor superfamily member on a cell. It is preferred that the at least two of the binding molecules bind different epitopes on said second membrane protein; or bind different epitopes on said first membrane protein and different epitopes on said second membrane protein. In a particularly preferred embodiment the at least two binding molecules bind the same epitope on said first membrane protein and different epitopes on said second membrane protein. In some Oligoclonics® embodiments the two binding molecules block the TNF-receptor superfamily member-ligand interaction. In other Oligoclonics® embodiments the two binding molecules do not block the TNF-receptor superfamily member-ligand interaction. Different epitopes on a first and second membrane protein are preferably such that simultaneous binding of a binding molecule that binds one of the epitopes and a binding molecule that binds to the different epitope is possible. In a preferred embodiment the different epitopes are non-competing epitopes. In a preferred embodiment a first and a second of said binding molecules can bind the same domain of CD137 or OX40. In a preferred embodiment said first and second binding molecule bind the same epitope on CD137 or OX40.

The second membrane protein is preferably a multimeric cytokine receptor, a member of the B7 family, a member of the CD28 family; a member of ATP-binding cassette transporters (ABC transporters); an aquaporin; a member of the serine/threonine kinase receptor family; a member of the receptor tyrosine kinase family. In a preferred embodiment the second membrane protein is a member of the B7 family. In a preferred embodiment the B7 family member is CD80; CD86; PD-L1; PD-L2; ICOSL; B7-H3; B7-H4; B7-H5; B7-H6; or B7-H7. It is preferred that the second membrane protein is a co-inhibitory protein of the B7-family. In this preferred embodiment it is preferred that the variable domain that binds the second membrane protein blocks the binding of the B7-family member to the binding partner thereof of the CD28 family. In this way a potential co-inhibitory signal provided by the second membrane protein to the first cell is reduced. In a particularly preferred embodiment the second membrane protein is PD-L1 or PD-L2, preferably PD-L1. In another preferred embodiment the second membrane protein is a member of the EGF receptor family (ErbB); the insulin receptor family; the IGF receptor family; the FGF receptor family; the VEGF receptors family; the HGF receptor family; or the AXL receptor family. The second membrane protein is preferably a member of the EGF receptor family (ErbB), preferably EGFR; ErbB-2 or ErbB-3, preferably ErbB-2. It is preferred that the variable domain that binds an EGFR, ErbB-3 or ErbB-4 member of the EGF receptor family blocks the binding of a growth factor to said member. In this embodiment the activity of the EGF receptor family member on said second cell is reduced.

In embodiments of the invention the second membrane protein is a member of a binding pair. For instance, the EGF receptor (EGFR) and EGF form a binding pair. Other non-limiting examples of suitable binding pairs are HER3 and heregulin; LGR5-Rspondin; LGR4-Rspondin; or a B7 family member ligand and a receptor thereof of the CD28 family. In a preferred embodiment of the invention a binding molecule as described herein blocks the binding of the second membrane protein to the complementary member of the binding pair. Such binding molecules typically stimulate activity of a member of the TNF receptor superfamily on the cell and block an activity of the second membrane protein. Such binding molecules are particularly well suited for situations wherein the second cell is a tumor cell, or treatment of individuals with cancer. In a preferred embodiment the second membrane protein is a member of the B7 family, preferably PD-L1 or PD-L2, preferably PD-L1 and said at least one binding molecule preferably blocks the binding of said B7 family member to its normal receptor of the CD28 family. In a preferred embodiment the second membrane protein is PD-L1 and said at least one binding molecule preferably blocks the binding of PD-L1 to PD-1.

The invention provides a method of enhancing a biological effect in a CD137 expressing cell, the method comprising providing a system with a first cell and a second cell, wherein said first cell comprises CD137 on the cell membrane, and said second cell comprises a protein on the cell membrane with two or more instances (i.e. two or more copies of the same epitope are present) of the same epitope on an extracellular part of said protein, and providing said system with a binding molecule that comprises a binding site for an extracellular part of CD137, and a binding site for said epitope, the method further comprising incubating said system under conditions that allow said biological activity to be enhanced. In some embodiments, said method is an in vitro method. In some embodiments, said CD137 expressing cell is an immune cell, preferably a T cell, and said second cell is a tumor cell. In some embodiments, said CD137 expressing cell is an immune cell, preferably a T cell, and said second cell is another immune cell. In some embodiments, said CD137 expressing cell is an immune cell, preferably a T cell, and said second cell is a cell of the myeloid lineage. In some embodiments, said CD137 expressing cell is an immune cell, preferably a T cell, and said second cell is an antigen presenting cell. Said antigen presenting cell preferably presents a tumor antigen or a pathogenic antigen in the context of MHC, preferably in the context of HLA.

A cell typically has a member of the TNF-receptor superfamily on the membrane if the member is expressed by the cell. Expression can be measured in various ways. Quantitative RNA specific PCR is often used. Immunohistochemistry or FACS analysis using immune-fluorescence is also often used.

A suitable system wherein the first cell and second cell are provided is a cell culture. Another suitable system is a non-human animal comprising the first cell and second cell. Other suitable systems are ex vivo systems wherein the cells are maintained in active form but wherein growth of the cells is not necessarily facilitated. A first and second cell can be incubated together under, for instance, assay conditions that not necessarily facilitate growth but allow biological activity to be measured.

Incubating said system under conditions that are permissive for cells expressing said biological activity mediated by the binding of said first membrane protein and said second membrane protein means that the system is maintained under conditions wherein the first and second cell can exhibit a biological activity as a result of the binding partners. In vivo or in vitro incubation does not have to involve more than passing of sufficient time to allow the biological activity to become apparent.

A variable domain that does not block the binding of a specific binding pair of membrane proteins as described herein typically does not reduce binding of the pair when compared to the binding in the absence of the variable domain. This is preferably measured in an in vitro assay. Typically this is done by incubating the variable domain with the membrane protein that it can bind to and subsequently incubating the mixture with the other member of the pair. The binding of the pair is then compared with the binding of the pair in the absence of the variable domain. A variable domain is considered not to block the binding of a specific binding pair of membrane proteins if it reduces binding of the pair by not more than 50%, preferably not more than 40%, preferably not more than 30%, preferably not more than 20%, and more preferably not more than 10%, when compared to the binding in the absence of the variable domain. Binding by a variable domain and the blocking or non-blocking of the binding to the other member of the binding pair is defined herein as the blocking obtained using a bivalent monoclonal antibody comprising said two of the same of said variable domains. The blocking or non-blocking is defined as obtained with a bivalent monospecific antibody comprising said two of the same of said variable domains.

Specific variable domains that can bind an extracellular domain of CD137 and that do not block the binding of CD137 to CD137L are variable domains that comprise the amino acid sequence of the VH of MF6860; MF6848; MF6805; MF6832; MF6870; MF6862; MF6875; or MF6873.

Specific variable domains that can bind an extracellular domain of PD-L1 and that do not block the binding of PD1 to PD-L1 are variable domains that comprise the amino acid sequence of the VH of MF5361.

Functional aspects of variable domains in kind not necessarily in amount, such as binding to an antigen, blocking capacity of receptor ligand interaction, biological activity of a variable domain, etc. can be can be determined in various ways. Suitable formats are a Fab fragment or an antibody. A suitable antibody format is a monospecific bivalent antibody comprising two of the variable domains. Another suitable format is for instance a bispecific antibody comprising the variable domain to be tested and another variable domain. The other variable domain is preferably a variable domain with a neutral specificity with respect to the assay to be performed. A suitable neutral variable domain is a variable domain that can bind tetanus toxoid.

An antibody or functional part, derivative and/or analogue thereof of the invention preferably comprises a variable domain that blocks the binding of its TNF receptor superfamily target membrane protein to a binding partner thereof. In some embodiments, an antibody or functional part, derivative and/or analogue thereof of the invention comprises a variable domain that blocks the binding of its TNF receptor superfamily target membrane protein to a binding partner thereof, and that, when provided in a monospecific bivalent antibody comprising two of said variable domains, does not stimulate activity of the TNF-receptor superfamily member on a cell. In some embodiments, an antibody or functional part, derivative and/or analogue thereof of the invention comprises a variable domain that blocks the binding of CD137 to CD137L, and that, when provided in a monospecific bivalent antibody comprising two of said variable domains, does not stimulate activity of CD137 on a cell.

The invention also provides a method for the treatment of an individual that has a cancer, the method comprising administering a binding molecule of the invention, preferably an antibody or a functional part, derivative and/or analogue of the invention or a bispecific antibody of the invention, to the individual in need thereof. The individual is preferably an individual that has cancer. In some embodiments the cancer is a cancer that comprises cancer cells that express said second membrane protein. In some embodiments the cancer is a cancer that comprises cancer cells that express a member of the B7 family. In some embodiments, immune cells and/or cells of the myeloid lineage of said individual express said second membrane protein, preferably a member of the B7 family. In some embodiments, antigen presenting cells (APCs) of said individual express said second membrane protein, preferably a member of the B7 family. According to these embodiments, the cancer cells may or may not express said second membrane protein. When APCs express said second membrane protein, antigens of said cancer are presented by such APCs of the individual and transactivation of immune cells (preferably T cells) can be induced by an antibody or a functional part, derivative and/or analogue of the invention, which is able to bind an immune cell and an immune cell, APC or tumor cell of the individual. In some embodiments, an antibody or a functional part, derivative and/or analogue of the invention is used that binds CD137 and a member of the B7 family, preferably PD-L1. Such an antibody or functional part, derivative and/or analogue of the invention can transactivate an immune cell by binding a CD137-expressing immune cell (preferably a T cell) and either a tumor cell and/or an immune cell and/or a cell of the myeloid lineage and/or an APC that expresses said member of the B7 family.

The cancer is preferably an adenocarcinoma. Preferred cancers are colorectal cancer; pancreatic cancer; lung cancer; breast cancer; liver cancer; prostate cancer; ovarian cancer; cervical cancer; endometrial cancer; head and neck cancer; melanoma; testis cancer; urothelial cancer; renal cancer; stomach cancer; or carcinoid cancer. In a preferred embodiment the cancer is colorectal cancer; pancreatic cancer; lung cancer; breast cancer; liver cancer; prostate cancer; ovarian cancer; cervical cancer; endometrial cancer; head and neck cancer; or melanoma. In a particularly preferred embodiment the cancer is colorectal cancer; pancreatic cancer; lung cancer; breast cancer; or liver cancer. In a particularly preferred embodiment the cancer is a gastrointestinal cancer. In a preferred embodiment the cancer is colorectal cancer. In this embodiment the binding molecule preferably an antibody or functional part, derivative and/or analogue thereof is preferably an antibody with a variable domain that can bind CD137 or OX40 and a variable domain that can bind PD-L1. The variable domain that binds CD137 or OX40 preferably blocks the binding of CD137 to CD137 ligand or, in case of OX40 blocks the binding of OX40 the OX40 ligand. The variable domain that binds PD-L1 preferably blocks the binding of PD-1 to PD-L1.

Further provided is an ex vivo system comprising an antibody or a functional part, derivative and/or analogue thereof or bispecific antibody or a functional part, derivative and/or analogue thereof the invention, and said first cell said second cell. The first and said second cell preferably express respectively said first and said second membrane protein on the cell membrane. The system is preferably a cell system suitable for the maintenance and/or the growth of said first cell. The cell system is preferably suitable for the maintenance and/or the growth of said second cell. Such as system is for instance suitable to raise and/or multiply immune cells that are directed towards aberrant cells. Such immune cells can subsequently be administered to an individual in need thereof, for instance a cancer patient. The immune cells preferably comprise a T-cell or NK-cell, preferably a cytotoxic T-cell. The immune cells are preferably autologous to the individual in need thereof.

Further provided is a method for stimulating an immune response in an individual against an aberrant cell in said individual, the method comprising providing said individual with an antibody or a functional part, derivative and/or analogue thereof of the invention. The aberrant cell is preferably a cancer cell, a virus-infected cell, a parasite or a parasite infected cell. In a preferred embodiment the cell is a cancer cell or a neoplastic cell. In this embodiment the antibody or functional part, derivative and/or analogue thereof is preferably an antibody with a variable domain that can bind an extracellular part of CD137 or OX40 and a variable domain that can bind PD-L1. The variable domain that binds CD137 or OX40 preferably blocks the binding of CD137 to CD137 ligand or, in case of OX40 blocks the binding of OX40 the OX ligand. The variable domain that binds PD-L1 preferably blocks the binding of PD-1 to PD-L1.

A neoplasm is an abnormal growth of tissue and when it also forms a mass is commonly referred to as a tumor. A neoplasm in the present invention typically forms a mass. A neoplastic cell is a cell from a neoplasm that has formed a mass. The World Health Organization (WHO) classifies neoplasms into four main groups: benign neoplasms, in situ neoplasms, malignant neoplasms, and neoplasms of uncertain or unknown behavior. Malignant neoplasms are also simply known as cancers.

Stimulating an immune response encompasses inducing an immune response and enhancing an already existing immune response. The immune response in an individual can be measured by measuring where applicable; the tumor load of the individual; the virus load of the individual; the parasite load of the individual.

Said virus-infected cell is preferably a cell infected with an immune-deficiency virus, a herpes virus, preferably a herpes simplex virus, a varicella-zostervirus, a cytomegalovirus or an Epstein-Barr virus, a papilloma virus, a hepatis virus, preferably a hepatitis A, B or C virus, a measles virus or an adenoviruses. The virus is preferably a virus known to be able to persist in an individual. Persistent infections are characterized as those in which the virus is not cleared but remains in specific cells of infected individuals. Persistent infections may involve stages of both silent and productive infection without rapidly killing or even producing excessive damage of the host cells. Persistent virus-host interaction may be a latent, a chronic and/or a slow infection.

A parasite-infected cell is a cell that is infected with an intracellular parasite. Such parasites are parasitic microorganisms that are capable of growing and reproducing inside the cells of a host. Some intracellular parasites can also live outside a cell. Such parasites are so-called facultative intracellular parasites. Non-limiting examples are *Listeria monocytogenes, Legionella*, certain species of *mycobacterium* and *Cryptococcus neoformans*. Preferred intracellular parasites are parasites that cannot grow outside host cells, preferred examples are *Chlamydia*, and closely related species, certain species of *mycobacterium* such as *Mycobacterium leprae*, certain protozoa, including: Apicomplexans (*Plasmodium* spp., *Toxoplasma gondii* and *Cryptosporidium parvum* and trypanosomatids.

The invention also provides a nucleic acid molecule that encodes an antibody heavy chain variable region according to the invention. The nucleic acid molecule (typically an in vitro, isolated or recombinant nucleic acid molecule) preferably encodes any one of the heavy chain variable regions as depicted in FIG. 3 or a heavy chain variable region as depicted in FIG. 3 having 1, 2, 3, 4 or 5 amino acid insertions, deletions, substitutions or combination thereof. In a preferred embodiment the nucleic acid molecule comprises a sequence as depicted in FIG. 3. The nucleic acid molecule preferably uses codons that are optimized for expression in the antibody producing cell that is to be used. Preferably the nucleic acid encoding a heavy chain variable region as depicted in FIG. 3 or a heavy chain variable region as depicted in FIG. 3 having 1, 2, 3, 4 or 5 amino acid insertions, deletions, substitutions or combination thereof is codon optimized for expression in a human cell preferably Per.C6™; or a Chinese hamster, preferably CHO. The invention further provides a nucleic acid molecule that codes for the mentioned heavy chain variable region together with a heavy chain constant region of FIG. 2.

A nucleic acid molecule as used in the invention is typically but not exclusively a ribonucleic acid (RNA) or a deoxyribonucleic acid (DNA). Alternative nucleic acids are available for a person skilled in the art. A nucleic acid molecule according to the invention is for instance comprised in a cell. When said nucleic acid molecule is expressed in said cell, said cell can produce an antibody according to the invention. Therefore, the invention in one embodiment provides a cell comprising an antibody according to the invention and/or a nucleic acid molecule according to the invention. An antibody is produced when said cell produces a heavy chain and a light chain. Provided is a cell that can produce an antibody of the invention. The cell preferably comprises a nucleic acid molecule that encodes an antibody heavy chain that comprises an antibody heavy chain variable region that, when combined with a common light chain, can bind said first membrane protein. Said cell preferably further comprises a nucleic acid molecule that encodes an antibody heavy chain that comprises an antibody heavy chain variable region that, when combined with a common light chain, can bind said second membrane protein. Said cell preferably further comprises a nucleic acid molecule that codes for a common light chain. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Also provided is a cell that comprises one or more nucleic acid molecules that alone or together encode an antibody of the invention. The one or more nucleic acid molecules are expressible nucleic acid molecules meaning that they contain the in cis required signals for RNA transcription and translation of protein coding domains. Preferably said cell (typically an in vitro, isolated or recombinant cell) produces said antibody. In a preferred embodiment said cell is a hybridoma cell, a Chinese hamster ovary (CHO) cell, an NS0 cell or a PER-C6™ cell. In a particularly preferred embodiment said cell is a CHO cell. Further provided is a cell culture that comprises a cell according to the invention. Various institutions and companies have developed cell lines for the large scale production of antibodies, for instance for clinical use. Non-limiting examples of such cell lines are CHO cells, NS0 cells or PER.C6™ cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention. The invention further provides a cell for producing an antibody comprising a nucleic acid molecule that codes for a VH, a VL, and/or a heavy chain as depicted in FIGS. 3, 1 and 2. Preferably said nucleic acid molecule comprises a sequence as depicted in FIGS. 1 and 2.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, a 293F cell, an NS0 cell or any other cell type known in the art for its suitability for antibody production for clinical purposes, in particular for the production of antibodies used for administration in humans. In a particularly preferred embodiment said cell is a human cell, preferably a cell that is transformed by an adenovirus E1 region or a functional equivalent thereof. A preferred example of such a cell line is the PER.C6™ cell line or equivalent thereof. In a particularly preferred embodiment said cell is a CHO cell or a variant thereof, preferably a variant that makes use of a Glutamine synthetase (GS) vector system for expression of an antibody.

The invention further provides a pharmaceutical composition comprising one or more antibodies or variants thereof according to the invention. The pharmaceutical composition preferably comprises a pharmaceutically acceptable excipient or carrier.

An antibody or variant thereof of the invention may further comprise a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800; IRDye 680RD; IRDye 680LT; IRDye 750; IRDye 700DX; IRDye 800RS IRDye 650; IRDye 700 phosphoramidite; IRDye 800 phosphoramidite (LI-COR USA; 4647 Superior Street; Lincoln, Nebr.).

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred. The dosage can be in range of the dosing regimen of Nivolumab. The dosage can also be lower.

In a tumor suppressive environment the expression of PD-L1 on surrounding cells is expected to reach a density threshold that will result in activation of CD137 on T cells as described in Example 8 (FIGS. 28A and 28B). As such the bispecific antibody will be able to activate T cells within the tumor and not—or to a significantly lesser extent—act on cells expressing low PD-L1 cell surface levels. In case the CD137xPD-L1 bispecific antibody contains a PD-L1 blocking Fab arm, the antibody will in addition overcome the PD-1/PD-L1 blockade. By acting in 'trans' the CD137xPD-L1 antibody will release the PD-1/PD-L1 blockade and simultaneously activate the T cell by activating CD137. As a result a CD137xPD-L1 antibody can enhance the local T-cell responses leading to the release of a plethora of cytokines (Example 9) that in turn can activate other immune cells in the tumor microenvironment and overcome at least in part the local immune suppression in the tumor. It has been shown by the present inventors that a bispecific antibody according to the invention often has better T cell activating properties as compared to antibodies that are based on prior art benchmark antibodies with the same kind of specificity, such as for instance antibodies based on Urelumab (anti-CD137) or based on Atezolizumab (anti-PD-L1) In the Examples, stronger T cell activating activity has been achieved with a bispecific antibody according to the invention in comparison with a mixture of two of such benchmark-based antibodies. This is for instance shown in the T cell transactivation assays and the SEB stimulation assays of the current Examples. It has also been demonstrated that a bispecific antibody according to the present invention is able to reverse immune suppression induced by tumor-associated M2 macrophages and is capable of (re)stimulating tumor specific T cells isolated from patient tumors in vitro. A bispecific antibody according to the present invention can (re)stimulate tumor-specific CD4+ effector memory T cells, tumor-specific CD8+ effector memory T cells and tumor-specific CD8+ terminally differentiated T cells, while a benchmark anti-PD-L1 antibody based on Atezolizumab typically only (re)stimulates CD4+ T cells. Hence, a bispecific antibody according to the present invention has a potency of (re)stimulating a more variable subset of antigen-specific T cells as compared to the benchmark antibody, including CD8+ T cells.

Next to reinvigorating existing cytotoxic T cell responses against the tumor by activating antigen-experienced CD8 T cells, CD137xPD-L1 bispecific antibodies may enhance de novo CD8+ T cell anti-tumor responses. Tumor (neo)antigens shed into the environment by dying tumor cells or tumor cells engulfed by antigen presenting cells are transported to draining lymph nodes or tertiary lymphoid structures, which are ectopic lymphoid formations found in tumoral tissues. In the local tumor environment, the tumor antigens are presented to naïve CD8+ T cells that will expand and differentiate upon antigen-recognition.

As shown in the Examples, an antibody according to the invention can enhance T cell expansion following CD8+ T cell priming to a higher extent as compared to benchmark antibodies based on Urelumab or based on Atezolizumab. In the Examples it has been demonstrated that an antibody according to the invention can induce both expansion and differentiation of antigen-specific CD8+ T cells, greater than a mixture of benchmark antibodies based on Urelumab and based on Atezolizumab, which will facilitate the generation of large populations of tumor-specific memory and terminally differentiated killer T cells.

An antibody or variant thereof and in particular a bispecific antibody or a variant thereof according to the invention may have fewer side effects than a combination of bivalent monospecific antibodies with the variable domains. Combinations of antibodies that block inhibitory and/or costimulatory molecules benefit patients that do not respond to existing immunotherapies. However, dual blockade of immuno-modulatory receptors (iMODs) has been shown to increase immune-related toxicity. An antibody or variant thereof and in particular a bispecific antibody or a variant thereof according to the invention is suited to address dual blockade of iMODs, as they can exert functional activities that cannot be reproduced by monoclonal antibody combinations, and can more selectively target specific cell populations, which reduces safety liabilities in patients. Without being bound to any theory, it is believed that the reduced chance of adverse side effects of a bispecific antibody or variant of the invention, as compared to (a combination of) monospecific antibodies, is at least in part because a bispecific antibody or variant of the invention typically exhibits T cell activation in trans, whereas it has a low in cis T cell activation activity. Use of an antibody with low in cis T cell activation activity in context of the present invention is preferred because this diminishes the potential non-specific T cell response. An antibody or bispecific antibody or a functional part, derivative and/or analogue thereof according to the invention has less immune-related toxicity than a combination of bivalent monospecific antibodies with the variable domains.

In view of the above, a bispecific antibody according to the present invention, or a functional part, derivative and/or analogue thereof, is preferred for therapeutic applications.

The antibodies were produced as bispecific antibodies by cloning them into complementary expression vectors that contain mutations in the CH3 region that drives heterodimerization of heavy chains. Many bispecific antibodies were produced at small scale and tested in binding and functional assays on cancer cell lines. An antibody of the invention, particularly a bispecific antibody of the invention can combine low toxicity profiles with high efficacy. An antibody of the invention can be useful in various types and lines of immune targeted therapies. An antibody of the invention can have an increased therapeutic window when compared to an antibody that binds the same antigen(s) with both arms.

Further provided is a use of a bispecific antibody according to the invention or a functional part, derivative and/or analogue thereof, for the preparation of a medicament for the treatment or prevention of aberrant cells, a tumor and/or the formation of metastases. The tumor from which said metastases originate is preferably a tumor that is positive for said second cell membrane protein, preferably positive for a member of the B7 family.

Antibodies of the invention can be produced at levels>50 mg/L after transient transfection in suspension 293F cells. The bispecific antibodies can be purified to greater than 98% purity with yields>70%. Analytical characterization studies show bispecific IgG1 antibody profiles that are comparable to bivalent monospecific IgG1.

The invention also provides a bispecific antibody or a functional part, derivative and/or analogue thereof that can bind to an extracellular part of a membrane associated member of the TNF receptor superfamily and an extracellular part of a membrane associated second membrane protein, preferably a member of the B7 family. In some embodiments said bispecific antibody or functional part, derivative or analogue thereof comprises one antigen binding site that can bind said member of the TNF receptor superfamily and one antigen binding site that can bind said second protein, preferably said member of the B7 family. In some preferred embodiments, the antigen binding part of said bispecific antibody or functional part, derivative or analogue of the invention consists of one immunoglobulin variable domain that can bind an extracellular part of said member of the TNF receptor superfamily and one immunoglobulin variable domain that can bind said member of the B7 family. Said bispecific antibody or functional part, derivative or analogue thereof is preferably monovalent for said member of the TNF receptor superfamily and monovalent for said member of the B7 family. Said bispecific antibody is preferably a full length antibody. In some embodiments, said bispecific antibody is a full length IgG, i.e. a full length IgG1, IgG2, IgG3 or IgG4, preferably a full length IgG1 or a full length IgG4.

The invention also provides a bispecific antibody or a functional part, derivative and/or analogue thereof, that can bind to an extracellular part of CD137 and an extracellular part of PD-L1. Said bispecific antibody or functional part, derivative or analogue thereof preferably comprises two antigen binding sites. Said bispecific antibody or functional part, derivative or analogue thereof preferably comprises one antigen binding site that can bind CD137 and one antigen binding site that can bind PD-L1. In some preferred embodiments, the antigen binding part of said bispecific antibody or functional part, derivative or analogue of the invention consists of one immunoglobulin variable domain that can bind an extracellular part of CD137 and one immunoglobulin variable domain that can bind PD-L1. Said bispecific antibody or functional part, derivative or analogue thereof is preferably monovalent for CD137 and monovalent for PD-L1. In some embodiments the antigen binding site that can bind CD137 is able to block the binding of CD137 to CD137L. In some embodiments the antigen binding site that can bind CD137 is not able to block the binding of CD137 to CD137L. In some embodiments the antigen binding site that can bind PD-L1 is able to block the binding of PD-L1 to PD-1. In some embodiments the antigen binding site that can bind PD-L1 is not able to block the binding of PD-L1 to PD-1. Said bispecific antibody is preferably a full length antibody. In some embodiments, said bispecific antibody is a full length IgG, i.e. a full length IgG1, IgG2, IgG3 or IgG4, preferably a full length IgG1 or a full length IgG4.

Also provided is a method for the treatment of an individual that has a cancer, the method comprising administering a binding molecule of the invention or a bispecific antibody or a functional part, derivative or analogue of the invention to the individual in need thereof.

The invention further provides a binding molecule of the invention or a bispecific antibody or a functional part, derivative or analogue of the invention, for use in the treatment of an individual that has cancer.

Further provided is a cell system comprising an antibody or a bispecific antibody or a functional part, derivative and/or analogue thereof of the invention, and a first cell that expresses a membrane associated member of the TNF receptor superfamily and a second cell that expresses a membrane associated second membrane protein, preferably a member of the B7 family.

The invention provides a method of stimulating activity of a member of the TNF receptor superfamily on a cell comprising providing a first cell and a second cell, wherein said first cell has said member on the cell membrane and said second cell has a second membrane protein on the cell membrane, the method comprising contacting said cells with a bispecific antibody or variant thereof that comprises two variable domains, wherein one variable domain comprises a first antigen binding site that can bind an extracellular part of said member of the TNF receptor superfamily, and wherein another variable domain comprises a second antigen binding site that can bind an extracellular part of said second membrane protein, thereby stimulating activity of said member on said first cell. In some embodiments, said bispecific antibody comprises one antigen binding site that can bind said member of the TNF receptor superfamily. In some embodiments, said method is an in vitro method. In a preferred embodiment said member of the TNF receptor superfamily is CD137 or OX40. Said second membrane protein is preferably not a member of the TNF receptor superfamily. Said bispecific antibody is preferably monovalent for said member of the TNF receptor superfamily and monovalent for said second membrane protein, preferably monovalent for a member of the B7 family. Said bispecific antibody is preferably a full length antibody. In some embodiments, said bispecific antibody is a full length IgG, i.e. a full length IgG1, IgG2, IgG3 or IgG4, preferably a full length IgG1 or a full length IgG4.

Said first cell preferably does not significantly express said second membrane protein on the cell membrane. Said second membrane protein is preferably a protein that is present in one or more zones on the cell membrane. Said zone is preferably a cluster, domain, micro-domain or compartment on the cell membrane, preferably an immunological synapse. Said second membrane protein is preferably present on the cell membrane as a part of a multimeric protein comprising two or more instances of said second membrane protein. In some embodiments said second membrane protein is present on the cell membrane as a part of a homodimer or a homotrimer. In a preferred embodiment said second membrane protein is a multimeric cytokine receptor, a member of the B7 family, a member of the CD28 family; a member of ATP-binding cassette transporters (ABC transporters); an aquaporin; a member of the serine/threonine kinase receptor family; a member of the receptor tyrosine kinase family. The second membrane protein is preferably a member of the B7-family, preferably PD-L1 or PD-L2, preferably PD-L1. In a preferred embodiment the second membrane protein is a member of the EGF receptor family (ErbB); the IGF receptor family; the FGF receptor family; the VEGF receptors family; the HGF receptor family; or the AXL receptor family. The second membrane protein is preferably a member of the EGF receptor family (ErbB), preferably EGFR; ErbB-2 or ErbB-3, preferably ErbB-2. Preferably the variable domain that binds the member of the TNF receptor superfamily, blocks the binding of a ligand to the member. The variable domain that binds an extracellular part of said member of the TNF receptor superfamily is preferably defined as a variable domain that, when in a bivalent monospecific antibody format that comprises two of said variable domains that bind said member of the TNF receptor superfamily, does not stimulate activity of said TNF receptor superfamily member on a cell. A method preferably further comprises providing a further bispecific antibody comprising an antigen binding site that can bind an extracellular part of said member of the TNF receptor superfamily and an antigen binding site that can bind an extracellular part of said second membrane protein, wherein said first and second bispecific antibodies bind:

different epitopes on said first membrane protein;
different epitopes on said second membrane protein; or
different epitopes on said first membrane protein and different epitopes on said second membrane protein;

the method further comprising incubating said first and second cell with said first and second bispecific antibodies, thereby stimulating activity of said member of the TNF receptor superfamily on said first cell. In some embodiments, said method is an in vitro method. In a preferred embodiment the TNF receptor superfamily member is CD137 or OX40. In some embodiments said first and said second bispecific antibody each comprise one antigen binding site that can bind said member of the TNF receptor superfamily. Said second membrane protein is preferably not a member of the TNF receptor superfamily. Said first and/or said second bispecific antibody are preferably monovalent for said member of the TNF receptor superfamily and monovalent for said second membrane protein, preferably monovalent for said member of the B7 family. Said first and/or said second bispecific antibody is/are preferably a full length antibody. In some embodiments, said first and/or said second bispecific antibody is/are a full length IgG, i.e. a full length IgG1, IgG2, IgG3 or IgG4, preferably a full length IgG1 or a full length IgG4.

The antigen binding sites of the first and second bispecific antibody that can bind said second membrane protein, preferably bind different epitopes on the extracellular part of said second membrane protein. The different epitopes on the extracellular part of said second membrane protein are preferably non-competing epitopes.

Also provided is a bispecific antibody that comprises an antigen binding site that can bind an extracellular part of CD137 or OX40 and an antigen binding site that can bind an extracellular part of a second membrane protein. In some embodiments said bispecific antibody comprises one antigen binding site that can bind said CD137 or OX40. Said second membrane protein is preferably not a member of the TNF receptor superfamily. The second membrane protein is preferably not to a significant extent expressed by a T-cell. The second membrane protein is preferably expressed on an immune cell, a cell of the myeloid lineage, an antigen presenting cell, a tumor cell, a virus infected cell or a parasite infected cell. Preferably said second membrane protein is a protein that is present in one or more zones on the cell membrane. The zone is preferably a cluster, domain, micro-domain or compartment on the cell membrane, preferably an immunological synapse. In some embodiments said second membrane protein is a protein that is present on the cell membrane as a part of a multimeric protein comprising two or more of said second membrane protein. In some embodiments said second membrane protein is present on the cell membrane as a part of a homodimer or a homotrimer. Preferably said second membrane protein is a multimeric cytokine receptor, a member of the B7 family, a member of the CD28 family; a member of ATP-binding cassette transporters (ABC transporters); an aquaporin; a member of the serine/threonine kinase receptor family; a member of the receptor tyrosine kinase family. The second membrane protein is preferably a member of the B7 family, preferably PD-L1 or PD-L2, preferably PD-L1. In some embodiments the second membrane protein is a member of the EGF receptor family (ErbB); the insulin receptor family; the IGF receptor family; the FGF receptor family; the VEGF receptors family; the HGF receptor family; or the AXL receptor family. In some embodiments the second membrane protein is a member of the EGF receptor family (ErbB), preferably EGFR; ErbB-2 or ErbB-3, preferably ErbB-2. The variable domain that binds said CD137 or OX40 preferably blocks the binding of a ligand to the member. The variable domain that binds an extracellular part of said CD137 or OX40 is preferably defined as a variable domain that, when in a bivalent monospecific antibody format that comprises two of said variable domains that bind said CD137 or OX40, does not stimulate activity of CD137 or OX40 on a cell. Said bispecific antibody is preferably monovalent for CD137 or OX40 and monovalent for said second membrane protein. Said bispecific antibody is preferably a full length antibody. In some embodiments, said bispecific antibody is a full length IgG, i.e. a full length IgG1, IgG2, IgG3 or IgG4, preferably a full length IgG1 or a full length IgG4.

The invention also provides a composition comprising one or more bispecific antibodies according to the invention. Also provided is a composition or kit of parts comprising two or more of the bispecific antibodies of the invention, wherein the antigen binding sites that can bind CD137 or OX40 of a first and a second bispecific antibody bind different epitopes on said CD137 or OX40. Also provided is a method of stimulating activity of CD137 or OX40 on a cell comprising providing a first cell and a second cell, wherein said first cell has said CD137 or OX40 (first membrane protein) on the cell membrane and said second cell has a second membrane protein on the cell membrane, the method comprising contacting said cells with a bispecific antibody according to the invention (first bispecific antibody) that comprises two variable domains, wherein one variable domain comprises a first antigen binding site that can bind an extracellular part of said first membrane protein and another variable domain comprises a second antigen binding site that can bind an extracellular part of said second membrane protein, thereby stimulating activity of said first membrane protein on said first cell. In some embodiments said bispecific antibody comprises one antigen binding site that can bind said first membrane protein. In some embodiments, said method is an in vitro method. The method preferably further comprises providing a further bispecific antibody according to the invention (second bispecific antibody) comprising a variable domain with an antigen binding site that can bind an extracellular part of said first membrane protein; and a variable domain with an antigen binding site that can bind an extracellular part of said second membrane protein, wherein said first and second bispecific antibody bind:
  different epitopes on said first membrane protein;
  different epitopes on said second membrane protein; or
  different epitopes on said first membrane protein; and
    different epitopes on said second membrane protein;
  the method further comprising incubating said first and second cell with said first and second bispecific antibody, thereby stimulating activity of CD137 or OX40 on said first cell. The second membrane protein is preferably a member of the B7 family, more preferably PD-L1.

An antibody that is defined by an MF sequence as indicated herein below is preferably a bispecific antibody that has two different variable domains, wherein one of these variable domains comprises the indicated sequence.

An antibody or a functional part, derivative and/or analogue thereof that comprises a variable domain that can bind to an extra-cellular part of CD137 preferably comprises a heavy chain variable region with a CDR3 region that comprises the amino acid sequence of the CDR3 region of the variable heavy chain region of MF6754; MF6763; MF6785; or MF6797 (FIG. 3).

An antibody or a functional part, derivative and/or analogue thereof that comprises a variable domain that can bind to an extra-cellular part of CD137 preferably comprises a heavy chain variable region with a CDR1, CDR2 and CDR3 region that comprises the amino acid sequence of the CDR1, CDR2 and CDR3 of a variable heavy chain region of one of the VH depicted for MF6754; MF6763; MF6785; or MF6797 (FIG. 3). The CDR1, CDR2 and CDR3 sequences are preferably selected from the same VH region.

An antibody or a functional part, derivative and/or analogue thereof that comprises a variable domain that can bind to an extra-cellular part of CD137 preferably comprises the amino acid sequence of the variable heavy chain region of MF6754; MF6763; MF6785; or MF6797 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF. The amino acid insertion(s), deletion(s), substitution(s) or a combination thereof, if any, are preferably not in the amino acid sequence of the CDR regions.

An antibody or a functional part, derivative and/or analogue thereof that comprises a variable domain that can bind to an extra-cellular part of PD-L1 preferably comprises a heavy chain variable region with a CDR3 region that comprises the amino acid sequence of the CDR3 region of the variable heavy chain region of MF5554; MF5576; MF5578; MF9375; MF9376; MF7702; MF5424; MF5561; MF5439; MF5553; MF5594; MF5426; MF5442 or MF5361 (FIG. 3).

An antibody or a functional part, derivative and/or analogue thereof that comprises a variable domain that can bind to an extra-cellular part of PD-L1 preferably comprises a heavy chain variable region with a CDR1, CDR2 and CDR3 region that comprises the amino acid sequence of the CDR1, CDR2 and CDR3 of a variable heavy chain region of one of the VH depicted for MF5554; MF5576; MF5578; MF9375; MF9376; MF7702; MF5424; MF5561; MF5439; MF5553; MF5594; MF5426; MF5442 or MF5361 (FIG. 3). The CDR1, CDR2 and CDR3 sequences are preferably selected from the same VH region.

An antibody or a functional part, derivative and/or analogue thereof that comprises a variable domain that can bind to an extra-cellular part of PD-L1 preferably comprises the amino acid sequence of the variable heavy chain region of MF5554; MF5576; MF5578; MF9375; MF9376; MF7702; MF5424; MF5561; MF5439; MF5553; MF5594; MF5426; MF5442 or MF5361 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF. The amino acid insertion(s), deletion(s), substitution(s) or a combination thereof, if any, are preferably not in the amino acid sequence of the CDR regions.

An antibody or a functional part, derivative and/or analogue thereof preferably comprises a variable domain that can bind to an extracellular part of CD137 that blocks the binding of CD137 to CD137 ligand and a variable domain that can bind to an extracellular part of PD-L1 that blocks the binding of PD-1 to PD-L1. The variable domain that binds an extracellular part of PD-L1 in this antibody or a functional part, derivative and/or analogue thereof preferably comprises a VH region with the amino acid sequence of the CDR3 or the amino acid sequence of the CDR1, CDR2 and CDR3 of one of the VH of MF5554; MF5576; MF5578; MF9375; MF9376; MF7702; MF5424; MF5561; MF5439; MF5553; MF5594; MF5426; MF5442 or MF5361 (FIG. 3). In a preferred embodiment, the variable domain that binds an extracellular part of PD-L1 comprises a VH region with the amino acid sequence of a VH of MF5554; MF5576; MF5578; MF9375; MF9376; MF7702; MF5424; MF5561; MF5439; MF5553; MF5594; MF5426; MF5442 or MF5361 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF.

The variable domain that binds an extracellular part of CD137 in this antibody or a functional part, derivative and/or analogue thereof preferably comprises a VH region with the amino acid sequence of the CDR3 or the amino acid sequence of the CDR1, CDR2 and CDR3 of one of the VH of MF6754; MF6763; MF6785; or MF6797 (FIG. 3). In a preferred embodiment, the variable domain that binds an extracellular part of CD137 comprises a VH region with the amino acid sequence of the VH of MF6754; MF6763; MF6785; or MF6797 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF. The amino acid insertion(s), deletion(s), substitution(s) or a combination thereof, if any, are preferably not in the amino acid sequence of the CDR regions. A particularly preferred combination in this antibody or functional part, derivative and/or analogue is the combination of variable domains that comprise the indicated sequence or variant thereof of MF6797 and MF7702; MF6763 and MF7702; MF6785 and MF7702; MF6797 and MF5553; MF6763 and MF5553; MF6785 and MF5553; MF6754 and MF5424; MF6763 and MF5561; MF6785 and MF5439; MF6797 and MF5553; MF6744 and MF5594; MF6744 and MF5361; MF6783 and MF5361; or MF6783 and MF5594.

An antibody or a functional part, derivative and/or analogue thereof as described herein preferably comprises
- a CD137 binding variable domain that comprises a VH region with the amino acid sequence of the CDR3 or the amino acid sequence of the CDR1, CDR2 and CDR3 of the VH of MF6754; and
- a PD-L1 binding variable domain that comprises a VH region with the amino acid sequence of the CDR3 or the amino acid sequence of the CDR1, CDR2 and CDR3 of the VH of MF5554; MF5576; MF5578; MF9375; MF9376; MF7702; MF5594; MF5424; MF5426; MF5553; MF5442; MF5561; MF5439 or MF5361 (FIG. 3).

An antibody or a functional part, derivative and/or analogue thereof preferably comprises
- a CD137 binding variable domain that comprises a VH region with the amino acid sequence of the VH of MF6754 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF6754 and;
- a PD-L1 binding variable domain that comprises a VH region with the amino acid sequence of the VH of MF5554; MF5576; MF5578; MF9375; MF9376; MF7702; MF5594; MF5424; MF5426; MF5553; MF5442; MF5561; MF5439 or MF5361 (FIG. 3) having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF.

An antibody or a functional part, derivative and/or analogue thereof as described herein preferably comprises
- a CD137 binding variable domain that comprises a VH region with the amino acid sequence of the CDR3 or the amino acid sequence of the CDR1, CDR2 and CDR3 of the VH of MF6763; and
- a PD-L1 binding variable domain that comprises a VH region with the amino acid sequence of the CDR3 or the amino acid sequence of the CDR1, CDR2 and CDR3 of the VH of MF5554; MF5576; MF5578; MF9375; MF9376; MF7702; MF5594; MF5424; MF5426; MF5553; MF5442; MF5561; MF5439 or MF5361 (FIG. 3).

An antibody or a functional part, derivative and/or analogue thereof preferably comprises
- a CD137 binding variable domain that comprises a VH region with the amino acid sequence of the VH of MF6763 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6763 and;
- a PD-L1 binding variable domain that comprises a VH region with the amino acid sequence of the VH of MF5554; MF5576; MF5578; MF9375; MF9376; MF7702; MF5594; MF5424; MF5426; MF5553; MF5442; MF5561; MF5439 or MF5361 (FIG. 3) having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF.

An antibody or a functional part, derivative and/or analogue thereof as described herein preferably comprises
- a CD137 binding variable domain that comprises a VH region with the amino acid sequence of the CDR3 or the amino acid sequence of the CDR1, CDR2 and CDR3 of the VH of MF6785; and
- a PD-L1 binding variable domain that comprises a VH region with the amino acid sequence of the CDR3 or the amino acid sequence of the CDR1, CDR2 and CDR3 of the VH of MF5554; MF5576; MF5578; MF9375; MF9376; MF7702; MF5594; MF5424; MF5426; MF5553; MF5442; MF5561; MF5439 or MF5361 (FIG. 3).

An antibody or a functional part, derivative and/or analogue thereof preferably comprises
- a CD137 binding variable domain that comprises a VH region with the amino acid sequence of the VH of MF6785 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF6785 and;
- a PD-L1 binding variable domain that comprises a VH region with the amino acid sequence of the VH of MF5554; MF5576; MF5578; MF9375; MF9376; MF7702; MF5594; MF5424; MF5426; MF5553; MF5442; MF5561; MF5439 or MF5361 (FIG. 3) having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF.

An antibody or a functional part, derivative and/or analogue thereof as described herein preferably comprises
- a CD137 binding variable domain that comprises a VH region with the amino acid sequence of the CDR3 or the amino acid sequence of the CDR1, CDR2 and CDR3 of the VH of MF6797; and
- a PD-L1 binding variable domain that comprises a VH region with the amino acid sequence of the CDR3 or the amino acid sequence of the CDR1, CDR2 and CDR3 of the VH of MF5554; MF5576; MF5578;

MF9375; MF9376; MF7702; MF5594; MF5424; MF5426; MF5553; MF5442; MF5561; MF5439 or MF5361 (FIG. 3).

An antibody or a functional part, derivative and/or analogue thereof preferably comprises
- a CD137 binding variable domain that comprises a VH region with the amino acid sequence of the VH of MF6797 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6797 and;
- a PD-L1 binding variable domain that comprises a VH region with the amino acid sequence of the VH of MF5554; MF5576; MF5578; MF9375; MF9376; MF7702; MF5594; MF5424; MF5426; MF5553; MF5442; MF5561; MF5439 or MF5361 (FIG. 3) having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF.

As shown in the Examples, an antibody with a PD-L1 binding variable domain that is based on MF5553 provides particularly good T cell activation results in combination with different CD137 binding variable domains, including MF6754, MF6763, MF6785 and MF6797.

Further provided is therefore a bispecific antibody or a functional part, derivative and/or analogue thereof that comprises:
- a CD137 binding variable domain that comprises a VH region with the amino acid sequence of the CDR3 region of the VH of MF6754; and
- a PD-L1 binding variable domain that comprises a VH region with the amino acid sequence of the CDR3 region of the VH of MF5553.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6754; and
- a PD-L1 binding variable domain that comprises a VH region with the amino acid sequence of the CDR1, CDR2 and CDR3 regions of the VH of MF5553.

Also provided is a bispecific antibody or a functional part, derivative and/or analogue thereof that comprises:
- a CD137 binding variable domain that comprises a VH region with the amino acid sequence of the VH of MF6754 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF6754 and;
- a PD-L1 binding variable domain that comprises a VH region with the amino acid sequence of the VH of MF5553 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5553.

Further provided is a bispecific antibody or a functional part, derivative and/or analogue thereof that comprises:
- a CD137 binding variable domain that comprises a VH region with the amino acid sequence of the CDR3 region of the VH of MF6763; and
- a PD-L1 binding variable domain that comprises a VH region with the amino acid sequence of the CDR3 region of the VH of MF5553.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6763; and
- a PD-L1 binding variable domain that comprises a VH region with the amino acid sequence of the CDR1, CDR2 and CDR3 regions of the VH of MF5553.

Also provided is a bispecific antibody or a functional part, derivative and/or analogue thereof that comprises:
- a CD137 binding variable domain that comprises a VH region with the amino acid sequence of the VH of MF6763 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6763 and;
- a PD-L1 binding variable domain that comprises a VH region with the amino acid sequence of the VH of MF5553 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5553.

Further provided is a bispecific antibody or a functional part, derivative and/or analogue thereof that comprises:
- a CD137 binding variable domain that comprises a VH region with the amino acid sequence of the CDR3 region of the VH of MF6785; and
- a PD-L1 binding variable domain that comprises a VH region with the amino acid sequence of the CDR3 region of the VH of MF5553.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6785; and
- a PD-L1 binding variable domain that comprises a VH region with the amino acid sequence of the CDR1, CDR2 and CDR3 regions of the VH of MF5553.

Also provided is a bispecific antibody or a functional part, derivative and/or analogue thereof that comprises:
- a CD137 binding variable domain that comprises a VH region with the amino acid sequence of the VH of MF6785 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6785 and;
- a PD-L1 binding variable domain that comprises a VH region with the amino acid sequence of the VH of MF5553 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5553.

Further provided is a bispecific antibody or a functional part, derivative and/or analogue thereof that comprises:
- a CD137 binding variable domain that comprises a VH region with the amino acid sequence of the CDR3 region of the VH of MF6797; and a PD-L1 binding variable domain that comprises a VH region with the amino acid sequence of the CDR3 region of the VH of MF5553.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6797; and
- a PD-L1 binding variable domain that comprises a VH region with the amino acid sequence of the CDR1, CDR2 and CDR3 regions of the VH of MF5553.

Also provided is a bispecific antibody or a functional part, derivative and/or analogue thereof that comprises:
- a CD137 binding variable domain that comprises a VH region with the amino acid sequence of the VH of MF6797 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6797 and;
- a PD-L1 binding variable domain that comprises a VH region with the amino acid sequence of the VH of MF5553 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5553.

It is furthermore shown in the Examples that an antibody with a PD-L1 binding variable domain that is based on MF7702 provides particularly good T cell activation results in combination with different CD137 binding variable domains, including MF6763, MF6785 and MF6797.

Further provided is therefore a bispecific antibody or a functional part, derivative and/or analogue thereof that comprises:
- a CD137 binding variable domain that comprises a VH region with the amino acid sequence of the CDR3 region of the VH of MF6797; and
- a PD-L1 binding variable domain that comprises a VH region with the amino acid sequence of the CDR3 region of the VH of MF7702.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6797; and
- a PD-L1 binding variable domain that comprises a VH region with the amino acid sequence of the CDR1, CDR2 and CDR3 regions of the VH of MF7702.

Also provided is a bispecific antibody or a functional part, derivative and/or analogue thereof that comprises:
- a CD137 binding variable domain that comprises a VH region with the amino acid sequence of the VH of MF6797 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6797 and;
- a PD-L1 binding variable domain that comprises a VH region with the amino acid sequence of the VH of MF7702 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF7702.

Further provided is a bispecific antibody or a functional part, derivative and/or analogue thereof that comprises:
- a CD137 binding variable domain that comprises a VH region with the amino acid sequence of the CDR3 region of the VH of MF6763; and
- a PD-L1 binding variable domain that comprises a VH region with the amino acid sequence of the CDR3 region of the VH of MF7702.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6763; and
- a PD-L1 binding variable domain that comprises a VH region with the amino acid sequence of the CDR1, CDR2 and CDR3 regions of the VH of MF7702.

Also provided is a bispecific antibody or a functional part, derivative and/or analogue thereof that comprises:
- a CD137 binding variable domain that comprises a VH region with the amino acid sequence of the VH of MF6763 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6763 and;
- a PD-L1 binding variable domain that comprises a VH region with the amino acid sequence of the VH of MF7702 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF7702.

Further provided is a bispecific antibody or a functional part, derivative and/or analogue thereof that comprises:
- a CD137 binding variable domain that comprises a VH region with the amino acid sequence of the CDR3 region of the VH of MF6785; and
- a PD-L1 binding variable domain that comprises a VH region with the amino acid sequence of the CDR3 region of the VH of MF7702.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6785; and
- a PD-L1 binding variable domain that comprises a VH region with the amino acid sequence of the CDR1, CDR2 and CDR3 regions of the VH of MF7702.

Also provided is a bispecific antibody or a functional part, derivative and/or analogue thereof that comprises:
- a CD137 binding variable domain that comprises a VH region with the amino acid sequence of the VH of MF6785 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6785 and;
- a PD-L1 binding variable domain that comprises a VH region with the amino acid sequence of the VH of MF7702 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF7702.

It is furthermore shown in the Examples that a bispecific antibody with a CD137 binding variable domain that is based on MF6744 and a PD-L1 binding variable domain that is based on MF5594 provides particularly good T cell activation; see for instance FIGS. 14-16. Importantly, such antibody has a stronger T cell activation potential as compared to an antibody that is based on the antibody Urelumab.

Further provided is therefore a bispecific antibody or a functional part, derivative and/or analogue thereof that comprises:
- a CD137 binding variable domain that comprises a VH region with the amino acid sequence of the CDR3 region of the VH of MF6744; and
- a PD-L1 binding variable domain that comprises a VH region with the amino acid sequence of the CDR3 region of the VH of MF5594.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6744; and
- a PD-L1 binding variable domain that comprises a VH region with the amino acid sequence of the CDR1, CDR2 and CDR3 regions of the VH of MF5594.

Also provided is a bispecific antibody or a functional part, derivative and/or analogue thereof that comprises:
- a CD137 binding variable domain that comprises a VH region with the amino acid sequence of the VH of MF6744 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6744 and;
- a PD-L1 binding variable domain that comprises a VH region with the amino acid sequence of the VH of MF5594 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5594.

It is furthermore shown in the Examples that a bispecific antibody with a CD137 binding variable domain that is based on MF6744 and a PD-L1 binding variable domain that is based on MF5361 provides particularly good T cell activation; see for instance FIGS. 14-16. Importantly, such antibody has a stronger T cell activation potential as compared to an antibody that is based on the antibody Urelumab.

Further provided is therefore a bispecific antibody or a functional part, derivative and/or analogue thereof that comprises:
- a CD137 binding variable domain that comprises a VH region with the amino acid sequence of the CDR3 region of the VH of MF6744; and
- a PD-L1 binding variable domain that comprises a VH region with the amino acid sequence of the CDR3 region of the VH of MF5361.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6744; and
- a PD-L1 binding variable domain that comprises a VH region with the amino acid sequence of the CDR1, CDR2 and CDR3 regions of the VH of MF5361.

Also provided is a bispecific antibody or a functional part, derivative and/or analogue thereof that comprises:
- a CD137 binding variable domain that comprises a VH region with the amino acid sequence of the VH of MF6744 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6744 and;
- a PD-L1 binding variable domain that comprises a VH region with the amino acid sequence of the VH of MF5361 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5361.

It is furthermore shown in the Examples that a bispecific antibody with a CD137 binding variable domain that is based on MF6783 and a PD-L1 binding variable domain that is based on MF5361 provides particularly good T cell activation; see for instance FIGS. 14-15. Importantly, such antibody has a stronger T cell activation potential as compared to an antibody that is based on the antibody Urelumab.

Further provided is therefore a bispecific antibody or a functional part, derivative and/or analogue thereof that comprises:
- a CD137 binding variable domain that comprises a VH region with the amino acid sequence of the CDR3 region of the VH of MF6783; and
- a PD-L1 binding variable domain that comprises a VH region with the amino acid sequence of the CDR3 region of the VH of MF5361.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6783; and
- a PD-L1 binding variable domain that comprises a VH region with the amino acid sequence of the CDR1, CDR2 and CDR3 regions of the VH of MF5361.

Also provided is a bispecific antibody or a functional part, derivative and/or analogue thereof that comprises:
- a CD137 binding variable domain that comprises a VH region with the amino acid sequence of the VH of MF6783 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6783 and;
- a PD-L1 binding variable domain that comprises a VH region with the amino acid sequence of the VH of MF5361 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5361.

It is furthermore shown in the Examples that a bispecific antibody with a CD137 binding variable domain that is based on MF6783 and a PD-L1 binding variable domain that is based on MF5594 provides particularly good T cell activation; see for instance FIGS. 14-15.

Further provided is therefore a bispecific antibody or a functional part, derivative and/or analogue thereof that comprises:
- a CD137 binding variable domain that comprises a VH region with the amino acid sequence of the CDR3 region of the VH of MF6783; and a PD-L1 binding variable domain that comprises a VH region with the amino acid sequence of the CDR3 region of the VH of MF5594.

Also provided is a bispecific antibody or a functional part, derivative and/or analogue thereof that comprises:
- a CD137 binding variable domain that comprises a VH region with the amino acid sequence of the CDR1, CDR2 and CDR3 regions of the VH of MF6783; and
- a PD-L1 binding variable domain that comprises a VH region with the amino acid sequence of the CDR1, CDR2 and CDR3 regions of the VH of MF5594.

Also provided is a bispecific antibody or a functional part, derivative and/or analogue thereof that comprises:
- a CD137 binding variable domain that comprises a VH region with the amino acid sequence of the VH of MF6783 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6783 and;
- a PD-L1 binding variable domain that comprises a VH region with the amino acid sequence of the VH of MF5594 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5594.

In addition, it is shown in the Examples that a combination of a bispecific antibody with a CD137 binding variable domain that is based on MF6744 and a PD-L1 binding variable domain that is based on MF5361, together with a bispecific antibody with a CD137 binding variable domain that is based on MF6744 and a PD-L1 binding variable domain that is based on MF5594 (applied as a dual bispecific, e.g., Oligoclonics® embodiment) provides a superior T cell activation (see FIGS. 14-16) and superior to an antibody that is based on Urelumab.

Further provided is therefore a mixture or kit of parts, comprising:
- a first bispecific antibody or a functional part, derivative and/or analogue thereof that comprises a CD137 binding variable domain comprising a VH region with the amino acid sequence of the CDR3 region of the VH of MF6744, and a PD-L1 binding variable domain comprising a VH region with the amino acid sequence of the CDR3 region of the VH of MF5594; and
- a second bispecific antibody or a functional part, derivative and/or analogue thereof that comprises a CD137 binding variable domain comprising a VH region with the amino acid sequence of the CDR3 region of the VH of MF6744 and a PD-L1 binding variable domain comprising a VH region with the amino acid sequence of the CDR3 region of the VH of MF5361.

Also provided is a mixture or kit of parts, comprising:
a first bispecific antibody or a functional part, derivative and/or analogue thereof that comprises a CD137 binding variable domain comprising a VH region with the amino acid sequence of the CDR1, CDR2 and CDR3 regions of the VH of MF6744, and a PD-L1 binding variable domain comprising a VH region with the amino acid sequence of the CDR1, CDR2 and CDR3 regions of the VH of MF5594; and
a second bispecific antibody or a functional part, derivative and/or analogue thereof that comprises a CD137 binding variable domain comprising a VH region with the amino acid sequence of the CDR1, CDR2 and CDR3 regions of the VH of MF6744, and a PD-L1 binding variable domain comprising a VH region with the amino acid sequence of the CDR1, CDR2 and CDR3 regions of the VH of MF5361.

Also provided is a mixture or kit of parts, comprising:
a first bispecific antibody or a functional part, derivative and/or analogue thereof that comprises a CD137 binding variable domain comprising a VH region with the amino acid sequence of the VH of MF6744 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF6744, and a PD-L1 binding variable domain comprising a VH region with the amino acid sequence of the VH of MF5594 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5594; and
a second bispecific antibody or a functional part, derivative and/or analogue thereof that comprises a CD137 binding variable domain comprising a VH region with the amino acid sequence of the VH of MF6744 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the VH of MF6744, and a PD-L1 binding variable domain that comprises a VH region with the amino acid sequence of the VH of MF5361 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5361.

In addition, it is shown in the Examples that a combination of a bispecific antibody with a CD137 binding variable domain that is based on MF6744 and a PD-L1 binding variable domain that is based on MF5361, together with a bispecific antibody with a CD137 binding variable domain that is based on MF6783 and a PD-L1 binding variable domain that is based on MF5594 (applied as a dual bispecific, e.g., Oligoclonics® embodiment) provides superior T cell activation as compared to an antibody that is based on Urelumab.

Further provided is therefore a mixture or kit of parts, comprising:
- a first bispecific antibody or a functional part, derivative and/or analogue thereof that comprises a CD137 binding variable domain comprising a VH region with the amino acid sequence of the CDR3 region of the VH of MF6783, and a PD-L1 binding variable domain comprising a VH region with the amino acid sequence of the CDR3 region of the VH of MF5594; and
- a second bispecific antibody or a functional part, derivative and/or analogue thereof that comprises a CD137 binding variable domain comprising a VH region with the amino acid sequence of the CDR3 region of the VH of MF6744 and a PD-L1 binding variable domain comprising a VH region with the amino acid sequence of the CDR3 region of the VH of MF5361.

Also provided is a mixture or kit of parts, comprising:
a first bispecific antibody or a functional part, derivative and/or analogue thereof that comprises a CD137 binding variable domain comprising a VH region with the amino acid sequence of the CDR1, CDR2 and CDR3 regions of the VH of MF6783, and a PD-L1 binding variable domain comprising a VH region with the amino acid sequence of the CDR1, CDR2 and CDR3 regions of the VH of MF5594; and a second bispecific antibody or a functional part, derivative and/or analogue thereof that comprises a CD137 binding variable domain comprising a VH region with the amino acid sequence of the CDR1, CDR2 and CDR3 regions of the VH of MF6744, and a PD-L1 binding variable domain comprising a VH region with the amino acid sequence of the CDR1, CDR2 and CDR3 regions of the VH of MF5361.

Also provided is a mixture or kit of parts, comprising:

a first bispecific antibody or a functional part, derivative and/or analogue thereof that comprises a CD137 binding variable domain comprising a VH region with the amino acid sequence of the VH of MF6783 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF6783, and a PD-L1 binding variable domain comprising a VH region with the amino acid sequence of the VH of MF5594 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5594; and a second bispecific antibody or a functional part, derivative and/or analogue thereof that comprises a CD137 binding variable domain comprising a VH region with the amino acid sequence of the VH of MF6744 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF6744, and a PD-L1 binding variable domain that comprises a VH region with the amino acid sequence of the VH of MF5361 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of MF5361.

It is also shown in the Examples that the binding of the CD137-specific VH of MF6797, which has good T cell activating properties, is associated with the presence of amino acids comprising Arg66, Gly70 and Phe72 of the CD137 amino acid sequence as depicted in FIG. 42.

The invention therefore also provides an isolated, synthetic or recombinant antibody, or a functional part, derivative and/or analogue thereof, that is able to bind to CD137, wherein the binding of said antibody or functional part, derivative or analogue to CD137 is associated with the presence of amino acids comprising Arg66, Gly70 and Phe72 of the CD137 amino acid sequence as depicted in FIG. 42. The binding of said antibody or functional part, derivative or analogue to CD137 is preferably also associated with an amino acid comprising Val71 of the CD137 amino acid sequence as depicted in FIG. 42.

The term "Arg66" refers to the arginine residue at position 66 of the CD137 sequence as depicted in FIG. 42. The term "Gly70" refers to the glycine residue at position 70 of the CD137 sequence as depicted in FIG. 42. The term "Val71" refers to the valine residue at position 71 of the CD137 sequence as depicted in FIG. 42. The term "Phe72" refers to the phenylalanine residue at position 72 of the CD137 sequence as depicted in FIG. 42.

The binding of an antibody or functional part, derivative or analogue to CD137 is associated with the presence of the recited amino acid residues if, when any one of these residues is substituted by alanine, binding of the antibody or functional part, derivative or analogue to the resulting CD137 protein is reduced.

Some embodiments provide an isolated, synthetic or recombinant antibody, or a functional part, derivative and/or analogue thereof, that is able to bind to CD137, wherein said antibody or functional part, derivative or analogue specifically binds amino acids Arg66, Gly70 and Phe72 of the CD137 amino acid sequence as depicted in FIG. 42. Said antibody or functional part, derivative or analogue preferably also specifically binds amino acid Val71 of the CD137 amino acid sequence as depicted in FIG. 42.

Some preferred embodiments provide a bispecific antibody, or a functional part, derivative and/or analogue thereof, that is able to bind to CD137 and to PD-L1 and that has a CD137 binding variable domain based on MF6797 and a PD-L1 binding variable domain based on MF7702. The binding of such bispecific antibody, which has particularly good T cell activating properties, to CD137 and PD-L1 is associated with amino acids comprising the above mentioned CD137 amino acid residues.

Now that the above mentioned CD137 amino acid residues have been identified, it has become possible to generate or select antibodies, or variants thereof, that specifically bind these amino acid residues. Generation and/or selection of binding molecules that specifically bind certain amino acid residues can be done using methods well known in the art, such as for instance by immunizing a transgenic non-human animal capable of generating antibodies with an antigen fragment containing the particular domain comprising the target amino acid residues. Alternatively, by screening an antibody phage display library, for phage that bind to identified amino acid residues.

Further provided is an antibody or a variant thereof that competes with antibody PB17311 for binding to CD137 and/or PD-L1. A competing antibody or variant thereof is for instance identified using a competition assay wherein cells comprising CD137 and/or PD-L1 are incubated with PB17311 and with candidate antibodies or variants thereof. Candidate antibodies or variants thereof that are capable of diminishing the amount of bound PB17311, as compared to a control wherein the cells comprising CD137 and/or PD-L1 are incubated with PB17311 without the candidate antibodies or variants thereof, are competing antibodies or variants.

Some embodiments provide an isolated, synthetic or recombinant antibody, or a functional part, derivative and/or analogue thereof, that competes with antibody PB17311 for binding to CD137 and/or PD-L1.

Some embodiments provide an isolated, synthetic or recombinant antibody, or a functional part, derivative and/or analogue thereof, that competes with antibody PB17311 for binding to amino acids Arg66, Gly70 and Phe72 of the CD137 amino acid sequence as depicted in FIG. 42, more preferably for binding to amino acids Arg66, Gly70, Val71 and Phe72 of the CD137 amino acid sequence as depicted in FIG. 42.

Some embodiments provide an isolated, synthetic or recombinant antibody, or a functional part, derivative and/or analogue thereof, that competes with antibody PB17309 for binding to CD137 and/or PD-L1.

Some embodiments provide an isolated, synthetic or recombinant antibody, or a functional part, derivative and/or analogue thereof, that competes with antibody PB17310 for binding to CD137 and/or PD-L1.

Antibodies or variants thereof that compete with PB17309 or PB17310 for binding to CD137 and/or PD-L1 are for instance isolated using a competition assay wherein binding of PB17309 or PB17310 to cells comprising CD137 and/or PD-L1 in the absence of a candidate antibody or variant thereof is compared with the binding of PB17309 or PB17310 to cells comprising CD137 and/or PD-L1 in the presence of said candidate antibody or variant thereof. A candidate antibody or variant thereof that is capable of diminishing the amount of bound PB17309 or PB17310, as compared to a control wherein the cells comprising CD137 and/or PD-L1 are incubated with PB17309 or PB17310 without said candidate antibody or variant thereof, is identified as a competing antibody or variant thereof.

An OX40 x PD-L1 bispecific antibody or a functional part, derivative and/or analogue thereof as described herein preferably comprises an OX40 binding variable domain that comprises a VH region with the amino acid sequence of the CDR3 or the amino acid sequence of the CDR1, CDR2 and CDR3 of the VH of MF6629; MF6630; MF6637; MF6643; MF6645; MF6648; MF6655; MF6658; MF6660; MF6675; MF6686; MF6690; MF6692; MF6700; MF6706; MF6714; MF6721; MF6722; MF6724; MF6728; MF6729; MF6826; MF6940; MF6942; MF6943; MF6944; MF6947; MF6949; MF7331; MF7332; MF7334; MF7341; MF7345; MF7350; MF7351; MF7352; MF7353; MF7356; MF7358; MF7365; MF7366; MF7371; MF7372; MF7374; MF7378; MF7382; MF7383; MF7394; MF7395; or MF7397; and a PD-L1 binding variable domain. The PD-L1 binding variable domain preferably comprises a VH region with the amino acid sequence of the CDR3 or the amino acid sequence of the CDR1, CDR2 and CDR3 of the VH of a PD-L1 specific VH as depicted in FIG. 3. In a preferred embodiment of a PD-L1 specific VH as depicted for MF5594; MF5424; MF5426; MF5553; MF5442; MF5561; MF5426; or MF5439 (FIG. 3).

An antibody or a functional part, derivative and/or analogue thereof preferably comprises an OX40 binding variable domain that comprises a VH region with the amino acid sequence of the VH of MF6629; MF6630; MF6637; MF6643; MF6645; MF6648; MF6655; MF6658; MF6660; MF6675; MF6686; MF6690; MF6692; MF6700; MF6706; MF6714; MF6721; MF6722; MF6724; MF6728; MF6729; MF6826; MF6940; MF6942; MF6943; MF6944; MF6947; MF6949; MF7331; MF7332; MF7334; MF7341; MF7345; MF7350; MF7351; MF7352; MF7353; MF7356; MF7358; MF7365; MF7366; MF7371; MF7372; MF7374; MF7378; MF7382; MF7383; MF7394; MF7395; or MF7397 having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the amino acid sequence of the indicated VH and;

a PD-L1 binding variable domain. The PD-L1 binding variable domain preferably comprises a VH region with the amino acid sequence of the VH of MF5594; MF5424; MF5426; MF5553; MF5442; MF5561; MF5426; or MF5439 (FIG. 3) having at most 15, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the amino acid sequence of the VH of the indicated MF (FIG. 3).

The mentioned at most 15, preferably 1, 2, 3, 4, 5, 6, 7, 8, 9 or 10 and preferably 1, 2, 3, 4 or 5 amino acid substitutions in the mentioned H, VH, L and VL regions are preferably conservative amino acid substitutions, the insertions, deletions, substitutions or a combination thereof are preferably not in the CDR3 region of the H, VH, L or VL chain, preferably not in the CDR1, CDR2 or CDR3 region of the VH or VL chain and preferably not in the FR4 region.

For the purpose of clarity and a concise description features are described herein as part of the same or separate embodiments, however, it will be appreciated that the scope of the invention may include embodiments having combinations of all or some of the features described.

The invention is further explained in the following examples. These examples do not limit the scope of the invention, but merely serve to clarify the invention.

BRIEF DESCRIPTION OF THE DRAWINGS

FIG. 1. Common light chain used in mono- and bispecific IgG.

FIG. 1A: Common light chain amino acid sequence. FIG. 1: Common light chain variable domain DNA sequence and translation (IGKV1-39/jk1). FIG. 1C: Common light chain constant region DNA sequence and translation. FIG. 1D: IGKV1-39/jk5 common light chain variable domain translation. FIG. 1E: V-region IGKV1-39A FIG. 2. IgG heavy chains for the generation of bispecific molecules. FIG. 2A: VH is nucleic acid encoding the amino acid sequence for an MF depicted in FIG. 3. FIG. 2B: CH1 region. FIG. 2C: hinge region. FIG. 2D: CH2 region. FIG. 2E: CH2 containing L235G and G238R substitutions. FIG. 2F: CH3 domain containing substitutions L351K and T366K (KK). FIG. 2G; CH3 domain containing substitutions L351D and L368E (DE)

FIG. 3. Amino acid sequences of heavy chain variable regions. FIG. 3A: VH sequences of CD137 specific clones. FIG. 3B: VH sequences of PD-L1 specific clones. FIG. 3C: VH sequences of OX40 specific clones. FIG. 3D: VH sequences of PD-L1 specific clones.

The notation MF refers to a fab containing a heavy chain variable region as depicted and a common light chain. The amino acid sequence of the light chain is indicated in FIG. 1A. The underlined sequences indicate per amino acid sequence respectively the CDR1, the CDR2 and the CDR3 region according to Kabat numbering.

Figure 4:
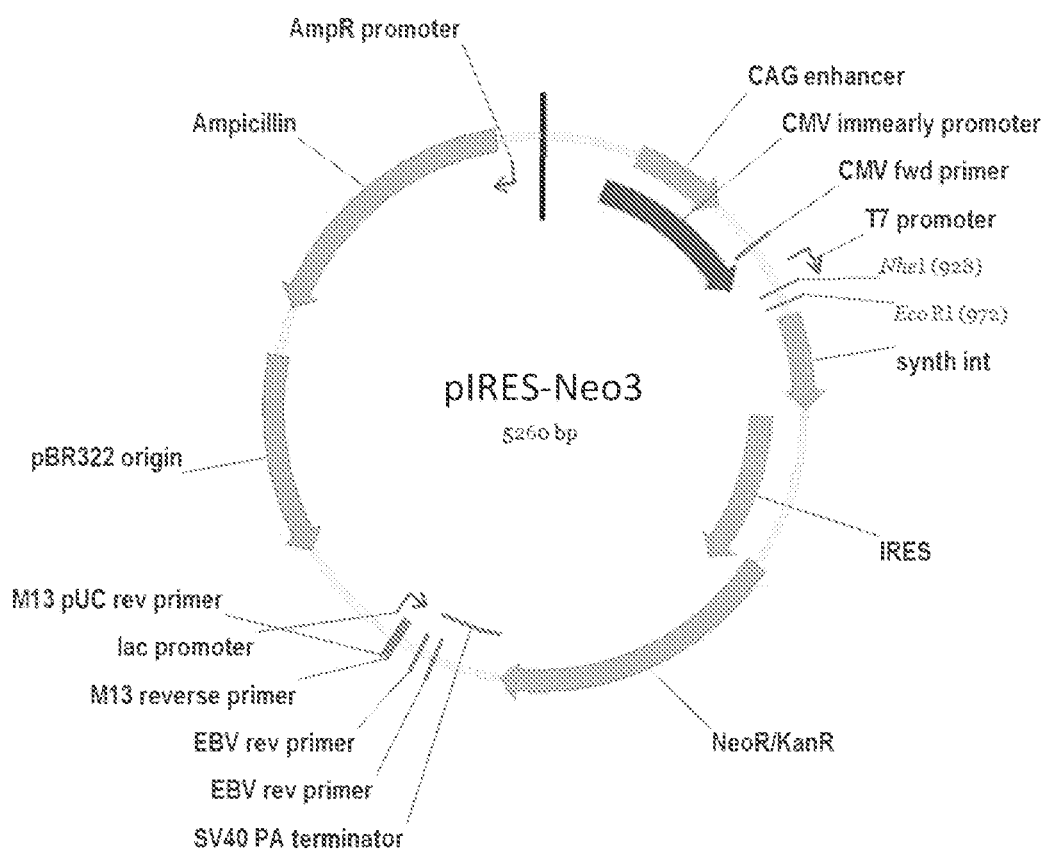

FIG. 4. Vector map and features of pIRES-Neo3 (MV1363).

Figure 5:
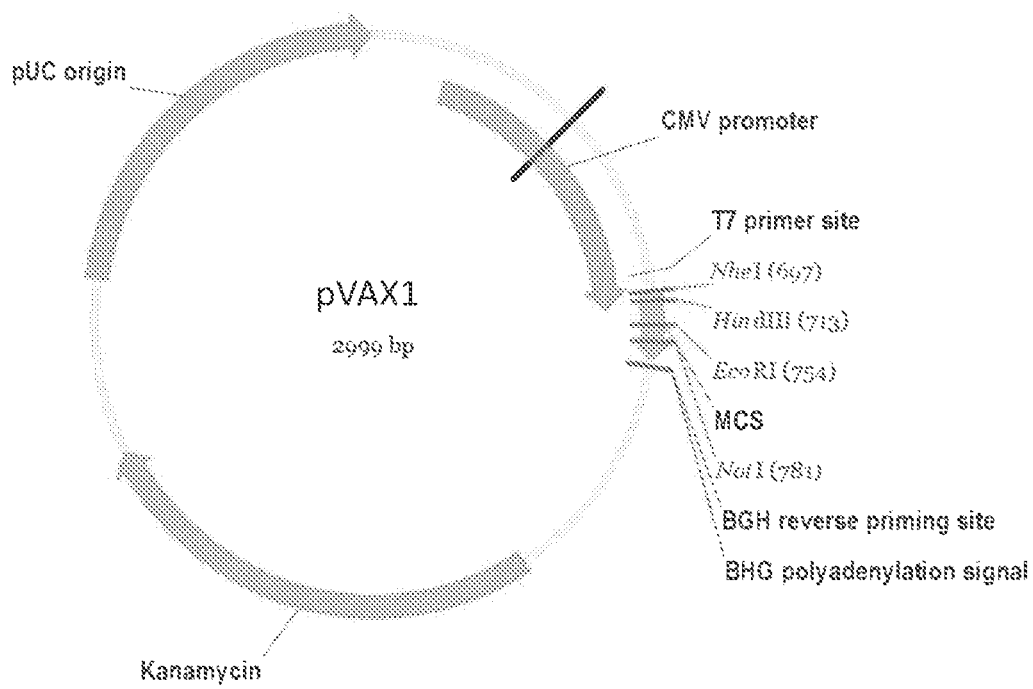

FIG. 5. Vector map and features of pVAX1.

Figure 6:
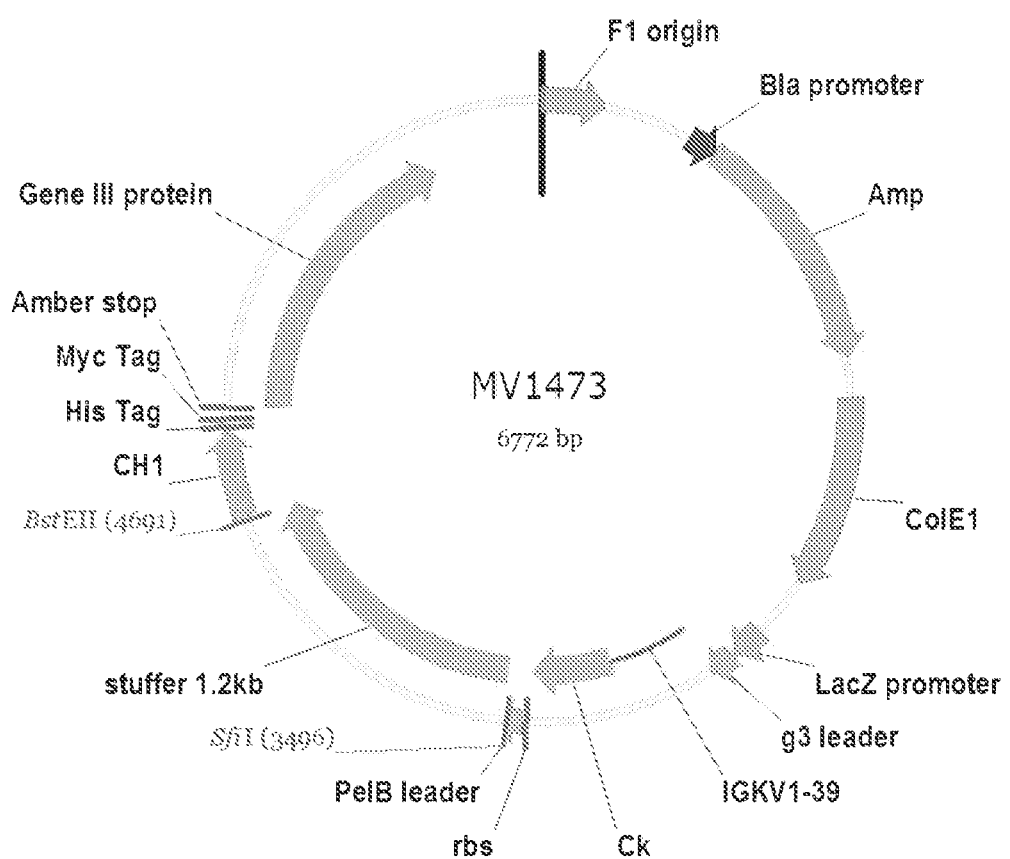

FIG. 6. Vector map and features of the phagemid vector MV1473 used to generate 'immune' phage display libraries.

Figures 7, 8:
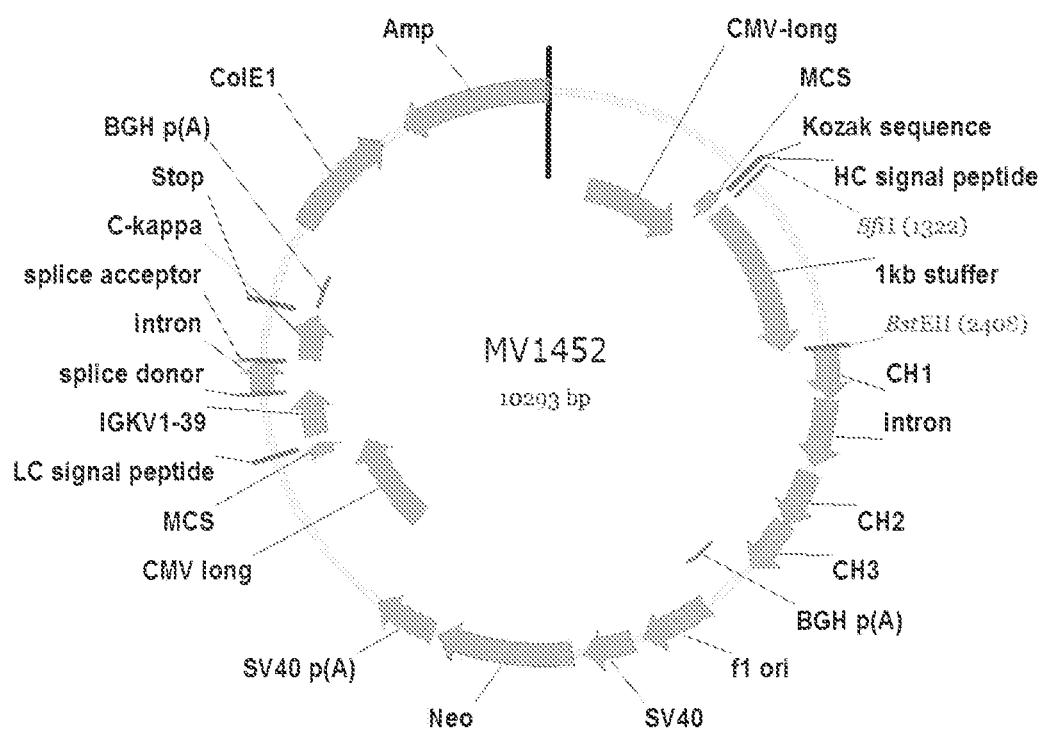

FIG. 7. Vector map and features of the IgG expression vector MV1452 or MV1453, that were used for expression of the CD137, PD-1, PD-L1 and OX40 specific Fab arms in the KK-variant heavy chain or the DE variant heavy chain, respectively, for bispecific IgG generation.

FIG. 8. Amino acid sequence of the VH gene that is tetanus toxin specific when combined with the common light chain as MF1337, and that is present in the DE-variant heavy chain that was used to generate PD-L1xTT bispecific IgG molecules. The underlined sequences indicate per amino acid sequence respectively the CDR1, the CDR2 and the CDR3 region.

Figure 9:
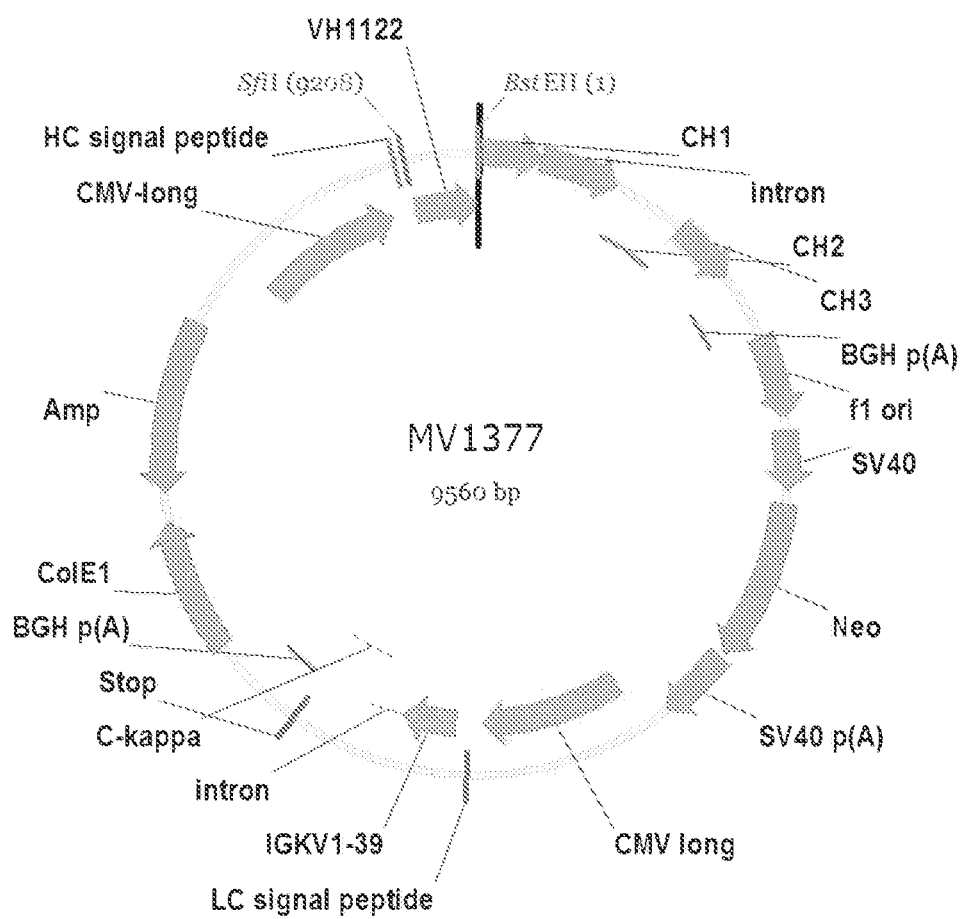

FIG. 9. Vector map and features of the IgG expression vector MV1377, that was used for expression of the TT specific Fab arm MF1337 in the DE-variant heavy chain for bispecific IgG generation.

Figure 10:
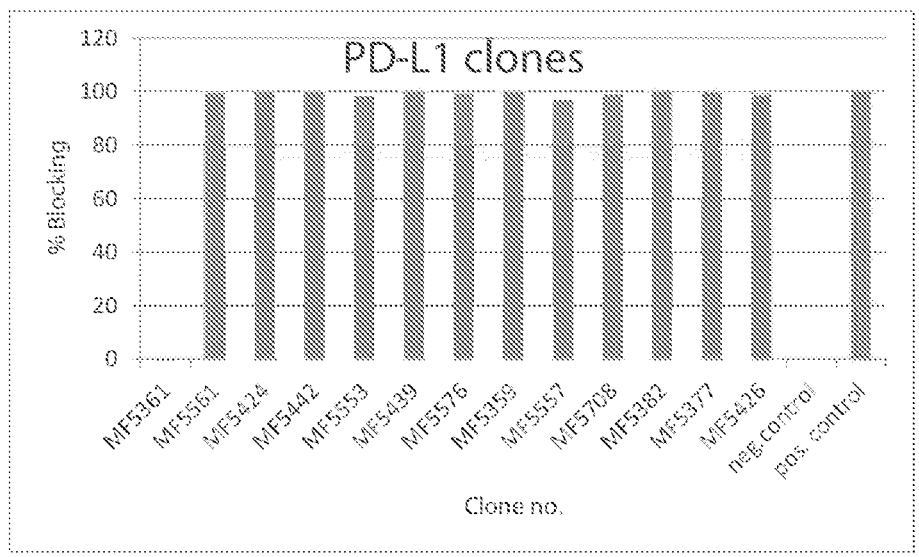

FIG. 10. PD-1/PD-L1 blocking assay.

Assessment of the capacity of the anti-PD-L1 antibody panel to block the interaction of PD-L1 to coated PD-1 at a concentration of 10 μg/ml bispecific IgG. Data are normalized to data obtained with the bivalent benchmark PD-L1 antibody MPDL3280A at a concentration of 10 μg/ml (100% blocking). A representative example is shown of the PD-L1 panel. Maximum binding (normalized to 0% blocking) was established by incubation with a non-PD-1/PD-L1 specific human isotype antibody. All PD-L1 variable domains comprising MF sequences depicted in FIG. 3 and not represented here block the PD-1/PD-L1 interaction>70%.

Figure 11:
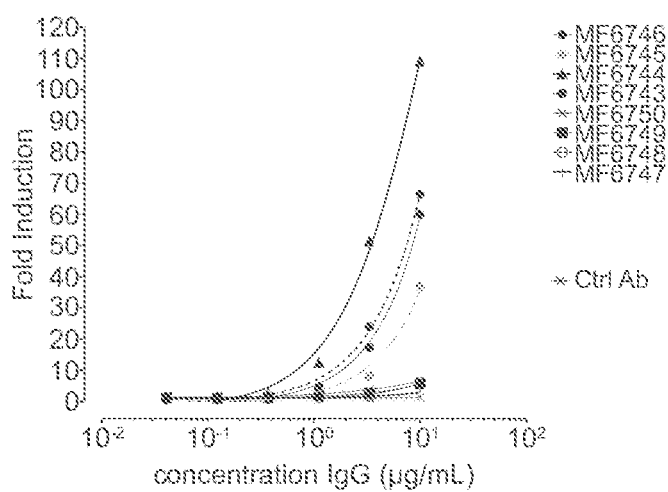

FIG. 11. Activation of CD137 in Jurkat CD137-NFkBluc cells by bivalent CD137 antibodies FIG. 12. Activation of CD137 in Jurkat CD137-NFkBluc cells by CD137xPD-L1 antibodies in the absence (left) or presence of a IgG cross linking antibody (right). MF numbers refer to CD137 Fabs present in the CD137xPD-L1 bispecific antibodies.

Figure 13:
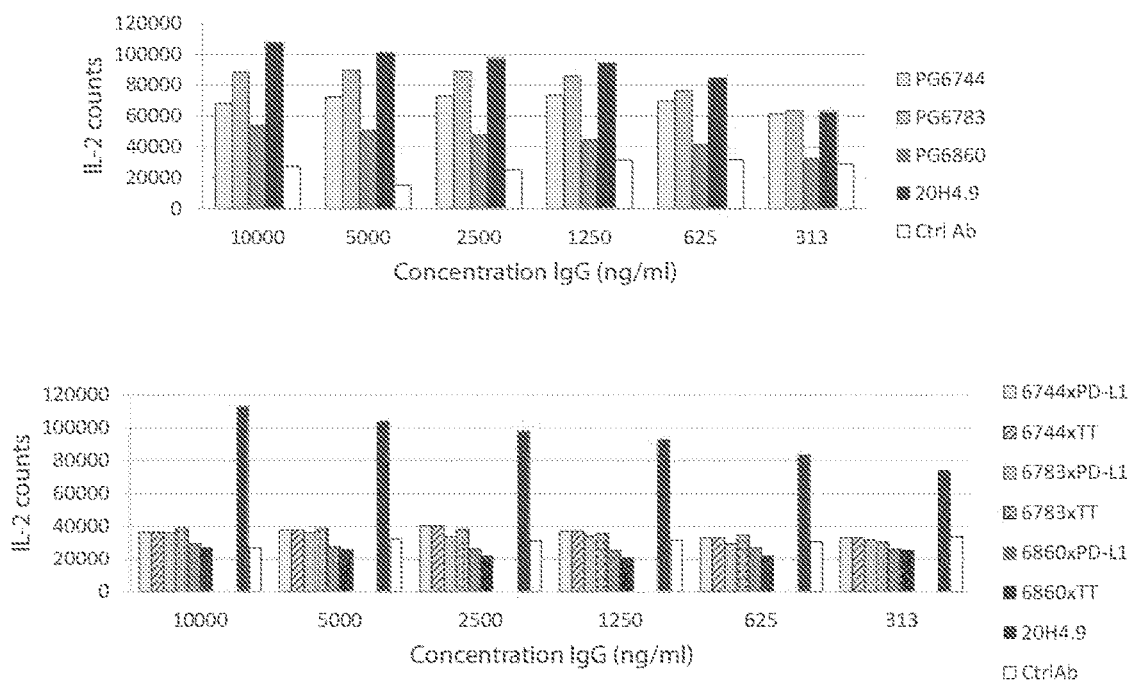

FIG. 13. Activation of primary T cells by bivalent CD137 antibodies (top) or monovalent antibodies (bottom) in combination with a PD-L1 Fab arm (MF5594) as measured by IL-2 release.

PG6744: bivalent CD137 antibody containing two MF6744 arms (also denoted as 6744x6744).

PG6783: bivalent CD137 antibody containing two MF6783 arms (also denoted as 6783x6783).

PG6860: bivalent CD137 antibody containing two MF6860 arms (also denoted as 6860x6860). 20H4.9: anti-CD137 reference antibody based on WO 2005/035584.

Figure 14:
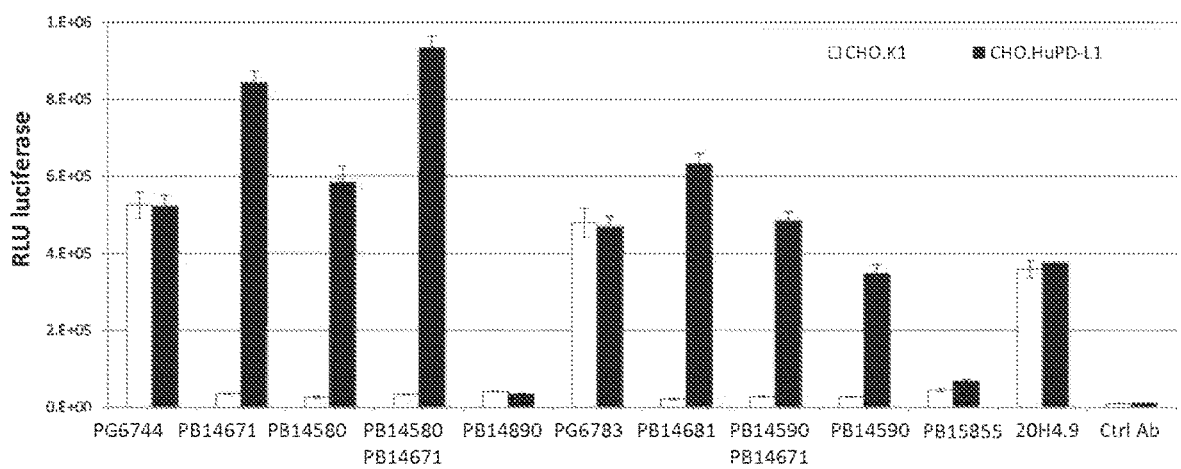

FIG. 14. Activation of CD137 on Jurkat-CD137-luc cells in the presence of CHO cells overexpressing PD-L1 or CHO wildtype cells. CD137 activation was measured by luciferase expression.

PG6744: bivalent CD137 antibody (6744x6744)
PB14671: bispecific CD137xPD-L1 antibody (6744x5361)
PB14580: bispecific CD137xPD-L1 antibody (6744x5594)
PB14890: bispecific CD137xTT antibody (6744x1337)
PG6783: bivalent CD137 antibody (6783x6783)
PB14681: bispecific CD137xPD-L1 antibody (6783x5361)
PB14590: bispecific CD137xPD-L1 antibody (6783x5594)
PB15855: bispecific CD137xTT antibody (6783x1337)
20H4.9: anti-CD137 reference antibody based on WO 2005/035584

Figure 15:
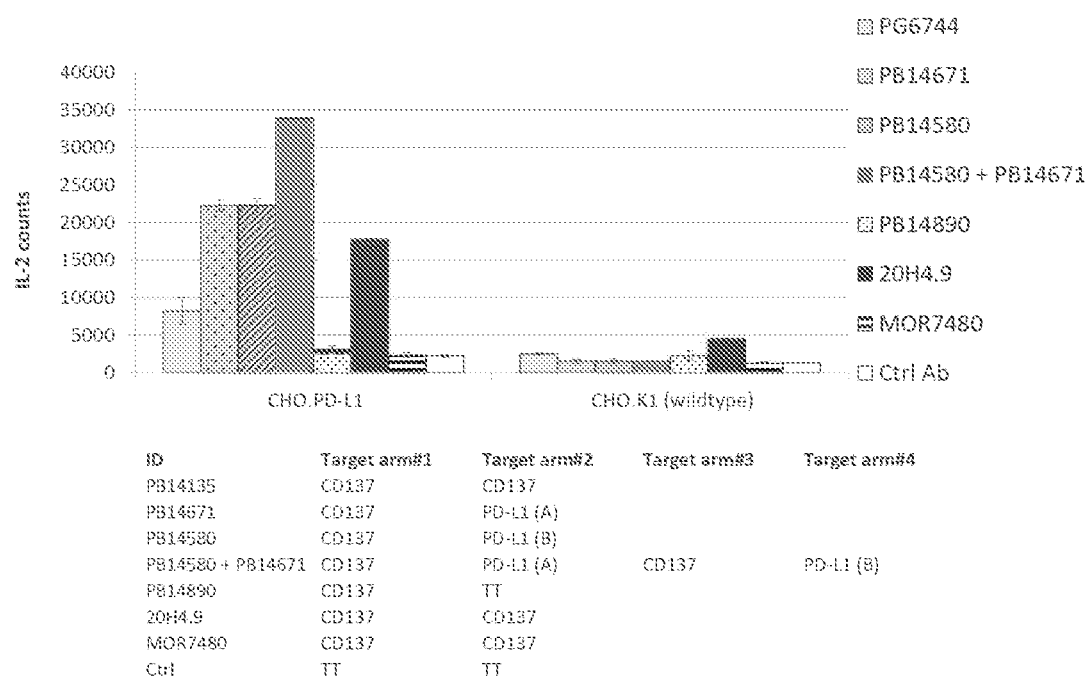

FIG. 15. Activation of primary T cells by bivalent CD137 antibodies, CD137xPD-L1 bispecific antibodies or CD137xPD-L1 Oligoclonics® combinations in the presence of CHO cells overexpressing PD-L1 or CHO wild type cells. Activation was measured by IL-2 release.

PG6744: bivalent CD137 antibody (6744x6744)
PB14671: bispecific CD137xPD-L1 antibody (6744x5361)
PB14580: bispecific CD137xPD-L1 antibody (6744x5594)
PB14890: bispecific CD137xTT antibody (6744x1337)
20H4.9: anti-CD137 reference antibody based on WO 2005/035584 MOR7480: anti-CD137 reference antibody based on U.S. Pat. No. 8,337,850

Figure 16:
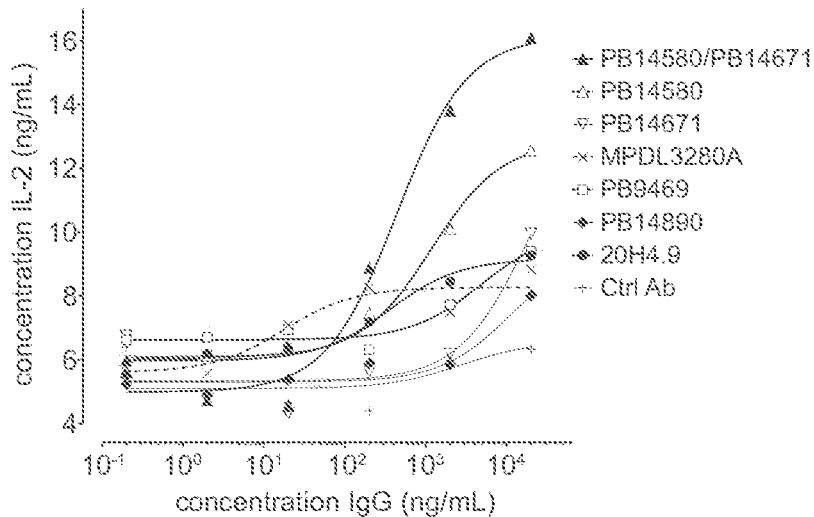

FIG. 16. SEB-stimulation of IL-2 production is enhanced by anti-CD137xPD-L1 bispecific antibody or anti-CD137xPD-L1 Oligoclonics® in healthy donor blood cells.

PB14580: bispecific CD137xPD-L1 antibody (6744x5594)
PB14671: bispecific CD137xPD-L1 antibody (6744x5361)
MPDL3280A: anti-PD-L1 reference antibody based on WO 2010/077634
PB9469: bispecific PD-L1xTT antibody (5594x1337)
PB14890: bispecific CD137xTT antibody (6744x1337)
20H4.9: anti-CD137 reference antibody based on WO 2005/035584
Ctrl Ab: PG2708p213; anti RSV-G FIG. 17. SEB-stimulation of IL-2 production in healthy donor blood cells is dramatically enhanced by anti-CD137xPD-L1 bispecific antibodies in comparison to the anti-CTLA-4 antibody 10D1 (which is based on ipilumumab) FIG. 18. Activation of OX-40 on Jurkat-OX-40 NFkB-luc cells in the presence of CHO cells overexpressing PD-L1 (left panel) or CHO wildtype cells (right panel). Activation was determined by measuring luciferase expression. PD-L1 Fab arm MF5561; PD-1 Fab arm MF6256 (sequence shown in FIG. 43).

Figure 19:
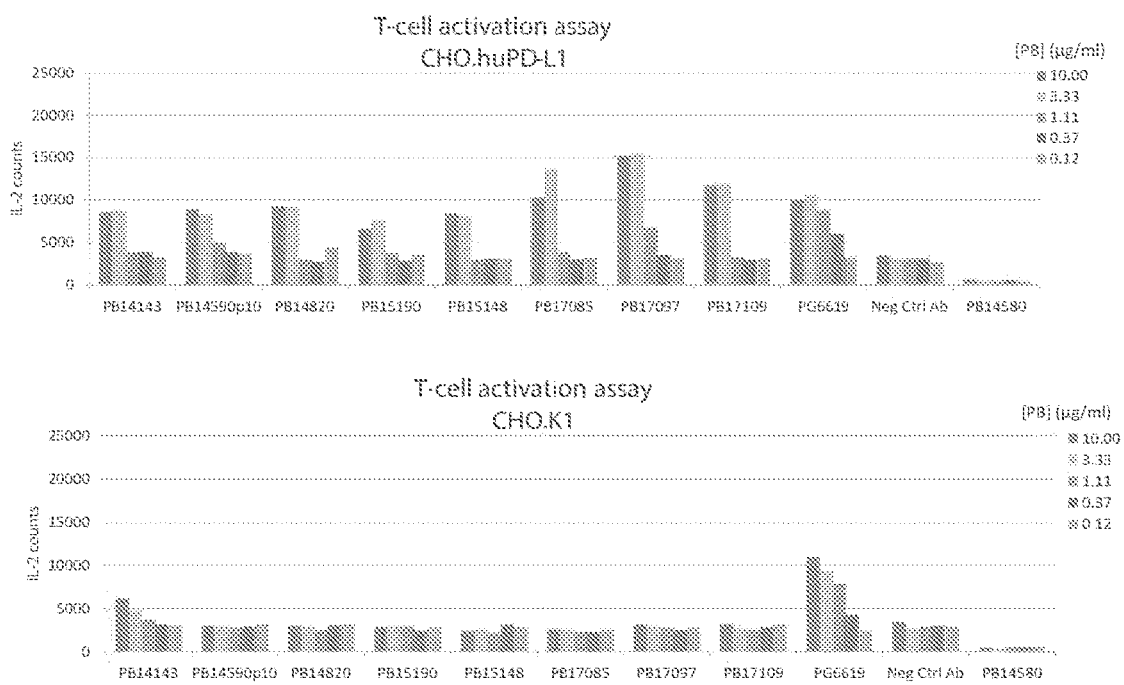
Figure 19:
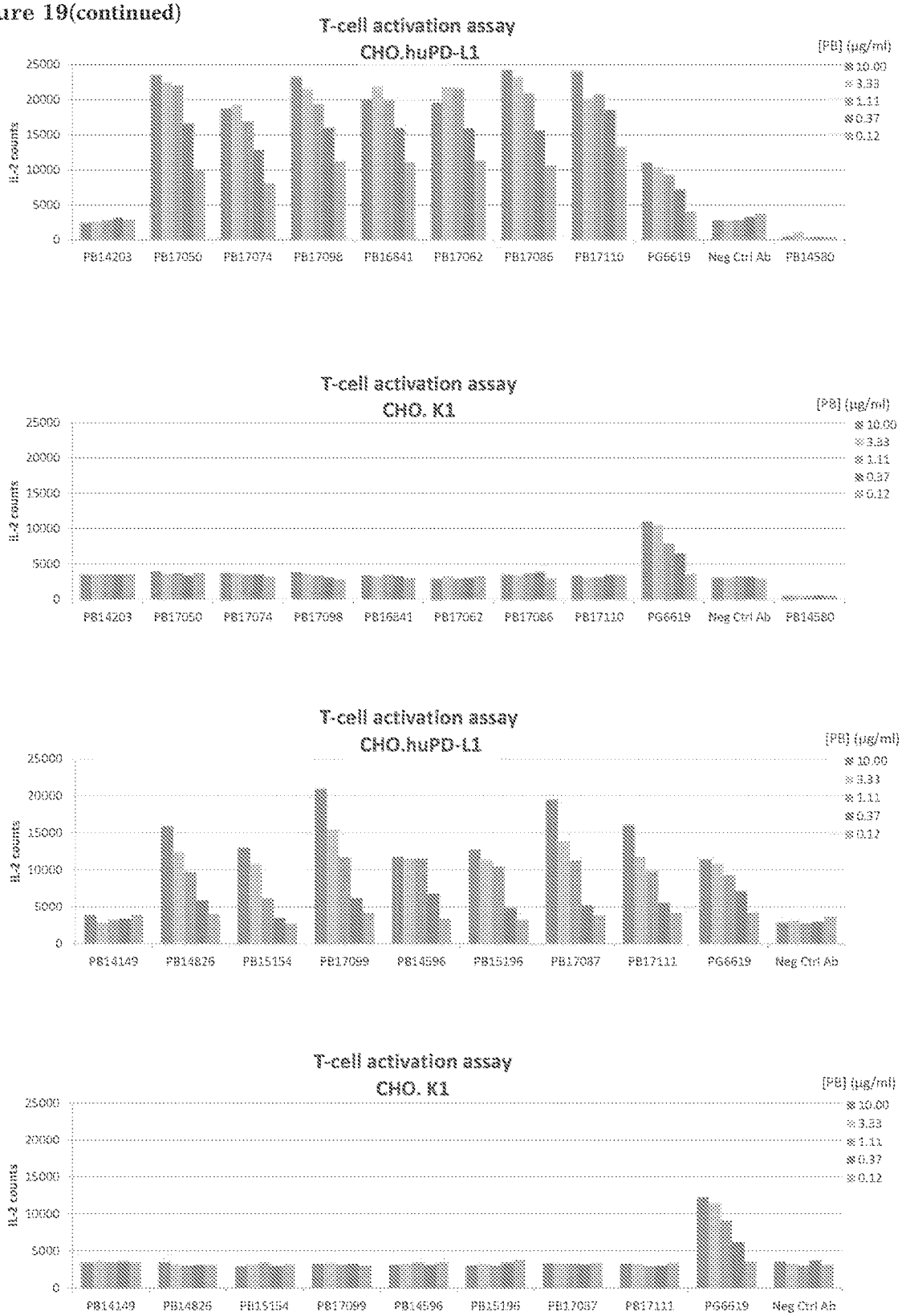
Figure 19:
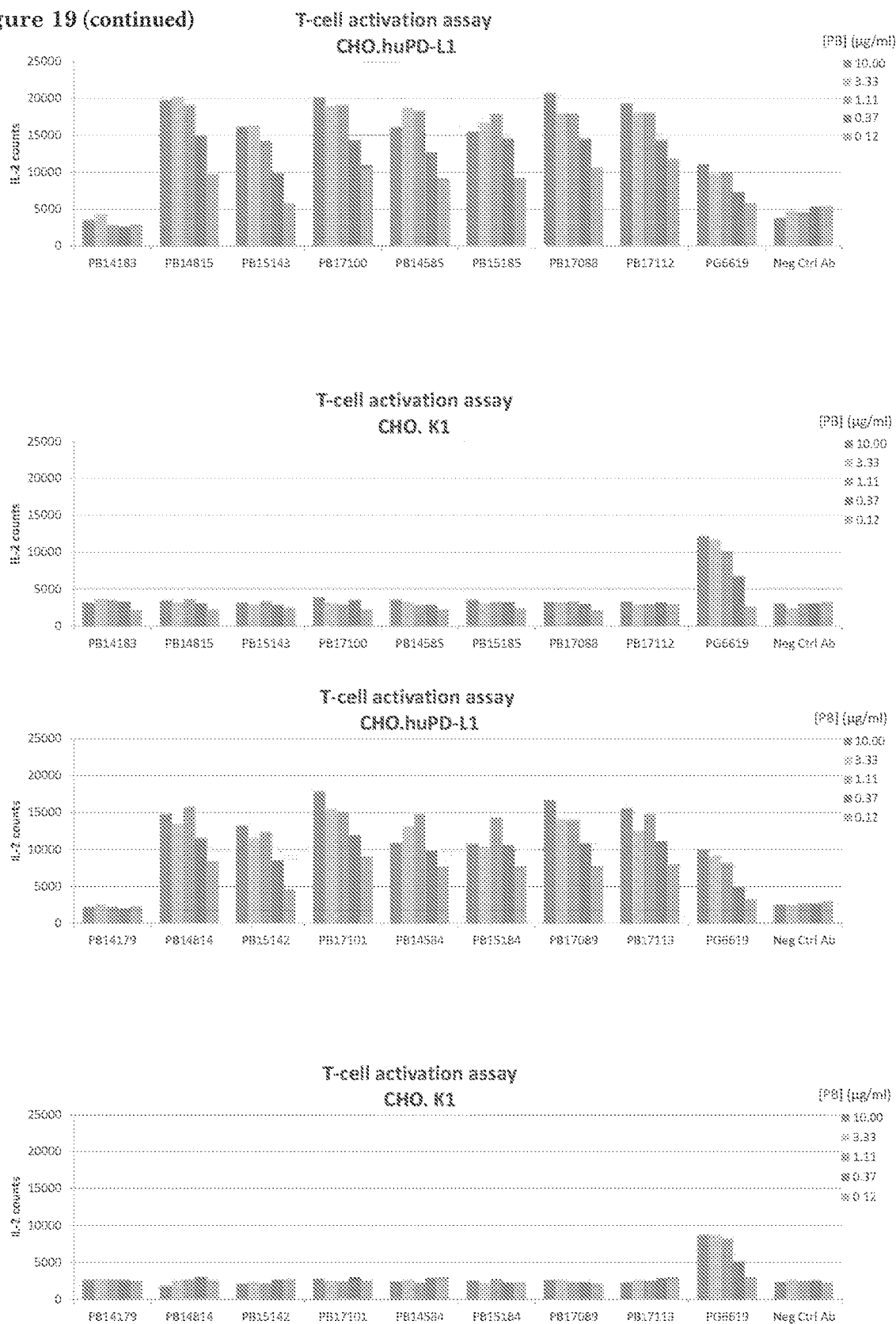
Figure 19:
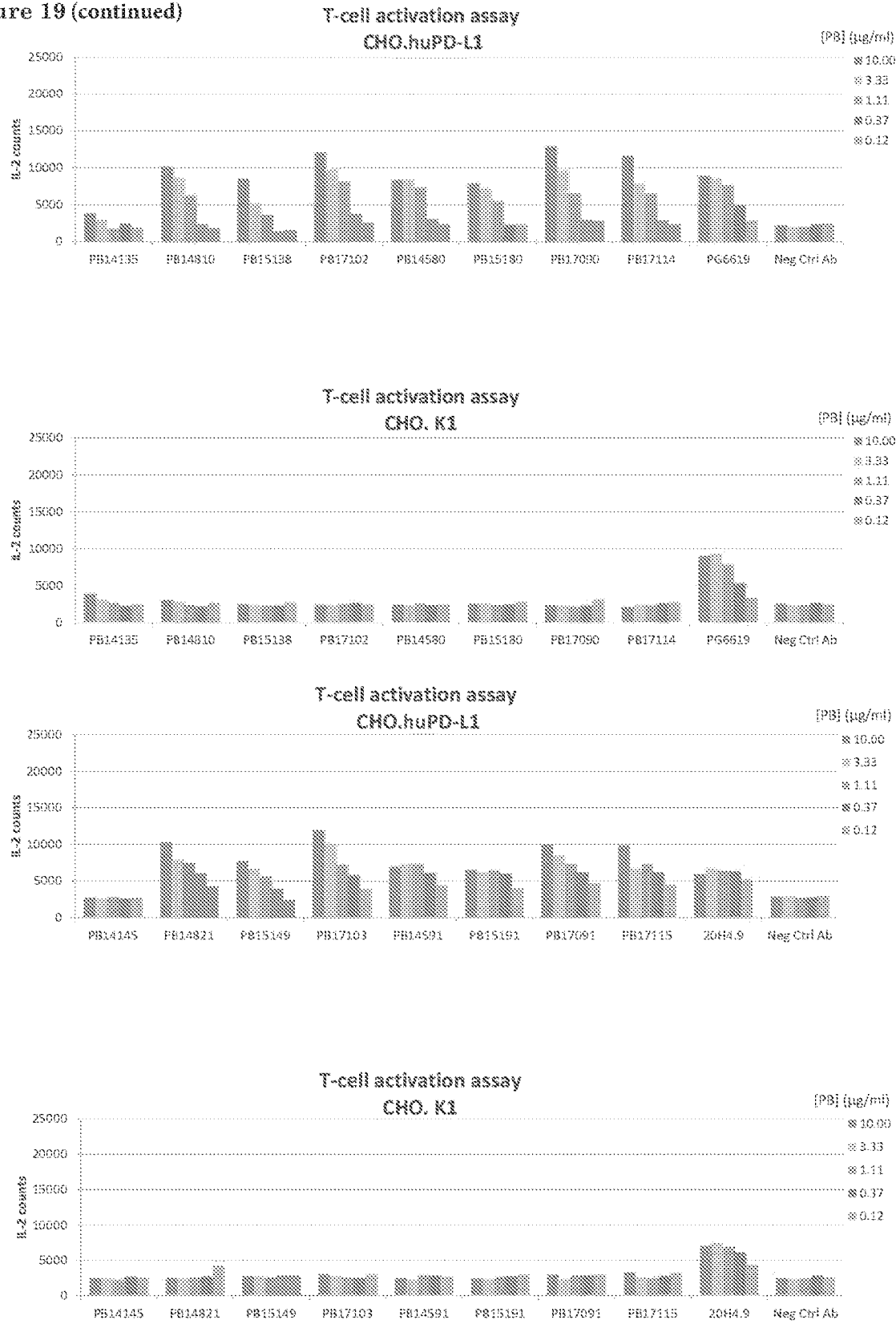
Figure 19:
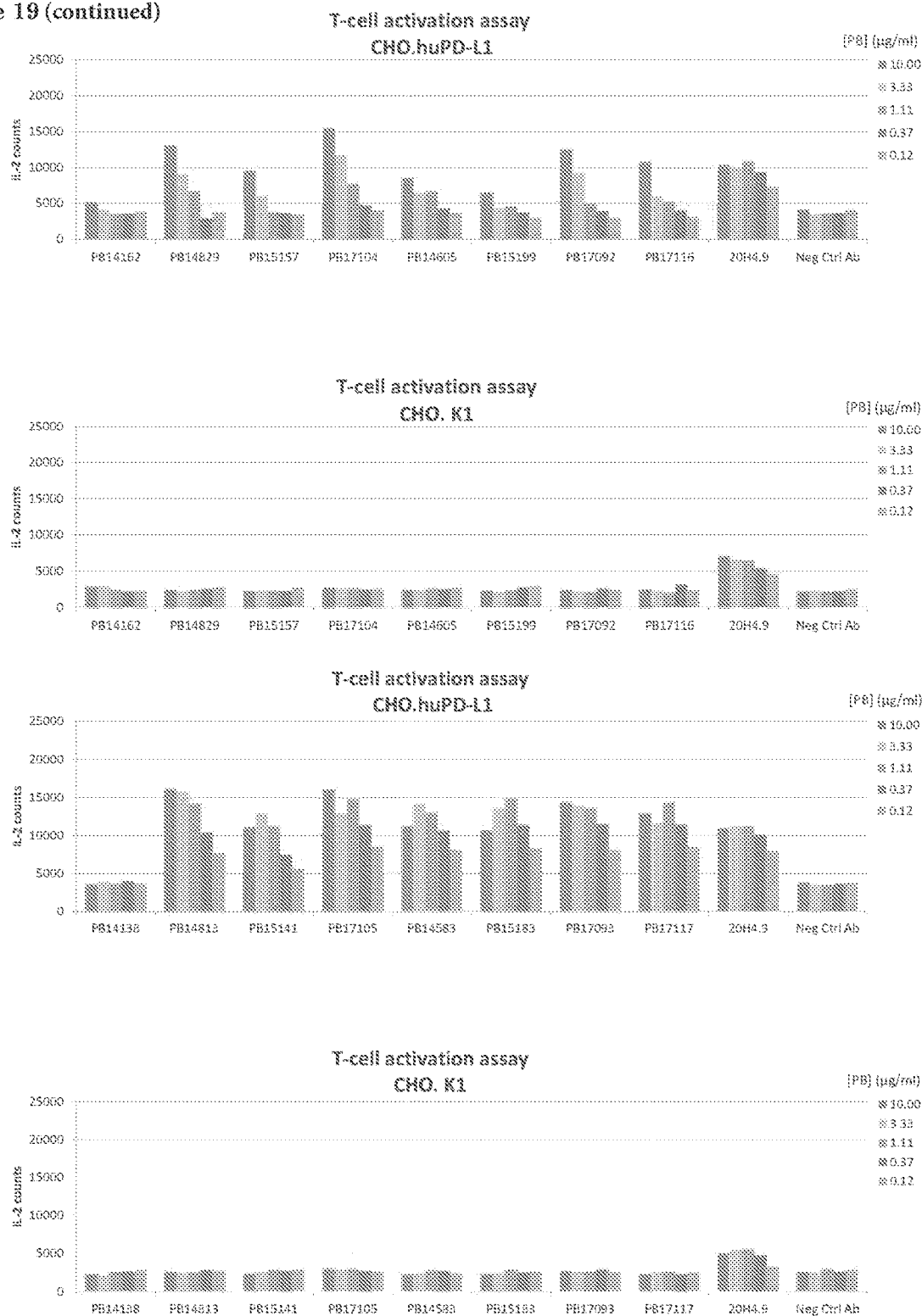
Figure 19:
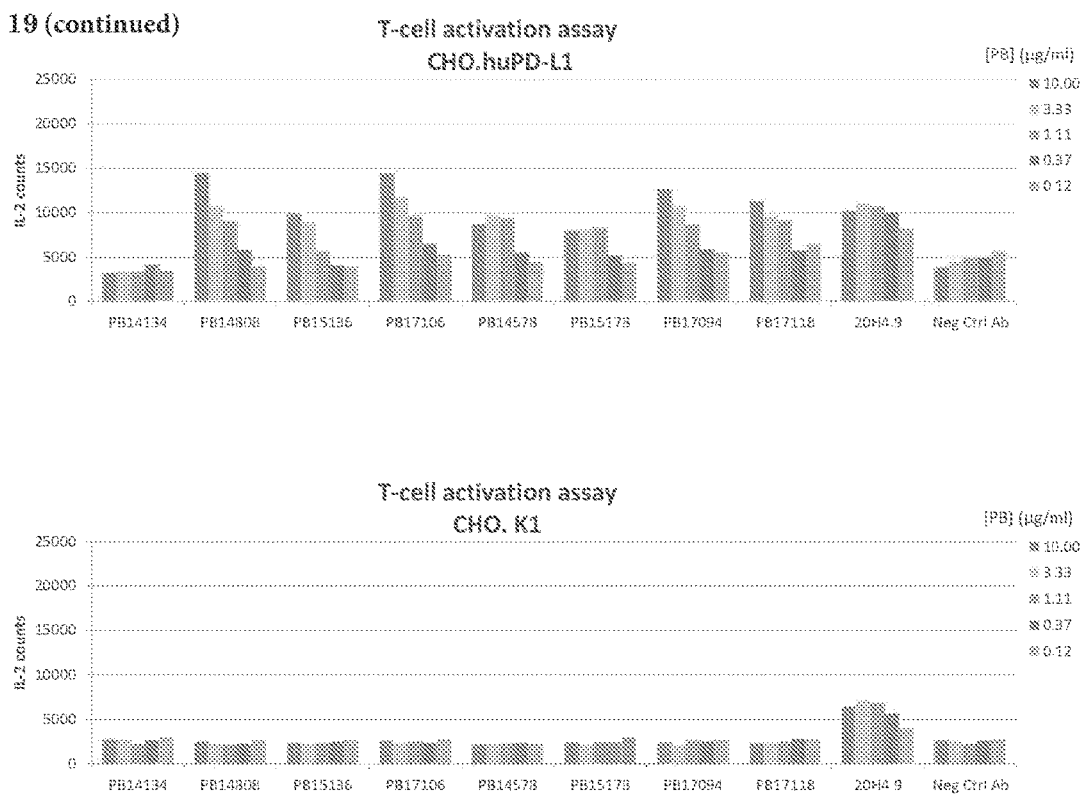
Figure 19:
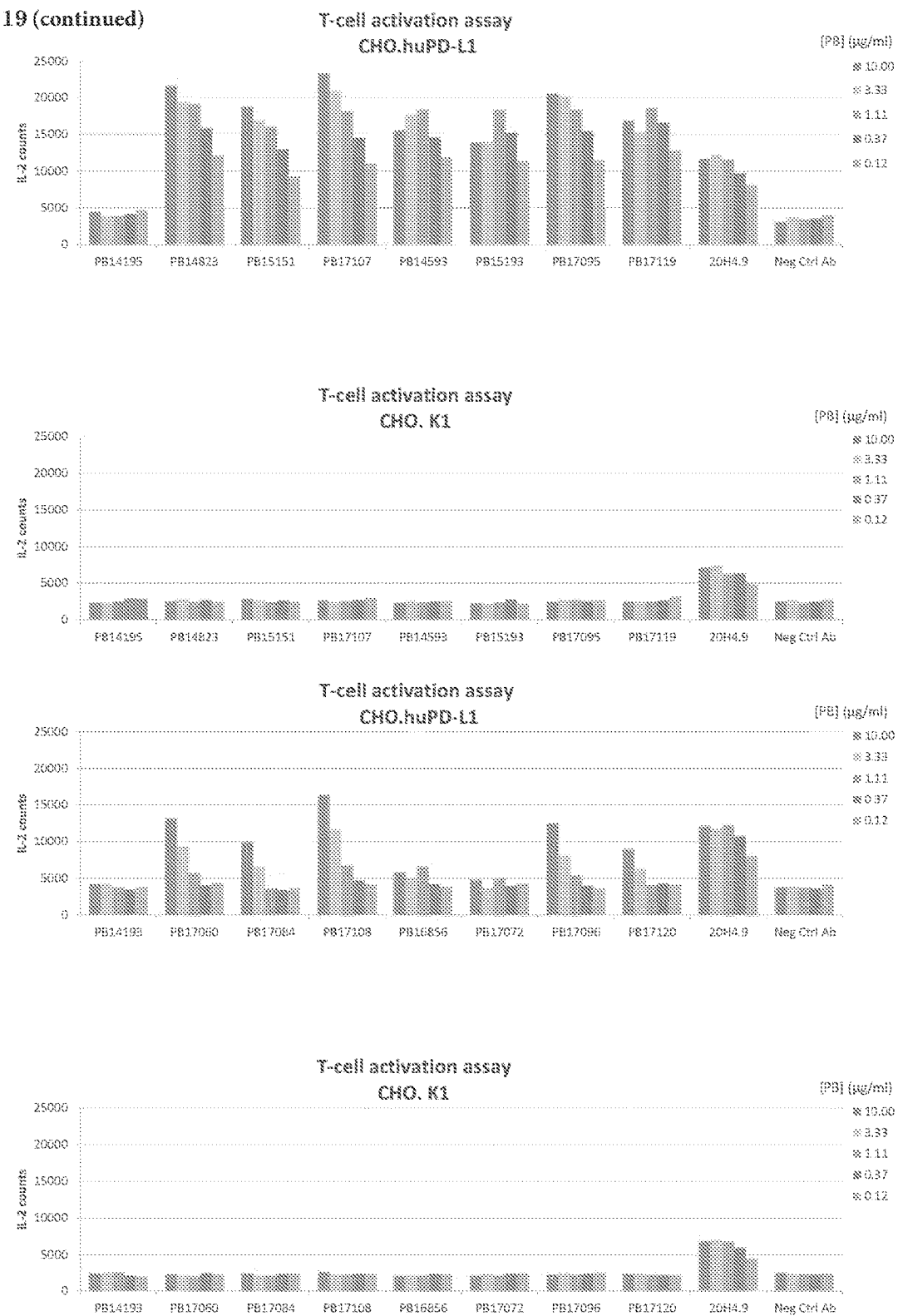

FIG. 19. Screening of CD137 x PD-L1 antibodies in T-cell activation assay (12 CD137 Fab arms). T cells from a single donor were stimulated for 72H at 37° C. with a dose dependent titration of the indicated antibody panel below in the presence of CHO cells overexpressing PD-L1 (upper panels) or CHO wildtype cells (lower panels). CD137 activation was measured by the release of IL-2 using AlphaLISA, expressed in IL-2 counts. Positive control antibody 20H4.9 (referred to in this Figure as PG6619), and the anti-TT negative control antibody PG1337 (Neg Ctrl Ab)

| PB | MF1 | MF2 | PB | MF1 | MF2 | PB | MF1 | MF2 | PB | MF1 | MF2 |
|---|---|---|---|---|---|---|---|---|---|---|---|
| PB14143 | MG6783 | MG6783 | PB14183 | MG6763 | MG6763 | PB14145 | MG6785 | MG6785 | PB14134 | MG6737 | MG6737 |
| PB14590 | MG6783 | MG5594 | PB14815 | MG6763 | MG5561 | PB14821 | MG6785 | MG5561 | PB14808 | MG6737 | MG5561 |
| PB14820 | MG6783 | MG5561 | PB15143 | MG6763 | MG5426 | PB15149 | MG6785 | MG5426 | PB15136 | MG6737 | MG5426 |
| PB15190 | MG6783 | MG5424 | PB17100 | MG6763 | MG5553 | PB17103 | MG6785 | MG5553 | PB17106 | MG6737 | MG5553 |
| PB15148 | MG6783 | MG5426 | PB14585 | MG6763 | MG5594 | PB14591 | MG6785 | MG5594 | PB14578 | MG6737 | MG5594 |
| PB17085 | MG6783 | MG5442 | PB15185 | MG6763 | MG5424 | PB15191 | MG6785 | MG5424 | PB15178 | MG6737 | MG5424 |
| PB17097 | MG6783 | MG5553 | PB17088 | MG6763 | MG5442 | PB17091 | MG6785 | MG5442 | PB17094 | MG6737 | MG5442 |
| PB17109 | MG6783 | MG5439 | PB17112 | MG6763 | MG5439 | PB17115 | MG6785 | MG5439 | PB17118 | MG6737 | MG5439 |
| PB14203 | MG6808 | MG6808 | PB14179 | MG6754 | MG5754 | PB14162 | MG6825 | MG6825 | PB14195 | MG6797 | MG6797 |
| PB17050 | MG6808 | MG5561 | PB14814 | MG6754 | MG5561 | PB14829p | MG6825 | MG5561 | PB14823 | MG6797 | MG5561 |
| PB17074 | MG6808 | MG5426 | PB15142 | MG6754 | MG5426 | PB15157 | MG6825 | MG5426 | PB15151 | MG6797 | MG5426 |
| PB17098 | MG6808 | MG5553 | PB17101 | MG6754 | MG5553 | PB17104 | MG6825 | MG5553 | PB17107 | MG6797 | MG5553 |
| PB16841 | MG6808 | MG5594 | PB14584 | MG6754 | MG5594 | PB14605 | MG6825 | MG5594 | PB14593 | MG6797 | MG5594 |
| PB17062 | MG6808 | MG5424 | PB15184 | MG6754 | MG5424 | PB15199 | MG6825 | MG5424 | PB15193 | MG6797 | MG5424 |
| PB17086 | MG6808 | MG5442 | PB17089 | MG6754 | MG5442 | PB17092 | MG6825 | MG5442 | PB17095 | MG6797 | MG5442 |
| PB17110 | MG6808 | MG5439 | PB17113 | MG6754 | MG5439 | PB17116 | MG6825 | MG5439 | PB17119 | MG6797 | MG5439 |

-continued

| PB | MF1 | MF2 | PB | MF1 | MF2 | PB | MF1 | MF2 | PB | MF1 | MF2 |
|---|---|---|---|---|---|---|---|---|---|---|---|
| PB14149 | MG6805 | MG6805 | PB14135 | MG6744 | MG6744 | PB14138 | MG6749 | MG6749 | PB14193 | MG6788 | MG6788 |
| PB14826 | MG6805 | MG5561 | PB14810 | MG6744 | MG5561 | PB14813 | MG6749 | MG5561 | PB17060 | MG6788 | MG5561 |
| PB15154 | MG6805 | MG5426 | PB15138p | MG6744 | MG5426 | PB15141 | MG6749 | MG5426 | PB17084 | MG6788 | MG5426 |
| PB17099 | MG6805 | MG5553 | PB17102 | MG6744 | MG5553 | PB17105 | MG6749 | MG5553 | PB17108 | MG6788 | MG5553 |
| PB14596 | MG6805 | MG5594 | PB14580p | MG6744 | MG5594 | PB14583 | MG6749 | MG5594 | PB16856 | MG6788 | MG5594 |
| PB15196 | MG6805 | MG5424 | PB15180 | MG6744 | MG5424 | PB15183 | MG6749 | MG5424 | PB17072 | MG6788 | MG5424 |
| PB17087 | MG6805 | MG5442 | PB17090 | MG6744 | MG5442 | PB17093 | MG6749 | MG5442 | PB17096 | MG6788 | MG5442 |
| PB17111 | MG6805 | MG5439 | PB17114 | MG6744 | MG5439 | PB17117 | MG6749 | MG5439 | PB17120 | MG6788 | MG5439 |

Figure 20:
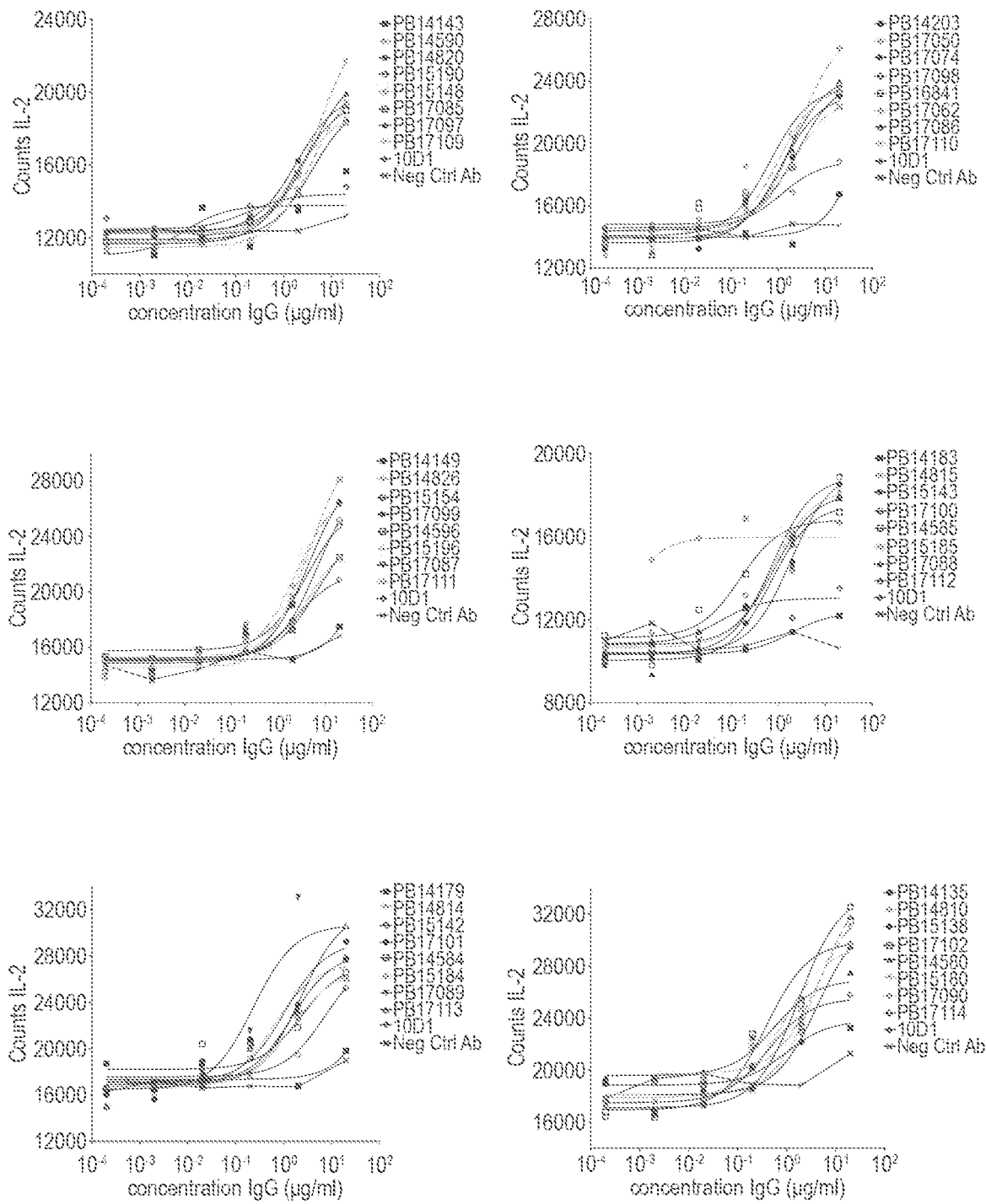
Figure 20:
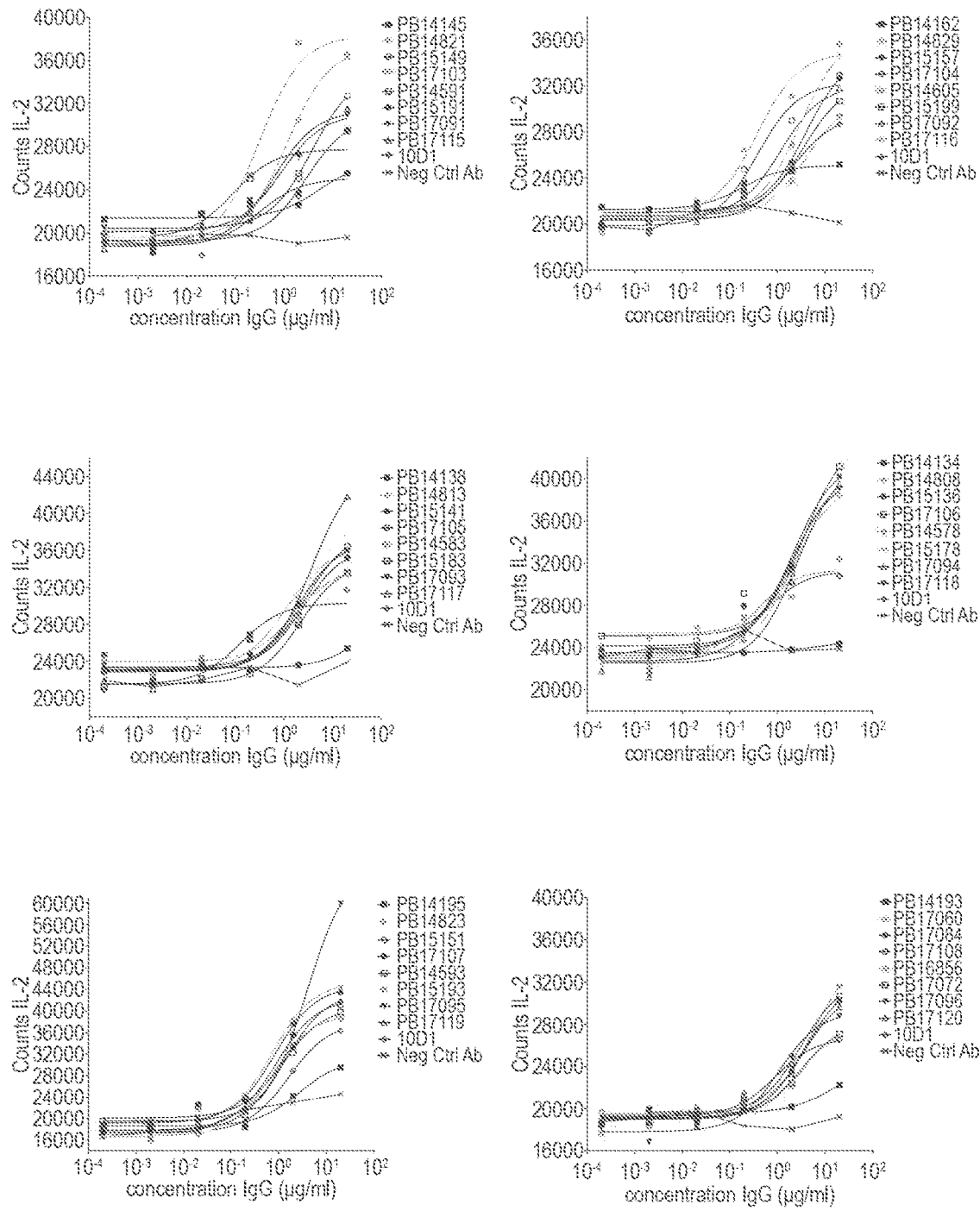

FIG. 20. Screening of CD137 x PD-L1 antibodies in SEB PBMC assay (12 CD137 Fab arms). CD137xPD-L1 antibodies were tested in SEB PBMC assay in the presence of 2 μg/ml SEB. CD137 activation was measured by the release of IL-2 using AlphaLISA, expressed in IL-2 counts. Positive control antibody; anti-CTLA-4 positive control antibody (based on Ipilimumab, 10D1) and the anti-RSV-G negative control antibody PG2708 (Neg Ctrl Ab).

| PB | MF1 | MF2 | PB | MF1 | MF2 | PB | MF1 | MF2 | PB | MF1 | MF2 |
|---|---|---|---|---|---|---|---|---|---|---|---|
| PB14143 | MG6783 | MG6783 | PB14183 | MG6763 | MG6763 | PB14145 | MG6785 | MG6785 | PB14134 | MG6737 | MG6737 |
| PB14590 | MG6783 | MG5594 | PB14815 | MG6763 | MG5561 | PB14821 | MG6785 | MG5561 | PB14808 | MG6737 | MG5561 |
| PB14820 | MG6783 | MG5561 | PB15143 | MG6763 | MG5426 | PB15149 | MG6785 | MG5426 | PB15136 | MG6737 | MG5426 |
| PB15190 | MG6783 | MG5424 | PB17100 | MG6763 | MG5553 | PB17103 | MG6785 | MG5553 | PB17106 | MG6737 | MG5553 |
| PB15148 | MG6783 | MG5426 | PB14585 | MG6763 | MG5594 | PB14591 | MG6785 | MG5594 | PB14578 | MG6737 | MG5594 |
| PB17085 | MG6783 | MG5442 | PB15185 | MG6763 | MG5424 | PB15191 | MG6785 | MG5424 | PB15178 | MG6737 | MG5424 |
| PB17097 | MG6783 | MG5553 | PB17088 | MG6763 | MG5442 | PB17091 | MG6785 | MG5442 | PB17094 | MG6737 | MG5442 |
| PB17109 | MG6783 | MG5439 | PB17112 | MG6763 | MG5439 | PB17115 | MG6785 | MG5439 | PB17118 | MG6737 | MG5439 |
| PB14203 | MG6808 | MG6808 | PB14179 | MG6754 | MG6754 | PB14162 | MG6825 | MG6825 | PB14195 | MG6797 | MG6797 |
| PB17050 | MG6808 | MG5561 | PB14814 | MG6754 | MG5561 | PB14829p | MG6825 | MG5561 | PB14823 | MG6797 | MG5561 |
| PB17074 | MG6808 | MG5426 | PB15142 | MG6754 | MG5426 | PB15157 | MG6825 | MG5426 | PB15151 | MG6797 | MG5426 |
| PB17098 | MG6808 | MG5553 | PB17101 | MG6754 | MG5553 | PB17104 | MG6825 | MG5553 | PB17107 | MG6797 | MG5553 |
| PB16841 | MG6808 | MG5594 | PB14584 | MG6754 | MG5594 | PB14605 | MG6825 | MG5594 | PB14593 | MG6797 | MG5594 |
| PB17062 | MG6808 | MG5424 | PB15184 | MG6754 | MG5424 | PB15199 | MG6825 | MG5424 | PB15193 | MG6797 | MG5424 |
| PB17086 | MG6808 | MG5442 | PB17089 | MG6754 | MG5442 | PB17092 | MG6825 | MG5442 | PB17095 | MG6797 | MG5442 |
| PB17110 | MG6808 | MG5439 | PB17113 | MG6754 | MG5439 | PB17116 | MG6825 | MG5439 | PB17119 | MG6797 | MG5439 |
| PB14149 | MG6805 | MG6805 | PB14135 | MG6744 | MG6744 | PB14138 | MG6749 | MG6749 | PB14193 | MG6788 | MG6788 |
| PB14826 | MG6805 | MG5561 | PB14810 | MG6744 | MG5561 | PB14813 | MG6749 | MG5561 | PB17060 | MG6788 | MG5561 |
| PB15154 | MG6805 | MG5426 | PB15138p | MG6744 | MG5426 | PB15141 | MG6749 | MG5426 | PB17084 | MG6788 | MG5426 |
| PB17099 | MG6805 | MG5553 | PB17102 | MG6744 | MG5553 | PB17105 | MG6749 | MG5553 | PB17108 | MG6788 | MG5553 |
| PB14596 | MG6805 | MG5594 | PB14580p | MG6744 | MG5594 | PB14583 | MG6749 | MG5594 | PB16856 | MG6788 | MG5594 |
| PB15196 | MG6805 | MG5424 | PB15180 | MG6744 | MG5424 | PB15183 | MG6749 | MG5424 | PB17072 | MG6788 | MG5424 |
| PB17087 | MG6805 | MG5442 | PB17090 | MG6744 | MG5442 | PB17093 | MG6749 | MG5442 | PB17096 | MG6788 | MG5442 |
| PB17111 | MG6805 | MG5439 | PB17114 | MG6744 | MG9439 | PB17117 | MG6749 | MG5439 | PB17120 | MG6788 | MG5439 |

Figure 21:
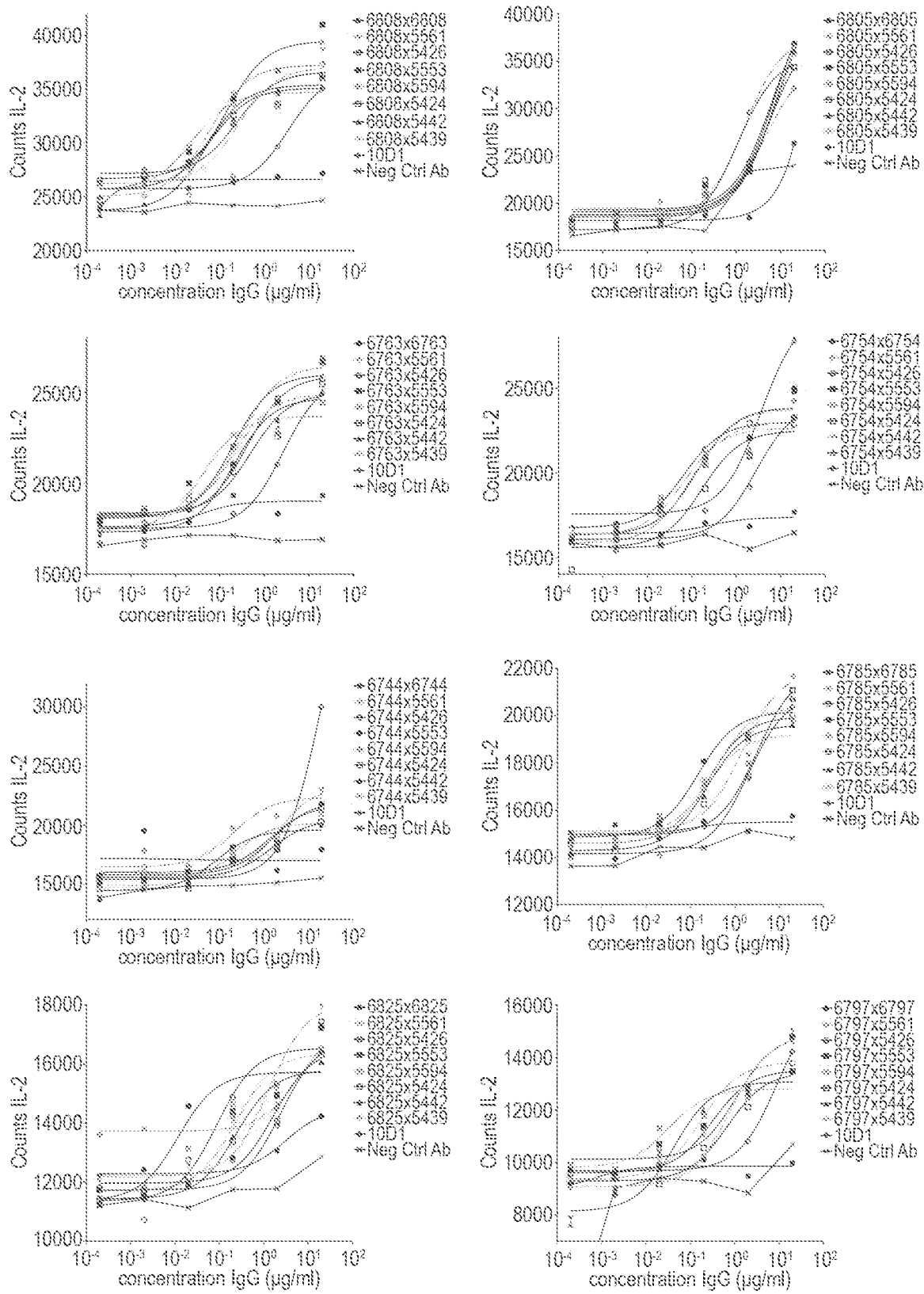

FIG. 21. Screening of CD137 x PD-L1 antibodies in SEB PBMC assay (8 CD137 Fab arms). CD137xPD-L1 antibodies were tested in SEB PBMC assay in the presence of 2 μg/ml SEB. CD137 activation was measured by the release of TL-2 using AlphaLISA, expressed in IL-2 counts. Positive control antibody; anti-CTLA-4 positive control antibody (based on Ipilimumab, 10D1) and the anti-RSV-G negative control antibody PG2708 (Neg Ctrl Ab).

| PB | MF1 | MF2 | PB | MF1 | MF2 | PB | MF1 | MF2 |
|---|---|---|---|---|---|---|---|---|
| PB14203 | MG6808 | MG6808 | PB17088 | MG6763 | MG5442 | PB14591 | MG6785 | MG5594 |
| PB17050 | MG6808 | MG5561 | PB17112 | MG6763 | MG5439 | PB15191 | MG6785 | MG5424 |
| PB17074 | MG6808 | MG5426 | PB14179 | MG6754 | MG6754 | PB17091 | MG6785 | MG5442 |
| PB17098 | MG6808 | MG5553 | PB14814 | MG6754 | MG5561 | PB17115 | MG6785 | MG5439 |
| PB16841 | MG6808 | MG5594 | PB15142 | MG6754 | MG5426 | PB14162 | MG6825 | MG6825 |
| PB17062 | MG6808 | MG5424 | PB17101 | MG6754 | MG5553 | PB14829 | MG6825 | MG5561 |
| PB17086 | MG6808 | MG5442 | PB14584 | MG6754 | MG5594 | PB15157 | MG6825 | MG5426 |
| PB17110 | MG6808 | MG5439 | PB15184 | MG6754 | MG5424 | PB17104 | MG6825 | MG5553 |
| PB14149 | MG6805 | MG6805 | PB17089 | MG6754 | MG5442 | PB14605 | MG6825 | MG5594 |
| PB14826 | MG6805 | MG5561 | PB17113 | MG6754 | MG5439 | PB15199 | MG6825 | MG5424 |
| PB15154 | MG6805 | MG5426 | PB14135 | MG6744 | MG6744 | PB17092 | MG6825 | MG5442 |
| PB17099 | MG6805 | MG5553 | PB14810 | MG6744 | MG5561 | PB17116 | MG6825 | MG5439 |
| PB14596 | MG6805 | MG5594 | PB15138 | MG6744 | MG5426 | PB14195 | MG6797 | MG6797 |
| PB15196 | MG6805 | MG5424 | PB17102 | MG6744 | MG5553 | PB14823 | MG6797 | MG5561 |
| PB17087 | MG6805 | MG5442 | PB14580 | MG6744 | MG5594 | PB15151 | MG6797 | MG5426 |
| PB17111 | MG6805 | MG5439 | PB15180 | MG6744 | MG5424 | PB17107 | MG6797 | MG5553 |
| PB14183 | MG6763 | MG6763 | PB17090 | MG6744 | MG5442 | PB14593 | MG6797 | MG5594 |

-continued

| PB | MF1 | MF2 | PB | MF1 | MF2 | PB | MF1 | MF2 |
|---|---|---|---|---|---|---|---|---|
| PB14815 | MG6763 | MG5561 | PB17114 | MG6744 | MG5439 | PB15193 | MG6797 | MG5424 |
| PB15143 | MG6763 | MG5426 | PB14145 | MG6785 | MG6785 | PB17095 | MG6797 | MG5442 |
| PB17100 | MG6763 | MG5553 | PB14821 | MG6785 | MG5561 | PB17119 | MG6797 | MG5439 |
| PB14585 | MG6763 | MG5594 | PB15149 | MG6785 | MG5426 | | | |
| PB15185 | MG6763 | MG5424 | PB17103 | MG6785 | MG5553 | | | |

Figure 22:
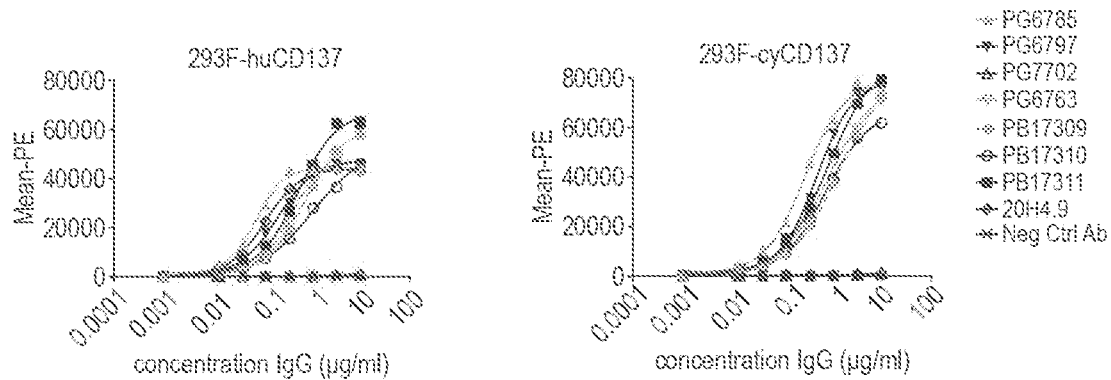

FIG. 22. Bispecific anti-CD137xPD-L1 antibodies and their parental bivalent anti-CD137 antibodies bind to human and cynomolgus CD137 as determined by flow cytometry.

Figure 23:
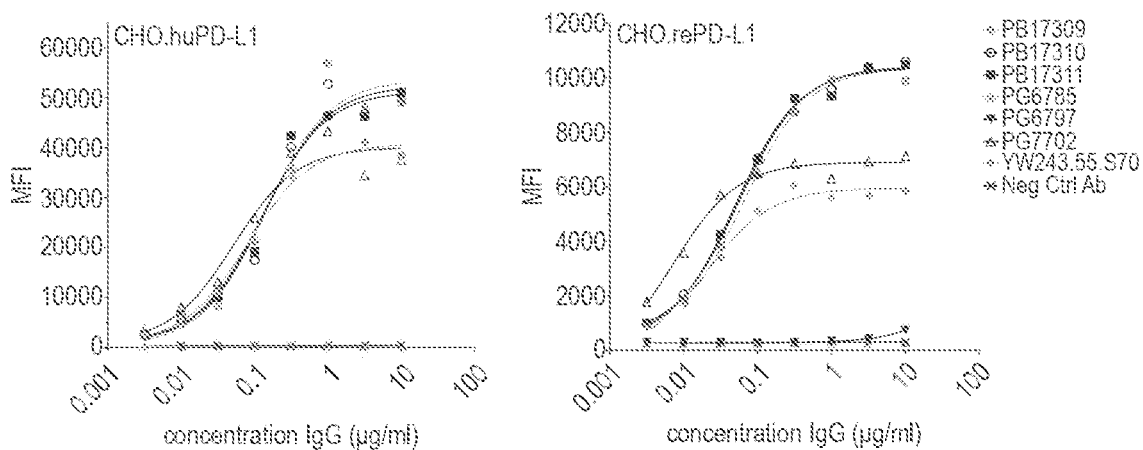

FIG. 23. Bispecific anti-CD137xPD-L1 antibodies and their parental bivalent anti-PD-L1 antibodies bind to human and rhesus macaque PD-L1 as determined by flow cytometry.

Figure 24:
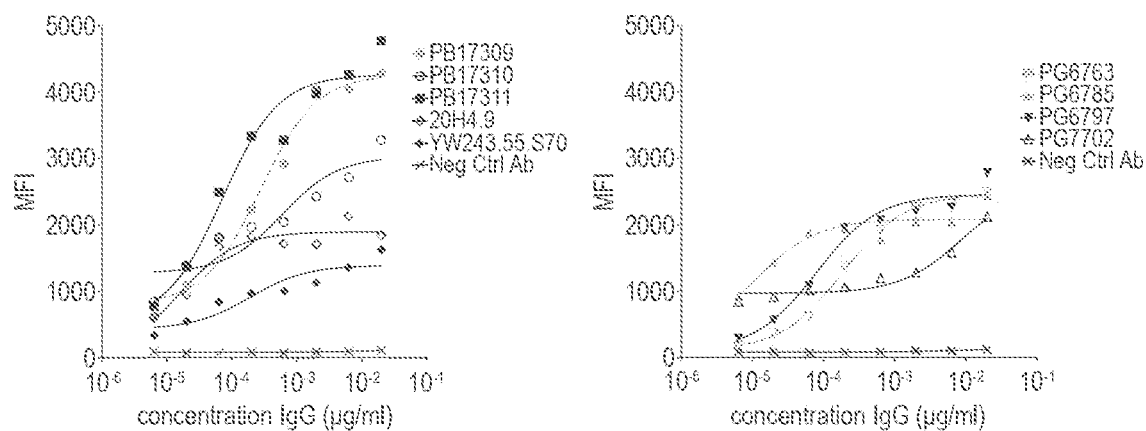

FIG. 24. Bispecific anti-CD137xPD-L1 antibodies and their parental bivalent antibodies bind to activated T cells as determined by flow cytometry.

Figure 25:
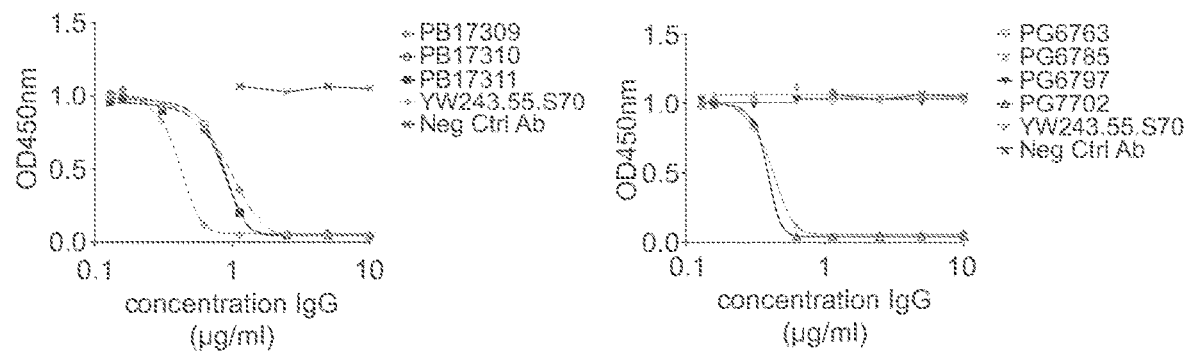

FIG. 25. Bispecific anti-CD137xPD-L1 antibodies and their parental bivalent anti-PD-L1 antibodies block PD-L1 ligand binding as determined by ELISA FIG. 26. Bispecific anti-CD137xPD-L1 antibodies and their parental bivalent anti-PD-L1 antibodies block CD137 ligand binding as determined by flow cytometry FIG. 27. Bispecific anti-CD137xPD-L1 antibodies and their parental bivalent antibodies block the interaction between PD-L1 and PD-1 in an in vitro blockade reporter assay.

FIG. 28 A. Transactivation of CD137 on Jurkat-CD137-luc cells in the presence of CHO cells expressing different PD-L1 binding sites per cell in comparison to CHO wildtype cells. CD137 activation was measured by luciferase expression.

FIG. 28 B. Transactivation of CD137 on Jurkat-CD137-luc cells in the presence of human tumor cells expressing different PD-L1 binding sites per cell PD-L1. CD137 activation was measured by luciferase expression FIG. 28 C. Transactivation of CD137 on Jurkat-CD137-luc cells in the presence of CHO-PD-L1, ES-2 or CHO wild type cells. IgG were tested in triplicate at 10 µg/ml. CD137 activation was measured by luciferase expression. Below the tested antibodies and their composition

| PB/PG | Target arm#1 | MF | Target arm#2 | MF |
|---|---|---|---|---|
| PG6763 | CD137 | 6763 | CD137 | 6763 |
| PB17309 | CD137 | 6763 | PD-L1 | 7702 |
| PB14879 | CD137 | 6763 | TT | 1337 |
| PG6785 | CD137 | 6785 | CD137 | 6785 |
| PB17310 | CD137 | 6785 | PD-L1 | 7702 |
| PB17200 | CD137 | 6785 | TT | 1337 |
| PG6797 | CD137 | 6797 | CD137 | 6797 |
| PB17311 | CD137 | 6797 | PD-L1 | 7702 |
| PB17207 | CD137 | 6797 | TT | 1337 |
| 40H4.9 | CD137 | NA | CD137 | NA |
| Ctrl Ab | TT | 1337 | TT | 1337 |

Figure 29:
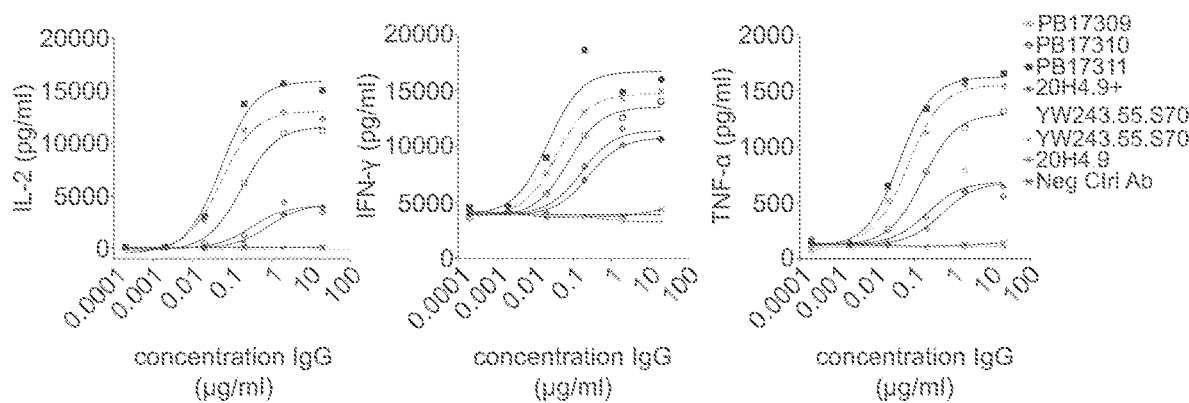

FIG. 29. Comparing CD137 x PD-L1 antibodies in T-cell activation assay to single and combination of reference controls. CD137 activation was measured as IL-2 and TNFα cytokine release and measured by Luminex analysis.

Figure 30:
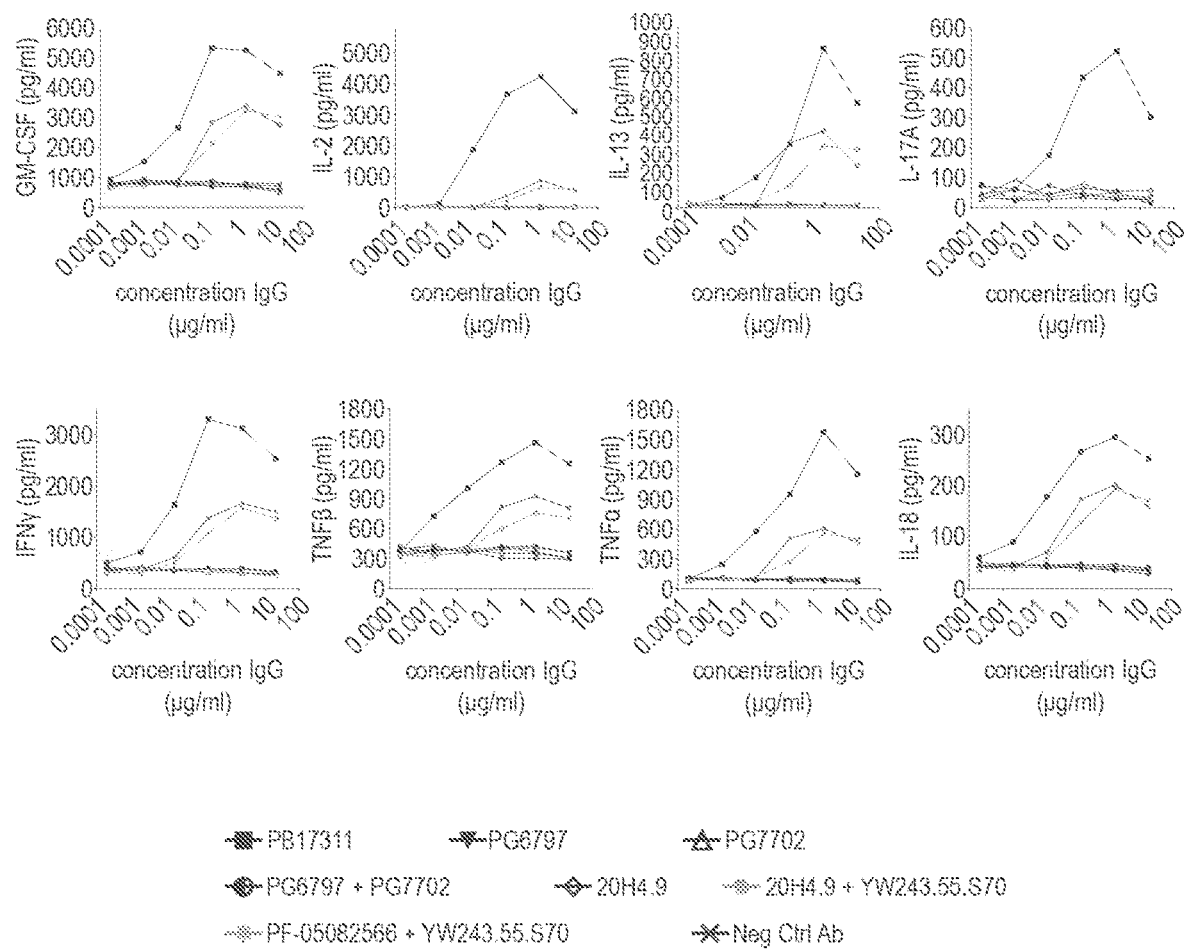
Figure 30:
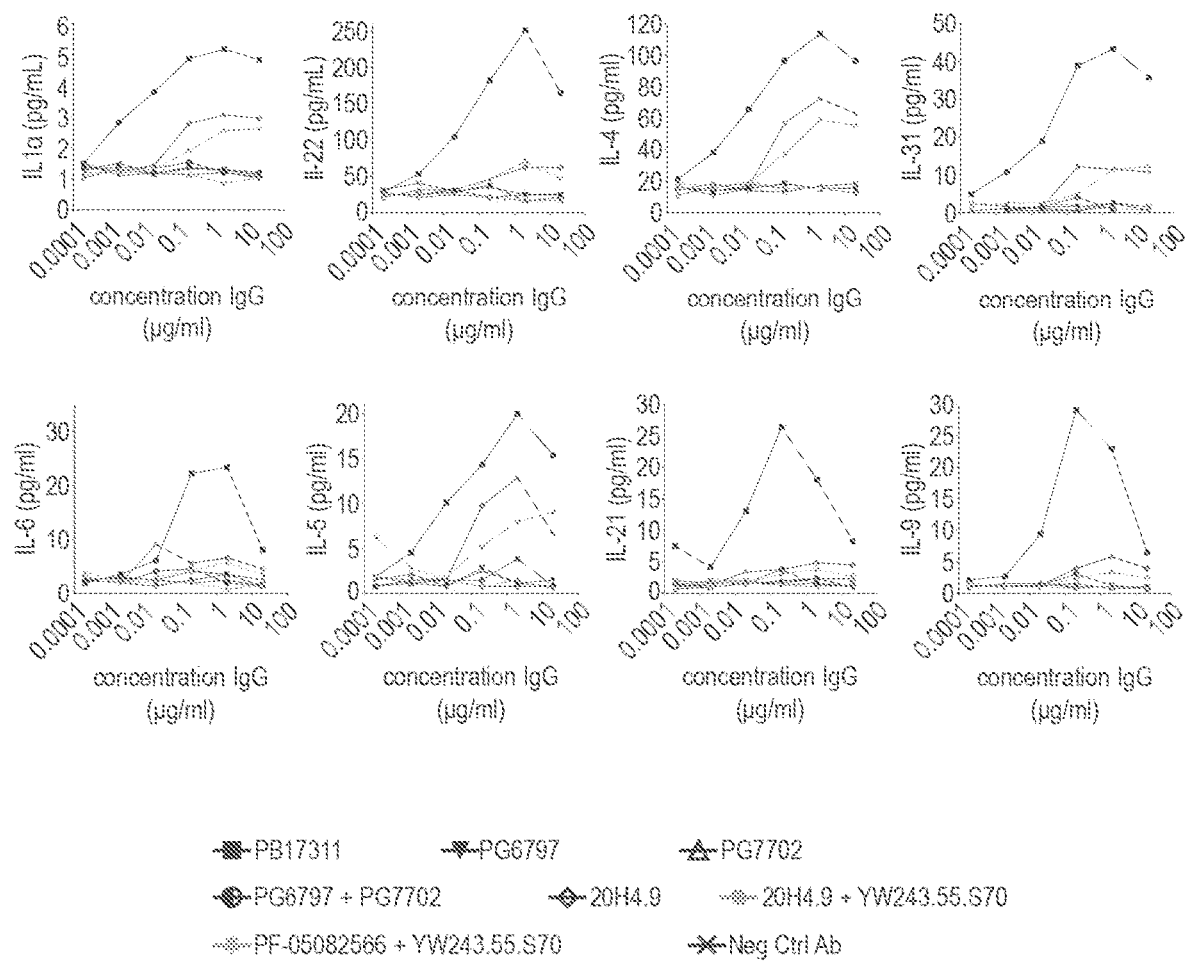

FIG. 30. Activity of CD137 x PD-L1 antibody PB17311 in T-cell activation assay in comparison to single and combination of reference control antibodies. CD137 activation was measured by multiple cytokine release and measured by Luminex analysis (25plex).

FIG. 31. Bispecific anti-CD137xPD-L1 antibodies consistently enhance IL-2 release by PBMCs during a SEB stimulation assay, regardless of PBMC donor or SEB concentration. CD137 activation was measured as IL-2 release and measured by Luminex analysis FIG. 32. Bispecific anti-CD137xPD-L1 antibodies are more potent than an anti-CD137 benchmark antibody or an equimolar mix of anti-CD137 and anti-PD-L1 benchmark antibodies at enhancing cytokine release during a SEB stimulation assay. CD137 activation was measured as IL-2, IFNγ and TNFα cytokine release and measured by Luminex analysis FIG. 33. PB17311 inhibits M2 macrophage-mediated suppression of anti-CD3/CD28-stimulated PBMCs as demonstrated by enhancement of IFNγ release.

Figure 34:
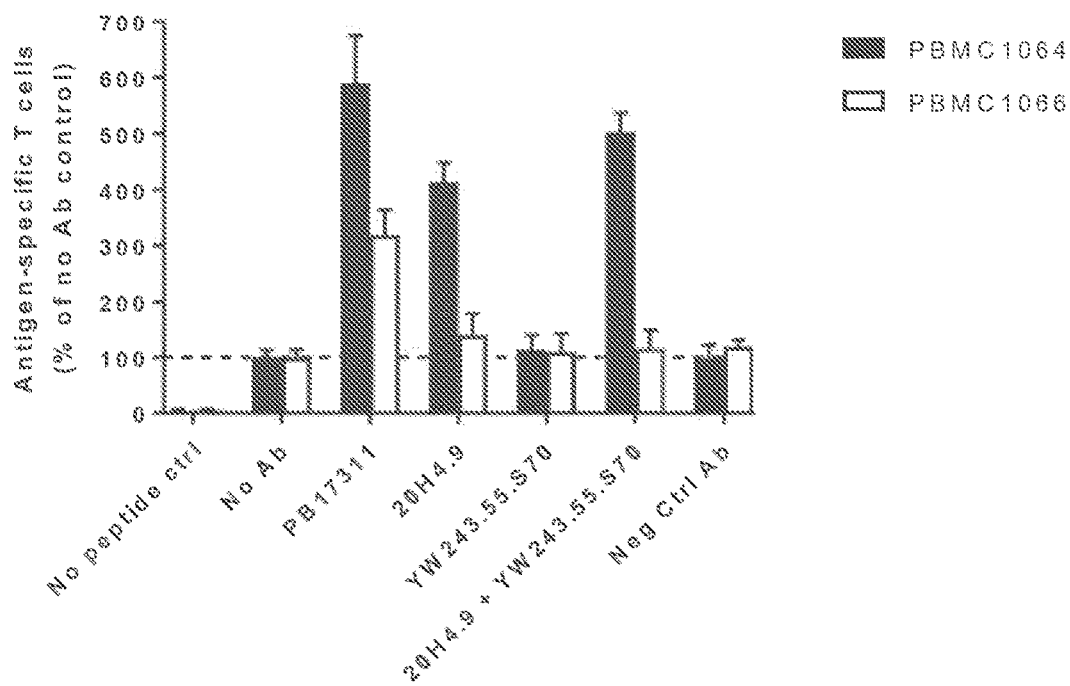

FIG. 34. PB17311 enhances T cell expansion following CD8+ T cell priming.

Figure 35:
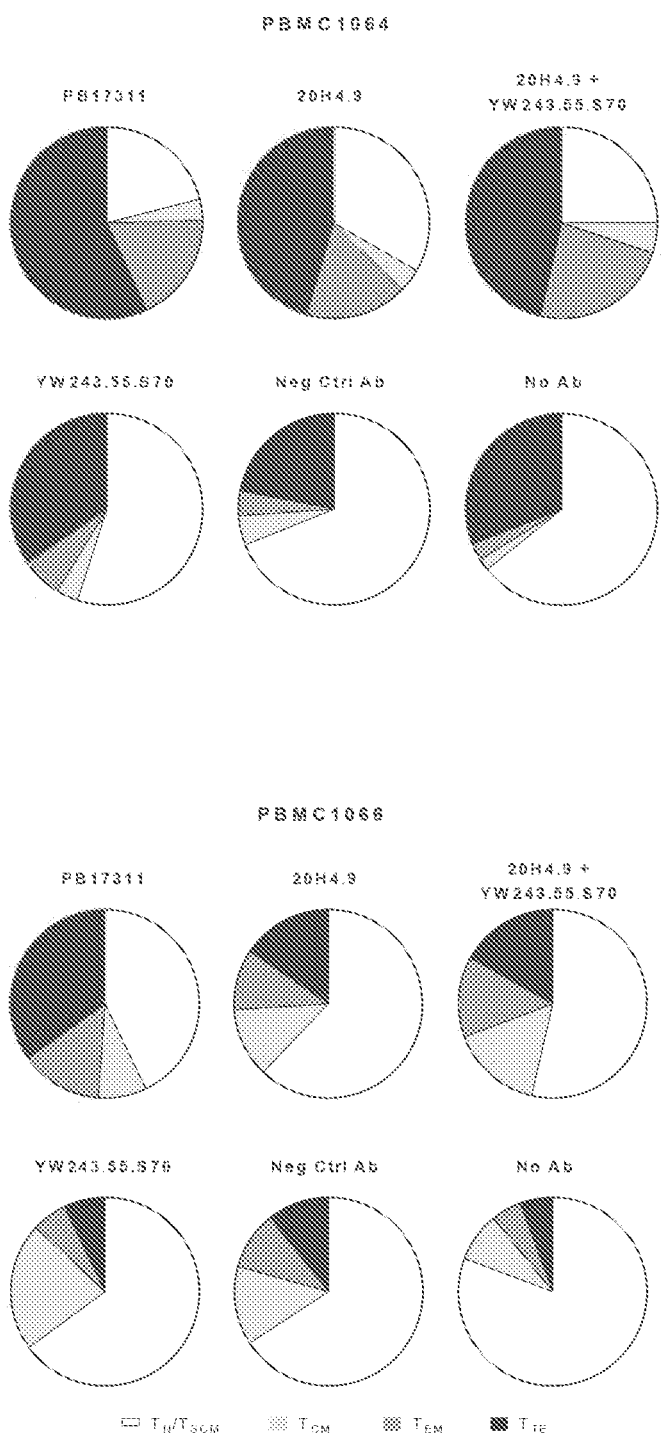

FIG. 35. PB17311 enhances differentiation of naïve T cells into central memory and effector T cells following priming. $T_{NSCM}$, Naive/Stem Cell Memory; $T_{CM}$, Central Memory, $T_{EM}$, Effector Memory; $T_E$, Terminal Effector cells.

Figure 36:
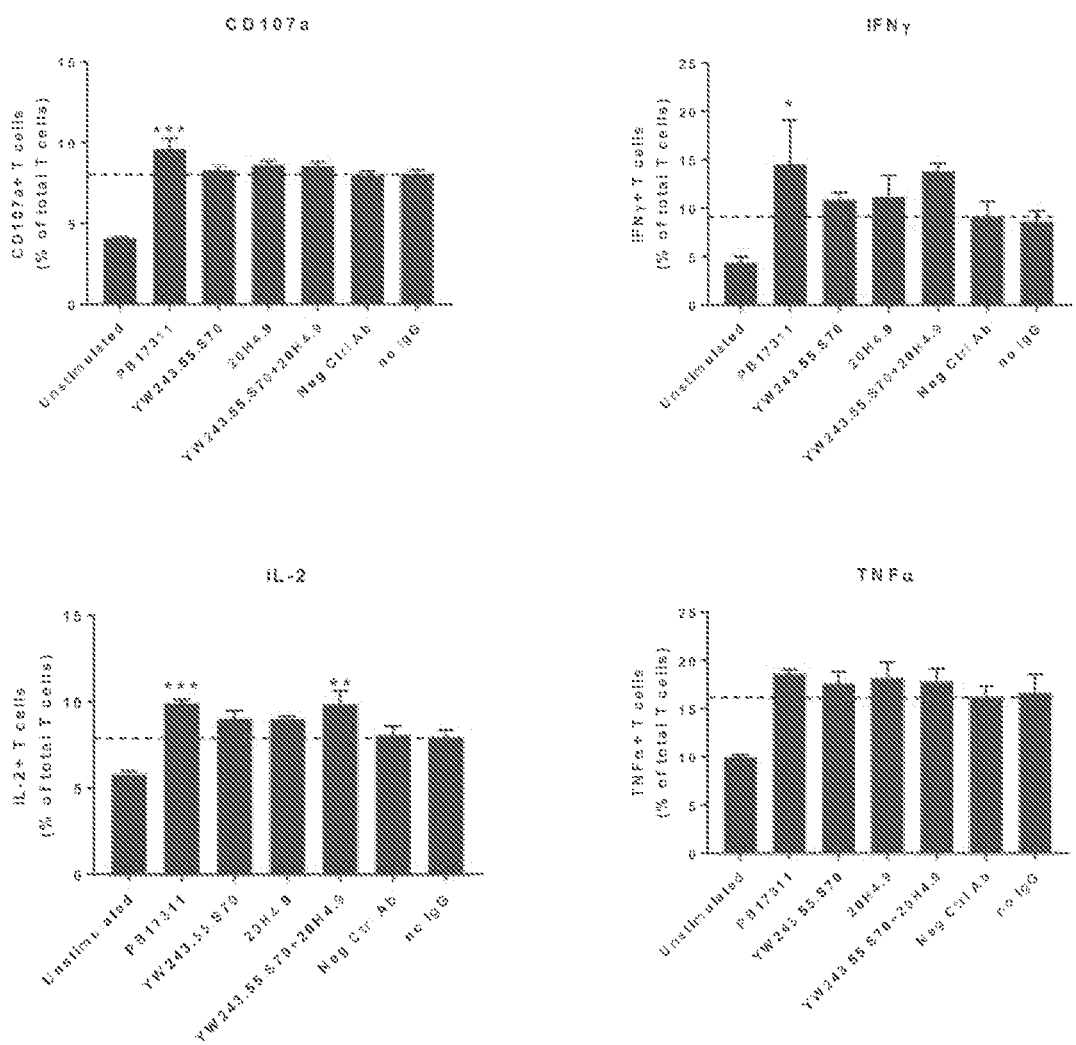

FIG. 36. Effect of PB17311 on the expression of CD107a and cytokines in the total T cell population. $T_{EM}$, Effector Memory; $T_E$, Terminal Effector cells FIG. 37. Effect of PB17311 on the expression of CD107a and cytokines in T cell subsets.

Figure 38:
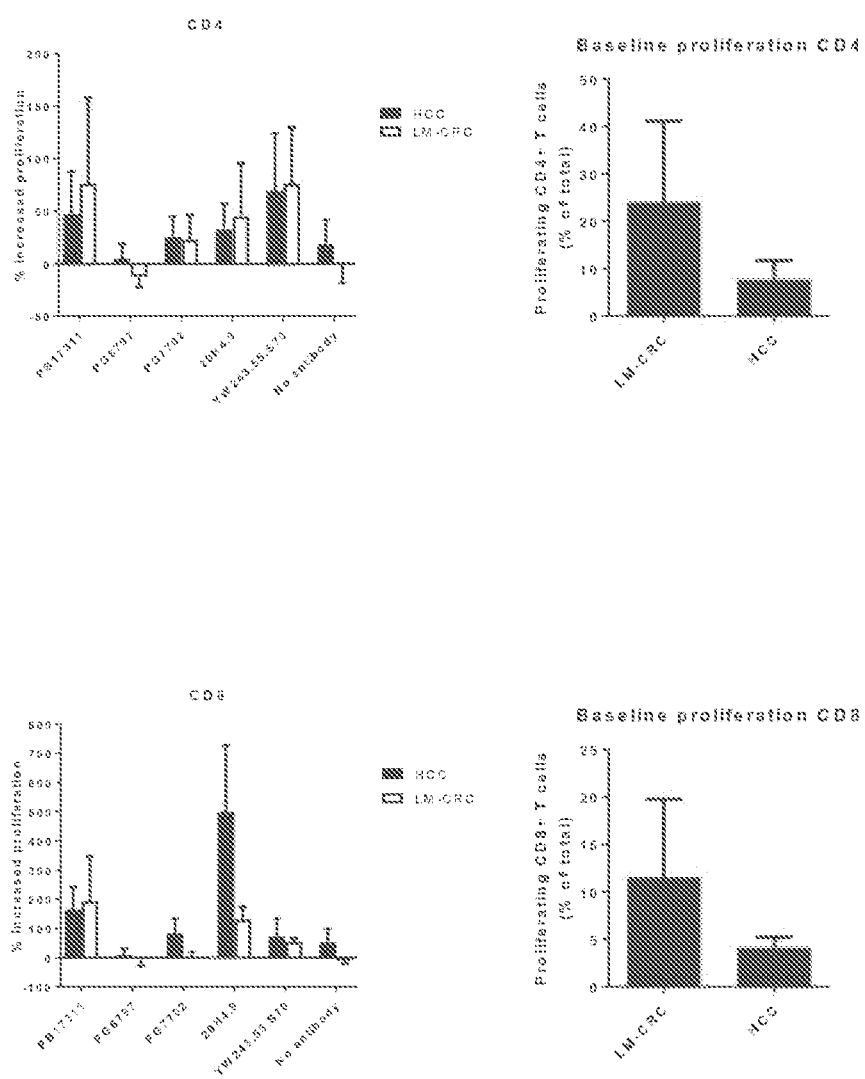

FIG. 38. Effect of PB17311 on the proliferation of tumor-infiltrating CD4 and CD8 T cells derived from liver metastasis in colorectal cancer (LM-CRC) and hepatic carcinoma (HCC).

FIG. 39. Identification and visualization of critical residues in CD137 for PB17311. (A) For each mutated clone, the mean binding value is plotted as a function of the clone's mean CD137 expression value (gray circles), as measured by control antibody binding. Binding is expressed as a percentage of that obtained with the WT clone. Dotted lines indicate thresholds used to identify critical clones (black dots). (B) The table lists the mean binding reactivities (and ranges) for all critical residues identified. Critical residues for PB17311 Ab binding (outlined in black) were negative for PB17311 Ab binding (<20% of binding to WT) but positive for the control antibody, 555955 MAb (>70% WT). (C) The critical residues (boxed outline) are visualized on a CD137 model based on the structure of murine OX40L bound to human OX40 (PDB ID #2HEY, Compaan et al., 2006). The non-validated residue, C133, is shown in gray.

Figure 40:
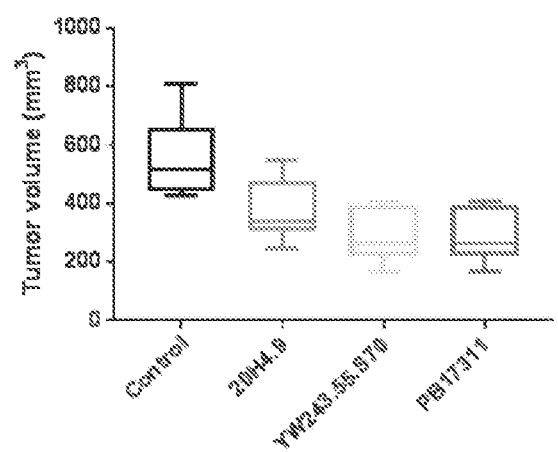

FIG. 40. Effect of CD137xPD-L1 bispecific antibody PB17311 on median tumor volume at day 19 in a xenograft mouse model. MTV, median tumor volume; TGI, tumor growth inhibition; statistical significance in Mann-Whitney test indicated by *(0.01<P<0.05) and ***(P<0.001) when compared with Group 1

Figure 41:
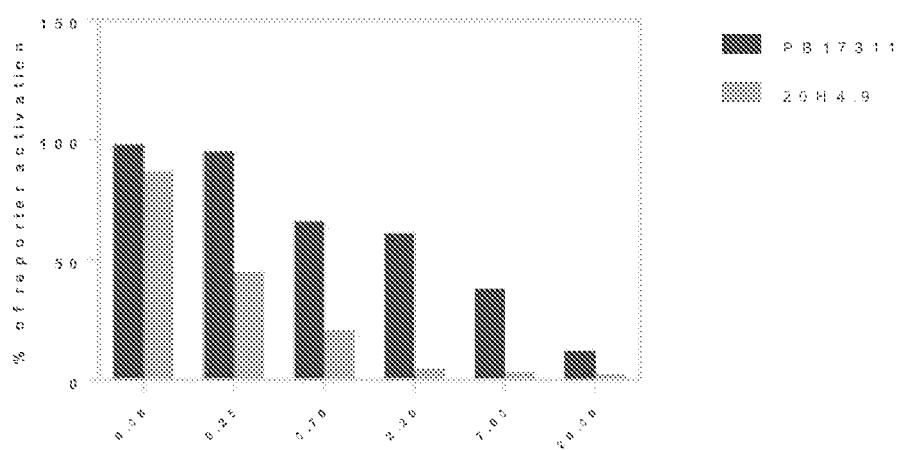

FIG. 41. Interference of sCD137 with T-cell activation. Assessment of effect of soluble CD137 on the ability of bispecific CD137xPD-L1 antibody to activate human primary T cells.

FIG. 42. Amino acid sequence of CD137 extracellular domain.

FIG. 43. Amino acid sequence of MF6256.

EXAMPLES

As used herein "MFXXXX" wherein X is independently a numeral 0-9, refers to a Fab comprising a variable domain wherein the VH has the amino acid sequence identified by the 4 digits. Unless otherwise indicated the light chain variable region of the variable domain typically has a sequence of FIG. 1A, typically 1B. "MFXXXX VH" refers to the amino acid sequence of the VH identified by the 4 digits. The MF further comprises a constant region of a light chain and a constant region of a heavy chain that normally interacts with a constant region of a light chain. PG refers to a monospecific antibody comprising identical heavy and light chains. PB refers to a bispecific antibody with two different heavy chains. The variable region of the heavy chains (VH) differs and typically also the CH3 region, wherein one of the heavy chains has a KK mutation of its CH3 domain and the other has the complementing DE mutation of its CH3 domain (see for reference PCT/NL2013/050294 (published as WO2013/157954).

Example 1

Generation of Materials for Selection and Screening
Culturing of Cell Lines

Human ES-2 cells (cat. no. CRL-1978) were purchased from ATCC and routinely maintained in McCoy's 5A (Gibco) supplemented with 10% FBS (Lonza). Freestyle 293F cells (cat. no. p/n51-0029) were obtained from Invitrogen and routinely maintained in 293 FreeStyle medium. HEK293T (cat. no. ATCC-CRL-11268), and CHO-K1 (cat. no. DSMZ ACC110) cell lines were purchased from ATCC and routinely maintained in DMEM/F12 (Gibco) supplemented with L-Glutamine (Gibco) and FBS (Lonza).

Generation of OX40, CD137 and PD-L1 Expression Vectors for Immunization, and for Generation of Stable Cell Lines Full length cDNA of each target including unique restriction sites for cloning and kozak consensus sequence for efficient translation was either synthetized, or obtained via PCR amplification on a commercially available expression construct, containing the target cDNA, with specific primers that introduced unique restriction sites for cloning and kozak consensus sequence for efficient translation. The cDNA of each target was cloned into a eukaryotic expression construct such as pIRES-Neo3 (Clontech; FIG. 4) or pVAX1 (Thermo Fisher Scientific; FIG. 5) via NheI/EcoRI, resulting in pIRES-Neo3_[TARGET_NAME] and pVAX1_[TARGET_NAME], respectively. The insert sequences were verified by comparison with NCBI Reference amino acid sequences. The pIRES-Neo3 constructs were used for generation of stable cell lines. The pVAX1 constructs were used for immunization purposes. See TABLE 1 for an overview of the names of the resulting constructs.

Amino acid sequence full length huCD137 insert (both in pIRES-Neo3 and pVAX1) for expression on the cell surface (Identical to GenBank: NP_001552.2):

MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

-continued

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL

Of which:

MGNSCYNIVATLLLVLNFERTRS: signal peptide.

LQDPCSNCPAGTFCDNNRNQICSPCPPNSFSSAGGQRTCDICRQCKGVFR

TRKECSSTSNAECDCTPGFHCLGAGCSMCEQDCKQGQELTKKGCKDCCFG

TFNDQKRGICRPWTNCSLDGKSVLVNGTKERDVVCGPSPADLSPGASSVT

PPAPAREPGHSPQ: ECD of huCD137.

IISFFLALTSTALLFLLFFLTLRFSVV: Predicted TM region.

KRGRKKLLYIFKQPFMRPVQTTQEEDGCSCRFPEEEEGGCEL:
Intracellular tail.

Amino acid sequence full length macaque (*Macaca fascicularis*) CD137 insert (both in pIRES-Neo3 and pVAX1) for expression on the cell surface (Identical to GenBank: ABY47575.1):

MGNSCYNIVATLLLVLNFERTRSLQDLCSNCPAGTFCDNNRSQICSPCPP

NSFSSAGGQRTCDICRQCKGVFKTRKECSSTSNAECDCISGYHCLGAECS

MCEQDCKQGQELTKKGCKDCCFGTFNNKRGICRPWTNCSLDGKSVLVNGT

KERDVVCGPSPADLSPGASSATPPAPAREPGHSPQIIFFLALTSTVVLFL

LFFLVLRFSVVKRSRKKLLYIFKQPFMRPVQTTQEEDGCSCRFPEEEEGG

CEL

Of which:

MGNSCYNIVATLLLVLNFERTRS: signal peptide.

LQDLCSNCPAGTFCDNNRSQICSPCPPNSFSSAGGQRTCDICRQCKGVFK

TRKECSSTSNAECDCISGYHCLGAECSMCEQDCKQGQELTKKGCKDCCFG

TFNDQKRGICRPWTNCSLDGKSVINNGTKERDVVCGPSPADLSPGASSAT

PPAPAREPGHSPQ: ECD of maCD137.

IIFFLALTSTVVLFLLFFLVLRFSVV: Predicted TM region.

KRSRKKLLYIFKQPFMRPVQTNEEDGCSCRFPEEEEGGCEL:
Intracellular tail.

Amino acid sequence full length rat CD137 insert (both in pIRES-Neo3 and pVAX1) for expression on the cell surface (Identical to GenBank: XP_008762505.1):

MGSSCYNMVVTVLLVVGTEEVRATRNPCDSCEAGTFCSKYPPVCTSCPPS

TYSSTGGQPNCDICRVCQGYFRFKKPCSSTHNAECECVEGFHCLGPKCTR

CEKDCRPGQELTEQGCKNCGLGTFNDQDGAGVCRPWTNCSLDGRSVLKNG

TKEKDVVCGPPVVSLSPSTTPSAVTTPERESGERPLQVLTLFLALTLALL

LFLIFIILWFSVPKWLRKKFPHIFKQPFKKAVRTAQEEDACSCRFPEEEE

GGGGSYEL

Of which:

MGSSCYNMVVTVLLVVGTEEVRA: signal peptide.

TRNPCDSCEAGTFCSKYPPVCTSCPPSTYSSTGGQPNCDICRVCQGYFRF
KKPCSSTHNAECECVEGFHCLGPKCTRCEKDCRPGQELTEQGCKNCGLGT
FNDQDGAGVCRPWTNCSLDGRSVLKNGTKEKDVVCGPPVVSLSPSTTPSA
VTTPERESGERPLQ: ECD of raCD137.

VLTLFLALTLALLLFLIFIILWF: Predicted TM region.

SVPKWLRKKFPHIFKQPFKKAVRTNEEDACSCRFPEEEEGGGGSYEL: Intracellular tail.

Amino acid sequence full length huPD-L1 insert (both in pIRES-Neo3 and pVAX1) for expression on the cell surface (Identical to GenBank: AAI13735.1):

MRIFAVFIFMTYWHLLNAFTVTVPKDLYVVEYGSNMTIECKFPVEKQLDL
AALIVYWEMEDKNIIQFVHGEEDLKVQHSSYRQRARLLKDQLSLGNAALQ
ITDVKLQDAGVYRCMISYGGADYKRITVKVNAPYNKINQRILVVDPVTSE
HELTCQAEGYPKAEVIWTSSDHQVLSGKTTTTNSKREEKLFNVTSTLRIN
TTTNEIFYCTFRRLDPEENHTAELVIPELPLAHPPNERTHLVILGAILLC
LGVALTFIFRLRKGRMMDVKKCGIQDTNSKKQSDTHLEET

Of which:

MRIFAVFIFMTYWHLLNA: signal peptide.

FTVTVPKDLYVVEYGSNMTIECKFPVEKQLDLAALIVYWEMEDKNIIQFV
HGEEDLKVQHSSYRQRARLLKDQLSLGNAALQITDVKLQDAGVYRCMISY
GGADYKRITVKVNAPYNKINQRILVVDPVTSEHELTCQAEGYPKAEVIWT
SSDHQVLSGKTTTTNSKREEKLFNVTSTLRINTTTNEIFYCTFRRLDPEE
NHTAELVIPELPLAHPPNER: ECD of huPD-L1.

THLVILGAILLCLGVALTFIF: Predicted TM region.

RLRKGRMMDVKKCGIQDTNSKKQSDTHLEET: Intracellular tail.

Amino acid sequence full length macaque (*macaca mulatta*) PD-L1 insert (both in pIRES-Neo3 and pVAX1) for expression on the cell surface (Identical to GenBank: AB033161.1):

MRIFAVFIFTIYWHLLNAFTVTVPKDLYVVEYGSNMTIECRFPVEKQLGL
TSLIVYWEMEDKNIIQFVHGEEDLKVQHSNYRQRAQLLKDQLSLGNAALR
ITDVKLQDAGVYRCMISYGGADYKRITVKVNAPYNKINQRILVVDPVTSE
HELTCQAEGYPKAEVIWTSSDHQVLSGKTTTTNSKREEKLLNVTSTLRIN
TTANEIFYCIFRRLGPEENHTAELVIPELPLALPPNERTHLVILGAIFLL
LGVALTFIFYLRKGRMMDMKKSGIRVTNSKKQRDTQLEET

Of which:

MRIFAVFIFTIYWHLLNA: signal peptide.

FTVTVPKDLYVVEYGSNMTIECRFPVEKQLGLTSLIVYWEMEDKNINFVH
GEEDLKVQHSNYRQRAQLLKDQLSLGNAALRITDVKLQDAGVYRCMISYG
GADYKRITVKVNAPYNKINQRILVVDPVTSEHELTCQAEGYPKAEVIWTS
SDHQVLSGKTTTTNSKREEKLLNVTSTLRINTTANEIFYCIFRRLGPEEN
HTAELVIPELPLALPPNER: ECD of maPD-L1.

THLVILGAIFLLLGVALTFIF: Predicted TM region.

YLRKGRMMDMKKSGIRVTNSKKQRDTQLEET: Intracellular tail.

Amino acid sequence full length human OX40 insert (both in pIRES-Neo3 and pVAX1) for expression on the cell surface (Identical to GenBank: NP_003318.1):

MCVGARRLGRGPCAALLLLGLGLSTVTGLHCVGDTYPSNDRCCHECRPGN
GMVSRCSRSQNTVCRPCGPCIFYNDVVSSKPCKPCTWCNLRSGSERKQLC
TATQDTVCRCRAGNPLDSYKPGVDCAPCPPGHFSPGDNQACKPWTNCTLA
GKHTIAPASNSSDAICEDRDPPATQPQETQGPPARPITVQPTEAWPRTSQ
GPSTRPVEVPGGRAVAAILGLGLVLGLLGPLAILLALYLLRRDQRLPPDA
HKPPGGGSFRTPIQEEQADAHSTLAKI

Of which:

MCVGARRLGRGPCAALLLLGLGLSTVTG: signal peptide.

LHCVGDTYPSNDRCCHECRPGNGMVSRCSRSQNTVCRPCGPGFYNDVVSS
KPCKPCTWCNLRSGSERKQLCTATQDTVCRCRAGTQPLDSYKPGVDCAPC
PPGHFSPGDNQACKPWTNCTLAGKHTLQPASNSSDAICEDRDPPATQPQE
TQGPPARPITVQPTEAWPRTSQGPSTRPVEVPGGRA: ECD.

VAAILGLGLVLGLLGPLAILL: Predicted TM region.

ALYLLRRDQRLPPDAHKPPGGGSFRTPIQEEQADAHSTLAKI: Intracellular tail.

Amino acid sequence full length rat (*Rattus norvegicus*) OX40 insert (both in pIRES-Neo3 and pVAX1) for expression on the cell surface (Identical to GenBank: NP_037181.1):

MYVWVQQPTAFLLLGLSLGVTVKLNCVKDTYPSGHKCCRECQPGHGMVSR
CDHTRDTVCHPCEPCIFYNEAVNYDTCKQCTQCNHRSGSELKQNCTPTED
TVCQCRPGTQPRQDSSHKLGVDCVPCPPGHFSPGSNQACKPWTNCTLSGK
QIRHPASNSLDTVCEDRSLLATLLWETQRTTFRPTTVPSTTVWPRTSQLP
STPTLVAPEGPAFAVILGLGLCILLAPLTVLLALYLLRKAWRSPNTPKPC
WGNSFRTPIQEEQTDTHFTLAKI

Of which:

MYVWVQQPTAFLLLGLSLG: signal peptide.

VTVKLNCVKDTYPSGHKCCRECQPGHGMVSRCDHTRDTVCHPCEPGFYNE
AVNYDTCKQCTQCNHRSGSELKQNCTPTEDTVCQCRPGTQPRQDSSHKLG
VDCVPCPPGHFSPGSNQACKPWTNCTLSGKQIRHPASNSLDTVCEDRSLL
ATLLWENRTTFRPTTVPSTTVWPRTSQLPSTPTLVAPEGP: ECD.

```
-continued
AFAVILGLGLGLLAPLTVLLALYLL: Predicted TM region.

RKAWRSPNTPKPCWGNSFRTPIQEEQTDTHFTLAKI:
Intracellular tail.
```

Amino acid sequence full length macaque (*Macaca fascicularis*) OX40 insert (both in pIRES-Neo3 and pVAX1) for expression on the cell surface (Identical to GenBank: XP_005545179.1):

```
MCVGARRLGRGPCAALLLLGLGLSTTAKLHCVGDTYPSNDRCCQECRPGN

GMVSRCNRSQNTVCRPCGPGFYNDVVSAKPCKACTWCNLRSGSERKQPCT

ATQDTVCRCRAGTQPLDSYKPGVDCAPCPPGHFSPGDNQACKPWTNCTLA

GKHTLQPASNSSDAICEDRDPPPTQPQETQGPPARPTTVQPTEAWPRTSQ

RPSTRPVEVPRGPAVAAILGLGLALGLLGPLAMLLALLLLRRDQRLPPDA

PKAPGGGSFRTPMEEQADAHSALAKI
```

Of which:

```
MCVCIARRLGRGPCAALLLLGLGLSTTAK: signal peptide.

LHCVGDTYPSNDRCCQECRPGNGMVSRCNRSQNTVCRPCGPGFYNDVVSA

KPCKACTWCNLRSGSERKQPCTATQDTVCRCRAGTQPLDSTKPGVDCAPC

PPGHFSPGDNQACKPWTNCTLAGKHTIAPASINSSDAICEDRDPPPTQPQ

ETQGPPARPTTVQPTEAWPRTSQRPSTRPVEVPRGPA: ECD.

VAAILCILGLALGLLGPLAMLL: Predicted TM region.

ALLLLRRDQRLPPDAPKAPGGGSTRTPIQEEQADARSALAKI:
Intracellular tail.
```

Generation of stable cell lines expressing CD137, OX40 or PD-L1 pIRES-Neo3_[TARGET_NAME] expression constructs (TABLE 1) were used to generate Freestyle 293F or CHO-K1 clones stably expressing the respective proteins. Constructs were transiently transfected in CHO-K1 cells using lipofectamine transfection, or using PEI transfection for Freestyle 293F cells and screened by FACS using antibodies reacting with the respective proteins. After confirmation of expression, transiently transfected cells were seeded in limiting dilution and cultured under selection pressure relevant for the used expression construct to obtain stable cell clones. After 2-3 weeks of selection, clones were screened by FACS. The selected clones were expanded by serial passage, retested in FACS and frozen to −150° C. The names of clones that stably express the heterologous proteins are CHO-K1_[TARGET_NAME] cells or Freestyle 293F_[TARGET_NAME] cells. See TABLE 1 for an overview of the constructs used to generate the stable cell lines and their resulting name.

Example 2

Immunization, Selection and Screening

Mice Used for Immunizations

For generation of human antibodies binding to huCD137, huOX40 and huPD-L1, mice transgenic for the human VK1-39 light chain (common light chain mice, see WO2009/157771) and for a human heavy chain (HG) minilocus (comprising a selection of human V gene segments, all human Ds and all human Js) were immunized with either recombinant protein or DNA encoding the proteins as briefly described below. These mice are referred to as 'MeMo®' mice.

Protein Immunizations

'MeMo®' mice were immunized by subcutaneous injections with recombinant protein and Gerbu adjuvant MM (Gerbu Biotechnik c #3001). Recombinant huPD-L1-His (SinoBiological; cat. no. 10084-H08H), huOX40-Fc (R&D; cat. no. 3388-OX) and huOX40-His (SinoBiological; cat. no. 10481-H08H) proteins were used for immunizations. No protein immunizations were performed for CD137 antibody panel generation. Mice were immunized with 40 μg recombinant protein in PBS mixed with 40 μl of adjuvant in a total volume of 100 μl. Subsequently mice were boosted on day 14 and 28 with 20 μg of recombinant protein in PBS together with 20 μl of adjuvant in a total volume of 50 μl. Mouse serum was collected at day 35 to determine serum titers. Mice with low serum titers received additional cycles of booster immunizations and serum analyses. Each cycle consisted of two weekly immunizations using 20 μg of recombinant protein in 50 μl PBS followed one week later by serum collection for titer analysis. Mice showing high serum titers against the human and macaque target received a final boost immunization consisting of daily injections with 20 μg of recombinant protein in 50 μl PBS on three consecutive days. One day after the final injection mouse lymphoid tissue was collected.

DNA Immunizations

MeMo®' mice were immunized by DNA tattooing using a micropigmentation device. DNA tattoo immunizations were performed with 20 μg plasmid DNA encoding the target antigen (pVAX1_[TARGET_NAME], TABLE 1). Mice were immunized with DNA encoding the human target only (PD-L1) or by alternating immunizations with DNA encoding the human and rat (CD137, OX40) target to obtain species cross-reactive antibodies. For PD-L1 immunizations, Treg cells were depleted four days prior to the start of immunization by injection of mice with 0.5 mg anti-CD25 antibody PC61.5 (Bioceros) to break tolerance. Mice were immunized at day 0, 3, 6, 14, 17, 28 and 31. Mouse serum was collected at day 35 to determine serum titers. Mice with low serum reactivity against the human and/or macaque target received additional cycles of booster immunizations with human, rat or macaque DNA antigen and serum analyses. Each cycle consisted of two weekly DNA immunizations followed one week later by serum collection for titer analysis. Mice showing strong serum reactivity against cells expressing the human and macaque target received a final boost immunization followed after 3 days by collection of lymphoid tissue.

Combination of Protein and DNA Immunizations (OX40 Only)

Mice were immunized with recombinant huOX40-His (SinoBiological; cat. no. 10481-H08H) and boosted by alternating DNA (pVAX1_raOX40) and protein (huOX40-His) immunizations to obtain species cross-reactive antibodies. Therefore, mice were immunized with 40 μg recombinant protein in PBS mixed with 40 μl of adjuvant in a total volume of 100 μl. Subsequently mice were boosted on day 14 and 17 by DNA tattooing with 20 μg pVAX1_raOX40, followed on day 28 by protein immunization with 20 μg of huOX40-His protein in PBS together with 20 μl of adjuvant in a total volume of 50 μl. Mouse serum was collected at day 35 to determine serum titers. Mice with low human and/or macaque serum titers received additional cycles of booster immunizations and serum analyses. Each cycle consisted of two weekly protein or DNA immunizations with 20 μg huOX40-His, pVAX1_raOX40 or pVAX1_maOX40 followed one week later by serum collection for titer analysis. Mice showing high serum titers against the human and macaque target received a final boost immunization consisting of daily injections with 20 µg of recombinant protein in 50 µl PBS on three consecutive days. One day after the final injection mouse lymphoid tissue was collected.

Determination of Serum Titers

Serum titers were determined by FACS analysis using cell lines expressing the human and macaque target antigens (Table 1).

Generation of Synthetic Phage Fab Libraries

Synthetic libraries were constructed based on a repertoire of germline human VH genes that were selected for frequent use in natural repertoires and canonical sequence diversity. Synthetic HCDR3 regions were added to these VH genes using PCR. This was done using forward primers that anneal to framework 1 of the VH genes and include a SfiI restriction site for cloning. Reverse primers included sequences to anneal to framework 3 of the VH genes, followed by randomized sequences to encode HCDR3 diversity and a framework 4 encoding sequence also containing a BstEII and XhoI restriction site for cloning. Synthetic CDR3 regions were either completely random or encoded a more restricted diversity based on the frequency of use of amino acid residues at certain positions within the HCDR3. PCR products encoding the VH genes were cloned into phage display vectors in fusion with phage M13 gene 3 protein using aforementioned restriction enzymes and also containing a common light chain encoding gene. Large scale ligation and transformation of E. coli TG1 resulted in large libraries of synthetic Fab fragments displayed on phage which were used for panning on antigens or cells to identify antigen-specific Fab fragments.

Generation of 'Immune' Phage Fab Libraries by RT-PCR from Tissues of Immunized Mice Spleen and draining lymph nodes were removed from mice for which a significant humoral response was observed against the respective target proteins. Single cell suspensions were generated from both spleen and inguinal lymph nodes and subsequently these tissues were lysed in Trizol LS Reagent (Thermo Scientific c #10296028) and stored at −80° C. until use.

From successfully immunized mice, the inguinal lymph nodes were used for the construction of 'immune' phage antibody repertoires. RNA was extracted from the single cell suspensions of the lymphoid tissue. 1 µg of total RNA was used in a RT reaction using an IgG-CH1 specific primer. The resulting cDNA was then used to amplify the polyclonal pool of VH-encoding cDNA using in-house adapted VH-specific primers essentially as described in Marks et al. (J Mol Biol. 1991 Dec. 5; 222(3):581-97). The resulting PCR product was then cloned in a phagemid vector (FIG. 6) for the display of Fab fragments on phage, as described in de Haard et al. (J Biol Chem. 1999 Jun. 25; 274(26):18218-30) with the exception that the light chain (FIGS. 1A and 1B) was the same for every antibody and was encoded by the vector. After ligation, the phagemids were used to transform E. coli TG1 bacteria and transformed bacteria were plated onto LB-agar plates containing ampicillin and glucose. All phage libraries contained >4×10$^5$ transformants and had an insert frequency of >90%. Bacteria were harvested after overnight growth and used to prepare phage according to established protocols (de Haard et al., J Biol Chem. 1999 Jun. 25; 274(26):18218-30).

Selection of Phage Carrying Fab Fragments Specifically Binding to Human Target Protein from Synthetic and 'Immune' Phage Fab Libraries Using Recombinant Proteins The phage Fab libraries that were generated were used to select target specific Fabs using phage display on directly coated recombinant proteins. For PD-L1, huPD-L1-His (Sinobiological; cat. no. 10084-H08H), huPD-L1-Fc (R&D; cat. no. 156-B7), and maPD-L1-His (Sinobiological; cat. no. 90251-C08H) were used. For CD137, huCD137-Fc (R&D; cat. no. 838-4B), raCD137-Fc (R&D; cat. no. 7968-4B), moCD137-Fc (R&D; cat. no. 937-4B), huCD137-His (Sino-Biological; cat. no. 10041-H08H) and huCD137-Fc (Enzo; cat. no. ALX-522-031-C050) were used, and for OX40, huOX40-Fc (R&D; cat. no. 3388-OX) and huOX40-His (Sinobiological; cat. no. 10481-H08H).

For selections with recombinant protein, proteins were coated onto the wells of a MAXISORP™ ELISA plate. The MAXISORP™ ELISA plates were blocked with 4% dried skimmed milk (Marvel) in PBS. Phage Fab libraries were also blocked with 4% Marvel and, when Fc tagged recombinant protein was used, also with excess of human IgG to deplete for Fc region binders prior to the addition of the phage library to the coated antigen.

Incubation of the phage library with the coated protein was performed for 1.5 hrs at room temperature under shaking conditions. Plates or tubes were then washed fifteen times with 0.05% Tween-20 in PBS followed by 5 times washing with PBS. Bound phage were eluted for 20 minutes using trypsin, after which trypsin was neutralized with AEBSF trypsin inhibitor (Sigma).

The eluates were added to E. coli TG-1 and incubated at 37° C. for phage infection. Subsequently infected bacteria were plated on agar plates containing Ampicillin and glucose, and incubated at 37° C. overnight. Single clones from the selection outputs were screened for target binding in ELISA or FACS depending on the target.

For selections with synthetic phage Fab libraries, a second round selection was performed after rescue of the first round selection output using the same protocol as outlined above for the first round selection.

Selection of Phage Carrying Fab Fragments Specifically Binding to Human Target from 'Immune' Phage Fab Libraries Using Cells Stably Expressing the Target Protein Phage Fab libraries that were generated from target immunized mice were selected using phage display on cells expressing the respective target. The stable cell lines expressing CD137, OX40 or PD-L1 (Table 1) were used for 1$^{st}$ round selections. Cells were blocked with 10% FBS in PBS. After blocking, the rescued phage were incubated with blocked cells. Cells plus phage were incubated for 1 hr at 4° C. Washing the cells (5 times) was performed using 1 ml of 10% FBS in PBS. Bound phage were eluted using trypsin for 20 minutes, after which trypsin was neutralized with AEBSF trypsin inhibitor (Sigma). The eluate was added to E. coli TG-1 and incubated at 37° C. for phage infection. Subsequently, phage-infected bacteria were plated on agar plates containing ampicillin and glucose, and incubated at 37° C. overnight.

For PD-L1, second round selections with ES-2 cells endogenously expressing huPD-L1 were performed with the same protocol as was used for the 1$^{st}$ round selection. After selection, single clones were screened for target binding in FACS.

Screening for Target Specific Fab Clones in ELISA

Of single clones, soluble Fab or phage were prepared (J Mol Biol. 1991 Dec. 5; 222(3):581-97; J Biol Chem. 1999 Jun. 25; 274(26):18218-30). Obtained soluble Fab or phage samples were diluted (1:5 or 1:10, respectively) in 4% dried skimmed milk (Marvel) in PBS (blockbuffer) and tested for binding in ELISA to wells coated with the same antigen as was used for selection, or with huCD137-Fc (R&D; cat. no.

838-4B) for all selection outputs performed with either raCD137-Fc (R&D; cat. no. 7968-4B) or moCD137-Fc (R&D; cat. no. 937-4B).

Bound Fabs were detected by staining with an anti-myc antibody (Roche; cat. no. 11667203001) diluted 1:1000 in blockbuffer, followed by a HRP-conjugated anti-mouse IgG antibody (Jackson Immunoresearch; cat. no. 715-035-150) diluted 1:5000 in blockbuffer. Bound phage were detected by staining with a HRP-conjugated monoclonal anti-M13 antibody (GE healthcare; cat. no. 27-9421-01) diluted 1:5000 in blockbuffer.

After each antibody staining, wells were washed with PBS-T (PBS-0.05% v/v Tween 20). Bound secondary antibody was visualized by $TMB/H_2O_2$ staining and staining was quantified by means of $OD_{450\ nm}$ measurement. Clones were considered to bind the target when the OD450 nm was at least three times above the background signal obtained with a negative control Fab.

The VH-encoding cDNA's of all target-specific clones were sequenced. A selection of unique clones based on sequence identity and cluster analysis was then analyzed in FACS on binding to the target expressed on cells as described below for the clones obtained from the cell selection outputs.

Screening for Target Specific Fab Clones in FACS

Of single clones, selected on cells expressing the respective target, soluble Fab or phage were prepared as described (J Mol Biol. 1991 Dec. 5; 222(3):581-97; J Biol Chem. 1999 Jun. 25; 274(26):18218-30). Fab samples were tested for binding in FACS to cells expressing the human and macaque target (Table 1) by incubation with a mix of 1:5 diluted Fab sample with 1:1000 diluted anti-myc antibody (Gentaur; cat. no. 04-CMYC-9E10) in FACS buffer (0.5% HI-FBS in PBS). Bound Fab/anti-myc complexes were detected by incubation with an APC-conjugated goat anti-mouse IgG antibody (BD Bioscience; cat. no. 550826) diluted 1:500 in FACS buffer.

Phage samples were tested for binding in FACS by diluting the phage samples 1:3 in blockbuffer and incubation with target expressing cells for 1 hour. Bound phage were detected by staining with a biotinylated anti-M13 antibody (Fitzgerald, cat. nr. 61R-M101ABTB62-FEZ, 1:125 in FACS buffer, 30 minutes on ice) and PE-labeled streptavidin (Invitrogen, cat. nr. SA1004-4; 1:400 in FACS buffer for 15 minutes on ice). After each antibody incubation, wells were washed three times with FACS buffer. Stained cells were analysed using a FACS Accuri C6 instrument (Becton and Dickinson). Clones were considered positive when the mean fluorescence intensity was at least three times above the background signal obtained with a negative control Fab.

Results

The VH sequences of 24 CD137-specific clones, 14 PD-L1-specific clones and 50 OX40-specific clones that were obtained by the above-mentioned methods are depicted in FIG. 3.

Example 3

Characterization huCD137, huOX40 and huPD-L1 Specific Fab Clones in IgG Format

Recloning Human CD137, OX40 and PD-L1 Specific Fab to IgG Format

A selection of unique clones, based on CDR3 sequence and VH germline differences, that bound human and macaque target protein expressed on cells, was then recloned to an IgG expression plasmid such as MV1452 (FIG. 7), which contained the common light chain (FIG. 1), using Sfi1-BstEII digestion and ligation of the pool of digested cDNA's according to standardized molecular biological techniques.

Expression of Bispecific IgG Containing a Human CD137, OX40 or PD-L1 Specific Fab and a Tetanus Toxin Specific Fab Bispecific antibodies were generated by transient co-transfection of two plasmids encoding IgG with different VH domains, using a proprietary CH3 engineering technology to ensure efficient hetero-dimerisation and formation of bispecific antibodies. The common light chain present on both plasmids containing the heavy chain is also co-transfected in the same cell. In our co-pending applications (e.g. WO2013/157954 and WO2013/157953; incorporated herein by reference) we have disclosed methods and means for producing bispecific antibodies from a single cell, whereby means are provided that favor the formation of bispecific antibodies over the formation of monospecific antibodies. These methods can also be favorably employed in the present invention. Specifically, preferred mutations to produce essentially only bispecific full length IgG molecules are amino acid substitutions at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa. It was previously demonstrated in our co-pending applications that the negatively charged DE-variant heavy chain and positively charged KK-variant heavy chain preferentially pair to form heterodimers (so-called 'DEKK' bispecific molecules). Homodimerization of DE-variant heavy chains (DE-DE homodimers) or KK-variant heavy chains (KK-KK homodimers) hardly occurs due to strong repulsion between the charged residues in the CH3-CH3 interface between identical heavy chains.

VH genes encoding the antibodies binding human CD137, OX40 and PD-L1 described above were cloned into an IgG expression vector such as MV1452 encoding the positively charged CH3 domain. A tetanus toxin (TT) targeting antibody (FIG. 8) was cloned into the MV1377 IgG expression vector (FIG. 9) encoding the negatively charged CH3 domain. For expression of the CD137 antibody panel in IgG format, the entire panel was also cloned into the negatively charged CH3 domain vector to be able to produce monospecific CD137xCD137 bivalent IgG.

Suspension growth-adapted 293F Freestyle cells were cultivated in T125 flasks on a shaker plateau until a density of $3.0 \times 10^6$ cells/ml. Cells were seeded at a density of $0.3-0.5 \times 10^6$ viable cells/ml in each well of a 24-deep well plate (24 well format). The cells were transiently transfected with a mix of two plasmids encoding different antibodies, cloned into the proprietary vector system. Seven days after transfection, the cellular supernatant was harvested and filtered through a 0.22 µM filter (Sartorius). The sterile supernatant was stored at 4° C. until purification of the antibodies.

Purification of (Bispecific) IgG

Purification of IgG was performed on a small scale (<500 µg), using protein-A affinity chromatography. Small scale purifications were performed under sterile conditions in 24 well filter plates using filtration. First, the pH of the medium was adjusted to pH 8.0 and subsequently, IgG-containing supernatants were incubated with protein A Sepharose CL-4B beads (50% v/v) (Pierce) for 2 hrs at 25° C. on a shaking platform at 600 rpm. Next, the beads were harvested by filtration. Beads were washed twice with PBS pH 7.4.

Bound IgG was then eluted at pH 3.0 with 0.1 M citrate buffer and the eluate was immediately neutralized using Tris pH 8.0. Buffer exchange was performed by centrifugation using multiscreen Ultracel 10 multiplates (Millipore). The samples were finally harvested in PBS pH7.4. The IgG concentration was measured using Octet. Protein samples were stored at 4° C.

IgG Quantification Using Octet

To determine the amount of IgG purified, the concentration of antibody was determined by means of Octet analysis using protein-A biosensors (Forte-Bio, according to the supplier's recommendations) using total human IgG (Sigma Aldrich, cat. nr. 14506) as standard.

Specificity Analysis huCD137xCD137 Bivalent IgG and huOX40xTT and huPD-L1xTT Bispecific IgG The huCD137xCD137 bivalent IgG and huOX40xTT and huPD-L1xTT bispecific IgG were tested for binding in FACS to the stable cell lines expressing the relevant human and macaque orthologs (Table 1) and the wt cells. Therefore, cells were harvested and diluted to $10^6$ cells/ml in FACS buffer (PBS/0.5% BSA/0.5 mM EDTA). $1$-$2 \times 10^5$ cells were added to each well in a U-bottom 96 well plate. Cells were centrifuged for 2 minutes at 300 g at 4° C. Supernatant was discarded by inverting the plate(s). 50 µl of each IgG sample at a concentration of 10 µg/ml was added and incubated for 1H on ice. Cells were centrifuged once, supernatant was removed and cells were washed twice with 150 µl of FACS buffer. 50 µl 1:400 diluted goat anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer (Becton and Dickinson) in a HTS setting. Binding of the antibodies to cells was assessed by measuring the mean fluorescence intensity (MFI) of the stained cell population. Antibodies were considered to bind their target when the MFI was at least five-fold that of the same cell population stained with a (negative control) non-binding antibody (directed to tetanus toxoid).

Binning huCD137 Specific Fab Arms Present in CD137xCD137 Bivalent IgG on the Ability to Block the CD137 Interaction with CD137L huCD137 binding clones in bivalent IgG format were tested for their ability to block the interaction of CD137 with CD137L. Therefore, wells of a Maxisorp 96 well plate were coated with recombinant CD137-Fc (R&D; cat. no. 838-4B) at 1.25 µg/ml in PBS and incubated overnight at 4° C. Wells were washed two times with PBST (0.05% v/v Tween20 in PBS), and subsequently blocked with 2% BSA in PBS (block buffer) for one hour at room temperature. Thereafter, wells were incubated for one hour at room temperature with 0.25 µg/ml CD137L-muCD8 biotin (Ancell; cat. no. 503-030) diluted in block buffer in the presence or absence of 20 µg/ml IgG. Next, wash steps were repeated and wells were incubated with HRP-conjugated streptavidin (Becton Dickinson; cat. no. 554066) diluted 1:2000 in blockbuffer for 30 minutes at room temperature. For detection of bound streptavidin, wells were washed three times with PBST and incubated with TMB substrate components A and B (1:1 ratio) (Becton Dickinson; cat. no. 51-2606KC and 51-2607KC, respectively). Reaction was stopped after 10 minutes with 1M $H_2SO_4$ and the $OD_{450\ nm}$ was measured using an ELISA plate reader. Based on the results, clones were binned in 4 different groups: "Blocking clones" were considered to fully block the interaction of CD137 with CD137L when the ELISA signal was reduced more than 70% at an IgG (CD137xCD137) concentration of 20 µg/ml, compared to a control in which a TT specific competition antibody was added (0% blocking); "Partially blocking clones" reduced the signal between 25-70%; "Non-blocking clones" showed an ELISA signal that was reduced upto 25%, or enhanced upto 25%; "Enhancing clones" showed an increase in ELISA signal over 25%. The results obtained with a representative selection of the CD137 antibody panel tested as CD137xCD137 bispecific molecules are indicated in Table 2.

Binning huCD137 Specific Fab Arms Present in CD137xCD137 Bivalent IgG on Domain Specificity The above mentioned huCD137 binding clones in bivalent IgG format were also tested for domain specificity in FACS on HEK293T cells that were transiently transfected with eight different pIRES-Neo3 mouse/human CD137 hybrid expression constructs, a FL mouse CD137 pIRES-Neo3 expression construct (see amino acid insert sequences below) or the pIRES-Neo3_huCD137 expression construct used for generation of stable huCD137 expressing Freestyle 293F cells (Table 1). The same FACS protocol was used as described above during specificity analysis of the antibody panel. For generation of the hybrid constructs the extracellular domain of mouse and human CD137 was divided in 5 domains; 4 cysteine rich domains based on Uniprot reference sequences Q07011 (huCD137) and P20334 (moCD137) and 1 hinge domain from end of cysteine rich domain 4 to the transmembrane domain. The following amino acid insert sequences were cloned into pIRES-Neo3 (FIG. 4) via NheI/EcoRI; Text in bold is the signal peptide. Underscored text is the sequence identical to human CD137. Text in Italics represent the transmembrane and intracellular domain sequences.

Amino acid sequence Full length mouse CD137.

MGNNCYNVVVIVLLLVGCEKVGAVQNSCDNCQPGTFCRKYNPVCKSCPPS

TFSSIGGQPNCNICRVCAGYFRFKKFCSSTHNAECECIEGFHCLGPQCTR

CEKDCRPGQELTKQGCKTCSLGTFNDQNGTGVCRPWTNCSLDGRSVLKTG

TTEKDVVCGPPVVSFSPSTTISVTPEGGPGGHSLQVL*TLFLALTSALLLA*

*LIFITLLFSVLKWIRKKFPHIFKQPFKKTTGAAQEEDACSCRCPQEEEGG*

*GGGYEL*

Amino acid sequence mo/huCD137 chimeric insert A (human cysteine rich domain 1; mouse sequence from cysteine rich domain 2 forward).

MGNSCYNIVATLLLVLNFERTRS<u>LQDPCSNCPAGTFCDNNRNQICSS</u>CPP

STFSSIGGQPNCNICRVCAGYFRFKKFCSSTHNAECECIEGFHCLGPQCT

RCEKDCRPGQELTKQGCKTCSLGTFNDQNGTGVCRPWTNCSLDGRSVLKT

GTTEKDVVCGPPVVSFSPSTTISVTPEGGPGGHSLQVL*TLFLALTSALLL*

*ALIFITLLFSVLKWIRKKFPHIFKQPFKKTTGAAQEEDACSCRCPQEEEG*

*GGGGYEL*

Amino acid sequence mo/huCD137 chimeric insert B (human cysteine rich domain 1 and 2; mouse sequence from cysteine rich domain 3 forward).

MGNSCYNIVATLLLVLNFERTRS<u>LQDPCSNCPAGTFCDNNRNQICSPCPP</u>

<u>NSFSSAGGQRTCDICRQCKGVFRTRKECSSTSNAECECIEGFHCLGPQCT</u>

RCEKDCRPGQELTKQGCKTCSLGTFNDQNGTGVCRPWTNCSLDGRSVLKT

GTTEKDVVCGPPVVSFSPSTTISVTPEGGPGGHSLQVL*TLFLALTSALLL*

Amino acid sequence mo/huCD137 chimeric insert C (human cysteine rich domain 1 to 3; mouse sequence from cysteine rich domain 4 forward).

MGNSCYNIVATLLLVLNFERTRSLQPCSNCPAGTFCDNNRNQICSPCPPN
SFSSAGGQRTCDICRQCKGVFRTRKECSSTSNAECDCTPGFHCLGAGCSM
CEQDCKQNELTKKGCKTCSLGTFNDQNGTGVCRPWTNCSLDGESVLKTGT
TEKDVVCGPPVVSFSPSTTISVTPEGGPGGHSLQVL*TLFLALTSALLLAL*
*IFITLLFSVLKWIRKKFPHIFKQPFKKTTGAAQEEDACSCRCPQEEEGGG*
*GGYEL*

Amino acid sequence mo/huCD137 chimeric insert D (human cysteine rich domain 1 to 4; mouse sequence from hinge domain forward).

MGNSCYNIVATLLLVLNFERTRSLQDPCSNCPAGTFCDNNRNQICSPCPP
NSFSSAGGQRTCDICRQCKGVFRTRKECSSTSNAECDCTPGFHCLGAGCS
MCEKQGQELTKKGCKDCCFGTFNDQKRGICRPWTNCSLDGKSVLVNGTKE
RDVVCGPPVVSFSPSTTISVTPEGGPGGHSLQVL*TLFLALTSALLLALIF*
*ITLLFSVLKWIRKKFPHIFKQPFKKTTGAAQEEDACSCRCPQEEEGGGG*
*YEL*

Amino acid sequence mo/huCD137 chimeric insert E (mouse cysteine rich domain 1; human sequence from cysteine rich domain 2 forward).

MGNNCYNVVVIVLLLVGCEKVGAVQNSCDNCQPGTFCRKYNPVCK*PCPPN*
*SFSSAGGQRTCDICRQCKGVFRTRKECSSTSNAECDCTPGFHCLGAGCSM*
*CEQDCKQGQELTKKGCKDCCFGTFNDQKRGICRPWTNCSLDGKSVLVNGT*
*KERDVVCGPSPADLSPGASSVTPPAPAREPGHSPQIISFFLALTSTALLF*
*LLFFLTLRFSVVKRGRKKLLYIFKQPFMRPVQTTQEEDGCSCRFPEEEEG*
*GCEL*

Amino acid sequence mo/huCD137 chimeric insert F (mouse cysteine rich domain 1 and 2; human sequence from cysteine rich domain 3 forward).

MGNNCYNVVVIVLLLVGCEKVGAVQNSCDNCQPGTFCRKYNPVCKSCPPS
TFSSIGGQPNCNICRVCAGYFRFKKFCSSTHNAEC*DCTPGFHCLGAGCSM*
*CEQDCKQGQELTKKGCKDCCFGTFNDQKRGICRPWTNCSLDGKSVLVNGT*
*KERDVVCGPSPADLSPGASSVTPPAPAREPGHSPQIISFFLALTSTALL*
*FLLFFLTLRFSVVKRGRKKLLYIFKQPFMRPVQTTQEEDGCSCRFPEEEE*
*GGCEL*

Amino acid sequence mo/huCD137 chimeric insert G (mouse cysteine rich domain 1 to 3; human sequence from cysteine rich domain 4 forward).

MGNNCYNVVVIVLLLVGCEKVGAVQNSCDNCQPGTFCRKYNPVCKSCPPST
FSSIGGQPNCNICRVCAGYFRFKKFCSSTHNAECECIEGFHCLGPQCTRCE
KDCRPGQELTKQGCK*DCCFGTFNDQKRGICRPWTNCSLDGKSVLVNGTKER*
*DVVCGPSPADLSPGASSVTPPAPAREPGHSPQIISFFLALTSTALLFLLFF*
*LTLRFSVVKRGRKKLLYIFKQPFMRPVQTTQEEDGCSCRFPEEEEGGCEL*

Amino acid sequence mo/huCD137 chimeric insert H (mouse cysteine rich domain 1 to 4; human sequence from hinge domain forward).

MGNNCYNVVVIVLLLVGCEKVGAVQNSCDNCQPGTFCRKYNPVCKSCPPS
TFSSIGGQPNCNICRVCAGYFRFKKFCSSTHNAECECIEGFHCLGPQCTR
CEKDCRPGQELTKQGCKTCSLGTFNDQNGTGVCRPWTNCSLDGRSVLKTG
TTEKDVVCG*PSPADLSPGASSVTPPAPAREPGHSPQIISFFLALTSTALL*
*FLLFFLTLRFSVVKRGRKKLLYIFKQPFMRPVQTTQEEDGCSCRFPEEEE*
*GGCEL*

Based on the FACS results obtained with the chimeric and full length mouse and human CD137 constructs, clones were binned based on the observed binding patterns. Antibodies were considered to bind (chimeric) CD137 when the MFI was at least three-fold that of the same cell population stained with a (negative control) non-binding antibody (directed to tetanus toxoid).

Results

The domain specificities of the CD137-specific Fab arms are depicted in Table 2.

Binning huOX40 Specific Fab Arms Present in OX40xTT Bispecific IgG on the Ability to Block the OX40 Interaction with OX40L huOX40 binding clones in bispecific IgG format (OX40xTT) were tested for their ability to block the interaction of OX40 with OX40L. Therefore, wells of a Maxisorp 96 well plate were coated with recombinant huOX40-Fc (R&D; cat. no. 3388-OX) at 0.156 µg/ml in PBS and incubated overnight at 4° C. Wells were washed two times with PBST (0.05% v/v Tween20 in PBS), and subsequently blocked with 4% dried skimmed milk (ELK) in PBS (block buffer) for one hour at room temperature. Thereafter, wells were incubated for one hour at room temperature with 0.016 µg/ml OX40L (R&D; cat. no. 1054-OX) diluted in block buffer in the presence or absence of bispecific OX40xTT IgG at 20 µg/ml. Next, wells were washed 3 times with PBST and subsequently incubated for one hour with a biotinylated anti-OX40L antibody (R&D; cat. no. BAF1054) diluted in 2% BSA/PBS to 0.5 µg/ml. Next, wash steps were repeated and wells were incubated with HRP-conjugated streptavidin (Becton Dickinson; cat. no. 554066) diluted 1:2000 in 2% BSA/PBS for 30 minutes at room temperature. For detection of bound streptavidin, wells were washed three times with PBST and incubated with TMB substrate components A and B (1:1 ratio) (Becton Dickinson; cat. no. 51-2606KC and 51-2607KC, respectively). Reaction was stopped after 10 minutes with 1M $H_2SO_4$ and the $OD_{450\ nm}$ was measured using an ELISA plate reader.

Based on the results, clones were binned in 2 different groups: "Blocking clones" reduced the ELISA signal>24% at an IgG (OX40xTT) concentration of 20 µg/ml, compared to a control in which a TT specific competition antibody was added (0% blocking); "Non-blocking clones" showed an ELISA signal that was less than 24% reduced or enhanced the ELISA signal. This experiment was performed twice, with different subsets of huOX40 binding clones in bispecific IgG format (OX40xTT). The results of the OX40 antibody panel tested as OX40xTT bispecific molecules are given in Table 5.

Binning huOX40 Specific Fab Arms Present in OX40xTT Bispecific IgG on Domain Specificity huOX40 binding clones in bispecific OX40xTT IgG format were tested for domain specificity in FACS on HEK293T cells that were transiently transfected with eight different pIRES-Neo3 rat/human OX40 hybrid expression constructs (see amino acid insert sequences below), the pIRES-Neo3_raOX40 or the pIRES-Neo3_huOX40 expression construct used for generation of stable raOX40 and huOX40 expressing Freestyle 293F cells (Table 1). The same FACS protocol was used as described above during specificity analysis of the antibody panel. For generation of the hybrid constructs the extracellular domain of rat and human OX40 was divided in 5 domains; 4 cysteine rich domains based on Uniprot reference sequences P43489 (huOX40) and P15725 (raOX40) and 1 hinge domain from end of cysteine rich domain 4 to the transmembrane domain. The following amino acid insert sequences were cloned into pIRES-Neo3 (FIG. 4) via NheI/EcoRI; Text in bold is the signal peptide. Underscored text is the sequence identical to human OX40. Text in Italics represent the transmembrane and intracellular domain sequences.

Amino acid sequence ra/huOX40 chimeric insert A (human cysteine rich domain 1; rat sequence from cysteine rich domain 2 forward).

MCVGARRLGRGPCAALLLLGLGLSTVTGL<u>HCVGDTYPSNDRCCHECRPGN</u>

<u>GMVSRCSRSQNTVCRP</u>CEPGFYNEAVNYDTCKQCTQCNHRSGSELKQNCT

PTEDTVCQCRPGTQPRQDSSHKLGVDCVPCPPGHFSPGSNQACKPWTNCT

LSGKQIRHPASNSLDTVCEDRSLLATLLWETQRTTFRPTTVPSTTVWPRT

SQLPSTPTLVAPEGP*AFAVILGLGLGLLAPLTVLLALYLLRKAWRSPNTP*

*KPCWGNSFRTPIQEEQTDTHFTLAKI*

Amino acid sequence ra/huOX40 chimeric insert B (human cysteine rich domain 1 and 2; rat sequence from cysteine rich domain 3 forward).

MCVGARRLGRGPCAALLLLGLGLSTVTGL<u>HCVGDTYPSNDRCCHECRPGN</u>

<u>GMVSRCSRSQNTVCRPCGPGFYNDVVSSKPCKPCTWCNLRSGSERKQLCT</u>

<u>ATQDTVC</u>QCRPGTQPRQDSSHKLGVDCVPCPPGHFSPGSNQACKPWTNCT

LSGKQIRHPASNSLDTVCEDRSLLATLLWETQRTTFRPTTVPSTTVWPRT

SQLPSTPTLVAPEGP*AFAVILGLGLGLLAPLTVLLALYLLRKAWRSPNTP*

*KPCWGNSFRTPIQEEQTDTHFTLAKI*

Amino acid sequence ra/huOX40 chimeric insert C (human cysteine rich domain 1 to 3; rat sequence from cysteine rich domain 4 forward).

MCVGARRLGRGPCAALLLLGLGLSTVTGL<u>HCVGDTYPSNDRCCHECRPGN</u>

<u>GMVSRCSRSQNTVCRPCGPGFYNDVVSSKPCKPCTWCNLRSGSERKQLCT</u>

<u>ATQDTVCRCRAGTQPLDSYKPGVDCA</u>PCPPGHFSPGSNQACKPWTNCTLS

GKQIRHPASNSLDTVCEDRSLLATLLWETQRTTFRPTTVPSTTVWPRTSQ

LPSTPTLVAPEGP*AFAVILGLGLGLLAPLTVLLALYLLRKAWRSPNTPKP*

*CWGNSFRTPIQEEQTDTHFTLAKI*

Amino acid sequence ra/huOX40 chimeric insert D (human cysteine rich domain 1 to 4; rat sequence from hinge domain forward).

MCVGARRLGRGPCAALLLLGLGLSTVTGL<u>HCVGDTYPSNDRCCHECRPGN</u>

<u>GMVSRCSRSQNTVCRPCGPGFYNDVVSSKPCKPCTWCNLRSGSERKQLCT</u>

<u>ATQDTVCRCRAGTQPLDSYKPGVDCAPCPPGHFSPGDNQACKPWTNCTLA</u>

<u>GKHTLQPASNSSDAI</u>CEDRSLLATLLWETQRTTFRPTTVPSTTVWPRTSQ

LPSTPTLVAPEGP*AFAVILGLGLGLLAPLTVLLALYLLRKAWRSPNTPKP*

*CWGNSFRTPIQEEQTDTHFTLAKI*

Amino acid sequence ra/huOX40 chimeric insert E (rat cysteine rich domain 1; human sequence from cysteine rich domain 2 forward).

MYVWVQQPTAFLLLGLSLGVTVKLNCVKDTYPSGHKCCRECQPGHGMVSR

CDHTRDTVCH<u>PCGPGFYNDVVSSKPCKPCTWCNLRSGSERKQLCTATQDT</u>

<u>VCRCRAGTQPLDSYKPGVDCAPCPPGHFSPGDNQACKPWTNCTLAGKHTL</u>

<u>QPASNSSDAICEDRDPPATQPQETQGPPARPITVQPTEAWPRTSQGPSTR</u>

<u>PVEVPGGRA</u>*VAAILGLGLVLGLLGPLAILLALYLLRRDQRLPPDAHKPPG*

*GGSFRTPIQEEQADAHSTLAKI*

Amino acid sequence ra/huOX40 chimeric insert F (rat cysteine rich domain 1 and 2; human sequence from cysteine rich domain 3 forward).

MYVWVQQPTAFLLLGLSLGVTVKLNCVKDTYPSGHKCCRECQPGHGMVSR

CDHTRDTVCHPCEPGFYNEAVNYDTCKQCTQCNHRSGSELKQNCTPTEDT

VC<u>RCRAGTQPLDSYKPGVDCAPCPPGHFSPGDNQACKPWTNCTLAGKHTL</u>

<u>QPASNSSDAICEDRDPPATQPQETQGPPARPITVQPTEAWPRTSQGPSTR</u>

<u>PVEVPGGRA</u>*VAAILGLGLVLGLLGPLAILLALYLLRRDQRLPPDAHKPPG*

*GGSFRTPIQEEQADAHSTLAKI*

Amino acid sequence ra/huOX40 chimeric insert G (rat cysteine rich domain 1 to 3; human sequence from cysteine rich domain 4 forward).

MYVWVQQPTAFLLLGLSLGVTVKLNCVKDTYPSGHKCCRECQPGHGMVSR

CDHTRDTVCHPCEPGFYNEAVNYDTCKQCTQCNHRSGSELKQNCTPTEDT

VCQCRPGTQPRQDSSHKLGVDCV<u>PCPPGHFSPGDNQACKPWTNCTLAGKH</u>

<u>TLQPASNSSDAICEDRDPPATQPQETQGPPARPITVQPTEAWPRTSQGPS</u>

<u>TRPVEVPGGRA</u>*VAAILGLGLVLGLLGPLAILLALYLLRRDQRLPPDAHKP*

*PGGGSFRTPIQEEQADAHSTLAKI*

Amino acid sequence ra/huOX40 chimeric insert H (rat cysteine rich domain 1 to 4; human sequence from hinge domain forward).

MYVWVQQPTAFLLLGLSLGVTVKLNCVKDTYPSGHKCCRECQPGHGMVSR
CDHTRDTVCHPCEPGFYNEAVNYDTCKQCTQCNHRSGSELKQNCTPTEDT
VCQCRPGTQPRQDSSHKLGVDCVPCPPGHFSPGSNQACKPWTNCTLSGKQ
IRHPASNSLDTVCE<u>DRDPPATQPQETQGPPARPITVQPTEAWPRTSQGPS</u>
<u>TRPVEVPGGRAVAA</u>ILGLGLVLGLLGPLAILLALYLLRRDQRLPPDAHKP
PGGGSFRTPIQEEQADAHSTLAKI

Based on the FACS results obtained with the chimeric and full length rat and human OX40 constructs, clones were binned based on the observed binding patterns. Antibodies were considered to bind (chimeric) OX40 when the MFI was at least three-fold that of the same cell population stained with a (negative control) non-binding antibody (directed to tetanus toxoid).

The results of the huOX40 binding clones in bispecific OX40xTT IgG format are given in Table 5.

Binning huPD-L1 Specific Fab Arms Present in the PD-L1xTT Bispecific IgG on the Ability to Block the PD-1/PD-L1 Interaction 14 huPD-L1 binding clones (VH sequences depicted in FIG. 3) were tested for their ability to block the interaction of PD-L1 with PD-1, and their ability to block the interaction between PD-L1 and CD80. Therefore PD1-Fc (R&D systems; cat. no. 1086-PD) or CD80-Fc (R&D systems; cat. no. 140-B1) was coated to a maxisorp plate at 1 and 3 µg/ml, respectively. Coated wells were blocked with 4% BSA in PBS. Thereafter, 0.55 µg/ml biotinylated PD-L1 (BPS bioscience; cat. no. 71105) was added in the presence or absence of huPD-L1xTT bispecific IgG in the range of 0.15 to 20 µg/ml. Bound biotinylated PD-L1 was detected with HRP-conjugated streptavidin (BD bioscience: cat. no. 554066) diluted 1:2000 in block buffer. After each incubation step, the ELISA plate was washed three times with PBS-T (PBS-0.05% v/v Tween 20). Bound streptavidin was visualized by $TMB/H_2O_2$ staining and staining was quantified by means of $OD_{450\ nm}$ measurement. Clones were considered to block the interaction of PD-1 with PD-L1 when the ELISA signal was reduced more than 70% at an IgG (PD-L1xTT) concentration of 10 µg/ml, compared to a control in which a TT specific competition antibody was added. See FIG. 10 for the results obtained with a representative selection of the PD-L1 antibody panel tested as PD-L1xTT bispecific molecules. Except for MF5361, PD-L1-specific Fab arms depicted in FIG. 10 block the PD-1/PD-L1 interaction>70%. In addition, all other PD-L1-specific Fab arms comprising MF sequences depicted in FIG. 3 also block the PD-1/PD-L1 interaction>70% (data not shown).

In conclusion, the tested huPD-L1 specific Fab arms block the PD-1/PD-L1 interaction, except for MF5361.

Affinity Ranking huCD137, huOX40 and huPD-L1 Specific Fab Arms Present in the CD137xCD137, OX40xTT and PD-L1xTT Bispecific IgG Bispecific antibodies that were shown to bind the respective human and macaque orthologs in FACS were ranked on apparent affinity for both orthologs in FACS. Therefore, the stable cell lines expressing the respective orthologs (Table 1) were harvested and diluted to $1\times10^6$ cells/ml in FACS buffer (PBS/0.5% BSA/0.5 mM EDTA). Cells were centrifuged for 2 minutes at 300 g at 4° C. Supernatant was discarded by inverting the plate(s). 50 µl of each IgG sample, in a 11-step, 2-fold dilution series ranging from 10 to 0.01 µg/ml, was added and incubated for 1H on ice. Cells were centrifuged once, supernatant was removed and cells were washed twice with 150 µl of FACS buffer. 50 µl diluted 1:400 goat anti human IgG PE (Invitrogen) was added and incubated for 30 minutes on ice in the dark. After adding FACS buffer, cells were centrifuged once, supernatant was removed and cells were washed twice with FACS buffer. Cells were analyzed on a FACSCanto Flow cytometer (Becton and Dickinson) in a HTS setting. Binding of the antibodies to cells was assessed by measuring the mean fluorescence intensity (MFI) of the stained cell population. Antibodies were considered to bind their target when the MFI was at least five-fold that of the same cell population stained with a (negative control) non-binding antibody (directed to tetanus toxoid).

Reference Antibodies

Antibodies that inhibit the function of PD-L1 and CD137 and CTLA-4 are known in the art. Monoclonal bivalent antibodies were constructed according to published information and expressed in 293F Freestyle or CHO-S cells. The anti-PD-L1 antibody MPDL3280A (surrogate based on Atezolizumab) was based on the information disclosed in WO2010077634A1. The information of the anti-CD137 antibodies 20H4.9 (surrogate based on Urelumab) and PF-05082566 (surrogate based on Utomilumab) were obtained from WO 2005/035584 and WO2015119923 respectively. VH information of MOR7480 was obtained from U.S. Pat. No. 8,337,850 B2 and recloned in an IgG1 backbone. The information with regard to the anti-CTLA-4 antibody 10D1 (surrogate based on Ipilimumab) was obtained from PCT Publication No. WO 01/14424.

Example 4

Materials & Methods

PBMC Isolation

Human whole blood was obtained from buffy coats (Sanquin) and was diluted 1:1 with PBS. Leucosep tubes (Greiner Bio-One cat. no. 227 290) were filled with 17.5 m Ficoll-Paque Plus (Amersham Biosciences cat. no. 17-1440-02) warmed at room temperature (RT). Ficoll-Paque Plus was spun down for 30 seconds at 1000×g at RT. 30 ml of diluted whole blood was poured on top. The tubes were spun at 1000×g for 10 minutes at RT and the mononuclear PBMC interface was harvested, washed twice in PBS and resuspended in 250 µl PBS. The PBMCs were counted and readjusted to 1×106/ml in tissue culture medium (DMEM with 10% FCS) and frozen down by adding an equal volume of ice-cold freeze medium (80% culture medium/20% DMSO). Cells were stored in 1 ml aliquots at −150° C. until further use.

T Cell Activation Assay

PBMCs were thawed and 9 volumes of culture medium (RPMI1640 with L-glutamine and 10% heat inactivated FBS) was added. Cells were centrifuged for 10 minutes at 150 g at RT. The cell pellet was resuspended in 10 ml culture medium and cells were allowed to rest by incubating overnight in a 50 ml falcon tube at 37° C., 5% CO, in 95% relative humidity. Next day, T lymphocytes were isolated using Easy Sep T cell enrichment (pan CD3) purification procedure as described by the manufacturer (Stem cell Technologies cat #19051). The EasySep procedure uses negative selection. Briefly, PBMCs were centrifuged for 10 minutes at 150 g at RT. The cell pellet was resuspended in 2 ml PBS+2% FBS with 1 mM EDTA. The cell suspension was filtered through a 30 µm mesh nylon strainer. Cells counted and readjusted to 5×107 cells/ml in PBS+2% FBS with 1 mM EDTA. 50 µl of EasySep Human T Cell Enrichment cocktail was added to each 2 ml cell volume, mixed and allowed to incubate for 10 minutes at RT. Next, 50 µl of EasySep D Magnetic Particles were added to each 2 ml cell volume and allowed to incubate for 5 minutes at RT. The total volume was brought to 2.5 ml with PBS+2% FBS with 1 mM EDTA. Next, the tube was placed into the magnet allowing the undesired cell fraction to be bound to the magnet for 5 minutes at RT. Next, the tube was inverted and the purified T cells fraction was poured off in a new tube, cells were harvested by 10 minutes centrifugation at 150 g at RT and subsequently resuspended at a concentration of 1×105 cells/ml in culture medium. For the T cell activation assay the inner wells of a 96 well plates (96 wells Flat Bottom plates-Cellstar #655180) were coated overnight with 30 µg/mL anti-CD3 UCHT1 in PBS. Next day, plates were washed with PBS. Antibody dilutions (80 µg/ml) were prepared and incubated at a 1:1 ratio with a cross linking antibody aHuIgG-Fc (Bethyl cat. no. #A80-104A) for 15 minutes at RT. Next, serial dilutions of the mixture were prepared. 100 µL of the crosslinked antibodies were added to each well followed by 100 µL purified T-cell suspension. Each plate contained a serial dilution of negative (PG1337) and positive control antibody (Urelumab) that served as reference controls. T cell cultures were stimulated for 3 days at 37° C., 5% CO2 in 95% relative humidity prior to being tested for IL-2 secretion and/or cell surface expression of antigens. The concentration of released IL-2 was determined by AlphaLISA (Perkin Elmer cat no #AL221C). Expression of cell surface antigens related to check point inhibition or co stimulatory antigens was determined by flow cytometry.

SEB Assay

The functional activity of the bispecific antibodies was determined by using PBMCs stimulated by *Staphylococcus enterotoxin* B (SEB). SEB specifically activates T cells expressing the VB3 and V68 T cell receptor chain. PBMCs from 3 donors were thawed, washed, counted and resuspended in culture medium (RPMI1640 plus 10% heat inactivated FBS) to a concentration of 2×106 cells/ml. Cells were seeded in flat bottom 96-well plates (2×105 cells/well) in the presence of SEB (2000 or 125 ng/ml). Antibody serial dilutions starting at 20 µg/ml were added. Each plate contained a serial dilution of negative (PG1337) and positive control antibody (based on ipilumumab) that served as reference controls. Cells were stimulated for 3 days at 37° C., 5% CO2 in 95% relative humidity prior to being tested for cytokine secretion and/or cell surface expression of antigens.

PD-1/PD-L1 Blockade Reporter Assay

The PD-1/PD-L1 blockade reporter assays used were developed by Promega and are based on a two cell system; CHO cells expressing PD-L1, and a T cell activator and a Jurkat/NFAT-RE Reporter Cell Line overexpressing PD-1. The PD-1/PD-L1 blockade reporter assays were performed using the thaw and use format of Promega. PD-L1 expressing CHO cells (cat. no. C187103) were thawed in 14.5 ml Cell Recovery Medium (DMEM/F12 containing 10% FBS). Next, 50 µl cell suspension was added to the inner wells of a 96 well half area plate (Corning, cat. no. 3688). Plates were incubated overnight at 37° C., 5% CO, in 95% relative humidity. Next day, culture medium was removed and 20 µl test antibody in assay medium (RPMI 1640 containing 4% FBS) in a serial dilution (starting concentration 10 µg/ml) was added to each well. Each plate contained a serial dilution of negative (PG1337) and positive control antibody (based on Nivolumab/MPDL3280A) that served as reference controls. PD-1 effector cells (cat no. C187105) were thawed in 5.9 ml Assay medium and 20 µl cell suspension was added to each well. Plates were incubated for 6 H or overnight at 37° C., 5% CO, in 95% relative humidity. 40 µl of luciferase (Bio-Glo Luciferase Assay System, cat. no. G794L) was added the next day and the amount of luciferase activity was measured using aBioTek Synergy 2 Multi-Mode Microplate Reader. Potency was measured as luciferase activity in comparison to the negative control antibody.

Screening of the PD-L1 Antibody Panel

VH from the PD-L1 antibody panel were recloned into the charged engineered Fc-silenced vectors such that upon expression of the antibody heavy chains hetero dimerisation of heavy chains is forced resulting in the generation of bispecific antibodies after transfection. The PD-L1 Fab arms were recloned in the MV1624 vector. PD-L1 antibodies were combined with MF1337, a TT targeting Fab arm, to generate bispecific antibodies targeting PD-L1 in a monovalent manner. The panel of PD-L1 antibodies in monovalent format was ranked for activity as shown in Table 3.

Cytokine Assays

ELISA: After stimulation of T-cells or PBMCs at various times, plates were centrifuged and media was removed. Cytokine levels were detected by AlphaLISA in accordance with the manufacturer's instructions (Perkin Elmer). Concentrations were calculated based on the standard curve.

Luminex assay: Another method used to determine cytokine production in vitro was using multiplex analysis developed by eBioscience. Levels of IFN-γ, IL-2, and TNF-α were measured in culture supernatants following manufacturers' instructions. Results were analyzed by eBioscience analysis software.

Generation of Jurkat CD137-NFkBluc

A Jurkat CD137-NFkBluc stable reporter cell line was generated by stably integrating a full length CD137 construct and a NF-κB luciferase reporter construct in Jurkat E6 cells. Therefore the full length CD137 MV1604 [pIRES-neo3](Clontech) was transfected and stable clones expressing CD137 were generated following antibiotic selection. Next, the NF-κB luciferase reporter construct pGL4.32 [luc2P/NF-κB-RE/Hygro] (Promega) was transfected in the clone with the highest CD137 expression and stable clones expressing both CD137 and NF-κB luciferase were selected following antibiotic selection. Clones were selected for their capacity to respond to CD137L after initial activation by plate bound CD3 antibodies (clone OKT-3) and PMA/ionomycin. The clone that showed the highest window of activation was used as a thaw and use format in the CD137 reporter assay.

CD137 Reporter Assay

For the direct CD137 activation assay 96 well plates (Costar, cat. no. 3917) were coated overnight with 2 µg/ml anti-CD3 (OKT3) in PBS. For the CD137 activation assay mediated by cross linking 96 well plates (Costar, cat. no. 3917) were coated overnight with 2 µg/ml anti-CD3 in PBS+10 µg/ml anti-human IgG (Bethyl, cat. no. A80-104A). Next day, plates were washed with PBS. The above-mentioned Jurkat CD137-NFkBluc cells were thawed and washed with DMEM/F12 medium containing 10% heat inactivated fetal bovine serum (assay medium). Cells were resuspended at a density of 2×106 cells/ml. 25 µl cell suspension was plated into the inner wells of the coated 96 well assay plate. 25 µl test antibody in a serial dilution was added to each well (starting concentration 20 µg/ml) followed by 25 µl assay medium. Each plate contained a serial dilution of negative (PG1337) and positive control antibody that served as reference controls. Plates were incubated overnight at 37° C., 5% CO2, in 95% relative humidity. 50 µl of luciferase (Promega, Bright-Glo™, cat. no. E2610)

was added the next day and the amount of luciferase activity was measured using aBioTek Synergy 2 Multi-Mode Microplate Reader.

Large Scale Bispecific Antibody Production

Proteins were produced in FreeStyle™ 293-F cells (Invitrogen) using polyetyleneimine (PEI) as transfection reagent with a PEI/DNA mass ratio of 2.5:1. Bispecific antibodies were transfected using a 1:1 DNA mass ratio at 0.4-2L scale. Cell supernatants were purified by batch-wise incubation with MabSelect SuRe LX sepharose (GE Healthcare), followed by acidic elution and neutralization using Tris. The proteins were consequently desalted and centrifuged followed by cation exchange purification using a Resource S (GE Healthcare) column equilibrated in 25 mM phosphate buffer pH 6.0. A gradient elution to 1M NaCl was used to elute the proteins and protein containing fractions were collected and analyzed using NuPAGE 4-12% Bis-Tris protein gels (Invitrogen). Fractions containing bispecific antibody were pooled and applied to a Superdex200 26/600 gel filtration column (GE Healthcare) equilibrated in PBS. Fractions were collected and analyzed on NuPAGE, after which monomeric antibody-containing fractions were pooled and sterile filtered (0.22 μm).

Results

CD137 Reporter Assay

The panel of CD137 bivalent antibodies was screened in the above-mentioned CD137 direct activation reporter assay. A representative figure of a selection of the antibodies is shown in FIG. 11. 60% of the antibody panel was capable to directly activate CD137 to variable degree.

Screening CD137xPD-L1 Antibody Panel

One limitation of CD137 bivalent antibodies in cancer drug development is systemic activation of CD137 expressing cells. This can lead to toxicity of the antibody, due to non-specific targeting [Melero, 2013]. Bispecific antibodies can overcome this limitation by selectively targeting cells, either by targeting cells that co-express both targets, such as two tumor antigens or by targeting two different cells each expressing one of the targets. The latter can only occur when cells are in close proximity to one another. To investigate the possibility of selective activation of CD137, bispecific antibodies were generated that are composed of one Fab arm targeting CD137 and one Fab arm targeting PD-L1. With PD-L1 representing both an antigen present at high concentrations on tumor cells as well as an antigen highly expressed on activated T cells present at the tumor site [Pulko et al, 2011]. As such the bispecific CD137xPD-L1 antibody would be able to activate CD137 in 'cis' when targeting CD137 and PD-L1 on the same cell or in 'trans' by targeting CD137 on immune cells and PD-L1 on adjacent cells. On top of this mechanism, the inclusion of a PD-1 blocking Fab arm would be able to turn an inhibitory signal into a stimulatory signal.

VH from the CD137 and PD-L1 antibody panel were recloned into the charged engineered Fc-silenced vectors such that upon expression of the antibody heavy chains heterodimerisation of heavy chains is forced resulting in the generation of bispecific antibodies after transfection. A total of 320 CD137xPD-L1 bispecific antibodies comprising 40 different CD137 Fab arms and the 8 different PD-L1 Fab arms depicted in Table 3 were produced in 24-well format and IgG purified. All antibodies were tested for their capacity to induce dose dependent luciferase expression in the CD137-luc reporter system directly or in the presence of an anti-human IgG cross linking antibody. Surrogate antibodies 20H4.9 and MOR7480 were included as reference antibodies in the respective assays.

Figure 12:
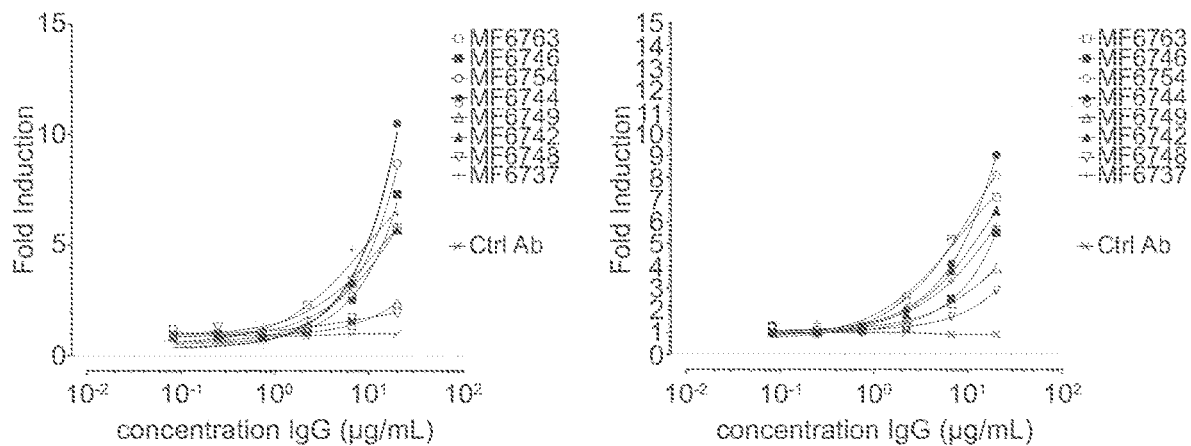

An example of the functional activity in the CD137-luc reporter assay of several CD137xPD-L1 bispecific antibodies in the absence or presence of the anti-human IgG cross linking antibody is shown in FIG. 12. The figure shows that the capacity of the CD137xPD-L1 bispecific antibodies to activate CD137 induced luciferase activity is highly dependent on cross linking by the anti-human IgG antibody since this increases the magnitude of luciferase activity by 25%. Significant enhancement of IFN-γ production after CD137 ligation also has been observed for the anti-CD137 antibody known in the art as 20H4.9 (WO 2005/035584). The top 25% CD137xPD-L1 of the bispecific antibody panel was composed of 22 CD137 Fab arms in combination with one to seven PD-L1 Fab arms of the total panel of eight PD-L1 Fab arms.

The top 25% CD137xPD-L1 bispecific antibody panel was next tested for their capacity to induce IL-2 release in a primary T cell activation assay in comparison to the bivalent parental CD137 antibodies and parental CD137 Fab arm combined with an irrelevant Fab arm targeting Tetanus Toxoid. In this experimental setup monovalent activation versus bivalent activation could be monitored. The top panel of FIG. 13 shows an example of a set of three antibodies that induce IL-2 secretion upon CD137 activation if present in a CD137x CD137 bivalent format in the range of the 20H4.9 reference antibody. In contrast, as shown in the bottom panel of FIG. 13, none of the CD137xPD-L1 bispecific antibodies was able to induce IL-2 secretion to the level of the bivalent CD137 parental Fab. All CD137xPD-L1 bispecific antibodies displayed the same activity as the CD137xTT variants indicating that CD137 signaling complexes could not be formed effectively by binding to CD137 and PD-L1 at the same cell surface (binding in 'cis'). The lack of in cisT cell activation of this CD137xPD-L1 bispecific antibody panel is advantageous, as this diminishes the potential of in vivo toxicity due to nonspecific T cell activation.

Transactivation Assay

To test whether bispecific CD137xPD-L1 antibodies would be able to activate CD137 in 'trans', bispecific antibodies were tested in a two cell assay whereby CD137 signaling in immune cells would occur through cross-linking by a second cell. The in vitro assay was composed of two different cell lines, i.e. CHO-PD-L1 cells mimicking tumor cells expressing PD-L1 and Jurkat CD137-luc reporter cells representing the immune cells. The same assay set-up was used as in the CD137-luc reporter with coated anti-CD3 providing the first T cell activation signal. The effector target cell ratio used was 4:1 with target cells being either CHO wildtype or CHO-PD-L1 cells. FIG. 14 shows an example whereby the CD137 bispecific antibodies PB14671 and PB14580, which are composed of the same CD137 Fab arm (MF6744) and two different PD-L1 Fab arms (MF5361 or MF5594, respectively) were both capable of inducing CD137 reporter cell activity in the presence of CHO-PD-L1 cells whereas no CD137 stimulation occurred in the presence of wild-type CHO wild-type cells. In addition, the CD137 bispecific antibodies PB14681 and PB14590, which are composed of the same CD137Fab arm (MF6783) and two different PD-L1 Fab arms (MF5361 or MF5594, respectively) were both capable of inducing CD137 reporter cell activity in the presence of CHO-PD-L1 cells whereas no CD137 stimulation occurred in the presence of wild-type CHO wild-type cells. Moreover, all CD137xPD-L1 bispecific antibodies were as potent as the reference control antibody 20H4.9. A combination of the CD137xPD-L1 bispecific antibodies PB14580 and PB14671 (Oligoclonics® format) induced a high luciferase activity.

Transactivation Assay with Primary T-Cells

The transactivation assay was reformatted to primary cells by adding CHO wildtype or CHO-PD-L1 cells in the T cell activation assay. An effector target cell ratio at the start of the assay of 1:1.8 for CHO-PD-L1 and CHO wildtype cells was used. For the T cell activation assay the inner wells of 96 well plates (96 wells Flat Bottom plates-Cellstar #655180) were coated overnight with 30 µg/mL anti-CD3 OKT-3 in PBS. Next day, plates were washed with PBS. 50 µL of antibody solution was added followed by 25 µL purified T-cell suspension of 2×106 cells/well and 25 µL purified CHO-K1 or CHO-PD-L1 in the ratio's as indicated above were added per well. Cultures were stimulated for 3 days at 37° C., 5% CO2 in 95% relative humidity prior to being tested for IL-2 secretion. The concentration of released IL-2 was determined by AlphaLISA (Perkin Elmer cat no #AL221C).

Two CD137xPD-L1 bispecific antibodies (PB14671 and PB14580) were tested, as well as the Oligoclonics® format and a CD137xTT format. The IL-2 release at day 3 depicted in FIG. 15 shows that the CD137xPD-L1 antibodies induced IL-2 production in T cells in the presence of CHO-PD-L1 cells to a higher extend than control antibody 20H4.9. Moreover, the CD137xTT format failed to induce IL-2 release. In the presence of CHO wild-type cells IL-2 levels are produced at background levels, with the exception of control antibody 20H4.9. A combination of the two CD137xPD-L1 bispecific antibodies (Oligoclonics® format) induced a high luciferase activity, thereby confirming the previous experiment. The Oligoclonics® format can be either targeting the same CD137 epitope and two different PD-L1 epitopes (as shown in FIGS. 14 and 15) or targeting two different CD137 domains and two different PD-L1 domains.

SEB Assay

To test the CD137xPD-L1 bispecific antibodies in a physiological setting where APCs are present that express PD-L1, both CD137xPD-L1 antibodies (PB14671 and PB14580), the CD137xTT antibodies and the Oligoclonics® format were tested in the SEB assay. One of the CD137xPD-L1 bispecific antibodies (PB14580) showed a higher activation in comparison to the negative control antibodies and was far more potent in comparison to the reference antibodies targeting either CD137 (20H4.9) or PD-L1 (MPDL3280A); see FIG. 16. Induction of IL-2 by the CD137xPD-L1 Oligoclonics® format was also potent.

Additional Testing

Figure 17:
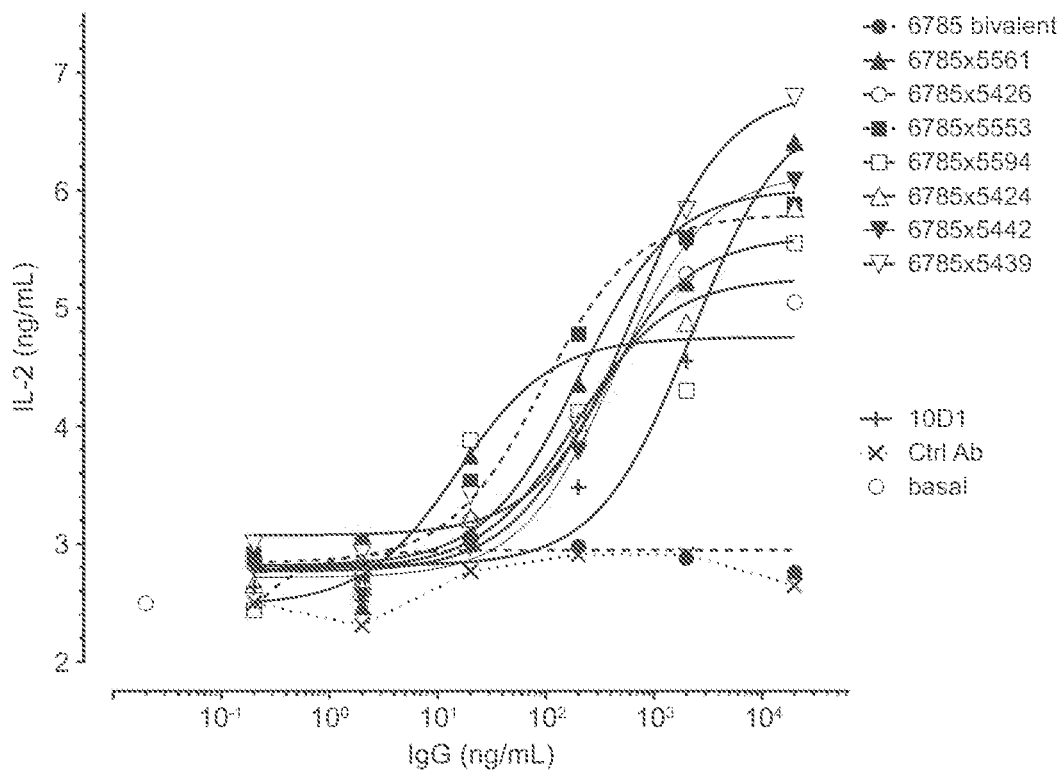

A panel of 24 anti-CD137 Fab arms representing the eleven different CD137 bins A-K (Table 2) were combined with seven PD-L1 specific, blocking Fab arms and one PD-L1 specific, non-blocking Fab arm (Table 3) and produced in 24-well format. The produced CD137xPD-L1 bispecific antibodies were subsequently tested in a serial titration for their capacity to induce dose dependent luciferase expression in the CD137-luc reporter system in the presence of CHO-PD-L1 cells or CHO wildtype cells. 20H4.9 and the negative control antibody were included as reference antibodies (FIG. 19). Antibodies (56 in total) that showed the highest induction of luciferase were selected and tested in a serial titration in the activated T cell assay in presence or absence of CHO-PD-L1 cells or CHO wildtype cells. In parallel the antibodies were tested in the SEB assay. As a read-out for CD137 activation, IL-2 release was measured. An overview of the characteristics and activity of the 24 bispecific antibodies tested in the T-cell-activation assay are shown in Table 7. The twelve CD137 Fab arms that were found to be active for both PD-L1 arms in both the activated T cell and SEB assay, were selected for combinations with 7 different PD-L1 Fab arms. As well as being produced as bivalent monospecific IgGs, the 12 CD137 arms were produced as bispecific/monovalent CD137xPD-L1 antibodies, each combined with one of the 7 different PD-L1 arms. Thus, a total of 84 bispecific CD137xPD-L1 antibodies were tested in a dose dependent titration in a SEB assay with IL-2 release as readout. The data in FIG. 20 show that when present in a CD137xPD-L1 format; four out of the twelve CD137 Fab arms (MF6783, MF6749, MF6737 and MF6788) showed a lower potency in the SEB assay compared to the other Fab arms. Therefore CD137xPD-L1 bispecific antibodies comprising these four CD137 Fab arms were excluded for further testing. During additional SEB testing CD137xPD-L1 combinations comprising MF6808, MF6763, MF6754, MF6785 and MF6797 induced the highest IL-2 cytokine release. (FIG. 21). CD137xPD-L1 combinations comprising MF6805, MF6744 and MF6825 induced a lesser amount of IL-2 cytokine secretion. The potency of CD137xPD-L1 combinations comprising MF6808, MF6763, MF6754, MF6785 and MF6797 was further analyzed during a SEB assay in a serial titration by measuring the induction of IL-2, IFNγ and TNFα release as determined by Luminex multiplex. Next, the antibodies were ranked upon EC50 values of IL-2 release (Table 4). A panel of 28 CD137xPD-L1 bispecific antibodies (Table 4) comprising four different CD137 Fab arms showed the highest activity in the SEB assay. These four CD137 Fab arms could be mapped to the same binding region in CD137 (binding domain 2) and moreover all were completely blocking the interaction between CD137 and CD137L. None of them showed agonistic activity in the Jurkat CD137 reporter screen as a bivalent monoclonal (FIG. 17). CIEX profiles of the 28 CD137xPD-L1 bispecific antibodies demonstrated that CD137xPD-L1 antibodies comprising a PD-L1 Fab arm based on MF5553 such as MF7702 had optimal CIEX profiles in terms of consideration as a lead candidate antibody for manufacturing.

Example 5

Affinity Ranking of Anti-CD137 Antibody Panel

The affinity of a panel of anti-CD137 Fabs that induced T cell activation in combination with the PD-L1 Fab arms in trans was determined by Biacore.

To this end, human recombinant CD137 protein was coupled to a chip and a Biacore T100 instrument analyzed the affinity of the different anti-CD137 antibodies in monovalent bispecific format: one Fab arm was specific for CD137 and the other for an irrelevant ligand, namely tetanus toxoid (TT).

In these experiments, bispecific anti-(CD137xTT) IgG was produced by means of transient transfection of the encoding constructs in Freestyle 293F cells in a small scale production (24 well format, see example 2). In each transfection, a construct encoding one of the selected anti-CD137 sequences was combined with MF1337 encoding the anti-TT sequence.

Surface plasmon resonance (SPR) on a Biacore T100 instrument was then used to determine the affinities of the antibodies. To this end, huCD137-Fc protein (RND Systems #838-4B) was diluted to 5 µg/ml in sodium acetate coupling buffer, pH 5.0, and coupled to the surface of cell 2 of a CM5 biosensor chip, to a level of 150 resonance units (RU). Flow cell 1 served as a negative control surface. To determine the kinetic dissociation rate constants ($K_{off}$ values), test antibodies were diluted in HEPES buffered saline (HBS) to 15

µg/ml (100 nM) and run over both flow cell 1 and 2 of the CD137-coated sensor chip at 30 µl/min. Regeneration was performed with a pulse of 10 µl of 100 mM HCl. The dissociation rate constant was determined from the obtained sensorgrams (i.e. graphs of response vs time) using curve fitting in BIAevaluation software.

To measure binding kinetics of the antibody panel and obtain kinetic association and dissociation rate constants of antibody binding to CD137, different concentrations of this subset of test antibodies were run over the surfaces of flow cells 1 and 2 of a newly coated chip. Antibodies were diluted in HBS to 200 nM (i.e. 30 µg/ml), serially diluted two-fold (4 dilutions, 100 nM-50 nM-25 nM-12.5 nM) and then tested for binding to the chip in a kinetic run at high flow rate (30 µl/min). Regeneration was performed with a pulse of 10 µl of 100 mM HCl. The obtained sensorgrams were analyzed using BIAevaluation software, and kinetic association ($K_a$) and dissociation ($K_d$) rate constants were determined, thereby generating data on the affinities ($K_D$ values) of the different anti-CD137 Fab arms. For each antibody concentration, the on-rates and off-rates were determined separately and then averaged.

The results are shown in Table 6. All tested anti-CD137 Fabs had an affinity in the low nM range.

Example 6

Generation of Jurkat OX40-NFkBluc

A Jurkat OX-40-NFkBluc stable reporter cell line was generated by stably integrating a full length OX-40 construct and a NF-κB luciferase reporter construct in Jurkat E6 cells. Therefore the full length OX-40 MV1616 [pIRESneo3] (Clontech) was transfected and stable clones expressing OX-40 were generated following antibiotic selection. Next, the NF-κB luciferase reporter construct pGL4.32[luc2P/NF-κB-RE/Hygro] (Promega) was transfected in the clone with the highest OX-40 expression and stable clones expressing both OX-40 and NF-κB luciferase were selected following antibiotic selection. Clones were selected for their capacity to respond to OX-40L after initial activation by plate bound CD3 antibodies (clone OKT-3) and PMA/ionomycin. The clone that showed the highest window of activation was used as a thaw and use format in the OX-40 reporter assay.

OX-40 Reporter Assay

For the direct OX-40 activation assay and the OX-40 activation assay mediated by cross linking, 96 well plates (Costar, cat. no. 3917) were coated overnight with 2 µg/ml anti-CD3 (OKT3) in PBS. Next day, plates were washed with PBS. Jurkat OX-40-NFkBluc were thawed and washed with DMEM/F12 medium containing 10% heat inactivated fetal bovine serum (assay medium). Cells were resuspended at a density of $5 \times 10^5$ cells/ml. 25 µl cell suspension was plated into the inner wells of the coated 96 well assay plate. Test antibody was combined with a 2.5 fold aHuIgG-Fc (Bethyl, cat. no. A80-104A) antibody and serial dilutions were prepared (start concentration test IgG 20 µg/ml). Antibody mixtures were incubated for 15 minutes at room temperature. Next 50 µl antibody mixture was added to the cells followed by 25 µl assay medium. Each plate contained a serial dilution of negative (PG1337) and positive control antibody that served as reference controls. Plates were incubated 6H at 37° C., 5% CO, in 95% relative humidity. 50 µl of luciferase (Promega, Bright-Glo™, cat. no. E2610) was added and the amount of luciferase activity was measured using aBioTek Synergy 2 Multi-Mode Microplate Reader.

Figure 18:
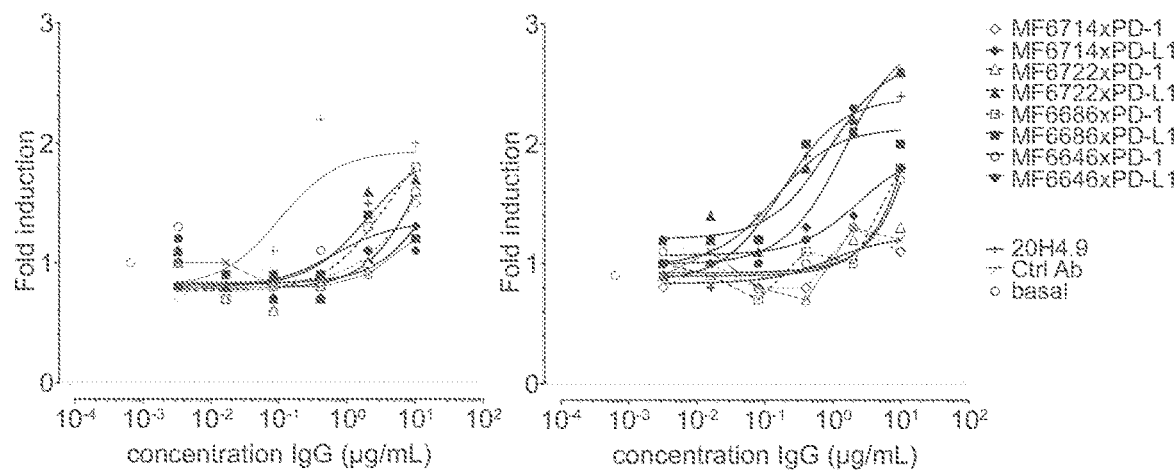

The panel of OX-40 bivalent antibodies was screened in the OX-40 direct activation reporter assay and in the T cell activation assay. Four different OX-40 Fab arms were selected to test whether bispecific OX40xPD-L1 or OX40xPD-1 antibodies would be able to activate OX40 in 'cis' or 'trans'. Therefore the bispecific antibodies were tested in a two cell system, using CHO cells overexpressing PD-L1 and Jurkat OX-40-NFkBluc. PD-L1 was provided in 'trans' on the CHO cells and PD-1 in 'cis' on activated Jurkat OX-40-NFkBluc reporter cells. The same assay set-up was used as in the Jurkat OX-40-NFkBluc assay with coated anti-CD3 providing the first T cell activation signal. The effector target cell ratio used was 4:1 with target cells being either CHO wildtype or CHO-PD-L1 cells. FIG. 18 shows an example of four different OX40 Fab arms combined with either a PD-L1 (MF5561) or PD-1 (MF6256) blocking Fab arm. OX40xPD-L1 antibodies induced OX40 reporter cell activity in the presence of CHO-PD-L1 cells to the same level as the anti-CTLA4 antibody based on ipilumumab. In contrast OX40xPD-1 antibodies showed a basal activity. In the absence of cells expressing PD-L1, the activity of OX40xPD-L1 antibodies returned to baseline.

Example 7

In Example 4, it was determined that five CD137-specific Fab arms are preferred in view of their T cell transactivation capacity.

In this Example a panel of three bispecific antibodies was used, consisting of three candidate CD137 arms (6763, 6785 and 6797), and one PD-L1 arm (7702).

Bispecific antibodies were produced in 293F Freestyle cells, and purified via protA, CIEX and gel filtration. Subsequently, the antibodies were tested in several assays. We tested the four Fab arms both in parental bivalent monospecific format (anti-CD137 or anti-PD-L1) and in bispecific format (anti-CD137xPD-L1) and compared these antibodies with the benchmark anti-CD137 antibody 20H4.9, the benchmark anti-PD-L1 antibody YW243.55.S70, and with a negative control antibody (anti-RSV antibody PG2708).

For the Materials & Methods of the assays described in this Example, reference is also made to Example 4.

The antibodies are listed below.

| Antibody name | MF sequences | Target |
| --- | --- | --- |
| PB17309 | 6763 × 7702 | CD137 × PD-L1 |
| PB17310 | 6785 × 7702 | CD137 × PD-L1 |
| PB17311 | 6797 × 7702 | CD137 × PD-L1 |
| PG6763 | 6763 × 6763 | CD137 |
| PG6785 | 6785 × 6785 | CD137 |
| PG6797 | 6797 × 6797 | CD137 |
| PG7702 | 7702 × 7702 | PD-L1 |

FACS Analysis

Antigen Specificity and Affinity

Binding of the monospecific and bispecific IgGs to human (hu) and cynomolgus (cy) CD137 was verified by FACS analysis using 293FF stable cell clones expressing either huCD137 or cyCD137. To this end, cells were incubated with an 8-step serial titration of antibody and binding intensity was analyzed through subsequent binding of a secondary antibody, anti-human IgG bound to the fluorescent dye phycoerythrin (PE). The binding intensity expressed as mean PE fluorescence for each of the antibodies tested is shown in FIG. 22. Of the monospecific parental anti-CD137 antibodies, PG6785 bound to human CD137 with the highest affinity, followed by PG6797 and then PG6763. Bispecific PB17311 (6797x7702) bound huCD137 with the highest affinity, followed by PB17309 (6763x7702) and then PB17310 (6785x7702). Of the parental anti-CD137 antibodies, PG6785 again bound to cynomolgus CD137 with the highest affinity, this time followed by PG6797 and then PG6763. Bispecific PB17311 (6797x7702) bound cyCD137 with the highest affinity, followed by PB17309 (6763x7702) and then PB17310 (6785x7702). Of note, as shown in FIG. 22, when the three CD137-specific Fab arms are present in a bispecific, monovalent antibody, they are able to bind both huCD137 and cyCD137 equally well, as also observed for the monospecific, bivalent parental antibodies.

Binding of the monospecific and bispecific IgGs to human (hu) and rhesus macaque (re) PD-L1 was verified by FACS analysis using CHO-K1 stable cell clones expressing huPD-L1 or rePD-L1. To this end, cells were incubated with an 8-step serial titration of antibody and binding intensity was analyzed through subsequent binding of a secondary antibody, anti-human IgG-PE. The binding intensity expressed as mean fluorescence intensity (MFI) for each of the antibodies tested is shown in FIG. 23. As expected, the parental anti-CD137 antibodies did not bind to human or rhesus macaque PD-L1, while the parental anti-PD-L1 PG7702 antibody did. Importantly, all three bispecific antibodies bound strongly to PD-L1, all with higher affinity than the positive control antibody. This means that even when present in a monovalent, bispecific antibody the MF7702 arm has a higher affinity for PD-L1 as compared to the bivalent control antibody YW243.55.S70.

Binding to Activated T Cells

We tested the binding affinity of the antibody panel for activated T cells. To this end, peripheral blood mononuclear cells (PBMCs) were collected from a donor and left to rest overnight. T cells were subsequently isolated and activated by incubating them for 3 days on plates coated with anti-CD3 antibody OKT3. The activated T cells were harvested and stained with a serial titration of the IgGs in the antibody panel and with control IgGs. Antibody binding was measured on FACS through subsequent binding of a secondary antibody, anti-human IgG-PE. The binding intensity expressed as MFI for each of the antibodies tested is shown in FIG. 24, with binding of the bispecific IgGs shown on the left and binding of monospecific IgGs on the right. PB17311 (6797x7702) showed the most potent binding. Importantly, the binding affinities of the positive control antibodies were lower than those of the bispecific antibodies. This means that the bispecific antibodies of the present invention have a higher affinity for activated T cells as compared to the PD-L1 specific benchmark antibody YW243.55.S70 (based on Atezolizumab) and the CD137 specific benchmark antibody 20H4.9 (which is based on Urelumab).

Ligand-Blocking Assays

PD-1/PD-L1 Competition Assay

The capacity of the bispecific and monospecific IgGs to block PD-L1 ligand binding was tested in a PD-1/PD-L1 competition ELISA, whereby increasing amounts of antibodies containing an anti-PD-L1 arm were expected to reduce the amount of biotinylated PD-L1 that could bind to a plate coated with PD-1 Fc. To this end, 1 µg/ml PD-1-Fc (R&D; #. 1086-PD) was coated to a maxisorp plate, and biotinylated PD-L1 (BPS Bioscience; cat. nr. 71105) was added in solution in the presence or absence of a serial dilution of each antibody starting at a concentration of 10 µg/ml. Bound PD-L1 was detected through subsequent binding of streptavidin conjugated to horseradish peroxidase (HRP), and addition of colorless substrate which HRP catalyzes into a colored product. The optical density (OD) of the solution, measured at 450 nm using an ELISA plate reader, is an indication of bound PD-L1. Binding curves are shown in FIG. 25, with binding of the bispecific IgGs shown on the left and binding of monospecific IgGs on the right. As expected, the positive control anti-PD-L1 antibody showed a high level of blocking activity, and the negative control antibody showed none. The monospecific anti-CD137 antibodies were also negative for PD-L1 blocking. For the IgGs containing at least one anti-PD-L1 arm, all were able to block PD-1/PD-L1 binding. The parental monospecific anti-PD-L1 antibody PG7702 was found to be just as effective as the benchmark anti-PD-L1 antibody YW243.55.S70 at blocking PD-L1 binding. The bispecific IgGs all had good, similar levels of blocking activity.

Cell-Based huCD137 Ligand Blocking Assay

The capacity of the bispecific and monospecific IgGs to block CD137 ligand binding was also tested. We tested the three candidate CD137 arms (6763, 6785 and 6797) and the PD-L1 arm (7702) both in parental bivalent monospecific format (anti-CD137 or anti-PD-L1) and in bispecific format (anti-CD137xPD-L1) and compared these antibodies with the benchmark anti-CD137 antibody 20H4.9 and PF-05082566 and with a negative control antibody (anti-RSV antibody PG2708).

To analyze CD137 ligand blocking under conditions that are physiologically relevant, the bispecific and monospecific IgGs were tested in a cell-based huCD137 ligand blocking assay using flow cytometry. In this assay, increasing amounts of antibodies containing an anti-CD137 arm were expected to reduce the amount of huCD137L recombinant protein that could bind to CHO-K1 cells stably expressing huCD137. To this end CHO(huCD137) cells were co-incubated with huCD137L protein together with serial dilutions of each antibody. Bound huCD137L was detected with a secondary biotin-conjugated anti-huCD137L antibody, followed by staining with streptavidin conjugated to phycoerythrin (PE).

Methods

CHO cells stably expressing huCD137 were harvested, counted and diluted in FACS buffer to $5 \times 10^5$ cells/ml and 200 µl (containing $1 \times 10^5$ cells) was added to each well of a U-bottom 96-well microtiter plate. Cells were kept on ice. Cells were spun for 3 min at 300 g at 4° C. and washed by adding 200 µl ice-cold FACS buffer. Cells were spun again for 3 min at 300 g at 4° C. and the pellet resuspended in 25 µl antibody dilution in FACS buffer (3-fold serial dilutions from 25 to 0.034 µg/ml) plus 25 µl of a solution of huCD137L-FLAG protein (Adipogen #AG-40A-0198T; end concentration 0.06 µg/ml). Plates were incubated for 60 min on ice in the dark. Cells were then washed twice by adding 200 µl ice-cold FACS buffer and spinning for 3 min at 300 g at 4° C. 50 µl/well of biotinylated polyclonal goat huCD137L antibody (R&D Systems #BAF2295) diluted to 1 µg/ml in ice-cold FACS buffer was then added. Cells were resuspended and plates incubated for 60 min on ice in the dark, followed by washing twice as before. 50 µl/well of streptavidin-PE diluted 1:200 in ice-cold FACS buffer was then added. Cells were resuspended and plates incubated for 30 min on ice in the dark, followed by washing twice as before. Cells were resuspended in 100 µl FACS buffer per well and fixed by the addition of 100 µl 4% paraformaldehyde (PFA) solution. Samples were measured using a BD FACSCanto flow cytometer according to instructions in the BD manuals. The degree of binding of huCD137 ligand was expressed as the mean fluorescence intensity (MFI) of bound streptavidin-PE.

Results

Figure 26:
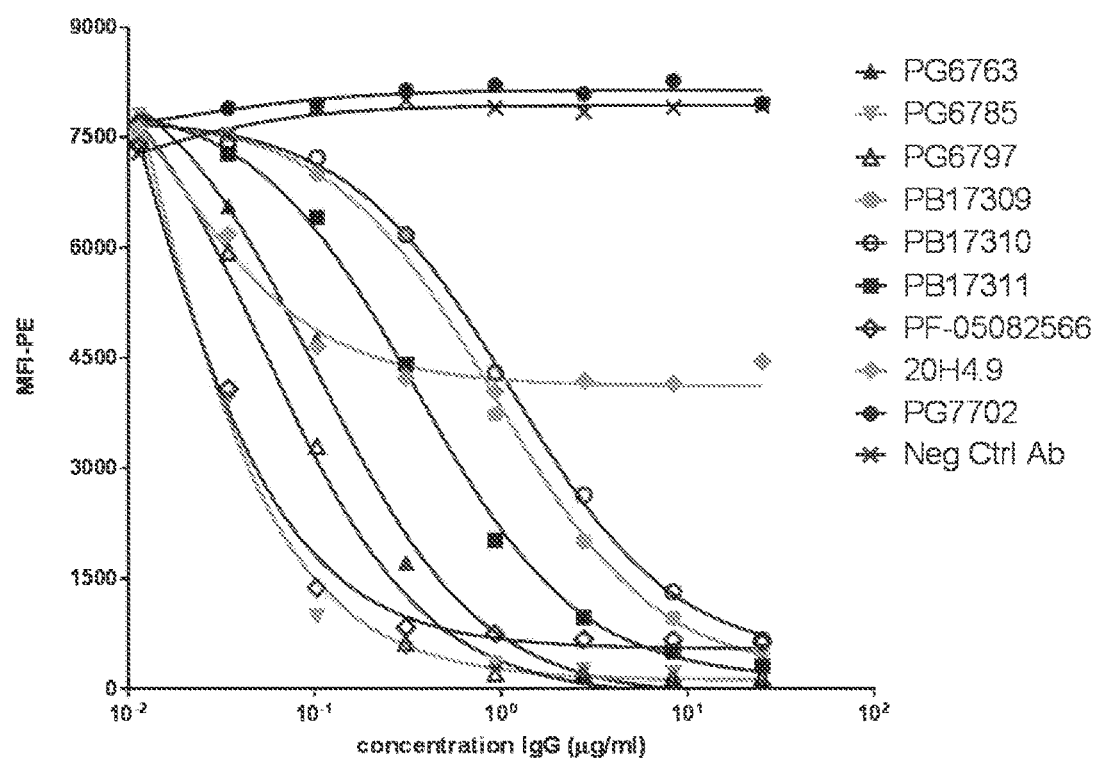

The binding curves obtained are shown in FIG. 26. As expected, the negative control did not block CD137 ligand binding. Blocking of ligand binding by the positive control antibodies differed: benchmark antibody PF-05082566 showed strong blocking, while 20H4.9 showed relatively weak and incomplete blocking. Of the three monospecific anti-CD137 antibodies, PG6785 was the best blocker and PG6797 (parent of PB17311) was the second best. The three corresponding bispecific anti-CD137 x anti-PD-L1 antibodies were also able to block CD137 ligand binding. Since this is a cell-based assay, these results are indicative for conditions that are physiologically relevant.

PD-1/PD-L1 Reporter Assay

Figure 27:
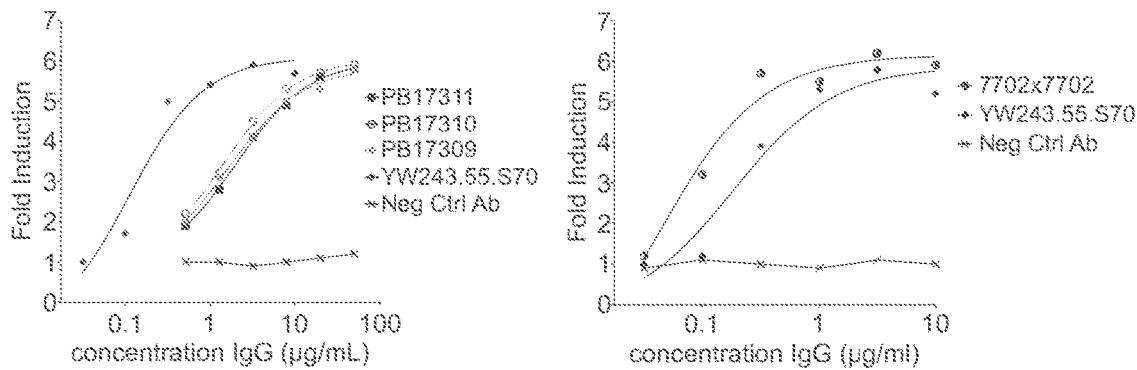

Another step in the characterization of the candidate anti-CD137xPD-L1 antibodies was to determine whether they could block the PD-1/PD-L1 pathway, and to compare this with the activity of a control antibody specific for PD-L1. This blocking activity was tested in vitro in a physiologically relevant PD-1/PD-L1 blockade reporter assay developed by Promega based on a two-cell system: CHO cells expressing PD-L1 and a T-cell receptor activator, and a Jurkat/NFAT-RE reporter cell line overexpressing PD-1. The Jurkat T cells contain a luciferase reporter gene that can become activated through the NFAT (nuclear factor of activated T-cells) pathway. Interaction of PD-1 with PD-L1 inhibits activation of this pathway. However, blocking the PD-1/PD-L1 interaction with antibodies against PD-1 or PD-L1 can activate the NFAT pathway. Therefore, the greater the degree of PD-1/PD-L1 blockade, the greater the activation of the luciferase reporter gene. To this end, serial dilutions of each antibody were added to PD-L1-expressing CHO cells before addition of Jurkat/NFAT-RE reporter cells overexpressing PD-1. The degree of blockade after 24 hours expressed as fold induction of the reporter gene is shown in FIG. 27, with binding of the bispecific IgGs shown on the left and binding of the monospecific anti-PD-L1 IgG on the right. Again, the bivalent parental antibody 7702 was more potent than the positive control benchmark antibody YW243.55.S70. The bispecific IgGs all had good, similar levels of blocking activity.

Example 8

Effect of PD-L1 Expression Level on Transactivation of CD137 by CD137xPD-L1 Bispecifics Culturing of Cell Lines MDA-MB231 cells (cat. no. CRM-HTB-26) were purchased from ATCC and routinely maintained in DMEM high glucose (Gibco) supplemented with 100 mM sodium pyruvate (Gibco) MEM non-essential amino acids (Gibco) and 10% FBS (Lonza). BxPC-3 cells (cat. no. CRL-1687) were obtained from ATCC and routinely maintained in RPMI-1640 (Gibco) supplemented with 10% FBS (Lonza).

Mode of Action CD137xPD-L1 Antibodies

Figure 28A:
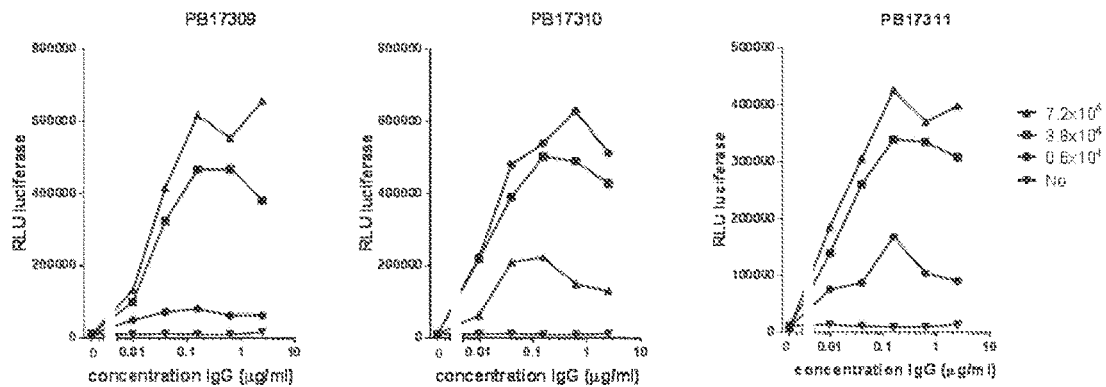

The Jurkat CD137-luc reporter transactivation assay was used to determine whether CD137xPD-L1 antibody-mediated transactivation would occur at physiological PD-L1 expression levels and whether it correlates to PD-L1 expression levels. Therefore, the number of PD-L1 binding sites on various CHO-PD-L1 cell lines and human tumor cells lines were determined by QIFIKIT analysis (DAKO). Three CHO-PD-L1 cell lines showing PD-L1 expression levels corresponding to human tumor cell lines expressing relatively high (ES-2 cells) intermediate (MDA-MB231) or low (BxPC-3) levels of PD-L1 were selected. FIG. 28A shows an example of three CD137xPD-L1 bispecific antibodies in using the three selected CHO cell lines expressing ~6,000 to ~72,000 PD-L1 binding sites per cell. The data show that CD137xPD-L1 bispecific antibodies show high activation when more than $3.8 \cdot 10^4$ PD-L1 copies are present on the cell. At low PD-L1 levels; in the presence of CHO cells expressing merely ~6000 PD-L1 binding sites per cell a low level of activation is observed. Hence, transactivation by CD137xPD-L1 bispecific antibodies will occur in the vicinity of cells expressing high levels of PD-L1 such as occur in an immunosuppressive tumor micro environment and therefore provide an optimal therapeutic window for the CD137xPD-L1 bispecific antibody.

FIG. 28A shows a positive correlation between CD137xPD-L1 bispecific antibody-mediated NF-kB activation and PD-L1 expression levels on CHO cells for all antibodies tested.

Figure 28B:
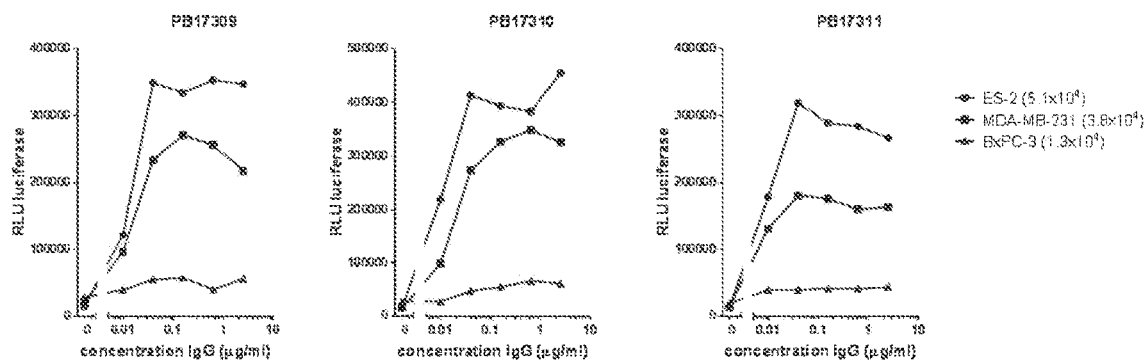

FIG. 28B shows an example of the Jurkat CD137-luc reporter transactivation assay wherein the CHO-PD-L1 cells were substituted for the human tumor cell lines expressing high, intermediate and low surface PD-L1 levels. This experiment confirmed that CD137xPD-L1 bispecific antibody-mediated transactivation is associated with accessory cell PD-L1 expression levels, and that the CD137xPD-L1 bispecific antibodies are capable of transactivation in the presence of tumor cells expressing high levels of PD-L1.

Figure 28C:
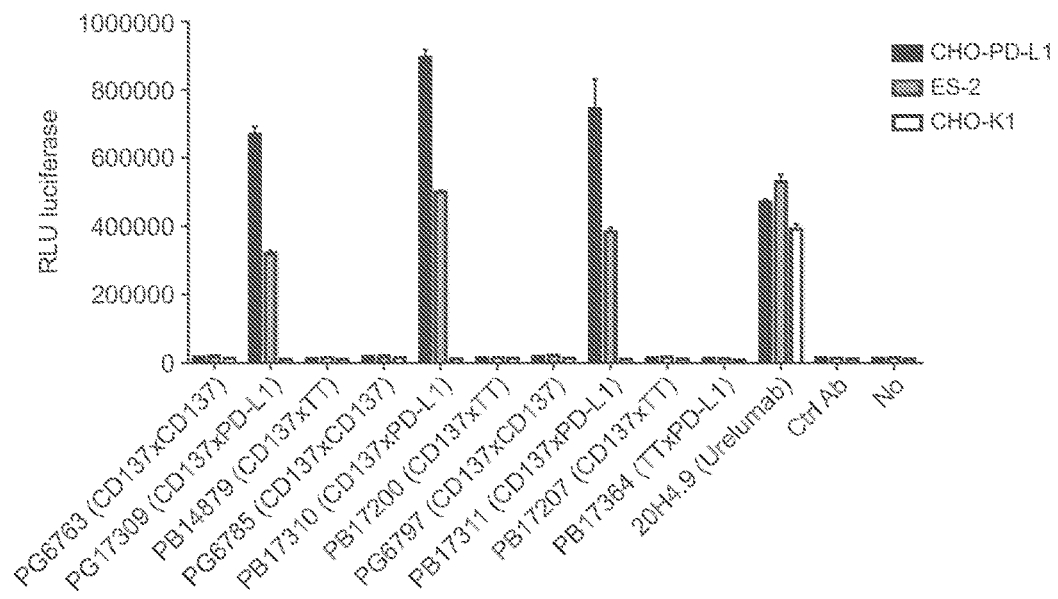

Next, it was assessed whether CD137 transactivation in the presence of PD-L1 expressing accessory cells was a specific trait of CD137xPD-L1 bispecific antibodies. FIG. 28C shows an example wherein Jurkat CD137-luc reporter cell transactivation in the presence of PD-L1 expressing accessory cells was assessed for CD137xPD-L1 bispecific antibodies, their parental monospecific bivalent (CD137xCD137) and parental monospecific monovalent CD137 (CD137xTT) and PD-L1 (TTxPD-L1) antibodies. All IgG were tested at 10 µg/ml. The data show that only CD137xPD-L1 bispecific antibodies mediated transactivation in the presence of PD-L1 expressing CHO or ES-2 cells. As expected, reference control antibody 20H4.9 directly activated Jurkat CD137-luc reporter cells and was independent of PD-L1 expression by accessory cells.

Example 9

CHO-PD-L1 x T Cell Transactivation Assay

To determine the added value of using a bispecific IgG, we assessed the ability of several bispecific anti-CD137xPD-L1 antibodies to induce cytokine release by T cells in a transactivation assay, and compared their activation with that of benchmark bivalent antibodies against PD-L1 (YW243.55.S70) and CD137 (20H4.9). These benchmark antibodies were tested alone and in equimolar combination. To this end, purified and activated T cells from a single healthy donor were co-incubated for 3 days with CHO-PD-L1 cells and a serial dilution of the test antibodies (see also Example 4 for a detailed description of this assay). Levels of IL-2, IFNγ and TNFα were subsequently measured in undiluted culture supernatants. The degree of cytokine release measured in this transactivation assay is shown in FIG. 29. As shown in FIG. 29, all three bispecific antibodies were more potent at inducing cytokine release than either one of the reference antibodies. Importantly, each one of the three bispecific antibodies was also more potent at inducing cytokine release than a combination of the two reference antibodies, demonstrating their superior T cell activating characteristics.

Cytokine Release During T Cell Transactivation Assay

To determine the added value of using a bispecific IgG, we compared one of the bispecific antibodies (PB17311; 6797×7702) with a mix of its parental monospecific bivalent parental IgGs and with benchmark bivalent antibodies against PD-L1 and CD137, in terms of their ability to activate cytokine release by T cells in a transactivation assay. These benchmark antibodies are based on therapeutic antibodies used in the clinic: anti-PD-L1 clone YW243.55.S70 is based on Atezoluzumab, anti-CD137 clone 20H4.9 is based on Urelumab and anti-CD137 clone PF-05082566 is based on Utomilumab. These benchmark antibodies were tested alone and in equimolar combination.

In these experiments, antibodies were tested in a 6-step 10-fold titration starting at 20 µg/ml. PBMCs from 2 donors were thawed and 9 volumes of culture medium (RPMI1640 with L-glutamine and 10% heat inactivated FBS) was added. Cells were centrifuged for 10 minutes at 150 g at RT. The cell pellet was resuspended in 10 ml culture medium and cells were allowed to rest by incubating overnight in a 50 ml falcon tube at 37° C., 5% CO, at 95% relative humidity. In preparation for the transactivation assay, the inner wells of a 96-well plate (Cellstar, cat. no. 655180) were coated overnight with 5 µg/mL anti-CD3 antibody (clone OKT3) in PBS.

Next day, T lymphocytes were isolated using the Easy Sep T cell enrichment (pan CD3) purification procedure as described by the manufacturer (Stem cell Technologies, cat. no. 19051). The EasySep procedure uses negative selection. Briefly, PBMCs were centrifuged for 10 minutes at 150 g at RT. The cell pellet was resuspended in 2 ml PBS+2% FBS with 1 mM EDTA. The cell suspension was filtered through a 30 µm mesh nylon strainer. The cells were counted and readjusted to $5 \times 10^7$ cells/ml in PBS+2% FBS with 1 mM EDTA. 50 µl of EasySep Human T Cell Enrichment cocktail was added to each 2 ml cell volume, mixed and allowed to incubate for 10 minutes at RT. Next, 50 µl of EasySep D Magnetic Particles were added to each 2 ml cell volume and allowed to incubate for 5 minutes at RT. The total volume was brought to 2.5 ml with PBS+2% FBS with 1 mM EDTA. Next, the tube was placed into the magnet allowing the undesired cell fraction to be bound to the magnet for 5 minutes at RT. Next, the tube was inverted and the purified T cells fraction was poured off into a new tube, cells were harvested by 10 minutes centrifugation at 150 g at RT and subsequently resuspended at a concentration of 106 cells/ml in culture medium.

The same day, the pre-coated 96-well plates were washed with PBS and 25 µl of the prediluted antibody was added, followed by 50 µl purified T cells (50,000 cells/well) and 25 µl CHO-PD-L1 cells (30,000 cells/well). Cells were allowed to incubate for 72 hrs at 37° C. Supernatant was then collected and tested fresh or stored at −80° C. Levels of cytokines were measured in undiluted culture supernatants by Luminex Multiplex assay following the manufacturers' instructions. Results were analyzed by eBioscience analysis software.

For a subset of 16 cytokines, the levels induced by PB17311 in the transactivation assay were higher than those induced by the benchmark anti-CD137 antibody 20H4.9 on its own or in combination with the benchmark anti-PD-L1 antibody YW243.55.S70 (see FIG. 30). The subset was composed of GM-CSF, IL-2, IL-13, IFNγ, TNFβ, IL-17A, TNFα, IL-18, IL-la, IL-22, IL-4, IL-31, IL-6, IL-5, IL-21 and IL-9. The greatest increase in cytokine levels induced by PB17311 was seen for GM-CSF, IL-2, IL-13, IL-17A, IFNγ, TNF-α, TNF-8, IL-18, IL-22, and IL-4. No notable antibody-mediated cytokine release was observed for IL-16, IL-IRA, IL-7, IL-10, IL-12p70, IL-15, IL-23, or IL-27. No increase in cytokine release was seen when cells were incubated with the anti-PD-L1 antibody YW243.55.S70 only, or with the anti-CD137 antibody PF-05082566 only, or with the parental 6797 (CD137) or PD-L1 (7702) bivalent antibodies.

In conclusion, this experiment shows that the bispecific antibody PB17311 has an improved T cell activation ability as compared to the benchmark anti-CD137 antibody 20H4.9 on its own or in combination with the benchmark anti-PD-L1 antibody YW243.55.S70.

An important advantage of PB17311 is that this bispecific antibody is more potent at activating T cells than a mixture of two benchmark antibodies.

Example 10

SEB Assay

To further characterize the three CD137xPD-L1 bispecific antibodies PB17309, PB17310 and PB17311, their ability to enhance cytokine release by PBMCs in the presence of staphylococcal enterotoxin B (SEB) was determined. To this end, purified PBMCs from 3 donors were incubated for 3 days in the presence of SEB (2000 or 125 ng/ml) and a serial dilution of the three candidate bispecific antibodies or control antibodies. The reference control antibody in this experiment was anti-CTLA4 antibody 10D1 that has been shown to induce a potent cytokine release in this assay.

Figure 32:
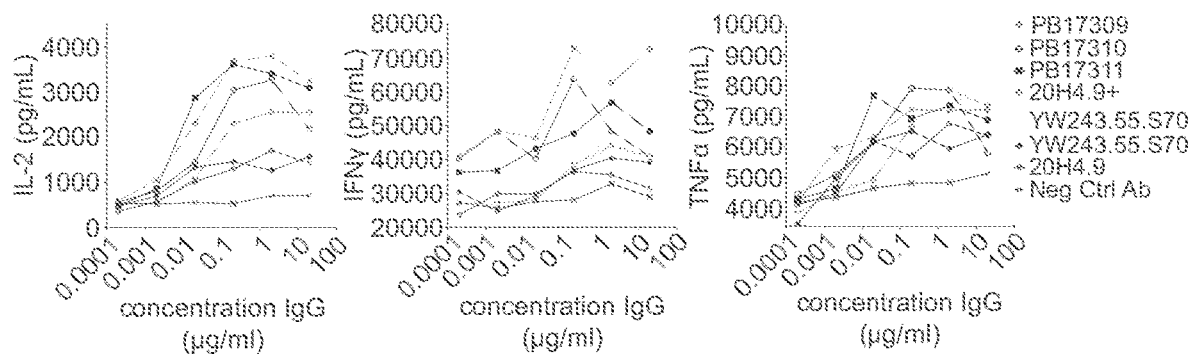

Cytokine levels were measured in culture supernatants by Luminex Multiplex assay. The results of IL-2 release by PBMCS from three different donors at the two different SEB concentrations are shown in FIG. 31. This comparison demonstrates that the activity profiles of all 3 bivalent CD137xPD-L1 antibodies were consistent among the three donors. They also show that PB17309 and PB17311 were the most effective of the bispecific antibodies. All three of PB17309 (6763x7702), PB17310 (6785x7702) and PB17311 (6797x7702) were more potent than the positive control antibodies. The results for levels of IL-2, IFNγ and TNFα released by PBMCs from a single donor (no. 1038) at a SEB concentration of 2000 ng/ml is shown in FIG. 32, whereby the cytokine release induced by the CD137xPD-L1 bispecific antibodies was compared with that induced by benchmark bivalent antibodies against CD137 (20H4.9) or PD-L1 (YW243.55.S70), either alone or in an equimolar mix. This comparison demonstrates that the CD137xPD-L1 bispecific antibodies are clearly more efficient at activating PBMCs than each of the benchmark bivalent antibodies. Importantly, each of the CD137xPD-L1 bispecific antibodies was also more efficient at activating PBMCs than a mixture of YW243.55.S70 and 20H4.9, again demonstrating the superior T cell activating characteristics of these bispecific antibodies in the presence of cells expressing PD-L1 that can provide activation in trans of the bispecific molecules.

Example 11

Effect of PB17309, PB17310 and PB17311 on M2 Macrophage-Mediated Suppression of Anti-CD3/CD28-Stimulated PBMCs Classically activated macrophages (M1 macrophages) can kill tumors during the early steps of carcinogenesis. However, during the transition from early transformation to advanced tumor stages, dynamic changes in the tumor microenvironment gradually drive the switch from M1 to M2 macrophages. Tumor-associated M2 macrophages secrete immunosuppressive cytokines and induce immune suppression by ligation to PD-1. As such, M2 macrophages inhibit T cell proliferation and cytokine production.

An M2 macrophage suppression assay developed by Aquila Biomedical has been used to demonstrate that an anti-PD-1 antibody can partially reverse the inhibitory effect of M2 macrophages on T cell proliferation. We used this assay to test the effect of PB17309, PB17310 and PB17311 on the repolarization of M2 macrophages, using IFN-γ expression as the read-out, and compared it with the effects mediated by a negative isotype control (anti-RSV-G antibody PG2708) and two reference antibodies (anti-CD137 benchmark antibody 20H4.9 and anti-PD-L1 benchmark antibody YW243.55.570).

M2 Suppression Assay

Peripheral blood mononuclear cells (PBMCs) were isolated from fresh blood collected from five healthy volunteers. Magnetic cell sorting was used to isolate monocytes by negative selection (without CD16 depletion). A subset of PBMCs from each of the 5 donors was also cryopreserved for use later in the assay for PBMC/M2 co-culture. M2 macrophages were generated by culturing isolated monocytes with M-CSF (50 ng/mL) in RPMI-10 (RPMI-1640, 10% heat inactivated FBS, 100 U/mL penicillin, 100 μg/mL streptomycin and 2 mM L-glutamine, 50 μM β-mercaptoethanol) for 8 days in 96-well round-bottom plates. During the culture period, cells were replenished with fresh RPMI-10 supplemented with M-CSF on day 3 and 6. On day 8, medium was removed, fresh medium (without M-CSF) added and the cells were activated with LPS (0.1 μg/mL) for 2 hours. The macrophages were then washed to remove LPS and replenished with fresh media (without M-CSF). The M2 macrophages were co-cultured with autologous PBMCs (thawed and washed) at a 4:1 ratio (PBMC:M2) in the presence or absence of test antibodies or isotype controls (10 μg/ml), in triplicate. After 24 hours of cross-talk, the cultures were stimulated with anti-CD3 (1 μg/mL) and anti-CD28 (2 μg/mL) for three days to activate T cells via the TCR receptor complex. IFN-γ was then measured in culture supernatant by ELISA with supernatants diluted 1:10 or 1:20 in the appropriate ELISA diluent to bring values within the detection range of the kits. Statistical analyses were made between test substance and appropriate control groups using either a ratio paired t-test, or one way-ANOVA for multiple comparisons with either post-hoc Dunnett's (for comparisons between a control and multiple groups) or Holm-Sidak (for comparisons between all groups) multiple comparisons test. Statistical significance was assumed when P<0.05.

Results

Figure 33:
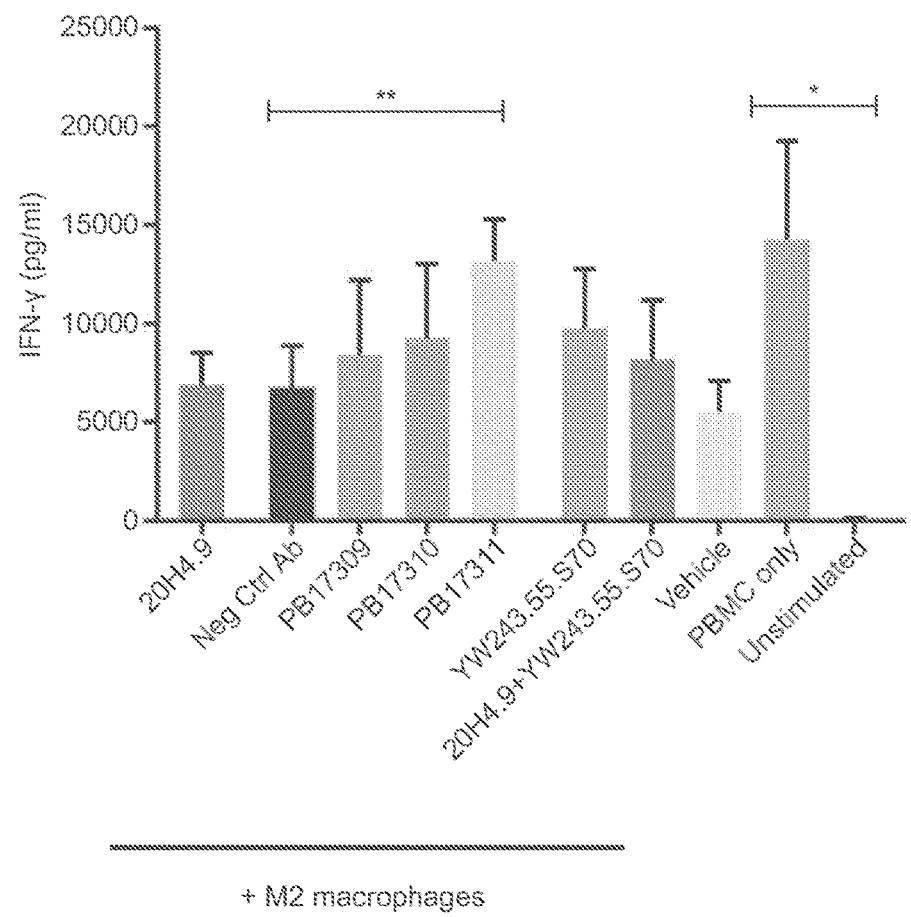

The results are shown in FIG. 33, with data presented as the mean levels of IFN-γ of the triplicates detected by ELISA after anti-CD3/CD28 stimulation of PBMCs. It is clear from these results that PBMCs cultured in the absence of M2 macrophages produced higher levels of IFN-γ after stimulation with CD3 and CD28 (compare "PBMC only" with "Unstimulated" condition; * indicates P<0.05). Despite the heterogeneity of the results obtained for the different donors, it is concluded that all three bispecific antibodies increased the production of IFN-γ in M2:PBMC co-cultures. Although not statistically significant, PB17309 and PB17310 show a tendency of increased IFN-γ production relative to those treated with PG2708 isotype control. Importantly, the addition of PB17311 significantly increased the production of IFN-γ in M2:PBMC co-cultures relative to those treated with PG2708 isotype control (** indicates P<0.01). The results that are obtained with PB17309 and PB17310 are comparable with the results obtained with anti-CD137 benchmark antibody 20H4.9 and with anti-PD-L1 benchmark antibody YW243.55.570. The results that are obtained with PB17309 and PB17310 are also comparable with the results obtained with a combination of both reference antibodies.

Example 12

Effect of PB17311 on Naïve Human CD8+ T Cell Priming

CD137 x PD-L1 bispecific antibodies according to the present invention induce activation of T cells by bridging CD137 on the T cell and PD-L1 on accessory cells. This is thought to result in CD137 signaling and to enhance antigen-dependent TCR activation by blocking the PD-1/PD-L1 pathway. In the presence of PD-L1 expressing tumors, CD137 x PD-L1 bispecific antibodies according to the present invention facilitate (re)activation of antigen-specific T cells, as shown in the current Examples. This is consistent with the fact that it is known that CD137 co-stimulation allows expansion, cytokine production and survival of T cells (Bertram et al 2004). However, we also wanted to demonstrate that CD137 x PD-L1 bispecific antibodies according to the present invention facilitate de novo effective T cell responses against tumor neoantigens. Priming of naive CD8+ T cells in mouse infection models has shown that CD137 co-stimulation facilitates the formation of central memory and effector T cell populations (Zhao et al 2012). We therefore assessed the effects mediated by one of our bispecific antibodies (PB17311; 6797 x 7702) on the priming of naïve human CD8+ T cells.

Due to the low numbers of naïve T cell precursor cells antigen-specific priming of human T cells is difficult to assess. However, an antigen overexpressed in melanoma—the tumor-associated antigen Melan-A—has been found to be particularly suitable for assessing naïve T-cell responses in human T cells. This is because levels of T cells specific for this HLA-A0201-restricted Melan-A 27-35 peptide epitope are about 10-fold higher than levels of T cells against other self- or tumor-associated antigens; the epitope is recognized by about 1 in 1000 naïve T cells. Based on this epitope, Wölfl and Greenberg (2014) have developed an in vitro priming system that reliably assesses priming conditions for CD8+ T cells. The method is known as antigen-specific activation and priming of human CD8 T cells, or ASAP-T8. In an ASAP-T8 assay, isolated naïve CD8+ T cells are co-cultured with peptide antigen-loaded autologous monocyte-derived dendritic cells for 10 days, followed by quantitative and qualitative analysis of antigen-specific T cells.

In this Example the ASAP-T8 assay was performed in accordance with the detailed methods described in Wölfi and Greenberg (2014) using peripheral blood mononuclear cells (PBMCs) from two independent donors (no. 1064 and 1066). The antibodies and controls tested in the assay were anti-CD137xPD-L1 antibody PB17311, anti-CD137 benchmark antibody 20H4.9, anti-PD-L1 benchmark antibody YW243.55.570, an equimolar mix of both benchmark antibodies and negative control anti-RSV-G antibody PG2708. Test antibodies were added from the start of the DC:T cell culture and again during the first feeding.

Generation of Monocyte-Derived Mature Dendritic Cells (mDCs)

Monocyte-derived mature dendritic cells were generated using a protocol following the detailed methods as described in Wölfl and Greenberg (2014). To this end, four days before the start of the ASAP-T8 assay, PBMCs from HLA-A2$^+$ donors were thawed, spun at 300 g for 5 min at RT, and resuspended in culture medium (CellGro Dendritic Cell Medium (CellGenix, cat. no. 2005)+1% human serum) to $1 \times 10^7$/ml. 2 ml of this cell suspension was then added to each well of a 6-well plate. After an incubation of 2-3 hrs at 37° C. to allow adherence to plastic, medium was removed and non-adherent cells removed through washing with PBS. 3 ml of warm culture medium supplemented with 10 ng/ml IL-4 and 1600 IU/ml GM-CSF was added to each well, followed by incubation for 2 days at 37° C. After further addition of 1.5 ml of fresh culture medium supplemented with IL-4 and GM-CSF, cells were incubated for an additional 24 hrs.

Immature DCs were then harvested by removal of 3 ml supernatant followed by vigorous resuspension of cells in remaining medium, and washing with ice-cold PBS to remove any remaining cells. Cells were pooled and counted and spun at 300 g for 5 min at RT. The pellet was resuspended at $1 \times 10^6$ cells/ml in pre-warmed culture medium, supplemented with GM-CSF (800 IU/ml), IL-4 (10 ng/ml), LPS (10 ng/ml) and IFNγ (100 IU/ml). 2 ml cell suspension ($2 \times 106$ cells) was added to the wells of a new 6-well plate. Melan-A antigen peptide (JPT, cat. no. SP-MHCI-0006) dissolved in DMSO to 5 µg/µl was added to the appropriate wells at 2.5 µg/ml and cells were incubated at 37° C. for 16 hrs.

After a check for DC morphology, mDCs were harvested through vigorous resuspension with a pipette and flushing of empty wells with ice-cold PBS to ensure removal of all adherent cells. mDC that had been pulsed with peptide and those that had not were pooled separately and live cells counted. Tubes with mDC were kept on ice at all times and irradiated with 30 Gy (3000 Rad) to prevent potential proliferation of contaminating cells during subsequent prolonged co-culture of the cells. Cells were then spun at 300 g for 5 min at RT, and resuspended in CellGro DC medium+ 5% human serum (HS) at $5 \times 10^5$ cells/ml.

Generation of Naïve CD8 T Cells

One day before the start of the ASAP-T8 assay, PBMCs from the same HLA-A2$^+$ donors as those used to generate mDCs were thawed, spun at 300 g for 5 min at RT, and resuspended in cold PBS/HS/EDTA buffer (PBS containing 2% HS and 1 mM EDTA) at $5 \times 10^7$ cells/ml. Cells were used for naïve CD8 T cell isolation using the EasySEP Human Naïve CD8+ T Cell Isolation Kit (STEMCELL, cat. no. 19258).

Per ml of cell sample, 50 µl EasySep Isolation Cocktail was added, followed by mixing and incubation at RT for 10 minutes. EasySep magnetic particles were then vortexed for 30 sec and 100 µl particles added per ml of sample to target unwanted cells for removal. After incubation at RT for 10 min, the cell suspension was made up to a total volume of 2.5 ml by addition of EasySep buffer, and cells were mixed by gentle pipetting followed by transfer to a 5 ml Falcon tube. The cap was removed and the tube placed into the EasySep magnet. After 5 minutes at RT, the desired fraction was poured off into a new 5 ml Falcon tube by inverting magnet and tube in one continuous motion, leaving magnetically labeled unwanted cells bound inside the original tube. The magnet and tube were left in an inverted position for 3 seconds before returning to an upright position, leaving any drops that remained hanging from the mouth of the tube. The old tube with unwanted cells was removed from the magnet and the new tube with the negatively enriched cell fraction was placed into the magnet for a second separation. After 5 minutes at RT, the desired fraction was poured off in the same manner.

The negatively selected enriched cells were counted and then spun at 300 g for 5 min at RT and resuspended at a final cell concentration of $3 \times 10^6$ cells/ml in CellGro DC culture medium supplemented with 5% HS, and containing 5 ng/ml IL-7 to allow for optimal T cell priming. The cells were transferred to 6-well plates at 2 ml/well and incubated overnight.

ASAP-T8 Assay

This assay was performed in triplicate for each donor, following the detailed methods as described in Wölfl and Greenberg (2014). T cells that had been pre-incubated with IL-7 were harvested, pooled and counted, then spun at 300 g for 5 min at RT. The pellet was resuspended in culture medium at $2 \times 10^6$ cells/ml and IL-21 added at 60 ng/ml to enhance CD8+ T cell priming. Two DC/T cell mixes were prepared by mixing peptide-pulsed mDC or non-pulsed DC with T cells at a 1:1 v/v ratio, resulting in a 4:1 T cell:DC ratio and a final IL-21 concentration of 30 ng/ml. Test antibodies were added at a final concentration of 10 µg/ml. 500 µl of each cell mix was then transferred to individual wells of 48-well plates.

The cells were co-cultured at 37° C. for a total of 10 days, which involved two feeding steps and a transfer to fresh plates. The cells were first fed after 72 hrs with an additional 500 µl warm culture medium containing 5% HS and 10 ng/ml IL-15 and 10 ng/ml IL-7 (final concentration of cytokines 5 ng/ml) in the presence or absence of 20 µg/ml test antibody (final IgG concentration 10 µg/ml) and incubated for 48 hrs. To allow more room for expansion and reduce the number of residual (plastic-adherent) myeloid cells from the DC preparation, the cells and medium were then transferred to fresh wells in a 24-well plate, to which 1 ml of medium containing 5% HS and 10 ng/ml IL-15 and IL-7 had already been added. After a further 120-hr incubation cells were ready for analysis.

On day 10 of co-culture, cells from individual wells were harvested and counted to determine absolute cell counts per well. T cells were then stained with a fluorescently-labeled Melan-A-specific dextramer (Immudex, cat. no. WB2162-APC). In this dextramer, the dextran polymer backbone carries>10 MHC-peptide complexes and fluorochrome molecules (allophycocyanin), thereby allowing for the detection of Melan-A-peptide-specific CD8+ T cells by FACS analysis. The cells were also stained with other antibodies against markers on specific T cell subsets. To this end, cells derived from individual wells were transferred to wells of a 96-well FACS plate at 50,000 cells/well. Cells were spun for 5 min at 300 g, the supernatant was removed, followed by the addition of 40 µl dextramer (1:50 dilution in PBS+5% FBS) and incubation in the dark for 20 min at RT. Additional antibodies specific for CD8, CD45RA and CCR7 (5× concentrated) were then added in 10 µl FACS buffer. Cells were incubated in the dark for 20 min at 4° C. then washed twice with FACS buffer. After incubation for 10 min at 4° C., cells were ready for analysis by FACS.

Results

T Cell Expansion

The dextramer-positive population represents antigen-specific cells that had expanded upon priming and constituted 5-24% of the total CD8 T cell population. The relative size of the dextramer-positive, CD8-positive T cell population and the absolute cell numbers were used to calculate the number of antigen-specific CD8+ T cells per well and the data from each donor was expressed as the number of antigen-specific CD8+ T cells in culture relative to the sample containing no antibody (see FIG. 34). The data shown is from an experiment performed in triplicate and error bars represent the standard deviation.

It is clear from these results that the population of dextramer-positive antigen-specific CD8+ T cells expanded when peptide antigen was present during priming (compare "No peptide ctrl" and "No Ab" conditions in FIG. 34).

The anti-CD137 reference antibody 20H4.9 enhanced expansion of antigen-specific CD8+ T cells relative to the negative control antibody, but only in one donor (PBMC1064).

Anti-PD-L1 reference antibody YW243.55.S70 did not affect expansion.

CD137xPD-L1 antibody PB17311 significantly enhanced expansion of antigen-specific CD8+ T cells in both donors relative to the negative control antibody. PB17311 enhanced expansion of antigen-specific CD8+ T cells to a higher extent than the anti-CD137 reference antibody 20H4.9. PB17311 had a higher CD8+ T cell expansion activity as compared to a combination of anti-PD-L1 antibody YW243.55.S70 and anti-CD137 reference antibody 20H4.9. This means that this CD137 x PD-L1 bispecific antibody is more potent in priming naïve CD8+ T cells than the CD137-specific and PD-L1-specific benchmark antibodies.

T Cell Differentiation

Upon antigen-specific priming, naïve T cells start to differentiate. During this differentiation process, the expression of CCR7 and CD45RA on the surface of the cells is downregulated, with CD45RA being re-expressed on terminally differentiated effector T cells. Downregulation of CCR7 and CD45RA expression is therefore an indication of differentiation. Expression of the differentiation markers CCR7 and CD45RA was analyzed by gating on CD8+ dextramer+ cells and then determining the relative numbers of cells within the different T cell subsets. Subsets were defined as T naïve/memory stem cells ($T_N/T_{SCM}$): CD45RA+CCR7+; central memory T cells ($T_{CM}$): CD45RA-CCR7+; effector memory T cells ($T_{EM}$): CD45RA-CCR7-; and terminally differentiated effector T cells ($T_{TE}$): CD45RA+CCR7-. Data from each donor were expressed as the percentage of each T cell subset within the CD8+dextramer+ T cell population (see FIG. 35). CD137xPD-L1 antibody PB17311 enhanced differentiation of antigen-specific CD8+ T cells in both donors relative to the negative control antibody. When we compared T cells that had been primed in the presence of the negative control antibody and those primed in the presence of antibody, we found that PB17311 reduced the relative numbers of antigen-specific CD8+ T cells with a naïve cell phenotype ($T_N/T_{SCM}$) and increased the relative numbers of effector memory and terminally differentiated effector cell populations ($T_{EM}$ and $T_{TE}$ in FIG. 35). PB17311 enhanced differentiation of antigen-specific CD8+ T cells to a higher extent than reference antibody 20H4.9, as shown by the increase in the relative numbers of effector memory and terminally differentiated effector cell populations within the PB17311 incubated CD8+ T cell population as compared to the 20H4.9 incubated CD8+ T cell population. PB17311 even enhanced differentiation of antigen-specific CD8+ T cells to a higher extent as compared to a combination of anti-PD-L1 antibody YW243.55.S70 and anti-CD137 reference antibody 20H4.9. This means that this CD137 x PD-L1 bispecific antibody is more potent in enhancing differentiation of naïve T cells upon priming than the CD137-specific and PD-L1-specific benchmark antibodies.

Without being bound to any theory, it is thought that the potent effects of CD137xPD-L1 antibody PB17311 on CD8+ T cell priming primarily depends on induction of CD137 signaling in T cells. By binding CD137 expressed on the T cell surface after antigen recognition and PD-L1 on mature DCs, PB17311 allows for CD137 receptor clustering required for CD137 signaling.

In summary, these results demonstrate that the CD137/PD-L1 bispecific antibody PB17311 enhances both the expansion and differentiation of naïve CD8+ T cells in vitro.

PB17311 has an increased expansion and differentiation potential as compared to (a combination of) anti-PD-L1 benchmark antibody YW243.55.S70 and anti-CD137 benchmark antibody 20H4.9. This demonstrates that PB17311 is more effective in inducing or enhancing novel T cell responses against existing tumors.

Example 13

Effect of PB17311 on CD107a and Cytokine Expression by T Cells

As demonstrated in Example 10, CD137xPD-L1 bispecific antibodies can enhance IL-2, TNFα and IFNγ production in the supernatant of SEB-activated PBMCs. Here we used intracellular cytokine staining and FACS analysis to identify the T cell subsets that are responsible for the enhanced cytokine production upon treatment with CD137xPD-L1 bispecific antibody PB17311. We also assessed CD107a expression as a marker for CD8+ T cell cytotoxicity. We compared the effect of PB17311 with that of anti-CD137 benchmark antibody 20H4.9, anti-PD-L1 benchmark antibody YW243.55.570, an equimolar mix of both reference antibodies, and negative control anti-RSV-G antibody PG2708.

To this end, PBMCs were stimulated with SEB (320 ng/ml) in the presence or absence of antibodies for 24 hrs, and stained for the markers CD3, CD4, CD8, CCR7, CD45RO and CD107a, for the cytokines IL-2, IFNγ and TNFα, and using a viability dye. PBMCs cultured in the absence of SEB and antibodies were included as a control for SEB stimulation (Unstimulated). The expression of CD107a and cytokines was analyzed in the total T cell population (CD3+ cells) and in the following CD4 and CD8 T cell subsets: naïve T cells (CD45RO-CCR7+), central memory T cells (CD45RO+CCR7+), effector memory T cells (CD45RO+CCR7-) and terminally differentiated effector T cells (CD45RO-CCR7-). Results are only shown for the subsets for which the most pronounced differences were observed: CD4 effector memory (EM) cells, CD8 EM cells and CD8 terminally differentiated effector (TE) cells.

Methods

List of antibodies used to detect intracellular and extracellular targets in FACS analysis.

| Target | Conjugate | Supplier | Cat. no. |
| --- | --- | --- | --- |
| CCR7 | BV605 | Biolegend | 353224 |
| CD45RO | BV785 | Biolegend | 304234 |
| CD3 | APC-H7 | BD | 560176 |
| CD4 | PerCP/Cy5.5 | BD | 560650 |
| CD8 | FITC | BD | 555634 |
| IFNγ | BV421 | BD | 562988 |
| IL-2 | PE | eBioscience | 12-7029-42 |
| TNFα | Pe-Cy7 | Biolegend | 502930 |
| CD107a* | AF647 | Biolegend | 328612 |

*added to cells during SEB stimulation

Cryopreserved PBMCs derived from a single healthy donor were thawed and left to rest overnight. The cells were then counted, centrifuged at 200 g for 12 min and the pellet resuspended to a concentration of $2\times10^6$ cells/ml in PBMC medium (RPMI1640, 10% heat inactivated FBS and 1 Penicillin-Streptomycin). 100 µl cell suspension was added to the wells of two 96-well round-bottom plates to which 100 µl PBMC medium containing SEB and test antibody had already been added. The final SEB concentration was 320 ng/ml. Each antibody was tested in triplicate at a single concentration of 1 µg/ml (except for the combination of YW243.55.570 and 20H4.9 which was tested at 0.5+0.5 µg/ml). Control wells without SEB or antibody were also included. Stimulation was for 24 hours at 37° C., 5% $CO_2$, 95% humidity. Anti-CD107a and a mixture of Brefeldin A (Golgiplug, BD) and Monensin (Golgistop, BD) were added to each well during the last 12 hours of incubation.

Duplicate plates were then pooled and PBMCs stained with antibodies specific for the relevant markers and cytokines (overview provided in the above list of antibodies). Since detection of CD3, CD4, and CD8 is not compromised after fixation, antibodies against these targets were added at the intracellular staining step, together with antibodies against the intracellular cytokines. Because of their known sensitivity to fixation, the extracellular targets CCR7 and CD45RO were stained before the fixation step. To this end, the plates were centrifuged at 350 g for 3 minutes, cells were resuspended in 100 µl PBS per well, and cells from the duplicate plates pooled. Plates were centrifuged as before and cells resuspended in 100 µl per well of 1:1000 diluted Fixable Viability Dye (eBioscience, cat. no. 65-0866). After a 10-min incubation at RT in the dark, 150 µl of FACS buffer (PBS pH 7.4, 0.5% BSA, 0.5 mM EDTA) was added to each well. Plates were centrifuged and cells resuspended in 25 µl of anti-CCR7 antibody diluted in FACS buffer. After a 15-min incubation at 37° C., 5% $CO_2$, 95% humidity, 25 µl of anti-CD45RO antibody diluted in FACS buffer was added. After a 30-min incubation at RT in the dark, 150 µl of FACS buffer was added to each well. Plates were centrifuged as before and cells resuspended in 200 µl of FACS buffer. Plates were centrifuged and cells resuspended in 100 µl of BD Fixation/Permeabilization solution (BD Biosciences, cat. no. 554714). After a 10-min incubation at RT in the dark, 100 µl of BD Perm/Wash buffer (BD Biosciences, cat. no. 554714) was added. Plates were then centrifuged at 350 g for 3 min and cells resuspended in 200 µl BD Perm/Wash buffer.

After this fixation and permeabilization step, plates were centrifuged at 500 g for 3 min and cells resuspended in 50 µl of a solution of BD Perm/Wash buffer containing antibodies specific for intracellular targets. This solution contained antibodies against the intracellular targets IFNγ, IL-2, and TNFα, and against CD3, CD4, and CD8. Plates were incubated for 1 hour at RT in the dark and 150 µl BD Perm/Wash buffer was then added to each well. Plates were then centrifuged at 350 g for 3 min and cells resuspended in 200 µl BD Perm/Wash buffer. Plates were again centrifuged at 350 g for 3 min, the cells resuspended in 100 µl fixative solution (PBS pH 7.4, 0.5% BSA, 0.5 mM EDTA, 1% formaldehyde) and stored at 4° C. until acquisition the next day.

Samples were measured using a BD Fortessa flow cytometer and the data analyzed using FlowJo software version 10. Cell populations were analyzed as follows: singlets were discriminated from doublets by plotting FSC-A versus FSC-H. Dead cells were excluded by gating on the population negative for viability staining. T cells were identified as CD3+ and divided into CD4+ and CD8+ subsets. These T cell subsets were further divided into naïve, central memory, effector memory, and terminally differentiated effector cells, based on the expression of CCR7 and CD45RO. The expression of cytokines and CD107a was assessed within the total T cell population and within the subpopulations and expressed as a percentage of the total population of T cells.

Results

Figure 37:
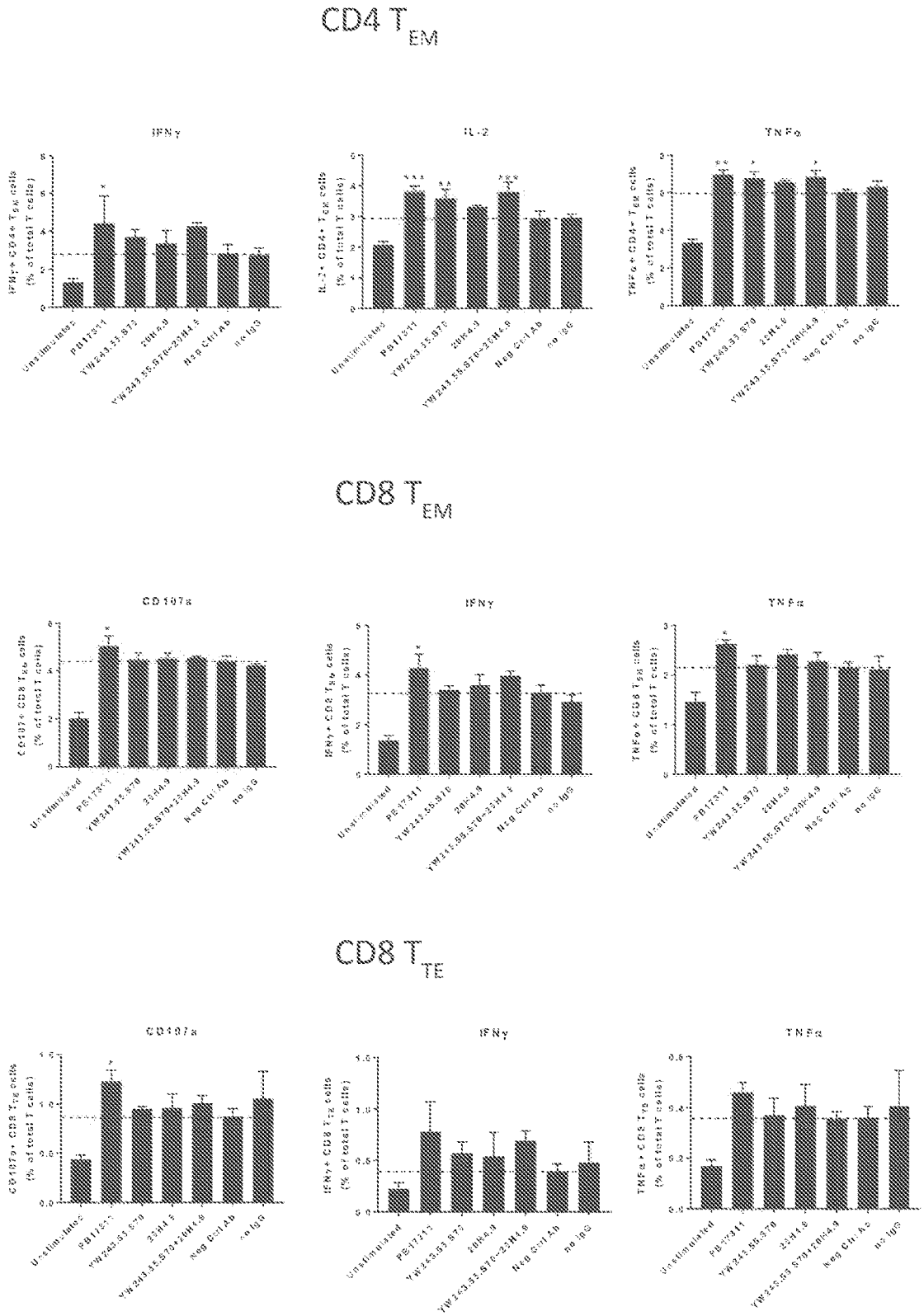

The intracellular levels of CD107a, IFNγ, IL-2 and TNFα in the total T cell population are shown in FIG. 36, with levels expressed by the three individual T cell subsets (CD4 $T_{EM}$, CD8 $T_{EM}$ and CD8 $T_{TE}$) shown in FIG. 37. In these figures, the dotted lines represent the mean percentage of cells positive for the indicated marker when stimulated with SEB and negative control antibody PG2708. The bars represent mean values f SD of an experiment performed in triplicate using cells derived from a single donor. To test for significant differences, each condition was compared to the negative control antibody PG2708 (Neg Ctrl Ab) by one-way ANOVA, followed by Dunnett's multiple comparisons test. P values are indicated with asterisks as follows: * $P<0.05$,  $P<0.01$, * $P<0.001$.

Relative to the negative control antibody, PB17311 enhanced CD107a, IL-2 and IFNγ production in the total T cell population (FIG. 36). Of note, CD107a production was more enhanced by PB17311 as compared to anti-CD137 benchmark antibody 20H4.9, anti-PD-L1 benchmark antibody YW243.55.570, and also as compared to an equimolar mix of both reference antibodies. From this it is concluded that CD8+ T cell cytotoxicity is more enhanced after incubation with PB17311 as compared to 20H4.9, YW243.55.570 or a mixture thereof. The production of IL-2 and IFNγ also appears to be higher after incubation with PB17311 as compared to 20H4.9 and YW243.55.570.

When we looked in more detail at the individual T cell subsets, we found that PB17311 enhanced expression of all three cytokines in CD4 $T_{EM}$ cells. PB17311 also boosted expression of CD107a in the CD8 $T_{EM}$ and $T_{TE}$ populations to a higher extent than the benchmark antibodies 20H4.9, YW243.55.570 and a mixture thereof, indicating that it enhances CD8 T cell cytotoxicity better than a mixture of these benchmark antibodies.

Conclusion

These results are in line with the earlier observation that CD137xPD-L1 bispecific antibodies enhance IL-2, TNFα and IFNγ production by PBMCs upon SEB stimulation. They demonstrate that PB17311 causes a significant increase in the numbers of T cells expressing cytokines, and that PB17311 induces expression of the cytotoxicity marker CD107a on CD8 $T_{EM}$ and $T_{TE}$ subsets more potently than the 20H4.9 and YW243.55.S70 benchmark antibodies. Of note, the IFNγ and TNFα production of the CD8 $T_{EM}$ and $T_{TE}$ populations were also higher after incubation with PB17311, as compared to the IFNγ and TNFα production after incubation with 20H4.9, YW243.55.570 or a mixture thereof, indicating that PB17311 has a higher potential of activating CD8+ T cells. The IL-2 production of the CD4 $T_{EM}$ population also appeared to be higher after incubation with PB17311, as compared to incubation with 20H4.9 and to a lesser extent YW243.55.570.

Example 14

Effect of PB17311 on the Proliferation of Tumor-Infiltrating T Cells

The initial screening of the anti-CD137xPD-L1 bispecific antibodies made use of assays based on primary T cells. However, such assays lack the complexity of the cellular interactions that drive the co-evolution of the tumor and its microenvironment. To test our bispecific antibodies in a tumor-related setting, we also made use of recently developed assays based on T cells isolated from patient tumor material. Zhou et al. have developed a method of obtaining fresh tumor material from patients with hepatocellular carcinoma (HCC) or colorectal cancer (CRC) and isolating tumor infiltrating cells (myeloid and lymphocytic cells) to test the effects of antibodies that target immune checkpoint inhibitors on the functions of tumor-infiltrating T cells (Zhou et al., 2017). Here we obtained material from patients with HCC or liver metastasis in CRC (LM-CRC) to test whether the anti-CD137xPD-L1 bispecific antibody PB17311 could reactivate tumor-infiltrating CD4 and CD8 T cells derived from these patients.

[Methods]

To this end, fresh tumor material was obtained from four patients with LM-CRC, and from three patients with HCC eligible for surgical resection of the tumor. None of the patients received chemotherapy or immunosuppressive treatment at least three months before surgery. The method as described by Zhou et al. (2017) was the following: tumor-infiltrating myeloid and lymphocytic cells were isolated from fresh tissue by cutting it into small pieces followed by digestion for 20-30 minutes at 37° C. in 0.5 mg/ml collagenase IV (Sigma-Aldrich, St. Louis, Mo.) and 0.2 mg/ml DNAse I (Roche, Indianapolis, Ind.). The resulting cell suspension was filtered through 100-μm pore cell strainers (BD Biosciences, Erembodegem, Belgium), and mononuclear leukocytes were obtained by Ficoll density gradient centrifugation. Viability was determined by trypan blue exclusion. The cells were then labeled with 0.1 μM of the fluorescent dye carboxyfluorescein diacetate succinimidyl ester (CFSE, Invitrogen) and suspended in RPMI medium supplemented with 10% human AB serum, 2 mM L-glutamine, 50 mM HEPES Buffer, 1% penicillin-streptomycin, 5 mM Sodium Pyruvate and 1% minimum essential medium non-essential amino acids (MEM NEAA). For HCC $1\times10^5$ cells and for LM-CRC $1\text{-}2\times10^5$ cells in 100 μl were then transferred to each well of a 96-well round-bottom plate. The tumor-infiltrating lymphocytes (TILs) were then stimulated to induce activation in the absence or presence of test antibody as follows: to wells containing TILs derived from HCC patients, 100 μl was added of the same medium containing test antibodies and $1\times10^5$ autologous CD40-activated B cell blasts that had been expanded and subsequently transfected with mRNA encoding the full-length tumor antigens glypican-3 (GPC3) or melanoma-associated antigen C2 (MAGEC2). These cells were co-incubated for six days. To the wells containing TILs derived from LM-CRC patients 100 μl of the same medium was added containing test antibodies and dynabeads coated with anti-human CD3/CD28 (Gibco-Life Technologies AS, Norway) for four days. After incubation, CFSE-labeled cells were harvested and stained with CD8, CD4, CD3 antibodies. Dead cells were excluded using 7-Aminoactinomycin D (7AAD; Invitrogen, Paisley UK), and T cell proliferation was determined based on CFSE dilution by flow cytometry analysis. Cells were measured by a FACSCanto II flow cytometer (BD Biosciences, San Diego, USA) and analyzed using FlowJo software.

CD137xPD-L1 bispecific antibody PB17311 was compared with its monospecific bivalent parental antibodies PG6797 and PG7702, and with anti-CD137 reference antibody 20H4.9, anti-PD-L1 reference antibody YW243.55.570, and negative control antibody PG2708 against the irrelevant RSV-G antigen. Samples without antibody were included as controls and all conditions were tested in duplo at an IgG concentration of 10 μg/ml.

For the samples derived from LM-CRC, CD4 T cell proliferation in the presence of antibodies could only be determined in three out of the four donors because the fourth donor's baseline level of CD4 T cell proliferation was already exceptionally high (>60% proliferating cells). CD8 T cell proliferation could be determined in samples from all four LM-CRC donors. Regarding the samples derived from HCC, autologous B cells expressing GPC3 were generated for all three donors, but MAGEC2 expression was only possible for two out of three. This resulted in a total of 5 proliferation experiments using the cells from the three HCC donors.

Results were presented as the means f SEM.

Results

The results are shown in FIG. 38. Baseline proliferation of CD4 TILs (upper right panel) and CD8 TILs (lower right panel) was determined by measuring the percentage of proliferating T cells (low levels of CFSE) in the presence of negative control antibody. CD4 (upper left) and CD8 (lower left) proliferation of samples was calculated as the percentage increase in proliferation over baseline. Values are mean f SEM (LM-CRC: CD4 n=3, CD8 n=4; HCC: CD4 and CD8 n=5).

CD137xPD-L1 bispecific antibody PB17311 clearly enhanced the proliferation of both CD4 and CD8 TILs in both tumor types, and the results indicate that it outperformed its parental antibodies PG6797 and PG7702. The results also indicate that YW243.55.S70 stimulated CD4 and CD8 T cell proliferation to the same level. PB17311 and 20H4.9 also enhanced proliferation of CD4 T cells, but more potently enhanced CD8 T cell proliferation.

These experiments demonstrate the added value of using a bispecific CD137 x PD-L1 antibody and that PB17311 enhances the proliferation of CD4 and CD8 TILs derived from patients with HCC and LM-CRC. Importantly, this means that a bispecific antibody according to the present invention can restimulate both antigen-specific CD4+ T cells and antigen-specific CD8+ T cells of a cancer patient, and that it can stimulate proliferation of CD8+ TILs more potently than the benchmark antibody YW243.55.S70.

Example 15

PB17311 Epitope Analysis Via Alanine-Scanning

Epitope analysis was performed to identify the sets of residues that comprise or are part of the epitopes recognized by the anti-CD137 Fab arm (MF6797) present in PB17311.

Analysis of the potentially non-linear epitope of the CD137 antigen to which PB17311 binds requires knowledge of the three-dimensional protein structure of CD137. CD137 is a relatively small protein of 25.4 kDa (17.3 kDa extracellular) with no clear distinct domains. However, defined 'repetitive regions' or cysteine-rich domains (CRDs) have been described for CD137. Reports in the literature concerning the protein structure of CD137 are limited. Yi et al. (2014) have described the ligand binding site of CD137 to be located in region 3 of CD137, based on binding studies with truncated expression constructs. While no crystal structure is available for CD137, a homology model has been published based on TNFR1 (Won et al., 2010). TNFR1 is a membrane-bound protein in the tumor necrosis factor receptor superfamily of which CD137 is also a member. The results of domain/swap experiments involving human/mouse CD137 chimeric constructs suggest that the anti-CD137 Fab arm (MF6797) binds to CRD 1 and/or 2. CD137L blocking data also suggest that the MF6797 epitope is near to or overlapping with the CD137 ligand binding site.

PD-L1 is also a relatively small protein of 31.1 kDa (25.2 kDa extracellular), for which no distinct regions or domains have been defined. However, the crystal structure of PD-L1 is known, as is that of its complex with PD-L1.

In these experiments, shotgun mutagenesis was used to generate a series of mutant proteins in which a single residue was mutated through substitution with an alanine residue. The mutant CD137 proteins were then expressed in human cells, allowing for the analysis of complex proteins, or proteins that can only be expressed and properly folded in human cells. Functional binding to the antibody was measured by fluorescent staining, resulting in binding maps and the identification of residues critical for antibody binding. The shotgun mutagenesis experiments and analysis were performed by Integral Molecular using methods described in Davidson and Doranz (2014).

First, based on a plasmid carrying wild-type CD137 cDNA, mutation libraries (Xxx to Ala, Ala to Ser) were generated for the target proteins. This resulted in 163 mutant cDNA clones for CD137, all of which were sequenced to verify the mutation. These mutant cDNA clones were consequently transfected into HEK-293T cells, along with wild-type (WT) constructs for comparison. HEK-293T cells expressing each of the mutant clones were subsequently analyzed by flow cytometry, whereby binding of each mutant protein to PB17311 was compared with binding to a control antibody specific for CD137 (mouse IgG1, BD Biosciences cat. no. 555955). This control antibody does not compete with PB17311 for binding. Fluorescently-labeled secondary antibodies against human or mouse IgG were used to detect binding of PB17311 or control antibody.

To identify clones that had high CD137 expression but gave low binding with PB17311, we compared PB17311 binding with that of the relevant control antibody (see FIG. 39A). For each clone, the mean binding value was plotted as a function of the clone's mean expression value as measured by control antibody binding. To identify preliminary critical clones, we applied thresholds of >70% WT binding to control antibody and <20% WT reactivity to PB17311 Ab. Preliminary critical clones identified using these thresholds are shown as black circles in FIG. 39A.

The results indicate that important residues in CD137 for binding of PB17311 are Arg66, Gly70, and Phe72. Val71 also appears to be involved with binding of PB17311 (see FIG. 39B). While Cys133 was initially identified as a critical residue based on the binding thresholds, it is relatively distant from the other critical residues, and cysteine mutations tend to cause slight aberrations in protein conformation due to disruption of disulfide bonds. Cys133 was therefore not considered part of the PB17311 epitope. The low reactivities with PB17311 of the proteins mutated at Arg66, Gly70 and Phe72 indicate that these residues are the major energetic contributors to PB17311 binding, with lesser contribution by Val71.

Example 16

Anti-Tumor Efficacy of CD137xPD-L1 Bispecific Antibody in a Xenograft Mouse Model To test the anti-tumor efficacy of an exemplary one of the clones, the CD137xPD-L1 bispecific antibody PB17311, in experimental animals and compare it with reference antibodies, antibody PB17311 was administered to mice bearing xenografted tumors. The mouse model chosen is one in which immunocompromised mice are humanized by engraftment with human peripheral blood mononuclear cells (PBMCs) before injection with a human cancer cell line. Subcutaneous solid tumor growth is then assessed over a period of 3 weeks.

The anti-CD137 and anti-PD-L1 Fabs of the CD137xPD-L1 bispecific antibody cross-react with human and cynomolgus orthologs, but not with mouse proteins.

The above model was chosen because it allows for the antibody's in vivo activity to be tested in a humanized system, whereby the antibody's anti-tumor response is mediated by human T cells and not mouse T cells. This type of model has been successfully used to evaluate various immunomodulatory targeted therapies, including several anti-CD137 monoclonal antibodies For example, the efficacy of 20H4.9 has been assessed in PBMC-humanized Rag2-/-IL2Rgnull mice bearing HT29 cells (Sanmamed et al 2015), Utomilumab efficacy has been assessed in SCID-beige mice xenografted with a mixture of PBMCs and human tumor cells PC3, LoVo or WM-266 (Fisher et al., 2012). In both models, the anti-CD137 monoclonal antibodies showed significant T-cell mediated anti-tumor activity compared to control IgG-treated animals.

In the xenograft mouse model used here, the cancer cells injected into the PBMC-humanized mice were RKO cells, a well-established human colon carcinoma cell line that expresses relatively high levels of PD-L1 but no CD137. The fact that PBMCs injected into immunocompromised mice have been shown to express CD137 as early as 5 days post-implantation and continuing to at least until day 22 (Sanmamed et al 2015) indicates that PBMC-humanized mice bearing RKO cells are an ideal model for expressing the targets of the CD137xPD-L1 bispecific antibody in a "trans" configuration (PD-L1 on RKO cells and CD137 on T cells). In addition, the PBMC donor does not lead to graft versus host disease for at least 40 days post-engraftment. This model is therefore robust for evaluating the efficacy of immunomodulatory agents.

Methods

Nine-week-old female NOD SCID Gamma (NSG) mice were engrafted with $3 \times 10^7$ human PBMCs by tail-vein injection. 7 days later, each test mouse received a subcutaneous injection of $5 \times 10^6$ RKO tumor cells in 0.1 mL 50% Matrigel in the right flank. Tumor growth was monitored by calipers as mean tumor volume approached the target range of 50 to 80 mm$^3$. Four days after tumor cell implantation, designated as Day 1 of the study, animals with individual tumor volumes from 40 to 63 mm$^3$ were sorted into four groups of eight animals. Tumor-bearing animals in each group received six intraperitoneal injections of antibody at a dose of 100 µg in 100 µL PBS on days 1, 4, 8, 11, 15 and 18. The four different groups received negative control (IgG), or benchmark antibody 20H4.9 (anti-CD137) or YW243.55.S70 (anti-PD-L1), or PB17311 (anti-CD137xPD-L1). Calipers were used to measure tumor volumes three times a week until the end of the study on Day 19, when inhibition of tumor growth was assessed.

Tumor growth inhibition (TGI) was defined as the percent difference between Day 19 median tumor volumes (MTVs) of treated and control mice, with differences between groups deemed statistically significant at $P<0.05$ using the Mann-Whitney test. Treatment tolerability was assessed by body weight measurements and frequent observations for clinical signs of treatment-related adverse events. FIG. 40 provides a box and whisker plot of tumor volume distribution by group. On Day 19, the median tumor volumes (MTVs) of the mice in IgG control was 517 mm$^3$, with an individual tumor volume range of 429 to 807 mm$^3$. Among the three treatment groups, PB17311 was as effective (with an MTV of 264 mm³, 49% TGI), as YW243.55.S70, with an MTV of 283 mm³, 45% TGI and 20H4.9, with an MTV of 339 mm³ and 34% TGI). All treatments resulted in MTVs significantly lower than those in the control Group (P<0.05 for 20H4.9; P<0.001 for PB17311 and YW243.55.S70). One animal receiving 20H4.9 died on Day 8; necropsy revealed pink lungs and a mottled liver. Animals in this group also experienced the largest mean BW loss (−8.0% at the lowest point on Day 15). Otherwise, treatments were well-tolerated.

In summary, the CD137xPD-L1 bispecific antibody PB17311 provided a statistically significant survival benefit as treatment for human RKO colon carcinoma in NSG mice engrafted with human PBMCs. Treatment results with PB17311 were better, with less side effects, as compared to 20H4.9.

Example 17

Interference of sCD137 with Agonistic Activity of CD137 Targeting Antibodies

Soluble CD137 Interferes Less with Agonistic Activity of Bispecific CD137xPD-L1 Antibody than with Bivalent CD137 Antibody CD137 expression is regulated by antigen shedding from the cell surface. The shed antigen (sCD137) is found in the blood as well as in the extra-cellular space and could therefore act as a competing sink for clearance of CD137 targeting antibodies.

Studies have shown that sCD137 is shed from immune cells expressing high levels of CD137, such as regulatory T cells (Ridgway et al., 2014), and that both sCD137 and sCD137L are produced by cancer cells of colorectal patients (Dimberg et al., 2006). In addition, exposure of tumor cell lines to hypoxic conditions promotes CD137 expression, the most predominant form being the soluble variant (Labiano et al, 2016). While average serum levels of sCD137 in healthy donors range from 0.02 to 0.2 ng/ml, levels are known to be higher in various disease states, ranging from 0.2 to 3.6 ng/ml (Michel et al, 1998; Shao et al, 2012). sCD137 appears to regulate activated T cells: when shed into the tumor microenvironment it dampens the activity of the immune system, thereby mediating immune escape. It is thought that sCD137 competes with membrane-bound CD137 for binding to CD137L, thereby blocking signaling through CD137 expressed on T cells.

Given the mechanisms described above, it was determined whether sCD137 would affect the ability of bispecific CD137xPD-L1 antibody PB17311 and reference antibodies to activate human primary T cells in vitro. Such activation was measured in a Jurkat reporter/CHO-PD-L1 trans-activation assay in the absence or presence of excess amounts of sCD137. In this assay, the Jurkat reporter T cell line expresses CD137 and the reporter gene is activated by antibodies specific for CD137. The T cells are co-cultured with CHO cells overexpressing PD-L1, which mimic tumor cells expressing PD-L1 and are required for activation of the T cells by the bispecific CD137xPD-L1 antibody.

To this end, flat-bottomed 96-well plates (Costar, cat. no. 3917) were coated overnight with 2 µg/mL anti-CD3 antibody OKT-3 (eBioscience, cat. no. 16-0037-85) in PBS. The next day, Jurkat CD137-NFkBluc reporter cells were thawed and washed with DMEM/F12 medium containing 10% heat inactivated fetal bovine serum (assay medium). Cells were resuspended at a density of 2×10⁶ cells/ml. The pre-coated 96 well plates were washed twice with PBS before addition of 25 µL test antibody (end concentration 200 ng/mL), followed by 25 µL of a mix of sCD137 (R&D, cat. no. 9220-4B) in a five-step, three-fold dilution starting at 20 µg/mL (end concentration). Then 25 µL Jurkat NFκBluc (50000 cells/well, 2×10⁶ cells/ml) were added, followed by 25 µL CHO-K1/CHO.huPD-L1 cells (12500 cells/well, 5×10⁵ cells/ml). The next day, plates were equilibrated to room temperature and 100 µl Bright-Glo/well (room temperature) was added (maximum 4 plates at a time) followed by 5 minutes incubation at room temperature. Plates were measured on the Biotek Synergy 2 Multi-Mode Microplate Reader (luminescence mode). Activation in terms of luciferase activity was expressed as a percentage of that obtained without addition of recombinant protein.

The results are shown in FIG. 41 and indicate that high concentrations of soluble CD137 can indeed interfere with the agonistic activity of both test antibodies. However, importantly, sCD137 competition appears to have a much greater effect on the anti-CD137 reference antibody (clone 20H4.9) than on the bispecific CD137xPD-L1 antibody PB17311. From this it is concluded that the in vivo effect of PB17311 will be less sensitive to immune suppressive mechanisms as compared to benchmark antibody 20H4.9

Tables

TABLE 1

Expression constructs for each target that were used for DNA immunization (pVAX1 vector based) and for generation of stable Freestyle 293F or CHO-K1 cell lines (pIRES-neo3 vector based or similar)

| Target | Vectors | Stable cell line |
|---|---|---|
| CD137 | pVAX1__huCD137 | NA |
|  | pVAX1__raCD137 | NA |
|  | pIRES-neo3__huCD137 | Freestyle 293F__huCD137 |
|  | pIRES-neo3__maCD137 | Freestyle 293F__maCD137 |
| OX40 | pVAX1__huOX40 | NA |
|  | pVAX1__raOX40 | NA |
|  | pVAX1__maOX40 | NA |
|  | pIRES-neo3__huOX40 | Freestyle 293F__huOX40 |
|  | pIRES-neo3__maOX40 | Freestyle 293F__maOX40 |
| PD-L1 | pVAX1__huPD-L1 | NA |
|  | pIRES-neo3__huPD-L1 | CHO-K1__huPD-L1 |
|  | pIRES-neo3__maPD-L1 | CHO-K1__maPD-L1 | hu = human,
ma = macaque,
NA = not applicable

TABLE 2

Panel of CD137 Fab arms describing binning based on FACS profiles, domain binding, agonistic activity as bivalent antibody and CD137 blocking activity.

| MF no. | Bin | Domain | Agonistic bivalent | % CD137L block | Denotation |
|---|---|---|---|---|---|
| MF6783 | A | 1/2 | X | 44 | Partially blocking |
| MF6860 | A | 1/2 | X | 6 | Non-blocking |
| MF6848 | B | 1/2 |  | −126 | Enhancing |
| MF6856 | B | 2 |  | 24 | Non-blocking |
| MF6861 | B | 1/2 |  | 50 | Partially blocking |
| MF6847 | C | 4 |  | 24 | Non-blocking |
| MF6795 | D | ND |  | 32 | Partially blocking |
| MF6808 | D | ND |  | 77 | Blocking |
| MF6798 | E | 1 |  | 44 | Partially blocking |
| MF6805 | E | 1 |  | 2 | Non-blocking |
| MF6832 | E | 1 | X | 8 | Non-blocking |
| MF6754 | F | 2 |  | 101 | Blocking |
| MF6763 | F | 2 |  | 101 | Blocking |

TABLE 2-continued

Panel of CD137 Fab arms describing binning based on FACS profiles, domain binding, agonistic activity as bivalent antibody and CD137 blocking activity.

| MF no. | Bin | Domain | Agonistic bivalent | % CD137L block | Denotation |
|---|---|---|---|---|---|
| MF6744 | G | 2/3 | X | 67 | Partially blocking |
| MF6785 | G | 2 |   | 99 | Blocking |
| MF6825 | G | 2 | X | 89 | Blocking |
| MF6737 | H | 3 | X | 76 | Blocking |
| MF6749 | H | 3 | X | 81 | Blocking |
| MF6870 | I | 4 |   | −16 | Non-blocking |
| MF6862 | J | ND | X | −80 | Enhancing |
| MF6875 | J | 1 |   | −22 | Non-blocking |
| MF6788 | K | 1 | X | 55 | Partially blocking |
| MF6797 | K | 1/2 |   | 102 | Blocking |
| MF6873 | K | 1/2 |   | −100 | Enhancing |

TABLE 3

Functional activity of PD-L1 Fab arms as measured in the PD-1/PD-L1 blockade reporter assay as a monovalent antibody expressed in AUC. Antibody affinities were determined by Biacore analysis. MF5361 is a non-blocking Fab, therefore AUC was not applicable (NA)

| ID | AUC | Affinity nM |
|---|---|---|
| MF5594 | 4.8 | 0.6 |
| MF5553 | 4.5 | ND |
| MF5424 | 3.6 | 4.6 |
| MF5561 | 3.6 | 4.1 |
| MF5426 | 3.4 | 2.5 |
| MF5439 | 3.2 | 5.5 |
| MF5442 | 3.1 | 6.0 |
| MF5361 | NA | 19.4 |

TABLE 4

Functional activity ($IC_{50}$ IL-2 release in SEB assay) of lead CD137 × PD-L1 panel (indicated using the PB prefix; each PB comprises a CD137 and a PD-L1 Fab arm as indicated in the table) compared to ipilumumab. Based on binding profiles using chimeric constructs CD137 could be distributed over different domain bins.

| ID | CD137 Fab arm | PD-L1 Fab arm | CD137 domain | AUC | IC50 (ng/ml) |
|---|---|---|---|---|---|
| PB14593 | 6797 | 5594 | 1/2 | 4.8 | 14.75 |
| PB14591 | 6785 | 5594 | 2 | 4.8 | 15.44 |
| PB14584 | 6754 | 5594 | 2 | 4.8 | 15.76 |
| PB15184 | 6754 | 5424 | 2 | 3.6 | 22.82 |
| PB15142 | 6754 | 5426 | 2 | 3.4 | 34.06 |
| PB17101 | 6754 | 5553 | 2 | 4.5 | 56.24 |
| PB17089 | 6754 | 5442 | 2 | 3.1 | 74.35 |
| PB17095 | 6797 | 5442 | 1/2 | 3.1 | 89.42 |
| PB17103 | 6785 | 5553 | 2 | 4.5 | 92.27 |
| PB14814 | 6754 | 5561 | 2 | 3.6 | 167.4 |
| PB15149 | 6785 | 5426 | 2 | 3.4 | 188.1 |
| PB14815 | 6763 | 5561 | 2 | 3.6 | 195.6 |
| PB14585 | 6763 | 5594 | 2 | 4.8 | 198 |
| PB14821 | 6785 | 5561 | 2 | 3.6 | 202.2 |
| PB15151 | 6797 | 5426 | 1/2 | 3.4 | 219.3 |
| PB15191 | 6785 | 5424 | 2 | 3.6 | 284.2 |
| PB15143 | 6763 | 5426 | 2 | 3.4 | 331.1 |
| PB15185 | 6763 | 5424 | 2 | 3.6 | 363 |
| PB14823 | 6797 | 5561 | 1/2 | 3.6 | 367.9 |
| PB17091 | 6785 | 5442 | 2 | 3.1 | 428.2 |
| PB17088 | 6763 | 5442 | 2 | 3.1 | 545.9 |
| PB17115 | 6785 | 5439 | 2 | 3.2 | 664.3 |
| PB17107 | 6797 | 5553 | 1/2 | 4.5 | 852.6 |
| PB17119 | 6797 | 5439 | 1/2 | 3.2 | 1030 |
| PB17112 | 6763 | 5439 | 2 | 3.2 | 1043 |
| PB17100 | 6763 | 5553 | 2 | 4.5 | 1382 |
| PB15193 | 6797 | 5424 | 1/2 | 3.6 | 1556 |
| PB17113 | 6754 | 5439 | 2 | 3.2 | 8145 |
| Ipilumumab |   |   |   |   | 9388 |

TABLE 5

Ligand blocking ability and domain specificity of the OX40 clones. Blocking ability was determined in two separate experiments.

| SEQ ID NO of indicated CDR3 | MF nr. | CDR3 | VH germline | Blocking Exp. 1 (%) | Blocking Exp. 2 (%) | OX40L blocking |
|---|---|---|---|---|---|---|
| SEQ ID NO: 26 | MF6629 | GWDF | VH5-51 | −1 | NA | no |
| SEQ ID NO: 27 | MF6630 | GGTMVRGVIDDWFDP | VH1-46 | 4 | NA | no |
| SEQ ID NO: 28 | MF6637 | VGGLRQAWYFDL | VH1-69 | 9 | NA | no |
| SEQ ID NO: 29 | MF6643 | GGWELLFNYFQQ | VH7-4-1 | 11 | NA | no |
| SEQ ID NO: 30 | MF6645 | SPPYYMDV | VH4-59 | 20 | NA | no |
| SEQ ID NO: 31 | MF6646 | GFDWYFTL | VH3-15 | 47 | 62 | yes |
| SEQ ID NO: 32 | MF6648 | GWGYSGYGPEGFDI | VH3-15 | 22 | NA | no |
| SEQ ID NO: 33 | MF6655 | IGGTGTTDWYFDL | VH1-69 | NA | 10 | no |
| SEQ ID NO: 34 | MF6658 | VGGYTSSSWFFDL | VH1-69 | 9 | NA | no |
| SEQ ID NO: 35 | MF6660 | VDGGNSDWYFDL | VH1-69 | 14 | NA | no |
| SEQ ID NO: 36 | MF6675 | VDGRSSGGNWHFDL | VH1-69 | 5 | NA | no |
| SEQ ID NO: 37 | MF6686 | DPYYFDSNGYPPFDD | VH1-69 | NA | 97 | yes |
| SEQ ID NO: 38 | MF6690 | GWDFFDS | VH7-4-1 | 7 | NA | no |
| SEQ ID NO: 39 | MF6692 | VGGLGTTPHWYFDL | VH1-69 | NA | 16 | no |

TABLE 5-continued

Ligand blocking ability and domain specificity of the OX40 clones. Blocking ability was determined in two separate experiments.

| SEQ ID NO of indicated CDR3 | MF nr. | CDR3 | VH germline | Blocking Exp. 1 (%) | Blocking Exp. 2 (%) | OX40L blocking |
|---|---|---|---|---|---|---|
| SEQ ID NO: 40 | MF6700 | PSYNWNRLYYYMDV | VH1-69 | 7 | NA | no |
| SEQ ID NO: 41 | MF6706 | SQPNLDFWSGYHFDY | VH2-5 | 99 | 97 | yes |
| SEQ ID NO: 42 | MF6714 | DPFFYDRSGYPPFDY | VH1-69 | 36 | 57 | yes |
| SEQ ID NO: 43 | MF6721 | GWGSG | VH3-15 | NA | 9 | no |
| SEQ ID NO: 44 | MF6722 | VGGYGNNYNFDY | VH1-69 | 24 | NA | no |
| SEQ ID NO: 45 | MF6724 | DPSGSYFYHYYMDV | VH3-15 | 75 | 92 | yes |
| SEQ ID NO: 46 | MF6728 | RRPNYDSWSGYYEDY | VH2-5 | 97 | 101 | yes |
| SEQ ID NO: 47 | MF6729 | GGWGLLREYFLQ | VH7-4-1 | 66 | 74 | yes |
| SEQ ID NO: 48 | MF6826 | HTGHYSGFDY | VH3-30 | 1 | NA | no |
| SEQ ID NO: 49 | MF6940 | VDGTGISNWYFDL | VH1-69 | 78 | 93 | yes |
| SEQ ID NO: 50 | MF6942 | GYSSIWHGENFQY | VH7-4-1 | 28 | 48 | yes |
| SEQ ID NO: 51 | MF6943 | DMDNWNYEGYYVMDV | VH7-4-1 | 90 | 87 | yes |
| SEQ ID NO: 52 | MF6944 | VEGWGSQWYFDL | VH1-69 | 18 | NA | no |
| SEQ ID NO: 53 | MF6947 | VEGTDSNWGWDF | VH1-69 | 22 | 41 | no/yes |
| SEQ ID NO: 54 | MF6949 | DDGTGTGDYVWGRYRYTLDF | VH7-4-1 | NA | 90 | yes |
| SEQ ID NO: 55 | MF7331 | DGYKLYAADGFDY | VH1-18 | NA | 18 | no |
| SEQ ID NO: 56 | MF7332 | DMDSYPFYRGFDY | VH1-18 | NA | 3 | no |
| SEQ ID NO: 57 | MF7334 | DDNTMWYSRPYAFDY | VH3-30 | 4 | NA | no |
| SEQ ID NO: 58 | MF7341 | DSPYWSLPGGFDY | VH1-18 | 15 | NA | no |
| SEQ ID NO: 59 | MF7345 | DQRWWYMDPGAGFDY | VH3-30 | 5 | NA | no |
| SEQ ID NO: 60 | MF7350 | DYSYSGTGSSSAFDY | VH1-18 | -8 | NA | no |
| SEQ ID NO: 61 | MF7351 | DYLHGSYYRGSAFDY | VH3-30 | NA | 11 | no |
| SEQ ID NO: 62 | MF7352 | DSWHGQYYYGKGFDY | VH3-30 | NA | 34 | yes |
| SEQ ID NO: 63 | MF7353 | DGLGWDPGYGFDY | VH3-30 | 19 | NA | no |
| SEQ ID NO: 64 | MF7356 | DNYQGMYYFGTGFDY | VH3-30 | 3 | NA | no |
| SEQ ID NO: 65 | MF7358 | DNHYYSPPTYWGFDY | VH3-30 | 2 | NA | no |
| SEQ ID NO: 66 | MF7365 | GGQSQYHSYPFGFDY | VH3-23 | NA | 46 | yes |
| SEQ ID NO: 67 | MF7366 | DWWQGHWYRSGGFDY | VH3-30 | NA | 35 | yes |
| SEQ ID NO: 68 | MF7371 | GQMDYYDDWYSAFDY | VH3-30 | NA | 1 | no |
| SEQ ID NO: 69 | MF7372 | DYYQGSHYFGPAFDY | VH3-30 | NA | -4 | no |
| SEQ ID NO: 70 | MF7374 | GDDNRMYSNPKGFDY | VH3-30 | 21 | NA | no |
| SEQ ID NO: 71 | MF7378 | DNTQGNYYRSRGFDY | VH3-30 | 2 | NA | no |
| SEQ ID NO: 72 | MF7382 | DGLQGSNYHLGGFDY | VH3-30 | NA | 5 | no |
| SEQ ID NO: 73 | MF7383 | GYDMYGGWGAWGFDY | VH3-23 | -6 | NA | no |
| SEQ ID NO: 74 | MF7394 | DYPAWAYSAFDY | VH1-18 | NA | 67 | yes |

TABLE 5-continued

Ligand blocking ability and domain specificity of the OX40 clones. Blocking ability was determined in two separate experiments.

| SEQ ID NO of indicated CDR3 | MF nr. | CDR3 | VH germline | Blocking Exp. 1 (%) | Blocking Exp. 2 (%) | OX40L blocking |
|---|---|---|---|---|---|---|
| SEQ ID NO: 75 | MF7395 | DYWYYLSDAFDY | VH3-30 | NA | 8 | no |
| SEQ ID NO: 76 | MF7397 | DHWGSFYGDFDY | VH3-23 | NA | 0 | no |

NA = not analyzed;
ND = not determined (domain specificity could not be determined because of binding to both rat and human OX40.

TABLE 6

| | 100 nM Ab | | | |
|---|---|---|---|---|
| MF ID | kon | koff | KD | KD (nM) |
| MF6797 | 2.49E+05 | 7.76E-04 | 3.11E-09 | 3.0 +/- 0.3 nM |
| MF6754 | 1.45E+06 | 0.001856 | 1.28E-09 | 2.1 +/- 1.1 nM |
| MF6763 | 3.54E+05 | 0.001033 | 2.92E-09 | 5.5 +/- 2.3 nM |
| MF6749 | 8.26E+05 | 0.002419 | 2.93E-09 | 2.7 +/- 1.1 nM |
| MF6737 | 1.56E+06 | 0.008839 | 5.68E-09 | 3.7 +/- 1.8 nM |
| MF6805 | 3.41E+05 | 6.29E-04 | 1.84E-09 | 2.2 +/- 0.5 nM |
| MF6785 | 3.48E+06 | 0.01575 | 4.52E-09 | 4.0 +/- 0.9 nM |
| MF6808 | 2.51E+05 | 3.98E-04 | 1.59E-09 | 1.4 +/- 0.5 nM |
| MF6744 | ND | | | |
| MF6788 | ND | | | |
| MF6825 | ND | | | |

TABLE 7

Activity of CD137xPD-L1 bispecific antibodies composed of 24 CD137 Fabs and 2 PD-L1 Fabs

| ME no. #1 | CDR3 | VH germline | Bin | Domain | Agonistic bivalent | % CD137L block | Reporter PD-L1 NB | PD-L1 B | T cell PD-L1 NB | PD-L1 B |
|---|---|---|---|---|---|---|---|---|---|---|
| MF6783 | DWGVIGGHYMDV (SEQ ID NO: 77) | VH7-4-1 | A | 1/2 | X | 44 | + | ++ | + | '+ |
| MF6860 | GLLWGKTDYYSGFDY (SEQ ID NO: 78) | VH5-51 | A | 1/2 | X | 6 | +/- | + | - | - |
| MF6861 | DSDGYGPKAFDY (SEQ ID NO: 79) | VH1-18 | B | 1/2 | | 50 | - | - | ND | ND |
| MF6856 | DWSGSWDYGSSAFDY (SEQ ID NO: 80) | VH3-23 | B | 1/2 | | 24 | - | - | ND | ND |
| MF6848 | DWSGWGSAYAFDY (SEQ ID NO: 81) | VH1-18 | B | 1/2 | | -126 | - | - | ND | ND |
| MF6847 | DSGYDSAYLAFDY (SEQ ID NO: 82) | VH1-18 | C | 4 | | 24 | - | - | ND | ND |
| MF6808 | GATYYYGSGTYYSINWFDP (SEQ ID NO: 83) | VH1-69 | D | ND | | 77 | + | ++ | ++ | +++ |
| MF6795 | FYTGIVGATGAFDV (SEQ ID NO: 84) | VH5-51 | D | ND | | 32 | - | - | ND | ND |
| MF6798 | DWASVMVRGDLDY (SEQ ID NO: 85) | VH7-4-1 | E | 1 | | 44 | +/- | +/- | ND | ND |
| MF6832 | GWNAFWFDY (SEQ ID NO: 86) | VH3-23 | E | 1 | X | 8 | +/- | + | - | - |
| MF6805 | TEYSYGYVFYY (SEQ ID NO: 87) | VH7-4-1 | E | 1 | | 2 | +/- | + | + | ++ |
| MF6754 | EGFDNYGSGIRGNWFDP (SEQ ID NO: 88) | VH1-24 | F | 2 | | 101 | + | ++ | ++ | +++ |
| MF6763 | EGVGVIRGNWFDP (SEQ ID NO: 89) | VH1-24 | F | 2 | | 101 | + | ++ | ++ | +++ |
| MF6785 | DLRLGASYYYSYMDV (SEQ ID NO: 90) | VH1-24 | G | 2/3 | | 99 | + | ++ | + | ++ |
| MF6825 | TLWGSDDVFDV (SEQ ID NO: 91) | VH2-5 | G | 2 | x | 89 | + | ++ | + | ++ |
| MF6744 | LGGYSGYAEDFVDF (SEQ ID NO: 92) | VH5-51 | G | 2 | X | 67 | + | ++ | + | ++ |
| MF6749 | HAGFIITSQNIDDY (SEQ ID NO: 93) | VH5-51 | H | 3 | X | 81 | + | ++ | + | +++ |
| MF6737 | HQGYSFSGSHIDDY (SEQ ID NO: 94) | VH5-51 | H | 3 | X | 76 | + | ++ | + | ++ |
| MF6870 | GSGHRFYQYRSGFDY (SEQ ID NO: 95) | VH3-23 | I | 4 | | -16 | - | - | ND | ND |
| MF6875 | GRWWFTYDGFDY (SEQ ID NO: 96) | VH3-23 | J | ND | | -22 | +/- | + | - | - |
| MF6862 | GRGWRNYFQWWGFDY (SEQ ID NO: 97) | VH3-30 | J | ND | X | -80 | +/- | + | - | - |

TABLE 7-continued

Activity of CD137xPD-L1 bispecific antibodies composed of 24 CD137 Fabs and 2 PD-L1 Fabs

| ME no. #1 | CDR3 | VH germline | Bin | Domain | Agonistic bivalent | % CD137L block | Reporter PD-L1 NB | PD-L1 B | T cell PD-L1 NB | PD-L1 B |
|---|---|---|---|---|---|---|---|---|---|---|
| MF6797 | EGIIGFLGGNWFDP (SEQ ID NO: 98) | VH2-5 | K | 1/2 | | 102 | + | ++ | + | ++ |
| MF6788 | DWGLVAIGYFDY (SEQ ID NO: 99) | VH7-4-1 | K | 1/2 | X | 55 | + | ++ | + | ++ |
| MF6873 | DRWSWYQGRGFGFDY (SEQ ID NO: 100) | VH1-18 | K | 1/2 | | −100 | − | − | ND | ND |

MF, unique ID Fab; CDR3, sequence of CDR3; VH germline, derived VH; Bin, specific grouping into bin (P1306-S33); Domain, CD137 domain to which antibody was mapped using mouse human swapped-domain constructs (1 or 2 means that the antibody could not be clearly mapped to one of the two domains); Agonistic bivalent, capacity of bivalent antibody to activate Jurkat-NFκB-luc-CD137; % CD137L block, capacity of Fab arm to block interaction with CD137; Reporter, data from reporter assay; T cell, data from T cell assay; PD-L1 NB, CD137 Fab in combination with PD-L1 non blocking Fab arm; PD-L1 B, CD137 Fab in combination with PD-L1 blocking Fab arm.

REFERENCES

Akbay, E. A., Koyama, S., Carretero, J., Altabef, A., Tchaicha, J. H., Christensen, C. L., Mikse, O. R., Cherniack, A. D., Beauchamp, E. M., Pugh, T. J., et al. (2013). Activation of the PD-1 Pathway Contributes to Immune Escape in EGFR-Driven Lung Tumors. Cancer Discov 3, 1355-1363

Arch, R. H., & Thompson, C. B. (1998). 4-1BB and Ox40 are members of a tumor necrosis factor (TNF)-nerve growth factor receptor subfamily that bind TNF receptor-associated factors and activate nuclear factor kappaB. Mol Cell Biol, 18(1), 558-65. http://doi.org/10.1016/j.bulcan.2015.03.022

Bernstein, M. B., Garnett, C. T., Zhang, H., Velcich, A., Wattenberg, M. M., Gameiro, S. R., Kalnicki, S., Hodge, J. W., and Guha, C. (2014). Radiation-induced modulation of costimulatory and coinhibitory T-cell signaling molecules on human prostate carcinoma cells promotes productive antitumor immune interactions. Cancer Biother Radiopharm 29, 153-161

Bertram et al. Role of T cell costimulation in anti-viral immunity. Seminars in Immunology, 16(3), 2004

Boland, J. M., Kwon, E. D., Harrington, S. M., Wampfler, J. A., Tang, H., Yang, P., and Aubry, M. C. (2013). Tumor B7-H1 and B7-H3 expression in squamous cell carcinoma of the lung. Clin Lung Cancer 14, 157-163.

Compaan, D. M., Hymowitz, S. G. (2006). The crystal structure of the costimulatory OX40-OX40L complex. Structure 14, 1321-1330.

Davidson, E. and Doranz, B. J. (2014) A high-throughput shotgun mutagenesis approach to mapping B-cell antibody epitope. Immunology 143, 13-20.

Dong, H., Strome, S. E., Salomao, D. R., Tamura, H., Hirano, F., Flies, D. B., Roche, P. C., Lu, J., Zhu, G., Tamada, K., et al. (2002). Tumor-associated B7-H1 promotes T-cell apoptosis: a potential mechanism of immune evasion. Nat Med 8, 793-800.

Makkouk A, Chester C, Kohrt H. Rationale for anti-CD137 cancer immunotherapy. Eur J of Cancer 54 (2016): 112-119

McNamara J, Kolonias D, Pastor F, Mittler R, Chen L, Giangrande P, Sullenger B, Gilboa E. Multivalent 4-1 BB binding aptamers costimulate CD8+ T cells and inhibit tumor growth in mice.

Melero I, Hirschhorn-Cymerman D, Morales-Kastresana A, Sanmamed M F, Wolchok J D. Agonist antibodies to TNFR molecules that costimulate T and NK cells. Clin Cancer Res 2013.

Michel, J., et al., A soluble form of CD137 (ILA/4-1BB), a member of the TNF receptor family, is released by activated lymphocytes and is detectable in sera of patients with rheumatoid arthritis. European Journal of Immunology, 1998. 28(1): p. 290-295.

Fisher et al. Targeting of 4-1BB by monoclonal antibody PF-05082566 enhances T-cell function and promotes antitumor activity. Cancer Immunology Immunotherapy, 61, 2012.

Pollok, K. E., Kim, Y. J., Zhou, Z., Hurtado, J., Kim, K. K., Pickard, R. T., & Kwon, B. S. (1993). Inducible T cell antigen 4-1BB. Analysis of expression and function. Journal of Immunology (Baltimore, Md.:1950), 150(3), 771-81. Retrieved from http://www.ncbi.nlm.nih.gov/pubmed/7678621

Pulko V, Harris K J, Liu X, Gibbons R M, Harrington S M, Krco C J, Kwon E D, Dong H J. B7-H1 expressed by activated CD8 T cells is essential for their survival. Immunol. 2011.

Sanmamed et al. Nivolumab and 20H4.9 enhance antitumor activity of human T lymphocytes engrafted in Rag2−/−IL2 R$\gamma^{null}$ immunodeficient mice. Cancer Research, 75(17), 2015.

Schwarz H. Biological activities of reverse signal transduction through CD137 ligand. J Leukoc Biol 77 (2005): 281-286

Shao, Z., et al., Admission levels of soluble CD137 are increased in patients with acute pancreatitis and are associated with subsequent complications. Experimental and Molecular Pathology, 2012. 92(1): p. 1-6.

Shao, Z., & Schwarz, H. (2011). CD137 ligand, a member of the tumor necrosis factor family, regulates immune responses via reverse signal transduction. Journal of Leukocyte Biology, 89(1), 21-29. http://doi.org/10.1189/jlb.0510615

Sharma, P., Hu-Lieskovan, S., Wargo, J. A., and Ribas, A. (2017). Primary, Adaptive, and Acquired Resistance to Cancer Immunotherapy. Cell 168, 707-723. Simon, H. U. (2001). Evidence for a pro-apoptotic function of CD137 in granulocytes. Swiss Medical Weekly, 131(31-32), 455-458. http://doi.org/2001/31/smw-09668

Sznol, M., and Chen, L. (2013). Antagonist antibodies to PD-1 and B7-H1 (PD-L1) in the treatment of advanced human cancer. Clin Cancer Res 19, 1021-1034.

Thompson, R. H., Gillett, M. D., Cheville, J. C., Lohse, C. M., Dong, H., Webster, W. S., Chen, L., Zincke, H., Blute, M. L., Leibovich, B. C., and Kwon, E. D. (2005). Costimulatory molecule B7-H1 in primary and metastatic clear cell renal cell carcinoma. Cancer 104, 2084-2091.

Tumeh, P. C., Harview, C. L., Yearley, J. H., Shintaku, I. P., Taylor, E. J. M., Robert, L., Chmielowski, B., Spasic, M., Henry, G., Ciobanu, V., et al. (2014). PD-1 blockade induces responses by inhibiting adaptive immune resistance. Nature 515, 568-571.

Velcheti, V., Schalper, K. A., Carvajal, D. E., Anagnostou, V. K., Syrigos, K. N., Sznol, M., Herbst, R. S., Gettinger, S. N., Chen, L., and Rimm, D. L. (2014). Programmed death ligand-1 expression in non-small cell lung cancer. Lab Invest 94, 107-116.

Vinay, D. S., & Kwon, B. S. (2011). 4-1BB signaling beyond T cells. Cellular & Molecular Immunology, 8(4), 281-4. http://doi.org/10.1038/cmi.2010.82

Wolf B., Morgan H., Krieg J., et al. A whole blood in vitro cytokine release assay with aqueous monoclonal antibody presentation for the prediction of therapeutic protein induced cytokine release syndrome in humans. Cytokine 60:828-831, 2012.

Wölfl and Greenberg. Antigen-specific activation and cytokine-facilitated expansion of naive, human CD8+ T cells. Nature protocols 9(4), 2014

Won, E. Y., Cha, K., Byun, J. S., Kim, D. U., Shin, S., Ahn, B., . . . Cho, H. S. (2010). The structure of the trimer of human 4-1BB ligand is unique among members of the tumor necrosis factor superfamily. Journal of Biological Chemistry, 285(12), 9202-9210. https://doi.org/10.1074/jbc.M109.084442

Yi, L., Zhao, Y., Wang, X., Dai, M., Hellström, K. E., Hellström, I., & Zhang, H. (2014). Human and mouse CD137 have predominantly different binding CRDs to their respective ligands. PLoS ONE, 9(1). https://doi.org/10.1371/journal.pone.0086337

Zhang, F., Wei, H., Wang, X., Bai, Y., Wang, P., Wu, J., Jiang, X., Wang, Y., Cai, H., Xu, T., Zhou, A. (2017). Structural basis of a novel PD-L1 nanobody for immune checkpoint blockade. Cell Discovery 3, 17004.

Zhao et al. Targeting 4-1BB (CD137) to enhance CD8 T cell responses with poxviruses and viral antigens. Frontiers in Immunology 3, 2012

Zhou et al. Antibodies Against Immune Checkpoint Molecules Restore Functions of Tumor-infiltrating T cells in Hepatocellular Carcinomas. Gastroenterology 2017 doi: 10.1053/j.gastro.2017.06.017.

---

The invention claimed is:

1. A bispecific antibody that comprises a first antigen binding site that can bind an extracellular part of CD137 and a second antigen binding site that can bind an extracellular part of PD-L1;
  wherein the first antigen binding site comprises a first heavy chain variable region comprising the complementarity determining regions CDR1 of SEQ ID NO:250, CDR2 of SEQ ID NO:251, and CDR3 of SEQ ID NO:252;
  wherein the second antigen binding site comprises a second heavy chain variable region comprising CDR1 of SEQ ID NO:253, CDR2 of SEQ ID NO:254, and CDR3 of SEQ ID NO:255; and
  wherein the first and second antigen binding site comprise a common light chain comprising CDR1 of SEQ ID NO:256, CDR2 of AAS, and CDR3 of SEQ ID NO:257.

2. The bispecific antibody of claim 1, wherein PD-L1 is expressed on an antigen presenting cell, a tumor cell, a virus infected cell or a parasite infected cell.

3. The bispecific antibody of claim 1, wherein PD-L1 is present in one or more zones on the cell membrane.

4. The bispecific antibody of claim 3, wherein said zone is a cluster, domain, micro-domain or compartment on the cell membrane.

5. The bispecific antibody of claim 1, wherein PD-L1 is present on the cell membrane as a part of a multimeric membrane protein comprising two or more copies of PD-L1.

6. The bispecific antibody of claim 1, wherein the variable domain that binds CD137 blocks the binding of a ligand to said CD137.

7. The bispecific antibody of claim 1, wherein the variable domain that binds an extracellular part of CD137 is defined as a variable domain that, when in a bivalent monospecific antibody format that comprises two of said variable domains that bind CD137, does not stimulate activity of CD137 on a cell.

8. A pharmaceutical composition comprising one or more bispecific antibodies according to claim 1, and a pharmaceutically acceptable excipient or carrier.

9. The bispecific antibody of claim 1, comprising a first heavy chain variable region that is at least 90% identical to SEQ ID NO: 129, and a second heavy chain variable region that is at least 90% identical to SEQ ID NO: 212.

10. The bispecific antibody of claim 9, wherein the first antigen binding site comprises a first heavy chain variable region comprising SEQ ID NO:129, and the second antigen binding site comprises a second heavy chain variable region comprising SEQ ID NO:212.

* * * * *

SEQUENCE LISTING

```
<160> NUMBER OF SEQ ID NOS: 257

<210> SEQ ID NO 1
<211> LENGTH: 255
<212> TYPE: PRT
<213> ORGANISM: Homo sapiens
<220> FEATURE:
<221> NAME/KEY: SIGNAL
<222> LOCATION: (1)..(23)
<220> FEATURE:
<221> NAME/KEY: DOMAIN
<222> LOCATION: (24)..(186)
<223> OTHER INFORMATION: ECD
<220> FEATURE:
<221> NAME/KEY: SIGNAL
<222> LOCATION: (187)..(214)
<223> OTHER INFORMATION: TM region
<220> FEATURE:
<221> NAME/KEY: SIGNAL
<222> LOCATION: (215)..(255)
<223> OTHER INFORMATION: intracellular tail

<400> SEQUENCE: 1

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110
```

```
Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255
```

<210> SEQ ID NO 2
<211> LENGTH: 254
<212> TYPE: PRT
<213> ORGANISM: Macaca fascicularis
<220> FEATURE:
<221> NAME/KEY: SIGNAL
<222> LOCATION: (1)..(23)
<220> FEATURE:
<221> NAME/KEY: DOMAIN
<222> LOCATION: (24)..(186)
<223> OTHER INFORMATION: ECD
<220> FEATURE:
<221> NAME/KEY: DOMAIN
<222> LOCATION: (187)..(214)
<223> OTHER INFORMATION: TM region
<220> FEATURE:
<221> NAME/KEY: DOMAIN
<222> LOCATION: (215)..(254)
<223> OTHER INFORMATION: intracellular tail

<400> SEQUENCE: 2

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Leu Cys Ser Asn Cys Pro
            20                  25                  30

Ala Gly Thr Phe Cys Asp Asn Asn Arg Ser Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Lys Thr Arg Lys Glu Cys Ser Ser
65                  70                  75                  80

Thr Ser Asn Ala Glu Cys Asp Cys Ile Ser Gly Tyr His Cys Leu Gly
                85                  90                  95

Ala Glu Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160
```

```
Ser Pro Ala Asp Leu Ser Pro Gly Ala Ser Ala Thr Pro Pro Ala
            165                 170                 175

Pro Ala Arg Glu Pro Gly His Ser Pro Gln Ile Ile Phe Phe Leu Ala
            180                 185                 190

Leu Thr Ser Thr Val Val Leu Phe Leu Leu Phe Phe Leu Val Leu Arg
            195                 200                 205

Phe Ser Val Val Lys Arg Ser Arg Lys Lys Leu Leu Tyr Ile Phe Lys
210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu
            245                 250

<210> SEQ ID NO 3
<211> LENGTH: 258
<212> TYPE: PRT
<213> ORGANISM: Rattus norvegicus
<220> FEATURE:
<221> NAME/KEY: SIGNAL
<222> LOCATION: (1)..(23)
<220> FEATURE:
<221> NAME/KEY: DOMAIN
<222> LOCATION: (24)..(187)
<223> OTHER INFORMATION: ECD
<220> FEATURE:
<221> NAME/KEY: DOMAIN
<222> LOCATION: (188)..(210)
<223> OTHER INFORMATION: TM region
<220> FEATURE:
<221> NAME/KEY: DOMAIN
<222> LOCATION: (211)..(258)
<223> OTHER INFORMATION: intracellular tail

<400> SEQUENCE: 3

Met Gly Ser Ser Cys Tyr Asn Met Val Val Thr Val Leu Leu Val Val
1               5                   10                  15

Gly Thr Glu Glu Val Arg Ala Thr Arg Asn Pro Cys Asp Ser Cys Glu
            20                  25                  30

Ala Gly Thr Phe Cys Ser Lys Tyr Pro Pro Val Cys Thr Ser Cys Pro
            35                  40                  45

Pro Ser Thr Tyr Ser Ser Thr Gly Gly Gln Pro Asn Cys Asp Ile Cys
50                  55                  60

Arg Val Cys Gln Gly Tyr Phe Arg Phe Lys Lys Pro Cys Ser Ser Thr
65                  70                  75                  80

His Asn Ala Glu Cys Glu Cys Val Glu Gly Phe His Cys Leu Gly Pro
            85                  90                  95

Lys Cys Thr Arg Cys Glu Lys Asp Cys Arg Pro Gly Gln Glu Leu Thr
            100                 105                 110

Glu Gln Gly Cys Lys Asn Cys Gly Leu Gly Thr Phe Asn Asp Gln Asp
            115                 120                 125

Gly Ala Gly Val Cys Arg Pro Trp Thr Asn Cys Ser Leu Asp Gly Arg
130                 135                 140

Ser Val Leu Lys Asn Gly Thr Lys Glu Lys Asp Val Val Cys Gly Pro
145                 150                 155                 160

Pro Val Val Ser Leu Ser Pro Ser Thr Thr Pro Ser Ala Val Thr Thr
            165                 170                 175

Pro Glu Arg Glu Ser Gly Glu Arg Pro Leu Gln Val Leu Thr Leu Phe
            180                 185                 190

Leu Ala Leu Thr Leu Ala Leu Leu Leu Phe Leu Ile Phe Ile Ile Leu
            195                 200                 205
```

```
Trp Phe Ser Val Pro Lys Trp Leu Arg Lys Lys Phe Pro His Ile Phe
            210                 215                 220

Lys Gln Pro Phe Lys Lys Ala Val Arg Thr Ala Gln Glu Glu Asp Ala
225                 230                 235                 240

Cys Ser Cys Arg Phe Pro Glu Glu Glu Gly Gly Gly Gly Ser Tyr
                245                 250                 255

Glu Leu

<210> SEQ ID NO 4
<211> LENGTH: 290
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: DOMAIN
<222> LOCATION: (19)..(238)
<223> OTHER INFORMATION: ECD
<220> FEATURE:
<221> NAME/KEY: DOMAIN
<222> LOCATION: (239)..(259)
<223> OTHER INFORMATION: TM region
<220> FEATURE:
<221> NAME/KEY: DOMAIN
<222> LOCATION: (260)..(290)
<223> OTHER INFORMATION: intracellular tail

<400> SEQUENCE: 4

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240
```

```
Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 5
<211> LENGTH: 290
<212> TYPE: PRT
<213> ORGANISM: Macaca mulatta
<220> FEATURE:
<221> NAME/KEY: SIGNAL
<222> LOCATION: (1)..(18)
<220> FEATURE:
<221> NAME/KEY: DOMAIN
<222> LOCATION: (19)..(238)
<223> OTHER INFORMATION: ECD
<220> FEATURE:
<221> NAME/KEY: DOMAIN
<222> LOCATION: (239)..(259)
<223> OTHER INFORMATION: TM region
<220> FEATURE:
<221> NAME/KEY: DOMAIN
<222> LOCATION: (260)..(290)
<223> OTHER INFORMATION: intracellular tail

<400> SEQUENCE: 5

Met Arg Ile Phe Ala Val Phe Ile Phe Thr Ile Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Arg Phe Pro Val Glu Lys Gln Leu
            35                  40                  45

Gly Leu Thr Ser Leu Ile Val Tyr Trp Glu Met Glu Asp Lys Asn Ile
    50                  55                  60

Ile Gln Phe Val His Gly Glu Glu Asp Leu Lys Val Gln His Ser Asn
65                  70                  75                  80

Tyr Arg Gln Arg Ala Gln Leu Leu Lys Asp Gln Leu Ser Leu Gly Asn
                85                  90                  95

Ala Ala Leu Arg Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Leu Asn
            180                 185                 190

Val Thr Ser Thr Leu Arg Ile Asn Thr Thr Ala Asn Glu Ile Phe Tyr
        195                 200                 205

Cys Ile Phe Arg Arg Leu Gly Pro Glu Glu Asn His Thr Ala Glu Leu
    210                 215                 220

Val Ile Pro Glu Leu Pro Leu Ala Leu Pro Pro Asn Glu Arg Thr His
```

```
            225                 230                 235                 240

Leu Val Ile Leu Gly Ala Ile Phe Leu Leu Gly Val Ala Leu Thr
                245                 250                 255

Phe Ile Phe Tyr Leu Arg Lys Gly Arg Met Met Asp Met Lys Lys Ser
                260                 265                 270

Gly Ile Arg Val Thr Asn Ser Lys Lys Gln Arg Asp Thr Gln Leu Glu
                275                 280                 285

Glu Thr
    290

<210> SEQ ID NO 6
<211> LENGTH: 277
<212> TYPE: PRT
<213> ORGANISM: Homo sapiens
<220> FEATURE:
<221> NAME/KEY: SIGNAL
<222> LOCATION: (1)..(28)
<220> FEATURE:
<221> NAME/KEY: DOMAIN
<222> LOCATION: (29)..(214)
<223> OTHER INFORMATION: ECD
<220> FEATURE:
<221> NAME/KEY: DOMAIN
<222> LOCATION: (215)..(235)
<223> OTHER INFORMATION: TM region
<220> FEATURE:
<221> NAME/KEY: DOMAIN
<222> LOCATION: (236)..(277)
<223> OTHER INFORMATION: intravellular tail

<400> SEQUENCE: 6

Met Cys Val Gly Ala Arg Arg Leu Gly Arg Gly Pro Cys Ala Ala Leu
1               5                  10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
                35                  40                  45

Gly Asn Gly Met Val Ser Arg Cys Ser Arg Ser Gln Asn Thr Val Cys
            50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220
```

```
Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
            245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 7
<211> LENGTH: 271
<212> TYPE: PRT
<213> ORGANISM: Rattus norvegicus
<220> FEATURE:
<221> NAME/KEY: SIGNAL
<222> LOCATION: (1)..(19)
<220> FEATURE:
<221> NAME/KEY: DOMAIN
<222> LOCATION: (20)..(210)
<223> OTHER INFORMATION: ECD
<220> FEATURE:
<221> NAME/KEY: DOMAIN
<222> LOCATION: (211)..(235)
<223> OTHER INFORMATION: TM region
<220> FEATURE:
<221> NAME/KEY: DOMAIN
<222> LOCATION: (236)..(271)
<223> OTHER INFORMATION: intracellular tail

<400> SEQUENCE: 7

Met Tyr Val Trp Val Gln Gln Pro Thr Ala Phe Leu Leu Gly Leu
1               5                   10                  15

Ser Leu Gly Val Thr Val Lys Leu Asn Cys Val Lys Asp Thr Tyr Pro
                20                  25                  30

Ser Gly His Lys Cys Cys Arg Glu Cys Gln Pro Gly His Gly Met Val
            35                  40                  45

Ser Arg Cys Asp His Thr Arg Asp Thr Val Cys His Pro Cys Glu Pro
50                  55                  60

Gly Phe Tyr Asn Glu Ala Val Asn Tyr Asp Thr Cys Lys Gln Cys Thr
65                  70                  75                  80

Gln Cys Asn His Arg Ser Gly Ser Glu Leu Lys Gln Asn Cys Thr Pro
                85                  90                  95

Thr Glu Asp Thr Val Cys Gln Cys Arg Pro Gly Thr Gln Pro Arg Gln
            100                 105                 110

Asp Ser Ser His Lys Leu Gly Val Asp Cys Val Pro Cys Pro Pro Gly
            115                 120                 125

His Phe Ser Pro Gly Ser Asn Gln Ala Cys Lys Pro Trp Thr Asn Cys
            130                 135                 140

Thr Leu Ser Gly Lys Gln Ile Arg His Pro Ala Ser Asn Ser Leu Asp
145                 150                 155                 160

Thr Val Cys Glu Asp Arg Ser Leu Leu Ala Thr Leu Leu Trp Glu Thr
                165                 170                 175

Gln Arg Thr Thr Phe Arg Pro Thr Thr Val Pro Ser Thr Thr Val Trp
            180                 185                 190

Pro Arg Thr Ser Gln Leu Pro Ser Thr Pro Thr Leu Val Ala Pro Glu
            195                 200                 205

Gly Pro Ala Phe Ala Val Ile Leu Gly Leu Gly Leu Gly Leu Leu Ala
        210                 215                 220

Pro Leu Thr Val Leu Leu Ala Leu Tyr Leu Leu Arg Lys Ala Trp Arg
225                 230                 235                 240
```

```
Ser Pro Asn Thr Pro Lys Pro Cys Trp Gly Asn Ser Phe Arg Thr Pro
                245                 250                 255

Ile Gln Glu Glu Gln Thr Asp Thr His Phe Thr Leu Ala Lys Ile
            260                 265                 270

<210> SEQ ID NO 8
<211> LENGTH: 277
<212> TYPE: PRT
<213> ORGANISM: Macaca fascicularis
<220> FEATURE:
<221> NAME/KEY: SIGNAL
<222> LOCATION: (1)..(28)
<220> FEATURE:
<221> NAME/KEY: DOMAIN
<222> LOCATION: (29)..(214)
<223> OTHER INFORMATION: ECD
<220> FEATURE:
<221> NAME/KEY: DOMAIN
<222> LOCATION: (215)..(235)
<223> OTHER INFORMATION: TM region
<220> FEATURE:
<221> NAME/KEY: DOMAIN
<222> LOCATION: (236)..(277)
<223> OTHER INFORMATION: intracellular tail

<400> SEQUENCE: 8

Met Cys Val Gly Ala Arg Arg Leu Gly Arg Gly Pro Cys Ala Ala Leu
1               5                   10                  15

Leu Leu Leu Gly Leu Gly Leu Ser Thr Thr Ala Lys Leu His Cys Val
            20                  25                  30

Gly Asp Thr Tyr Pro Ser Asn Asp Arg Cys Cys Gln Glu Cys Arg Pro
        35                  40                  45

Gly Asn Gly Met Val Ser Arg Cys Asn Arg Ser Gln Asn Thr Val Cys
    50                  55                  60

Arg Pro Cys Gly Pro Gly Phe Tyr Asn Asp Val Val Ser Ala Lys Pro
65                  70                  75                  80

Cys Lys Ala Cys Thr Trp Cys Asn Leu Arg Ser Gly Ser Glu Arg Lys
                85                  90                  95

Gln Pro Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Thr Gln Pro
                165                 170                 175

Gln Glu Thr Gln Gly Pro Pro Ala Arg Pro Thr Thr Val Gln Pro Thr
            180                 185                 190

Glu Ala Trp Pro Arg Thr Ser Gln Arg Pro Ser Thr Arg Pro Val Glu
        195                 200                 205

Val Pro Arg Gly Pro Ala Val Ala Ala Ile Leu Gly Leu Gly Leu Ala
    210                 215                 220

Leu Gly Leu Leu Gly Pro Leu Ala Met Leu Leu Ala Leu Leu Leu Leu
225                 230                 235                 240

Arg Arg Asp Gln Arg Leu Pro Pro Asp Ala Pro Lys Ala Pro Gly Gly
                245                 250                 255

Gly Ser Phe Arg Thr Pro Ile Gln Glu Glu Gln Ala Asp Ala His Ser
```

```
                    260                 265                 270

Ala Leu Ala Lys Ile
        275

<210> SEQ ID NO 9
<211> LENGTH: 256
<212> TYPE: PRT
<213> ORGANISM: Mus musculus

<400> SEQUENCE: 9

Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65              70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
        195                 200                 205

Ser Val Leu Lys Trp Ile Arg Lys Lys Phe Pro His Ile Phe Lys Gln
    210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255

<210> SEQ ID NO 10
<211> LENGTH: 257
<212> TYPE: PRT
<213> ORGANISM: Artificial Sequence
<220> FEATURE:
<223> OTHER INFORMATION: mo/huCD137 chimeric insert A

<400> SEQUENCE: 10

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Ser Cys
        35                  40                  45
```

```
Pro Pro Ser Thr Phe Ser Ser Ile Gly Gly Gln Pro Asn Cys Asn Ile
    50                  55                  60

Cys Arg Val Cys Ala Gly Tyr Phe Arg Phe Lys Phe Cys Ser Ser
65                  70                  75                  80

Thr His Asn Ala Glu Cys Glu Cys Ile Glu Gly Phe His Cys Leu Gly
                85                  90                  95

Pro Gln Cys Thr Arg Cys Glu Lys Asp Cys Arg Pro Gly Gln Glu Leu
                100                 105                 110

Thr Lys Gln Gly Cys Lys Thr Cys Ser Leu Gly Thr Phe Asn Asp Gln
                115                 120                 125

Asn Gly Thr Gly Val Cys Arg Pro Trp Thr Asn Cys Ser Leu Asp Gly
    130                 135                 140

Arg Ser Val Leu Lys Thr Gly Thr Thr Glu Lys Asp Val Val Cys Gly
145                 150                 155                 160

Pro Pro Val Val Ser Phe Ser Pro Ser Thr Thr Ile Ser Val Thr Pro
                165                 170                 175

Glu Gly Gly Pro Gly Gly His Ser Leu Gln Val Leu Thr Leu Phe Leu
                180                 185                 190

Ala Leu Thr Ser Ala Leu Leu Leu Ala Leu Ile Phe Ile Thr Leu Leu
        195                 200                 205

Phe Ser Val Leu Lys Trp Ile Arg Lys Lys Phe Pro His Ile Phe Lys
    210                 215                 220

Gln Pro Phe Lys Lys Thr Thr Gly Ala Ala Gln Glu Glu Asp Ala Cys
225                 230                 235                 240

Ser Cys Arg Cys Pro Gln Glu Glu Glu Gly Gly Gly Gly Tyr Glu Leu
                245                 250                 255

Leu
```

<210> SEQ ID NO 11
<211> LENGTH: 257
<212> TYPE: PRT
<213> ORGANISM: Artificial Sequence
<220> FEATURE:
<223> OTHER INFORMATION: mo/huCD137 chimeric insert B

<400> SEQUENCE: 11

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
                35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Glu Cys Ile Glu Gly Phe His Cys Leu Gly
                85                  90                  95

Pro Gln Cys Thr Arg Cys Glu Lys Asp Cys Arg Pro Gly Gln Glu Leu
                100                 105                 110

Thr Lys Gln Gly Cys Lys Thr Cys Ser Leu Gly Thr Phe Asn Asp Gln
                115                 120                 125

Asn Gly Thr Gly Val Cys Arg Pro Trp Thr Asn Cys Ser Leu Asp Gly
    130                 135                 140
```

```
Arg Ser Val Leu Lys Thr Gly Thr Thr Glu Lys Asp Val Val Cys Gly
145                 150                 155                 160

Pro Pro Val Val Ser Phe Ser Pro Ser Thr Thr Ile Ser Val Thr Pro
                165                 170                 175

Glu Gly Gly Pro Gly Gly His Ser Leu Gln Val Leu Thr Leu Phe Leu
            180                 185                 190

Ala Leu Thr Ser Ala Leu Leu Ala Leu Ile Phe Ile Thr Leu Leu
            195                 200                 205

Phe Ser Val Leu Lys Trp Ile Arg Lys Lys Phe Pro His Ile Phe Lys
        210                 215                 220

Gln Pro Phe Lys Lys Thr Thr Gly Ala Ala Gln Glu Glu Asp Ala Cys
225                 230                 235                 240

Ser Cys Arg Cys Pro Gln Glu Glu Glu Gly Gly Gly Gly Tyr Glu
                245                 250                 255

Leu
```

<210> SEQ ID NO 12
<211> LENGTH: 257
<212> TYPE: PRT
<213> ORGANISM: Artificial Sequence
<220> FEATURE:
<223> OTHER INFORMATION: mo/huCD137 chimeric insert C

<400> SEQUENCE: 12

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Thr Cys Ser Leu Gly Thr Phe Asn Asp Gln
        115                 120                 125

Asn Gly Thr Gly Val Cys Arg Pro Trp Thr Asn Cys Ser Leu Asp Gly
    130                 135                 140

Arg Ser Val Leu Lys Thr Gly Thr Thr Glu Lys Asp Val Val Cys Gly
145                 150                 155                 160

Pro Pro Val Val Ser Phe Ser Pro Ser Thr Thr Ile Ser Val Thr Pro
                165                 170                 175

Glu Gly Gly Pro Gly Gly His Ser Leu Gln Val Leu Thr Leu Phe Leu
            180                 185                 190

Ala Leu Thr Ser Ala Leu Leu Ala Leu Ile Phe Ile Thr Leu Leu
            195                 200                 205

Phe Ser Val Leu Lys Trp Ile Arg Lys Lys Phe Pro His Ile Phe Lys
        210                 215                 220

Gln Pro Phe Lys Lys Thr Thr Gly Ala Ala Gln Glu Glu Asp Ala Cys
225                 230                 235                 240

Ser Cys Arg Cys Pro Gln Glu Glu Glu Gly Gly Gly Gly Tyr Glu
```

-continued

```
                245                 250                 255
Leu

<210> SEQ ID NO 13
<211> LENGTH: 256
<212> TYPE: PRT
<213> ORGANISM: Artificial Sequence
<220> FEATURE:
<223> OTHER INFORMATION: mo/huCD137 chimeric insert D

<400> SEQUENCE: 13

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
        195                 200                 205

Ser Val Leu Lys Trp Ile Arg Lys Lys Phe Pro His Ile Phe Lys Gln
210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255

<210> SEQ ID NO 14
<211> LENGTH: 254
<212> TYPE: PRT
<213> ORGANISM: Artificial Sequence
<220> FEATURE:
<223> OTHER INFORMATION: mo/huCD137 chimeric insert E

<400> SEQUENCE: 14

Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Pro Cys Pro
```

```
                35                  40                  45
Pro Asn Ser Phe Ser Ser Ala Gly Gly Gln Arg Thr Cys Asp Ile Cys
 50                  55                  60
Arg Gln Cys Lys Gly Val Phe Arg Thr Arg Lys Glu Cys Ser Ser Thr
 65                  70                  75                  80
Ser Asn Ala Glu Cys Asp Cys Thr Pro Gly Phe His Cys Leu Gly Ala
                 85                  90                  95
Gly Cys Ser Met Cys Glu Gln Asp Cys Lys Gln Gly Gln Glu Leu Thr
                100                 105                 110
Lys Lys Gly Cys Lys Asp Cys Cys Phe Gly Thr Phe Asn Asp Gln Lys
                115                 120                 125
Arg Gly Ile Cys Arg Pro Trp Thr Asn Cys Ser Leu Asp Gly Lys Ser
                130                 135                 140
Val Leu Val Asn Gly Thr Lys Glu Arg Asp Val Val Cys Gly Pro Ser
145                 150                 155                 160
Pro Ala Asp Leu Ser Pro Gly Ala Ser Ser Val Thr Pro Pro Ala Pro
                165                 170                 175
Ala Arg Glu Pro Gly His Ser Pro Gln Ile Ile Ser Phe Phe Leu Ala
                180                 185                 190
Leu Thr Ser Thr Ala Leu Leu Phe Leu Leu Phe Phe Leu Thr Leu Arg
                195                 200                 205
Phe Ser Val Val Lys Arg Gly Arg Lys Lys Leu Leu Tyr Ile Phe Lys
210                 215                 220
Gln Pro Phe Met Arg Pro Val Gln Thr Thr Gln Glu Glu Asp Gly Cys
225                 230                 235                 240
Ser Cys Arg Phe Pro Glu Glu Glu Glu Gly Gly Cys Glu Leu
                245                 250

<210> SEQ ID NO 15
<211> LENGTH: 254
<212> TYPE: PRT
<213> ORGANISM: Artificial Sequence
<220> FEATURE:
<223> OTHER INFORMATION: mo/huCD137 chimeric insert F

<400> SEQUENCE: 15

Met Gly Asn Asn Cys Tyr Asn Val Val Ile Val Leu Leu Leu Val
1               5                   10                  15
Gly Cys Glu Lys Val Gly Ala Val Gln Asn Ser Cys Asp Asn Cys Gln
                 20                  25                  30
Pro Gly Thr Phe Cys Arg Lys Tyr Asn Pro Val Cys Lys Ser Cys Pro
                 35                  40                  45
Pro Ser Thr Phe Ser Ser Ile Gly Gly Gln Pro Asn Cys Asn Ile Cys
 50                  55                  60
Arg Val Cys Ala Gly Tyr Phe Arg Phe Lys Lys Phe Cys Ser Ser Thr
 65                  70                  75                  80
His Asn Ala Glu Cys Asp Cys Thr Pro Gly Phe His Cys Leu Gly Ala
                 85                  90                  95
Gly Cys Ser Met Cys Glu Gln Asp Cys Lys Gln Gly Gln Glu Leu Thr
                100                 105                 110
Lys Lys Gly Cys Lys Asp Cys Cys Phe Gly Thr Phe Asn Asp Gln Lys
                115                 120                 125
Arg Gly Ile Cys Arg Pro Trp Thr Asn Cys Ser Leu Asp Gly Lys Ser
                130                 135                 140
Val Leu Val Asn Gly Thr Lys Glu Arg Asp Val Val Cys Gly Pro Ser
```

```
                145                 150                 155                 160
Pro Ala Asp Leu Ser Pro Gly Ala Ser Ser Val Thr Pro Pro Ala Pro
                165                 170                 175

Ala Arg Glu Pro Gly His Ser Pro Gln Ile Ile Ser Phe Phe Leu Ala
                180                 185                 190

Leu Thr Ser Thr Ala Leu Leu Phe Leu Leu Phe Phe Leu Thr Leu Arg
                195                 200                 205

Phe Ser Val Val Lys Arg Gly Arg Lys Lys Leu Leu Tyr Ile Phe Lys
                210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu
                245                 250

<210> SEQ ID NO 16
<211> LENGTH: 254
<212> TYPE: PRT
<213> ORGANISM: Artificial Sequence
<220> FEATURE:
<223> OTHER INFORMATION: mo/huCD137 chimeric insert G

<400> SEQUENCE: 16

Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
                20                  25                  30

Pro Gly Thr Phe Cys Arg Lys Tyr Asn Pro Val Cys Lys Ser Cys Pro
                35                  40                  45

Pro Ser Thr Phe Ser Ser Ile Gly Gly Gln Pro Asn Cys Asn Ile Cys
                50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
                100                 105                 110

Lys Gln Gly Cys Lys Asp Cys Cys Phe Gly Thr Phe Asn Asp Gln Lys
                115                 120                 125

Arg Gly Ile Cys Arg Pro Trp Thr Asn Cys Ser Leu Asp Gly Lys Ser
                130                 135                 140

Val Leu Val Asn Gly Thr Lys Glu Arg Asp Val Val Cys Gly Pro Ser
145                 150                 155                 160

Pro Ala Asp Leu Ser Pro Gly Ala Ser Ser Val Thr Pro Pro Ala Pro
                165                 170                 175

Ala Arg Glu Pro Gly His Ser Pro Gln Ile Ile Ser Phe Phe Leu Ala
                180                 185                 190

Leu Thr Ser Thr Ala Leu Leu Phe Leu Leu Phe Phe Leu Thr Leu Arg
                195                 200                 205

Phe Ser Val Val Lys Arg Gly Arg Lys Lys Leu Leu Tyr Ile Phe Lys
                210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu
                245                 250
```

```
<210> SEQ ID NO 17
<211> LENGTH: 255
<212> TYPE: PRT
<213> ORGANISM: Artificial Sequence
<220> FEATURE:
<223> OTHER INFORMATION: mo/huCD137 chimeric insert H

<400> SEQUENCE: 17

Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
            35                  40                  45

Pro Ser Thr Phe Ser Ser Ile Gly Gly Gln Pro Asn Cys Asn Ile Cys
50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
            115                 120                 125

Gly Thr Gly Val Cys Arg Pro Trp Thr Asn Cys Ser Leu Asp Gly Arg
130                 135                 140

Ser Val Leu Lys Thr Gly Thr Thr Glu Lys Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 18
<211> LENGTH: 276
<212> TYPE: PRT
<213> ORGANISM: Artificial Sequence
<220> FEATURE:
<223> OTHER INFORMATION: ra/huOX40 chimeric insert A

<400> SEQUENCE: 18

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
50                  55                  60
```

Arg Pro Cys Glu Pro Gly Phe Tyr Asn Glu Ala Val Asn Tyr Asp Thr
65                  70                  75                  80

Cys Lys Gln Cys Thr Gln Cys Asn His Arg Ser Gly Ser Glu Leu Lys
            85                  90                  95

Gln Asn Cys Thr Pro Thr Glu Asp Thr Val Cys Gln Cys Arg Pro Gly
            100                 105                 110

Thr Gln Pro Arg Gln Asp Ser Ser His Lys Leu Gly Val Asp Cys Val
            115                 120                 125

Pro Cys Pro Pro Gly His Phe Ser Pro Gly Ser Asn Gln Ala Cys Lys
            130                 135                 140

Pro Trp Thr Asn Cys Thr Leu Ser Gly Lys Gln Ile Arg His Pro Ala
145                 150                 155                 160

Ser Asn Ser Leu Asp Thr Val Cys Glu Asp Arg Ser Leu Leu Ala Thr
            165                 170                 175

Leu Leu Trp Glu Thr Gln Arg Thr Thr Phe Arg Pro Thr Thr Val Pro
            180                 185                 190

Ser Thr Thr Val Trp Pro Arg Thr Ser Gln Leu Pro Ser Thr Pro Thr
            195                 200                 205

Leu Val Ala Pro Glu Gly Pro Ala Phe Ala Val Ile Leu Gly Leu Gly
            210                 215                 220

Leu Gly Leu Leu Ala Pro Leu Thr Val Leu Leu Ala Leu Tyr Leu Leu
225                 230                 235                 240

Arg Lys Ala Trp Arg Ser Pro Asn Thr Pro Lys Pro Cys Trp Gly Asn
                245                 250                 255

Ser Phe Arg Thr Pro Ile Gln Glu Glu Gln Thr Asp Thr His Phe Thr
            260                 265                 270

Leu Ala Lys Ile
        275

<210> SEQ ID NO 19
<211> LENGTH: 276
<212> TYPE: PRT
<213> ORGANISM: Artificial Sequence
<220> FEATURE:
<223> OTHER INFORMATION: ra/huOX40 chimeric insert B

<400> SEQUENCE: 19

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
            85                  90                  95

Gln Leu Cys Thr Ala Thr Gln Asp Thr Val Cys Gln Cys Arg Pro Gly
            100                 105                 110

Thr Gln Pro Arg Gln Asp Ser Ser His Lys Leu Gly Val Asp Cys Val
            115                 120                 125

Pro Cys Pro Pro Gly His Phe Ser Pro Gly Ser Asn Gln Ala Cys Lys
            130                 135                 140

```
Pro Trp Thr Asn Cys Thr Leu Ser Gly Lys Gln Ile Arg His Pro Ala
145                 150                 155                 160

Ser Asn Ser Leu Asp Thr Val Cys Glu Asp Arg Ser Leu Leu Ala Thr
            165                 170                 175

Leu Leu Trp Glu Thr Gln Arg Thr Thr Phe Arg Pro Thr Thr Val Pro
        180                 185                 190

Ser Thr Thr Val Trp Pro Arg Thr Ser Gln Leu Pro Ser Thr Pro Thr
    195                 200                 205

Leu Val Ala Pro Glu Gly Pro Ala Phe Ala Val Ile Leu Gly Leu Gly
210                 215                 220

Leu Gly Leu Leu Ala Pro Leu Thr Val Leu Leu Ala Leu Tyr Leu Leu
225                 230                 235                 240

Arg Lys Ala Trp Arg Ser Pro Asn Thr Pro Lys Pro Cys Trp Gly Asn
                245                 250                 255

Ser Phe Arg Thr Pro Ile Gln Glu Glu Gln Thr Asp Thr His Phe Thr
            260                 265                 270

Leu Ala Lys Ile
        275

<210> SEQ ID NO 20
<211> LENGTH: 274
<212> TYPE: PRT
<213> ORGANISM: Artificial Sequence
<220> FEATURE:
<223> OTHER INFORMATION: ra/huOX40 chimeric insert C

<400> SEQUENCE: 20

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Ser Asn Gln Ala Cys Lys Pro Trp
    130                 135                 140

Thr Asn Cys Thr Leu Ser Gly Lys Gln Ile Arg His Pro Ala Ser Asn
145                 150                 155                 160

Ser Leu Asp Thr Val Cys Glu Asp Arg Ser Leu Leu Ala Thr Leu Leu
                165                 170                 175

Trp Glu Thr Gln Arg Thr Thr Phe Arg Pro Thr Thr Val Pro Ser Thr
            180                 185                 190

Thr Val Trp Pro Arg Thr Ser Gln Leu Pro Ser Thr Pro Thr Leu Val
        195                 200                 205

Ala Pro Glu Gly Pro Ala Phe Ala Val Ile Leu Gly Leu Gly Leu Gly
    210                 215                 220
```

Leu Leu Ala Pro Leu Thr Val Leu Leu Ala Leu Tyr Leu Leu Arg Lys
225                 230                 235                 240

Ala Trp Arg Ser Pro Asn Thr Pro Lys Pro Cys Trp Gly Asn Ser Phe
            245                 250                 255

Arg Thr Pro Ile Gln Glu Glu Gln Thr Asp Thr His Phe Thr Leu Ala
            260                 265                 270

Lys Ile

<210> SEQ ID NO 21
<211> LENGTH: 274
<212> TYPE: PRT
<213> ORGANISM: Artificial Sequence
<220> FEATURE:
<223> OTHER INFORMATION: ra/huOX40 chimeric insert D

<400> SEQUENCE: 21

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
            85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
            130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Ser Leu Leu Ala Thr Leu Leu
                165                 170                 175

Trp Glu Thr Gln Arg Thr Thr Phe Arg Pro Thr Thr Val Pro Ser Thr
            180                 185                 190

Thr Val Trp Pro Arg Thr Ser Gln Leu Pro Ser Thr Pro Thr Leu Val
            195                 200                 205

Ala Pro Glu Gly Pro Ala Phe Ala Val Ile Leu Gly Leu Gly Leu Gly
210                 215                 220

Leu Leu Ala Pro Leu Thr Val Leu Leu Ala Leu Tyr Leu Leu Arg Lys
225                 230                 235                 240

Ala Trp Arg Ser Pro Asn Thr Pro Lys Pro Cys Trp Gly Asn Ser Phe
            245                 250                 255

Arg Thr Pro Ile Gln Glu Glu Gln Thr Asp Thr His Phe Thr Leu Ala
            260                 265                 270

Lys Ile

<210> SEQ ID NO 22
<211> LENGTH: 272
<212> TYPE: PRT
<213> ORGANISM: Artificial Sequence
<220> FEATURE:
<223> OTHER INFORMATION: ra/huOX40 chimeric insert E

<400> SEQUENCE: 22

Met Tyr Val Trp Val Gln Gln Pro Thr Ala Phe Leu Leu Leu Gly Leu
1               5                   10                  15

Ser Leu Gly Val Thr Val Lys Leu Asn Cys Val Lys Asp Thr Tyr Pro
            20                  25                  30

Ser Gly His Lys Cys Cys Arg Glu Cys Gln Pro Gly His Gly Met Val
        35                  40                  45

Ser Arg Cys Asp His Thr Arg Asp Thr Val Cys His Pro Cys Gly Pro
    50                  55                  60

Gly Phe Tyr Asn Asp Val Val Ser Ser Lys Pro Cys Lys Pro Cys Thr
65                  70                  75                  80

Trp Cys Asn Leu Arg Ser Gly Ser Glu Arg Lys Gln Leu Cys Thr Ala
                85                  90                  95

Thr Gln Asp Thr Val Cys Arg Cys Arg Ala Gly Thr Gln Pro Leu Asp
            100                 105                 110

Ser Tyr Lys Pro Gly Val Asp Cys Ala Pro Cys Pro Pro Gly His Phe
        115                 120                 125

Ser Pro Gly Asp Asn Gln Ala Cys Lys Pro Trp Thr Asn Cys Thr Leu
    130                 135                 140

Ala Gly Lys His Thr Leu Gln Pro Ala Ser Asn Ser Ser Asp Ala Ile
145                 150                 155                 160

Cys Glu Asp Arg Asp Pro Pro Ala Thr Gln Pro Gln Glu Thr Gln Gly
                165                 170                 175

Pro Pro Ala Arg Pro Ile Thr Val Gln Pro Thr Glu Ala Trp Pro Arg
            180                 185                 190

Thr Ser Gln Gly Pro Ser Thr Arg Pro Val Glu Val Pro Gly Gly Arg
        195                 200                 205

Ala Val Ala Ala Ile Leu Gly Leu Gly Leu Val Leu Gly Leu Leu Gly
    210                 215                 220

Pro Leu Ala Ile Leu Leu Ala Leu Tyr Leu Leu Arg Arg Asp Gln Arg
225                 230                 235                 240

Leu Pro Pro Asp Ala His Lys Pro Pro Gly Gly Ser Phe Arg Thr
                245                 250                 255

Pro Ile Gln Glu Glu Gln Ala Asp Ala His Ser Thr Leu Ala Lys Ile
                260                 265                 270

<210> SEQ ID NO 23
<211> LENGTH: 272
<212> TYPE: PRT
<213> ORGANISM: Artificial Sequence
<220> FEATURE:
<223> OTHER INFORMATION: ra/huOX40 chimeric insert F

<400> SEQUENCE: 23

Met Tyr Val Trp Val Gln Gln Pro Thr Ala Phe Leu Leu Leu Gly Leu
1               5                   10                  15

Ser Leu Gly Val Thr Val Lys Leu Asn Cys Val Lys Asp Thr Tyr Pro
            20                  25                  30

Ser Gly His Lys Cys Cys Arg Glu Cys Gln Pro Gly His Gly Met Val
        35                  40                  45

Ser Arg Cys Asp His Thr Arg Asp Thr Val Cys His Pro Cys Glu Pro
    50                  55                  60

Gly Phe Tyr Asn Glu Ala Val Asn Tyr Asp Thr Cys Lys Gln Cys Thr

```
            65                  70                  75                  80
        Gln Cys Asn His Arg Ser Gly Ser Glu Leu Lys Gln Asn Cys Thr Pro
                        85                  90                  95

Thr Glu Asp Thr Val Cys Arg Cys Arg Ala Gly Thr Gln Pro Leu Asp
                        100                 105                 110

Ser Tyr Lys Pro Gly Val Asp Cys Ala Pro Cys Pro Gly His Phe
                        115                 120                 125

Ser Pro Gly Asp Asn Gln Ala Cys Lys Pro Trp Thr Asn Cys Thr Leu
                130                 135                 140

Ala Gly Lys His Thr Leu Gln Pro Ala Ser Asn Ser Ser Asp Ala Ile
        145                 150                 155                 160

Cys Glu Asp Arg Asp Pro Pro Ala Thr Gln Pro Gln Glu Thr Gln Gly
                        165                 170                 175

Pro Pro Ala Arg Pro Ile Thr Val Gln Pro Thr Glu Ala Trp Pro Arg
                        180                 185                 190

Thr Ser Gln Gly Pro Ser Thr Arg Pro Val Glu Val Pro Gly Gly Arg
                        195                 200                 205

Ala Val Ala Ala Ile Leu Gly Leu Gly Leu Val Leu Gly Leu Leu Gly
                210                 215                 220

Pro Leu Ala Ile Leu Leu Ala Leu Tyr Leu Leu Arg Arg Asp Gln Arg
        225                 230                 235                 240

Leu Pro Pro Asp Ala His Lys Pro Pro Gly Gly Gly Ser Phe Arg Thr
                        245                 250                 255

Pro Ile Gln Glu Glu Gln Ala Asp Ala His Ser Thr Leu Ala Lys Ile
                        260                 265                 270

<210> SEQ ID NO 24
<211> LENGTH: 274
<212> TYPE: PRT
<213> ORGANISM: Artificial Sequence
<220> FEATURE:
<223> OTHER INFORMATION: ra/huOX40 chimeric insert G

<400> SEQUENCE: 24

Met Tyr Val Trp Val Gln Gln Pro Thr Ala Phe Leu Leu Gly Leu
        1               5                   10                  15

Ser Leu Gly Val Thr Val Lys Leu Asn Cys Val Lys Asp Thr Tyr Pro
                        20                  25                  30

Ser Gly His Lys Cys Cys Arg Glu Cys Gln Pro Gly His Gly Met Val
                        35                  40                  45

Ser Arg Cys Asp His Thr Arg Asp Thr Val Cys His Pro Cys Glu Pro
                50                  55                  60

Gly Phe Tyr Asn Glu Ala Val Asn Tyr Asp Thr Cys Lys Gln Cys Thr
        65                  70                  75                  80

Gln Cys Asn His Arg Ser Gly Ser Glu Leu Lys Gln Asn Cys Thr Pro
                        85                  90                  95

Thr Glu Asp Thr Val Cys Gln Cys Arg Pro Gly Thr Gln Pro Arg Gln
                        100                 105                 110

Asp Ser Ser His Lys Leu Gly Val Asp Cys Val Pro Cys Pro Pro Gly
                        115                 120                 125

His Phe Ser Pro Gly Asp Asn Gln Ala Cys Lys Pro Trp Thr Asn Cys
                        130                 135                 140

Thr Leu Ala Gly Lys His Thr Leu Gln Pro Ala Ser Asn Ser Ser Asp
        145                 150                 155                 160

Ala Ile Cys Glu Asp Arg Asp Pro Pro Ala Thr Gln Pro Gln Glu Thr
```

```
                      165                 170                 175
Gln Gly Pro Pro Ala Arg Pro Ile Thr Val Gln Pro Thr Glu Ala Trp
            180                 185                 190
Pro Arg Thr Ser Gln Gly Pro Ser Thr Arg Pro Val Glu Val Pro Gly
        195                 200                 205
Gly Arg Ala Val Ala Ala Ile Leu Gly Leu Gly Leu Val Leu Gly Leu
    210                 215                 220
Leu Gly Pro Leu Ala Ile Leu Leu Ala Leu Tyr Leu Leu Arg Arg Asp
225                 230                 235                 240
Gln Arg Leu Pro Pro Asp Ala His Lys Pro Pro Gly Gly Gly Ser Phe
            245                 250                 255
Arg Thr Pro Ile Gln Glu Glu Gln Ala Asp Ala His Ser Thr Leu Ala
        260                 265                 270
Lys Ile

<210> SEQ ID NO 25
<211> LENGTH: 274
<212> TYPE: PRT
<213> ORGANISM: Artificial Sequence
<220> FEATURE:
<223> OTHER INFORMATION: ra/huOX40 chimeric insert H

<400> SEQUENCE: 25

Met Tyr Val Trp Val Gln Gln Pro Thr Ala Phe Leu Leu Leu Gly Leu
1               5                   10                  15
Ser Leu Gly Val Thr Val Lys Leu Asn Cys Val Lys Asp Thr Tyr Pro
            20                  25                  30
Ser Gly His Lys Cys Cys Arg Glu Cys Gln Pro Gly His Gly Met Val
        35                  40                  45
Ser Arg Cys Asp His Thr Arg Asp Thr Val Cys His Pro Cys Glu Pro
    50                  55                  60
Gly Phe Tyr Asn Glu Ala Val Asn Tyr Asp Thr Cys Lys Gln Cys Thr
65                  70                  75                  80
Gln Cys Asn His Arg Ser Gly Ser Glu Leu Lys Gln Asn Cys Thr Pro
            85                  90                  95
Thr Glu Asp Thr Val Cys Gln Cys Arg Pro Gly Thr Gln Pro Arg Gln
        100                 105                 110
Asp Ser His Lys Leu Gly Val Asp Cys Val Pro Cys Pro Pro Gly
    115                 120                 125
His Phe Ser Pro Gly Ser Asn Gln Ala Cys Lys Pro Trp Thr Asn Cys
    130                 135                 140
Thr Leu Ser Gly Lys Gln Ile Arg His Pro Ala Ser Asn Ser Leu Asp
145                 150                 155                 160
Thr Val Cys Glu Asp Arg Asp Pro Pro Ala Thr Gln Pro Gln Glu Thr
                165                 170                 175
Gln Gly Pro Pro Ala Arg Pro Ile Thr Val Gln Pro Thr Glu Ala Trp
            180                 185                 190
Pro Arg Thr Ser Gln Gly Pro Ser Thr Arg Pro Val Glu Val Pro Gly
        195                 200                 205
Gly Arg Ala Val Ala Ala Ile Leu Gly Leu Gly Leu Val Leu Gly Leu
    210                 215                 220
Leu Gly Pro Leu Ala Ile Leu Leu Ala Leu Tyr Leu Leu Arg Arg Asp
225                 230                 235                 240
Gln Arg Leu Pro Pro Asp Ala His Lys Pro Pro Gly Gly Gly Ser Phe
            245                 250                 255
```

Arg Thr Pro Ile Gln Glu Glu Gln Ala Asp Ala His Ser Thr Leu Ala
            260                 265                 270

Lys Ile

<210> SEQ ID NO 26
<211> LENGTH: 4
<212> TYPE: PRT
<213> ORGANISM: Artificial Sequence
<220> FEATURE:
<223> OTHER INFORMATION: CDR3 of OX40 clone

<400> SEQUENCE: 26

Gly Trp Asp Phe
1

<210> SEQ ID NO 27
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 27

Gly Gly Thr Met Val Arg Gly Val Ile Asp Asp Trp Phe Asp Pro
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 28

Val Gly Gly Leu Arg Gln Ala Trp Tyr Phe Asp Leu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 29

Gly Gly Trp Glu Leu Leu Phe Asn Tyr Phe Gln Gln
1               5                   10

<210> SEQ ID NO 30
<211> LENGTH: 8
<212> TYPE: PRT
<213> ORGANISM: Artificial Sequence
<220> FEATURE:
<223> OTHER INFORMATION: CDR3 of OX40 clone

<400> SEQUENCE: 30

Ser Pro Pro Tyr Tyr Met Asp Val
1               5

<210> SEQ ID NO 31
<211> LENGTH: 8
<212> TYPE: PRT
<213> ORGANISM: Artificial Sequence
<220> FEATURE:
<223> OTHER INFORMATION: CDR3 of OX40 clone

```
<400> SEQUENCE: 31

Gly Phe Asp Trp Tyr Phe Thr Leu
1               5

<210> SEQ ID NO 32
<211> LENGTH: 14
<212> TYPE: PRT
<213> ORGANISM: Artificial Sequence
<220> FEATURE:
<223> OTHER INFORMATION: CDR3 of OX40 clone

<400> SEQUENCE: 32

Gly Trp Gly Tyr Ser Gly Tyr Gly Pro Glu Gly Phe Asp Ile
1               5                   10

<210> SEQ ID NO 33
<211> LENGTH: 13
<212> TYPE: PRT
<213> ORGANISM: Artificial Sequence
<220> FEATURE:
<223> OTHER INFORMATION: CDR3 of OX40 clone

<400> SEQUENCE: 33

Ile Gly Gly Thr Gly Thr Thr Asp Trp Tyr Phe Asp Leu
1               5                   10

<210> SEQ ID NO 34
<211> LENGTH: 13
<212> TYPE: PRT
<213> ORGANISM: Artificial Sequence
<220> FEATURE:
<223> OTHER INFORMATION: CDR3 of OX40 clone

<400> SEQUENCE: 34

Val Gly Gly Tyr Thr Ser Ser Ser Trp Phe Phe Asp Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 35

Val Asp Gly Gly Asn Ser Asp Trp Tyr Phe Asp Leu
1               5                   10

<210> SEQ ID NO 36
<211> LENGTH: 14
<212> TYPE: PRT
<213> ORGANISM: Artificial Sequence
<220> FEATURE:
<223> OTHER INFORMATION: CDR3 of OX40 clone

<400> SEQUENCE: 36

Val Asp Gly Arg Ser Ser Gly Gly Asn Trp His Phe Asp Leu
1               5                   10

<210> SEQ ID NO 37
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 37
```

Asp Pro Tyr Tyr Phe Asp Ser Asn Gly Tyr Pro Pro Phe Asp Asp
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: CDR3 of OX40 clone

<400> SEQUENCE: 38

Gly Trp Asp Phe Phe Asp Ser
1               5

<210> SEQ ID NO 39
<211> LENGTH: 14
<212> TYPE: PRT
<213> ORGANISM: Artificial Sequence
<220> FEATURE:
<223> OTHER INFORMATION: CDR3 of OX40 clone

<400> SEQUENCE: 39

Val Gly Gly Leu Gly Thr Thr Pro His Trp Tyr Phe Asp Leu
1               5                   10

<210> SEQ ID NO 40
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 40

Pro Ser Tyr Asn Trp Asn Arg Leu Tyr Tyr Tyr Tyr Met Asp Val
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 41

Ser Gln Pro Asn Leu Asp Phe Trp Ser Gly Tyr His Phe Asp Tyr
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 42

Asp Pro Phe Phe Tyr Asp Arg Ser Gly Tyr Pro Pro Phe Asp Tyr
1               5                   10                  15

<210> SEQ ID NO 43
<211> LENGTH: 5
<212> TYPE: PRT
<213> ORGANISM: Artificial Sequence
<220> FEATURE:
<223> OTHER INFORMATION: CDR3 of OX40 clone

<400> SEQUENCE: 43

```
Gly Trp Gly Ser Gly
1               5

<210> SEQ ID NO 44
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 44

Val Gly Gly Tyr Gly Asn Asn Tyr Asn Phe Asp Tyr
1               5                   10

<210> SEQ ID NO 45
<211> LENGTH: 14
<212> TYPE: PRT
<213> ORGANISM: Artificial Sequence
<220> FEATURE:
<223> OTHER INFORMATION: CDR3 of OX40 clone

<400> SEQUENCE: 45

Asp Pro Ser Gly Ser Tyr Phe Tyr His Tyr Tyr Met Asp Val
1               5                   10

<210> SEQ ID NO 46
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 46

Arg Arg Pro Asn Tyr Asp Ser Trp Ser Gly Tyr Tyr Glu Asp Tyr
1               5                   10                  15

<210> SEQ ID NO 47
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 47

Gly Gly Trp Gly Leu Leu Arg Glu Tyr Phe Leu Gln
1               5                   10

<210> SEQ ID NO 48
<211> LENGTH: 10
<212> TYPE: PRT
<213> ORGANISM: Artificial Sequence
<220> FEATURE:
<223> OTHER INFORMATION: CDR3 of OX40 clone

<400> SEQUENCE: 48

His Thr Gly His Tyr Ser Gly Phe Asp Tyr
1               5                   10

<210> SEQ ID NO 49
<211> LENGTH: 13
<212> TYPE: PRT
<213> ORGANISM: Artificial Sequence
<220> FEATURE:
<223> OTHER INFORMATION: CDR3 of OX40 clone

<400> SEQUENCE: 49

Val Asp Gly Thr Gly Ile Ser Asn Trp Tyr Phe Asp Leu
```

```
<210> SEQ ID NO 50
<211> LENGTH: 13
<212> TYPE: PRT
<213> ORGANISM: Artificial Sequence
<220> FEATURE:
<223> OTHER INFORMATION: CDR3 of OX40 clone

<400> SEQUENCE: 50

Gly Tyr Ser Ser Ile Trp His Gly Glu Asn Phe Gln Tyr
1               5                   10

<210> SEQ ID NO 51
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 51

Asp Met Asp Asn Trp Asn Tyr Glu Gly Tyr Tyr Val Met Asp Val
1               5                   10                  15

<210> SEQ ID NO 52
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 52

Val Glu Gly Trp Gly Ser Gln Trp Tyr Phe Asp Leu
1               5                   10

<210> SEQ ID NO 53
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 53

Val Glu Gly Thr Asp Ser Asn Trp Gly Trp Asp Phe
1               5                   10

<210> SEQ ID NO 54
<211> LENGTH: 20
<212> TYPE: PRT
<213> ORGANISM: Artificial Sequence
<220> FEATURE:
<223> OTHER INFORMATION: CDR3 of OX40 clone

<400> SEQUENCE: 54

Asp Asp Gly Thr Gly Thr Gly Asp Tyr Val Trp Gly Arg Tyr Arg Tyr
1               5                   10                  15

Thr Leu Asp Phe
            20

<210> SEQ ID NO 55
<211> LENGTH: 13
<212> TYPE: PRT
<213> ORGANISM: Artificial Sequence
<220> FEATURE:
<223> OTHER INFORMATION: CDR3 of OX40 clone

<400> SEQUENCE: 55
```

```
Asp Gly Tyr Lys Leu Tyr Ala Ala Asp Gly Phe Asp Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: CDR3 of OX40 clone

<400> SEQUENCE: 56

Asp Met Asp Ser Tyr Pro Phe Tyr Arg Gly Phe Asp Tyr
1               5                   10

<210> SEQ ID NO 57
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 57

Asp Asp Asn Thr Met Trp Tyr Ser Arg Pro Tyr Ala Phe Asp Tyr
1               5                   10                  15

<210> SEQ ID NO 58
<211> LENGTH: 13
<212> TYPE: PRT
<213> ORGANISM: Artificial Sequence
<220> FEATURE:
<223> OTHER INFORMATION: CDR3 of OX40 clone

<400> SEQUENCE: 58

Asp Ser Pro Tyr Trp Ser Leu Pro Gly Gly Phe Asp Tyr
1               5                   10

<210> SEQ ID NO 59
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 59

Asp Gln Arg Trp Trp Tyr Met Asp Pro Gly Ala Gly Phe Asp Tyr
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 60

Asp Tyr Ser Tyr Ser Gly Thr Gly Ser Ser Ser Ala Phe Asp Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 61
```

Asp Tyr Leu His Gly Ser Tyr Tyr Arg Gly Ser Ala Phe Asp Tyr
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 62

Asp Ser Trp His Gly Gln Tyr Tyr Tyr Gly Lys Gly Phe Asp Tyr
1               5                   10                  15

<210> SEQ ID NO 63
<211> LENGTH: 13
<212> TYPE: PRT
<213> ORGANISM: Artificial Sequence
<220> FEATURE:
<223> OTHER INFORMATION: CDR3 of OX40 clone

<400> SEQUENCE: 63

Asp Gly Leu Gly Trp Asp Pro Gly Tyr Gly Phe Asp Tyr
1               5                   10

<210> SEQ ID NO 64
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 64

Asp Asn Tyr Gln Gly Met Tyr Tyr Phe Gly Thr Gly Phe Asp Tyr
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 65

Asp Asn His Tyr Tyr Ser Pro Pro Thr Tyr Trp Gly Phe Asp Tyr
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 66

Gly Gly Gln Ser Gln Tyr His Ser Tyr Pro Phe Gly Phe Asp Tyr
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 67

Asp Trp Trp Gln Gly His Trp Tyr Arg Ser Gly Gly Phe Asp Tyr

<210> SEQ ID NO 68
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 68

Gly Gln Met Asp Tyr Tyr Asp Asp Trp Tyr Ser Ala Phe Asp Tyr
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 69

Asp Tyr Tyr Gln Gly Ser His Tyr Phe Gly Pro Ala Phe Asp Tyr
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 70

Gly Asp Asp Asn Arg Met Tyr Ser Asn Pro Lys Gly Phe Asp Tyr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 71

Asp Asn Thr Gln Gly Asn Tyr Tyr Arg Ser Arg Gly Phe Asp Tyr
1               5                   10                  15

<210> SEQ ID NO 72
<211> LENGTH: 14
<212> TYPE: PRT
<213> ORGANISM: Artificial Sequence
<220> FEATURE:
<223> OTHER INFORMATION: CDR3 of OX40 clone

<400> SEQUENCE: 72

Asp Gly Leu Gln Ser Asn Tyr His Leu Gly Gly Phe Asp Tyr
1               5                   10

<210> SEQ ID NO 73
<211> LENGTH: 15
<212> TYPE: PRT
<213> ORGANISM: Artificial Sequence
<220> FEATURE:
<223> OTHER INFORMATION: CDR3 of OX40 clone

<400> SEQUENCE: 73

Gly Tyr Asp Met Tyr Gly Gly Trp Gly Ala Trp Gly Phe Asp Tyr
1               5                   10                  15

```
<210> SEQ ID NO 74
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 74

Asp Tyr Pro Ala Trp Ala Tyr Ser Ala Phe Asp Tyr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 75

Asp Tyr Trp Tyr Tyr Leu Ser Asp Ala Phe Asp Tyr
1               5                   10

<210> SEQ ID NO 76
<211> LENGTH: 12
<212> TYPE: PRT
<213> ORGANISM: Artificial Sequence
<220> FEATURE:
<223> OTHER INFORMATION: CDR3 of OX40 clone

<400> SEQUENCE: 76

Asp His Trp Gly Ser Phe Tyr Gly Asp Phe Asp Tyr
1               5                   10

<210> SEQ ID NO 77
<211> LENGTH: 12
<212> TYPE: PRT
<213> ORGANISM: Artificial Sequence
<220> FEATURE:
<223> OTHER INFORMATION: CDR3 of CD137xPD-L1 antibody

<400> SEQUENCE: 77

Asp Trp Gly Val Ile Gly Gly His Tyr Met Asp Val
1               5                   10

<210> SEQ ID NO 78
<211> LENGTH: 15
<212> TYPE: PRT
<213> ORGANISM: Artificial Sequence
<220> FEATURE:
<223> OTHER INFORMATION: CDR3 of CD137xPD-L1 antibody

<400> SEQUENCE: 78

Gly Leu Leu Trp Gly Lys Thr Asp Tyr Tyr Ser Gly Phe Asp Tyr
1               5                   10                  15

<210> SEQ ID NO 79
<211> LENGTH: 12
<212> TYPE: PRT
<213> ORGANISM: Artificial Sequence
<220> FEATURE:
<223> OTHER INFORMATION: CDR3 of CD137xPD-L1 antibody

<400> SEQUENCE: 79

Asp Ser Asp Gly Tyr Gly Pro Lys Ala Phe Asp Tyr
1               5                   10
```

<210> SEQ ID NO 80
<211> LENGTH: 15
<212> TYPE: PRT
<213> ORGANISM: Artificial Sequence
<220> FEATURE:
<223> OTHER INFORMATION: CDR3 of CD137xPD-L1 antibody

<400> SEQUENCE: 80

```
Asp Trp Ser Gly Ser Trp Asp Tyr Gly Ser Ser Ala Phe Asp Tyr
1               5                   10                  15
```

<210> SEQ ID NO 81
<211> LENGTH: 13
<212> TYPE: PRT
<213> ORGANISM: Artificial Sequence
<220> FEATURE:
<223> OTHER INFORMATION: CDR3 of CD137xPD-L1 antibody

<400> SEQUENCE: 81

```
Asp Trp Ser Gly Trp Gly Ser Pro Tyr Ala Phe Asp Tyr
1               5                   10
```

<210> SEQ ID NO 82
<211> LENGTH: 13
<212> TYPE: PRT
<213> ORGANISM: Artificial Sequence
<220> FEATURE:
<223> OTHER INFORMATION: CDR3 of CD137xPD-L1 antibody

<400> SEQUENCE: 82

```
Asp Ser Gly Tyr Asp Ser Ala Tyr Leu Ala Phe Asp Tyr
1               5                   10
```

<210> SEQ ID NO 83
<211> LENGTH: 19
<212> TYPE: PRT
<213> ORGANISM: Artificial Sequence
<220> FEATURE:
<223> OTHER INFORMATION: CDR3 of CD137xPD-L1 antibody

<400> SEQUENCE: 83

```
Gly Ala Thr Tyr Tyr Tyr Gly Ser Gly Thr Tyr Tyr Ser Ile Asn Trp
1               5                   10                  15

Phe Asp Pro
```

<210> SEQ ID NO 84
<211> LENGTH: 14
<212> TYPE: PRT
<213> ORGANISM: Artificial Sequence
<220> FEATURE:
<223> OTHER INFORMATION: CDR3 of CD137xPD-L1 antibody

<400> SEQUENCE: 84

```
Phe Tyr Thr Gly Ile Val Gly Ala Thr Gly Ala Phe Asp Val
1               5                   10
```

<210> SEQ ID NO 85
<211> LENGTH: 12
<212> TYPE: PRT
<213> ORGANISM: Artificial Sequence
<220> FEATURE:
<223> OTHER INFORMATION: CDR3 of CD137xPD-L1 antibody

<400> SEQUENCE: 85

```
Asp Trp Ala Ser Val Met Arg Gly Asp Leu Asp Tyr
1               5                   10
```

<210> SEQ ID NO 86
<211> LENGTH: 9
<212> TYPE: PRT
<213> ORGANISM: Artificial Sequence
<220> FEATURE:
<223> OTHER INFORMATION: CDR3 of CD137xPD-L1 antibody

<400> SEQUENCE: 86

Gly Trp Asn Ala Phe Trp Phe Asp Tyr
1               5

<210> SEQ ID NO 87
<211> LENGTH: 11
<212> TYPE: PRT
<213> ORGANISM: Artificial Sequence
<220> FEATURE:
<223> OTHER INFORMATION: CDR3 of CD137xPD-L1 antibody

<400> SEQUENCE: 87

Thr Glu Tyr Ser Tyr Gly Tyr Val Phe Tyr Tyr
1               5                   10

<210> SEQ ID NO 88
<211> LENGTH: 17
<212> TYPE: PRT
<213> ORGANISM: Artificial Sequence
<220> FEATURE:
<223> OTHER INFORMATION: CDR3 of CD137xPD-L1 antibody

<400> SEQUENCE: 88

Glu Gly Phe Asp Asn Tyr Gly Ser Gly Ile Arg Gly Asn Trp Phe Asp
1               5                   10                  15

Pro

<210> SEQ ID NO 89
<211> LENGTH: 13
<212> TYPE: PRT
<213> ORGANISM: Artificial Sequence
<220> FEATURE:
<223> OTHER INFORMATION: CDR3 of CD137xPD-L1 antibody

<400> SEQUENCE: 89

Glu Gly Val Gly Val Ile Arg Gly Asn Trp Phe Asp Pro
1               5                   10

<210> SEQ ID NO 90
<211> LENGTH: 15
<212> TYPE: PRT
<213> ORGANISM: Artificial Sequence
<220> FEATURE:
<223> OTHER INFORMATION: CDR3 of CD137xPD-L1 antibody

<400> SEQUENCE: 90

Asp Leu Arg Leu Gly Ala Ser Tyr Tyr Tyr Ser Tyr Met Asp Val
1               5                   10                  15

<210> SEQ ID NO 91
<211> LENGTH: 11
<212> TYPE: PRT
<213> ORGANISM: Artificial Sequence
<220> FEATURE:
<223> OTHER INFORMATION: CDR3 of CD137xPD-L1 antibody

<400> SEQUENCE: 91

Thr Leu Trp Gly Ser Asp Asp Val Phe Asp Val

-continued

```
1               5                   10

<210> SEQ ID NO 92
<211> LENGTH: 14
<212> TYPE: PRT
<213> ORGANISM: Artificial Sequence
<220> FEATURE:
<223> OTHER INFORMATION: CDR3 of CD137xPD-L1 antibody

<400> SEQUENCE: 92

Leu Gly Gly Tyr Ser Gly Tyr Ala Glu Asp Phe Val Asp Phe
1               5                   10

<210> SEQ ID NO 93
<211> LENGTH: 14
<212> TYPE: PRT
<213> ORGANISM: Artificial Sequence
<220> FEATURE:
<223> OTHER INFORMATION: CDR3 of CD137xPD-L1 antibody

<400> SEQUENCE: 93

His Ala Gly Phe Ile Ile Thr Ser Gln Asn Ile Asp Asp Tyr
1               5                   10

<210> SEQ ID NO 94
<211> LENGTH: 14
<212> TYPE: PRT
<213> ORGANISM: Artificial Sequence
<220> FEATURE:
<223> OTHER INFORMATION: CDR3 of CD137xPD-L1 antibody

<400> SEQUENCE: 94

His Gln Gly Tyr Ser Phe Ser Gly Ser His Ile Asp Asp Tyr
1               5                   10

<210> SEQ ID NO 95
<211> LENGTH: 15
<212> TYPE: PRT
<213> ORGANISM: Artificial Sequence
<220> FEATURE:
<223> OTHER INFORMATION: CDR3 of CD137xPD-L1 antibody

<400> SEQUENCE: 95

Gly Ser Gly His Arg Phe Tyr Gln Tyr Arg Ser Gly Phe Asp Tyr
1               5                   10                  15

<210> SEQ ID NO 96
<211> LENGTH: 12
<212> TYPE: PRT
<213> ORGANISM: Artificial Sequence
<220> FEATURE:
<223> OTHER INFORMATION: CDR3 of CD137xPD-L1 antibody

<400> SEQUENCE: 96

Gly Arg Trp Trp Phe Thr Tyr Asp Gly Phe Asp Tyr
1               5                   10

<210> SEQ ID NO 97
<211> LENGTH: 15
<212> TYPE: PRT
<213> ORGANISM: Artificial Sequence
<220> FEATURE:
<223> OTHER INFORMATION: CDR3 of CD137xPD-L1 antibody

<400> SEQUENCE: 97

Gly Arg Gly Trp Arg Asn Tyr Phe Gln Trp Trp Gly Phe Asp Tyr
1               5                   10                  15
```

-continued

```
<210> SEQ ID NO 98
<211> LENGTH: 14
<212> TYPE: PRT
<213> ORGANISM: Artificial Sequence
<220> FEATURE:
<223> OTHER INFORMATION: CDR3 of CD137xPD-L1 antibody

<400> SEQUENCE: 98

Glu Gly Ile Ile Gly Phe Leu Gly Gly Asn Trp Phe Asp Pro
1               5                   10

<210> SEQ ID NO 99
<211> LENGTH: 12
<212> TYPE: PRT
<213> ORGANISM: Artificial Sequence
<220> FEATURE:
<223> OTHER INFORMATION: CDR3 of CD137xPD-L1 antibody

<400> SEQUENCE: 99

Asp Trp Gly Leu Val Ala Ile Gly Tyr Phe Asp Tyr
1               5                   10

<210> SEQ ID NO 100
<211> LENGTH: 15
<212> TYPE: PRT
<213> ORGANISM: Artificial Sequence
<220> FEATURE:
<223> OTHER INFORMATION: CDR3 of CD137xPD-L1 antibody

<400> SEQUENCE: 100

Asp Arg Trp Ser Trp Tyr Gln Gly Arg Gly Phe Gly Phe Asp Tyr
1               5                   10                  15

<210> SEQ ID NO 101
<211> LENGTH: 214
<212> TYPE: PRT
<213> ORGANISM: Artificial Sequence
<220> FEATURE:
<223> OTHER INFORMATION: Common IgG light chain

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 102
<211> LENGTH: 321
<212> TYPE: DNA
<213> ORGANISM: Artificial Sequence
<220> FEATURE:
<223> OTHER INFORMATION: Common light chain variable domain DNA sequence
<220> FEATURE:
<221> NAME/KEY: CDS
<222> LOCATION: (1)..(321)

<400> SEQUENCE: 102 gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac      96
Asp Arg Val Thr Ile Thr Cys Arg Ala Ser Gln Ser Ile Ser Ser Tyr
                20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
            35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
        50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa                         321
Thr Phe Gly Gln Gly Thr Lys Val Glu Ile Lys
            100                 105

<210> SEQ ID NO 103
<211> LENGTH: 107
<212> TYPE: PRT
<213> ORGANISM: Artificial Sequence
<220> FEATURE:
<223> OTHER INFORMATION: Synthetic Construct

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105
```

<210> SEQ ID NO 104
<211> LENGTH: 324
<212> TYPE: DNA
<213> ORGANISM: Artificial Sequence
<220> FEATURE:
<223> OTHER INFORMATION: Common light chain constant region DNA sequence
<220> FEATURE:
<221> NAME/KEY: CDS
<222> LOCATION: (1)..(324)

<400> SEQUENCE: 104

```
cga act gtg gct gca cca tct gtc ttc atc ttc ccg cca tct gat gag    48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc    96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa   144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc   192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag   240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg   288
Lys His Lys Val Tyr Ala Cys Glu Val Thr His Gln Gly Leu Ser Ser
                85                  90                  95 ccc gtc aca aag agc ttc aac agg gga gag tgt tag                   324
Pro Val Thr Lys Ser Phe Asn Arg Gly Glu Cys
            100                 105
```

<210> SEQ ID NO 105
<211> LENGTH: 107
<212> TYPE: PRT
<213> ORGANISM: Artificial Sequence
<220> FEATURE:
<223> OTHER INFORMATION: Synthetic Construct

<400> SEQUENCE: 105

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 106
<211> LENGTH: 108
<212> TYPE: PRT
<213> ORGANISM: Artificial Sequence
<220> FEATURE:
<223> OTHER INFORMATION: IGKV1-39/jk5 common light chain variable domain

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 107
<211> LENGTH: 95
<212> TYPE: PRT
<213> ORGANISM: Artificial Sequence
<220> FEATURE:
<223> OTHER INFORMATION: region IGKV1-39A

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 108
<211> LENGTH: 294
<212> TYPE: DNA
<213> ORGANISM: Artificial Sequence
<220> FEATURE:
<223> OTHER INFORMATION: IgG heavy chain CH1 region
<220> FEATURE:
<221> NAME/KEY: CDS
<222> LOCATION: (1)..(294)

<400> SEQUENCE: 108 gct agc acc aag ggc cca tcg gtc ttc ccc ctg gca ccc tcc tcc aag    48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac    96
Ser Thr Ser Gly Gly Thr Ala Ala Leu Gly Cys Leu Val Lys Asp Tyr
            20                  25                  30
```

```
ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
 50                  55                  60 ctc agc agc gtc gtg acc gtg ccc tcc agc agc ttg ggc acc cag acc      240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                85                  90                  95 aga gtt                                                              294
Arg Val <210> SEQ ID NO 109
<211> LENGTH: 98
<212> TYPE: PRT
<213> ORGANISM: Artificial Sequence
<220> FEATURE:
<223> OTHER INFORMATION: Synthetic Construct

<400> SEQUENCE: 109

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 110
<211> LENGTH: 45
<212> TYPE: DNA
<213> ORGANISM: Artificial Sequence
<220> FEATURE:
<223> OTHER INFORMATION: IgG heavy chain hinge region
<220> FEATURE:
<221> NAME/KEY: CDS
<222> LOCATION: (1)..(45)

<400> SEQUENCE: 110 gag ccc aaa tct tgt gac aaa act cac aca tgc cca ccg tgc cca         45
Glu Pro Lys Ser Cys Asp Lys Thr His Thr Cys Pro Pro Cys Pro
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthetic Construct

<400> SEQUENCE: 111

Glu Pro Lys Ser Cys Asp Lys Thr His Thr Cys Pro Pro Cys Pro
1               5                   10                  15
```

<210> SEQ ID NO 112
<211> LENGTH: 330
<212> TYPE: DNA
<213> ORGANISM: Artificial Sequence
<220> FEATURE:
<223> OTHER INFORMATION: IgG heavy chain CH2 region
<220> FEATURE:
<221> NAME/KEY: CDS
<222> LOCATION: (1)..(330)

<400> SEQUENCE: 112

```
gca cct gaa ctc ctg ggg gga ccg tca gtc ttc ctc ttc ccc cca aaa      48
Ala Pro Glu Leu Leu Gly Gly Pro Ser Val Phe Leu Phe Pro Pro Lys
1               5                   10                  15 ccc aag gac acc ctc atg atc tcc cgg acc cct gag gtc aca tgc gtg      96
Pro Lys Asp Thr Leu Met Ile Ser Arg Thr Pro Glu Val Thr Cys Val
                20                  25                  30 gtg gtg gac gtg agc cac gaa gac cct gag gtc aag ttc aac tgg tac     144
Val Val Asp Val Ser His Glu Asp Pro Glu Val Lys Phe Asn Trp Tyr
            35                  40                  45 gtg gac ggc gtg gag gtg cat aat gcc aag aca aag ccg cgg gag gag     192
Val Asp Gly Val Glu Val His Asn Ala Lys Thr Lys Pro Arg Glu Glu
50                  55                  60 cag tac aac agc acg tac cgt gtg gtc agc gtc ctc acc gtc ctg cac     240
Gln Tyr Asn Ser Thr Tyr Arg Val Val Ser Val Leu Thr Val Leu His
65                  70                  75                  80 cag gac tgg ctg aat ggc aag gag tac aag tgc aag gtc tcc aac aaa     288
Gln Asp Trp Leu Asn Gly Lys Glu Tyr Lys Cys Lys Val Ser Asn Lys
                85                  90                  95 gcc ctc cca gcc ccc atc gag aaa acc atc tcc aaa gcc aaa             330
Ala Leu Pro Ala Pro Ile Glu Lys Thr Ile Ser Lys Ala Lys
                100                 105                 110
```

<210> SEQ ID NO 113
<211> LENGTH: 110
<212> TYPE: PRT
<213> ORGANISM: Artificial Sequence
<220> FEATURE:
<223> OTHER INFORMATION: Synthetic Construct

<400> SEQUENCE: 113

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110
```

<210> SEQ ID NO 114
<211> LENGTH: 330
<212> TYPE: DNA
<213> ORGANISM: Artificial Sequence
<220> FEATURE:
<223> OTHER INFORMATION: IgG heavy chain CH3 domain containing L235G and

```
                    G236R silencing substitutions
<220> FEATURE:
<221> NAME/KEY: CDS
<222> LOCATION: (1)..(330)

<400> SEQUENCE: 114 gca cct gaa ctc ggc agg gga ccg tca gtc ttc ctc ttc ccc cca aaa        48
Ala Pro Glu Leu Gly Arg Gly Pro Ser Val Phe Leu Phe Pro Pro Lys
1               5                   10                  15 ccc aag gac acc ctc atg atc tcc cgg acc cct gag gtc aca tgc gtg        96
Pro Lys Asp Thr Leu Met Ile Ser Arg Thr Pro Glu Val Thr Cys Val
                20                  25                  30 gtg gtg gac gtg agc cac gaa gac cct gag gtc aag ttc aac tgg tac       144
Val Val Asp Val Ser His Glu Asp Pro Glu Val Lys Phe Asn Trp Tyr
            35                  40                  45 gtg gac ggc gtg gag gtg cat aat gcc aag aca aag ccg cgg gag gag       192
Val Asp Gly Val Glu Val His Asn Ala Lys Thr Lys Pro Arg Glu Glu
    50                  55                  60 cag tac aac agc acg tac cgt gtg gtc agc gtc ctc acc gtc ctg cac       240
Gln Tyr Asn Ser Thr Tyr Arg Val Val Ser Val Leu Thr Val Leu His
65                  70                  75                  80 cag gac tgg ctg aat ggc aag gag tac aag tgc aag gtc tcc aac aaa       288
Gln Asp Trp Leu Asn Gly Lys Glu Tyr Lys Cys Lys Val Ser Asn Lys
                85                  90                  95 gcc ctc cca gcc ccc atc gag aaa acc atc tcc aaa gcc aaa               330
Ala Leu Pro Ala Pro Ile Glu Lys Thr Ile Ser Lys Ala Lys
                100                 105                 110

<210> SEQ ID NO 115
<211> LENGTH: 110
<212> TYPE: PRT
<213> ORGANISM: Artificial Sequence
<220> FEATURE:
<223> OTHER INFORMATION: Synthetic Construct

<400> SEQUENCE: 115

Ala Pro Glu Leu Gly Arg Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 116
<211> LENGTH: 321
<212> TYPE: DNA
<213> ORGANISM: Artificial Sequence
<220> FEATURE:
<223> OTHER INFORMATION: IgG heavy chain CH3 domain containing
      substitutions L351K and T366K
<220> FEATURE:
<221> NAME/KEY: CDS
<222> LOCATION: (1)..(321)

<400> SEQUENCE: 116
```

```
ggg cag ccc cga gaa cca cag gtg tac acc aag ccc cca tcc cgg gag      48
Gly Gln Pro Arg Glu Pro Gln Val Tyr Thr Lys Pro Pro Ser Arg Glu
1               5                   10                  15 gag atg acc aag aac cag gtc agc ctg aag tgc ctg gtc aaa ggc ttc      96
Glu Met Thr Lys Asn Gln Val Ser Leu Lys Cys Leu Val Lys Gly Phe
                20                  25                  30 tat ccc agc gac atc gcc gtg gag tgg gag agc aat ggg cag ccg gag     144
Tyr Pro Ser Asp Ile Ala Val Glu Trp Glu Ser Asn Gly Gln Pro Glu
            35                  40                  45 aac aac tac aag acc acg cct ccc gtg ctg gac tcc gac ggc tcc ttc     192
Asn Asn Tyr Lys Thr Thr Pro Pro Val Leu Asp Ser Asp Gly Ser Phe
        50                  55                  60 ttc ctc tat agc aag ctc acc gtg gac aag agc agg tgg cag cag ggg     240
Phe Leu Tyr Ser Lys Leu Thr Val Asp Lys Ser Arg Trp Gln Gln Gly
65                  70                  75                  80 aac gtc ttc tca tgc tcc gtg atg cat gag gct ctg cac aac cac tac     288
Asn Val Phe Ser Cys Ser Val Met His Glu Ala Leu His Asn His Tyr
                85                  90                  95 acg cag aag agc ctc tcc ctg tct ccg ggt tga                         321
Thr Gln Lys Ser Leu Ser Leu Ser Pro Gly
                100                 105
```

<210> SEQ ID NO 117
<211> LENGTH: 106
<212> TYPE: PRT
<213> ORGANISM: Artificial Sequence
<220> FEATURE:
<223> OTHER INFORMATION: Synthetic Construct

<400> SEQUENCE: 117

```
Gly Gln Pro Arg Glu Pro Gln Val Tyr Thr Lys Pro Pro Ser Arg Glu
1               5                   10                  15

Glu Met Thr Lys Asn Gln Val Ser Leu Lys Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
                100                 105
```

<210> SEQ ID NO 118
<211> LENGTH: 321
<212> TYPE: DNA
<213> ORGANISM: Artificial Sequence
<220> FEATURE:
<223> OTHER INFORMATION: IgG heavy chain CH3 domain containing
      substitutions L351D and L368E
<220> FEATURE:
<221> NAME/KEY: CDS
<222> LOCATION: (1)..(321)

<400> SEQUENCE: 118

```
ggg cag ccc cga gaa cca cag gtg tac acc gac ccc cca tcc cgg gag      48
Gly Gln Pro Arg Glu Pro Gln Val Tyr Thr Asp Pro Pro Ser Arg Glu
1               5                   10                  15 gag atg acc aag aac cag gtc agc ctg acc tgc gag gtc aaa ggc ttc      96
```

```
Glu Met Thr Lys Asn Gln Val Ser Leu Thr Cys Glu Val Lys Gly Phe
            20                  25                  30 tat ccc agc gac atc gcc gtg gag tgg gag agc aat ggg cag ccg gag        144
Tyr Pro Ser Asp Ile Ala Val Glu Trp Glu Ser Asn Gly Gln Pro Glu
            35                  40                  45 aac aac tac aag acc acg cct ccc gtg ctg gac tcc gac ggc tcc ttc        192
Asn Asn Tyr Lys Thr Thr Pro Pro Val Leu Asp Ser Asp Gly Ser Phe
 50                  55                  60 ttc ctc tat agc aag ctc acc gtg gac aag agc agg tgg cag cag ggg        240
Phe Leu Tyr Ser Lys Leu Thr Val Asp Lys Ser Arg Trp Gln Gln Gly
 65                  70                  75                  80 aac gtc ttc tca tgc tcc gtg atg cat gag gct ctg cac aac cac tac        288
Asn Val Phe Ser Cys Ser Val Met His Glu Ala Leu His Asn His Tyr
                85                  90                  95 acg cag aag agc ctc tcc ctg tct ccg ggt tga                            321
Thr Gln Lys Ser Leu Ser Leu Ser Pro Gly
                100                 105
```

<210> SEQ ID NO 119
<211> LENGTH: 106
<212> TYPE: PRT
<213> ORGANISM: Artificial Sequence
<220> FEATURE:
<223> OTHER INFORMATION: Synthetic Construct

<400> SEQUENCE: 119

```
Gly Gln Pro Arg Glu Pro Gln Val Tyr Thr Asp Pro Pro Ser Arg Glu
1               5                   10                  15

Glu Met Thr Lys Asn Gln Val Ser Leu Thr Cys Glu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
                100                 105
```

<210> SEQ ID NO 120
<211> LENGTH: 123
<212> TYPE: PRT
<213> ORGANISM: Artificial Sequence
<220> FEATURE:
<223> OTHER INFORMATION: MF6737

<400> SEQUENCE: 120

```
Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Ser Phe Thr Asn Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80
```

```
Leu Gln Trp His Thr Leu Lys Ala Ser Asp Thr Ala Met Tyr Tyr Cys
                85                  90                  95

Ala Arg His Gln Gly Tyr Ser Phe Ser Gly Ser His Ile Asp Asp Tyr
            100                 105                 110

Trp Gly Gln Gly Thr Leu Val Thr Val Ser Ser
        115                 120

<210> SEQ ID NO 121
<211> LENGTH: 123
<212> TYPE: PRT
<213> ORGANISM: Artificial Sequence
<220> FEATURE:
<223> OTHER INFORMATION: MF6744

<400> SEQUENCE: 121

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Phe Pro Asp Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Pro Ser Asp Thr Ala Met Tyr Tyr Cys
                85                  90                  95

Val Arg Leu Gly Gly Tyr Ser Gly Tyr Ala Glu Asp Phe Val Asp Phe
            100                 105                 110

Trp Gly Gln Gly Thr Leu Val Thr Val Ser Ser
        115                 120

<210> SEQ ID NO 122
<211> LENGTH: 123
<212> TYPE: PRT
<213> ORGANISM: Artificial Sequence
<220> FEATURE:
<223> OTHER INFORMATION: MF6749

<400> SEQUENCE: 122

Glu Val Gln Leu Val Gln Ser Gly Ala Glu Val Arg Lys Pro Gly Glu
1               5                   10                  15

Ser Leu Lys Ile Ser Cys Lys Gly Ser Gly Tyr Ser Phe Thr Thr Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Val Tyr
65                  70                  75                  80

Leu Gln Trp Ser Ser Leu Lys Ala Ser Asp Thr Ala Met Tyr Tyr Cys
                85                  90                  95

Ala Arg His Ala Gly Phe Ile Ile Thr Ser Gln Asn Ile Asp Asp Tyr
            100                 105                 110

Trp Gly Gln Gly Thr Leu Val Thr Val Ser Ser
        115                 120

<210> SEQ ID NO 123
```

-continued

```
<211> LENGTH: 126
<212> TYPE: PRT
<213> ORGANISM: Artificial Sequence
<220> FEATURE:
<223> OTHER INFORMATION: MF6754

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Ser Glu Leu
            20                  25                  30

Ser Ile His Trp Val Arg Gln Ala Pro Gly Lys Gly Val Glu Trp Met
        35                  40                  45

Gly Gly Phe Tyr Pro Glu Asp Val Glu Pro Ile Tyr Ala Arg Lys Phe
    50                  55                  60

Gln Gly Arg Val Thr Met Thr Glu Asp Thr Ser Thr Asp Thr Ala Tyr
65                  70                  75                  80

Met Glu Leu Asn Ser Leu Arg Ser Glu Asp Thr Ala Val Tyr Tyr Cys
                85                  90                  95

Ala Ala Glu Gly Phe Asp Asn Tyr Gly Ser Gly Ile Arg Gly Asn Trp
            100                 105                 110

Phe Asp Pro Trp Gly Gln Gly Thr Leu Val Thr Val Ser Ser
        115                 120                 125

<210> SEQ ID NO 124
<211> LENGTH: 122
<212> TYPE: PRT
<213> ORGANISM: Artificial Sequence
<220> FEATURE:
<223> OTHER INFORMATION: MF6763

<400> SEQUENCE: 124

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ser Pro Gly Lys Gly Leu Glu Trp Met
        35                  40                  45

Gly Ser Phe Tyr Pro Glu Asp Gly Glu Thr Ile Tyr Ala Gln Lys Phe
    50                  55                  60

Gln Gly Arg Ile Thr Met Thr Glu Asp Thr Ser Ala Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Gly Val Gly Val Ile Arg Gly Asn Trp Phe Asp Pro Trp
            100                 105                 110

Gly Gln Gly Thr Leu Val Thr Val Ser Ser
        115                 120

<210> SEQ ID NO 125
<211> LENGTH: 121
<212> TYPE: PRT
<213> ORGANISM: Artificial Sequence
<220> FEATURE:
<223> OTHER INFORMATION: MF6783

<400> SEQUENCE: 125

Gln Val Gln Leu Val Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Asn Phe
            20                  25                  30

Ala Met Asn Trp Val Arg Arg Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Trp Gly Val Ile Gly Gly His Tyr Met Asp Val Trp Gly
            100                 105                 110

Lys Gly Thr Thr Val Thr Val Ser Ser
            115                 120
```

<210> SEQ ID NO 126
<211> LENGTH: 124
<212> TYPE: PRT
<213> ORGANISM: Artificial Sequence
<220> FEATURE:
<223> OTHER INFORMATION: MF6785

<400> SEQUENCE: 126

```
Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Lys Leu
            20                  25                  30

Ser Met His Trp Val Arg Gln Ala Pro Gly Lys Gly Leu Glu Trp Met
        35                  40                  45

Gly Gly Phe Glu Pro Glu Asp Gly Glu Thr Ile Asn Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Arg Leu Gly Ala Ser Tyr Tyr Ser Tyr Met Asp
            100                 105                 110

Val Trp Gly Arg Gly Thr Met Val Thr Val Ser Ser
            115                 120
```

<210> SEQ ID NO 127
<211> LENGTH: 121
<212> TYPE: PRT
<213> ORGANISM: Artificial Sequence
<220> FEATURE:
<223> OTHER INFORMATION: MF6788

<400> SEQUENCE: 127

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Asp Phe
    50                  55                  60

Thr Gly Arg Phe Val Phe Ser Leu Asp Thr Ser Gly Asn Thr Ala Tyr
65                  70                  75                  80
```

Leu Gln Ile Ser Ser Leu Lys Ala Glu Asp Thr Ala Val Tyr Tyr Cys
                85                  90                  95

Ala Arg Asp Trp Gly Leu Val Ala Ile Gly Tyr Phe Asp Tyr Trp Gly
            100                 105                 110

Gln Gly Thr Leu Val Thr Val Ser Ser
        115                 120

<210> SEQ ID NO 128
<211> LENGTH: 123
<212> TYPE: PRT
<213> ORGANISM: Artificial Sequence
<220> FEATURE:
<223> OTHER INFORMATION: MF6795

<400> SEQUENCE: 128

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Phe Tyr Thr Gly Ile Val Gly Ala Thr Gly Ala Phe Asp Val
            100                 105                 110

Trp Gly Gln Gly Thr Thr Val Thr Val Ser Ser
        115                 120

<210> SEQ ID NO 129
<211> LENGTH: 124
<212> TYPE: PRT
<213> ORGANISM: Artificial Sequence
<220> FEATURE:
<223> OTHER INFORMATION: MF6797

<400> SEQUENCE: 129

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Thr
            20                  25                  30

Gly Val Gly Val Asn Trp Ile Arg Gln Pro Pro Gly Glu Ala Leu Glu
        35                  40                  45

Trp Leu Ala Leu Ile Tyr Trp Asn Asp Asp Thr Tyr Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Glu Gly Ile Ile Gly Phe Leu Gly Gly Asn Trp Phe Asp
            100                 105                 110

Pro Trp Gly Gln Gly Thr Leu Val Thr Val Ser Ser
        115                 120

<210> SEQ ID NO 130
<211> LENGTH: 122
<212> TYPE: PRT
<213> ORGANISM: Artificial Sequence
<220> FEATURE:
<223> OTHER INFORMATION: MF6798

<400> SEQUENCE: 130

```
Gln Val Gln Leu Val Gln Ser Gly Ser Glu Leu Lys Lys Pro Gly Ala
1               5                   10                  15

Ser Val Lys Val Ser Cys Arg Ala Ser Gly Tyr Thr Phe Thr Asn Phe
            20                  25                  30

Ala Met Thr Trp Val Arg Gln Ala Pro Gly Gln Gly Pro Glu Tyr Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Trp Ala Ser Val Met Val Arg Gly Asp Leu Asp Tyr Trp
            100                 105                 110

Gly Gln Gly Thr Leu Val Thr Val Ser Ser
        115                 120
```

<210> SEQ ID NO 131
<211> LENGTH: 120
<212> TYPE: PRT
<213> ORGANISM: Artificial Sequence
<220> FEATURE:
<223> OTHER INFORMATION: MF6805

<400> SEQUENCE: 131

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Ala Met Asn Trp Val Arg Gln Ala Pro Gly Gln Gly Leu Glu Trp Met
        35                  40                  45

Gly Trp Ile His Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Gln Ala Glu Asp Thr Ala Val Tyr Tyr Cys
                85                  90                  95

Val Arg Thr Glu Tyr Ser Tyr Gly Tyr Val Phe Tyr Tyr Trp Gly Gln
            100                 105                 110

Gly Thr Leu Val Thr Val Ser Ser
        115                 120
```

<210> SEQ ID NO 132
<211> LENGTH: 128
<212> TYPE: PRT
<213> ORGANISM: Artificial Sequence
<220> FEATURE:
<223> OTHER INFORMATION: MF6808

<400> SEQUENCE: 132

```
Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Asp
            20                  25                  30

Ala Ile Ser Trp Val Arg Gln Ala Pro Gly Gln Gly Leu Glu Trp Met
        35                  40                  45

Gly Gly Met Ile Pro Ile Leu Gly Thr Ala Asn Tyr Ala Gln Lys Phe
 50                  55                  60

Gln Gly Arg Val Thr Ile Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Gly Ala Thr Tyr Tyr Tyr Gly Ser Gly Thr Tyr Tyr Ser Ile
            100                 105                 110

Asn Trp Phe Asp Pro Trp Gly Gln Gly Thr Leu Val Thr Val Ser Ser
        115                 120                 125

<210> SEQ ID NO 133
<211> LENGTH: 121
<212> TYPE: PRT
<213> ORGANISM: Artificial Sequence
<220> FEATURE:
<223> OTHER INFORMATION: MF6825

<400> SEQUENCE: 133

Gln Ile Thr Leu Lys Glu Ser Gly Pro Thr Leu Val Lys Pro Thr Gln
1               5                   10                  15

Thr Leu Thr Leu Ser Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Leu Ile Tyr Trp Asn Asp Asp Lys Tyr Phe Ser Pro Ser
 50                  55                  60

Leu Lys Ser Arg Leu Thr Ile Thr Lys Asp Thr Ser Lys Asn Gln Val
65                  70                  75                  80

Val Leu Thr Leu Thr Asn Met Asp Pro Val Asp Thr Ala Thr Tyr Tyr
                85                  90                  95

Cys Ala His Thr Leu Trp Gly Ser Asp Asp Val Phe Asp Val Trp Gly
            100                 105                 110

Gln Gly Thr Met Val Thr Val Ser Ser
        115                 120

<210> SEQ ID NO 134
<211> LENGTH: 118
<212> TYPE: PRT
<213> ORGANISM: Artificial Sequence
<220> FEATURE:
<223> OTHER INFORMATION: MF6832

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
```

-continued

```
                65                  70                  75                  80
Leu Gln Met Asn Ser Leu Arg Ala Glu Asp Thr Ala Val Tyr Tyr Cys
                85                  90                  95

Ala Arg Gly Trp Asn Ala Phe Trp Phe Asp Tyr Trp Gly Gln Gly Thr
            100                 105                 110

Leu Val Thr Val Ser Ser
        115

<210> SEQ ID NO 135
<211> LENGTH: 122
<212> TYPE: PRT
<213> ORGANISM: Artificial Sequence
<220> FEATURE:
<223> OTHER INFORMATION: MF6847

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Gly Tyr Asp Ser Ala Tyr Leu Ala Phe Asp Tyr Trp
            100                 105                 110

Gly Gln Gly Thr Leu Val Thr Val Ser Ser
        115                 120

<210> SEQ ID NO 136
<211> LENGTH: 122
<212> TYPE: PRT
<213> ORGANISM: Artificial Sequence
<220> FEATURE:
<223> OTHER INFORMATION: MF6848

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Trp Ser Gly Trp Gly Ser Pro Tyr Ala Phe Asp Tyr Trp
            100                 105                 110

Gly Gln Gly Thr Leu Val Thr Val Ser Ser
        115                 120
```

<210> SEQ ID NO 137
<211> LENGTH: 124
<212> TYPE: PRT
<213> ORGANISM: Artificial Sequence
<220> FEATURE:
<223> OTHER INFORMATION: MF6856

<400> SEQUENCE: 137

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Ser Gly Ser Trp Asp Tyr Gly Ser Ser Ala Phe Asp
            100                 105                 110

Tyr Trp Gly Gln Gly Thr Leu Val Thr Val Ser Ser
        115                 120
```

<210> SEQ ID NO 138
<211> LENGTH: 124
<212> TYPE: PRT
<213> ORGANISM: Artificial Sequence
<220> FEATURE:
<223> OTHER INFORMATION: MF6860

<400> SEQUENCE: 138

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Lys Gly Leu Leu Trp Gly Lys Thr Asp Tyr Tyr Ser Gly Phe Asp
            100                 105                 110

Tyr Trp Gly Gln Gly Thr Leu Val Thr Val Ser Ser
        115                 120
```

<210> SEQ ID NO 139
<211> LENGTH: 121
<212> TYPE: PRT
<213> ORGANISM: Artificial Sequence
<220> FEATURE:
<223> OTHER INFORMATION: MF6861

<400> SEQUENCE: 139

```
Gln Val Gln Leu Val Gln Ser Gly Ala Glu Val Lys Lys Pro Gly Ala
```

-continued

```
                1               5                   10                  15
Ser Val Lys Val Ser Cys Lys Ala Ser Gly Tyr Thr Phe Thr Ser Tyr
                    20                  25                  30

Gly Ile Ser Trp Val Arg Gln Ala Pro Gly Gln Gly Leu Glu Trp Met
                    35                  40                  45

Gly Trp Ile Ser Ala Tyr Asn Gly Asn Thr Asn Tyr Ala Gln Lys Leu
                    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                    85                  90                  95

Ala Arg Asp Ser Asp Gly Tyr Gly Pro Lys Ala Phe Asp Tyr Trp Gly
                    100                 105                 110

Gln Gly Thr Leu Val Thr Val Ser Ser
                    115                 120

<210> SEQ ID NO 140
<211> LENGTH: 124
<212> TYPE: PRT
<213> ORGANISM: Artificial Sequence
<220> FEATURE:
<223> OTHER INFORMATION: MF6862

<400> SEQUENCE: 140

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                    20                  25                  30

Gly Met His Trp Val Arg Gln Ala Pro Gly Lys Gly Leu Glu Trp Val
                    35                  40                  45

Ala Val Ile Ser Tyr Asp Gly Ser Asn Lys Tyr Tyr Ala Asp Ser Val
                    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Gly Arg Gly Trp Arg Asn Tyr Phe Gln Trp Trp Gly Phe Asp
                    100                 105                 110

Tyr Trp Gly Gln Gly Thr Leu Val Thr Val Ser Ser
                    115                 120

<210> SEQ ID NO 141
<211> LENGTH: 124
<212> TYPE: PRT
<213> ORGANISM: Artificial Sequence
<220> FEATURE:
<223> OTHER INFORMATION: MF6870

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                    20                  25                  30

Ala Met Ser Trp Val Arg Gln Ala Pro Gly Lys Gly Leu Glu Trp Val
                    35                  40                  45

Ser Ala Ile Ser Gly Ser Gly Gly Ser Thr Tyr Tyr Ala Asp Ser Val
                    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly His Arg Phe Tyr Gln Tyr Arg Ser Gly Phe Asp
            100                 105                 110

Tyr Trp Gly Gln Gly Thr Leu Val Thr Val Ser Ser
            115                 120

<210> SEQ ID NO 142
<211> LENGTH: 124
<212> TYPE: PRT
<213> ORGANISM: Artificial Sequence
<220> FEATURE:
<223> OTHER INFORMATION: MF6873

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg Trp Ser Trp Tyr Gln Gly Arg Gly Phe Gly Phe Asp
            100                 105                 110

Tyr Trp Gly Gln Gly Thr Leu Val Thr Val Ser Ser
            115                 120

<210> SEQ ID NO 143
<211> LENGTH: 121
<212> TYPE: PRT
<213> ORGANISM: Artificial Sequence
<220> FEATURE:
<223> OTHER INFORMATION: MF6875

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Trp Trp Phe Thr Tyr Asp Gly Phe Asp Tyr Trp Gly
            100                 105                 110

Gln Gly Thr Leu Val Thr Val Ser Ser
            115                 120

<210> SEQ ID NO 144
<211> LENGTH: 124
<212> TYPE: PRT
<213> ORGANISM: Artificial Sequence
<220> FEATURE:
<223> OTHER INFORMATION: MF5359

<400> SEQUENCE: 144

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Asn Thr Tyr
            20                  25                  30

Ser Ile Thr Trp Val Arg Gln Ala Pro Gly Gln Gly Leu Glu Trp Met
        35                  40                  45

Gly Ser Ile Val Pro Ile Phe Gly Thr Ile Asn Asn Ala Gln Lys Phe
    50                  55                  60

Gln Gly Arg Val Thr Ile Thr Ala Asp Lys Ser Ala Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asn Thr Met Val Arg Gly Val Asp Tyr Tyr Met Asp
            100                 105                 110

Val Trp Gly Lys Gly Thr Met Val Thr Val Ser Ser
        115                 120
```

<210> SEQ ID NO 145
<211> LENGTH: 121
<212> TYPE: PRT
<213> ORGANISM: Artificial Sequence
<220> FEATURE:
<223> OTHER INFORMATION: MF5361

<400> SEQUENCE: 145

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ser Leu Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Ser Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Thr Arg Asp His Asp Phe Arg Arg Gly Arg Ser Leu Asp Val Trp Gly
            100                 105                 110

Lys Gly Thr Thr Val Thr Val Ser Ser
        115                 120
```

<210> SEQ ID NO 146
<211> LENGTH: 121
<212> TYPE: PRT
<213> ORGANISM: Artificial Sequence
<220> FEATURE:
<223> OTHER INFORMATION: MF5377

<400> SEQUENCE: 146

Glu Val Gln Leu Val Gln Ser Gly Ala Glu Val Lys Lys Pro Gly Ser
1               5                   10                  15

Ser Val Lys Val Ser Cys Lys Ala Ser Gly Ile Phe Ser Thr Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Asp Thr Pro Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Lys Asn Val Arg Gly Tyr Ser Ala Tyr Asp Leu Asp Tyr Trp Gly
            100                 105                 110

Gln Gly Thr Leu Val Thr Val Ser Ser
            115                 120

<210> SEQ ID NO 147
<211> LENGTH: 119
<212> TYPE: PRT
<213> ORGANISM: Artificial Sequence
<220> FEATURE:
<223> OTHER INFORMATION: MF5382

<400> SEQUENCE: 147

Glu Val Gln Leu Val Gln Ser Gly Ala Glu Val Lys Asn Pro Gly Ser
1               5                   10                  15

Ser Val Lys Val Ser Cys Lys Ala Thr Gly Gly Thr Phe Asn Thr Tyr
            20                  25                  30

Gly Thr Asn Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Thr Thr Ala Tyr
65                  70                  75                  80

Met Glu Val Ser Ser Leu Arg Ser Glu Asp Thr Ala Val Tyr Tyr Cys
                85                  90                  95

Ala Arg Gly Gly Ala Asp Met Gly Thr Leu Asp Tyr Trp Gly Gln Gly
            100                 105                 110

Thr Leu Val Thr Val Ser Ser
        115

<210> SEQ ID NO 148
<211> LENGTH: 120
<212> TYPE: PRT
<213> ORGANISM: Artificial Sequence
<220> FEATURE:
<223> OTHER INFORMATION: MF5424

<400> SEQUENCE: 148

Glu Val Gln Leu Val Gln Ser Gly Ala Glu Val Met Arg Pro Gly Ser
1               5                   10                  15

Ser Val Lys Val Ser Cys Lys Ala Ser Gly Ile Phe Asn Thr Tyr
            20                  25                  30

Thr Ile Ile Trp Val Arg Gln Ala Pro Gly Gln Gly Leu Glu Trp Met
            35                  40                  45

Gly Gly Ile Ile Pro Ile Phe Asp Thr Pro Asn Phe Ala Gln Lys Phe
50                  55                  60

```
Gln Gly Arg Leu Thr Ile Thr Ala Asp Lys Ser Thr Asn Thr Ala Tyr
 65                  70                  75                  80

Met Glu Leu Thr Ser Leu Arg Ser Glu Asp Thr Ala Val Tyr Tyr Cys
                 85                  90                  95

Ala Arg Glu Gly Cys Asn His Gly Val Cys Tyr Pro Tyr Trp Gly Gln
            100                 105                 110

Gly Thr Leu Val Thr Val Ser Ser
            115                 120
```

<210> SEQ ID NO 149
<211> LENGTH: 121
<212> TYPE: PRT
<213> ORGANISM: Artificial Sequence
<220> FEATURE:
<223> OTHER INFORMATION: MF5426

<400> SEQUENCE: 149

```
Gln Val Gln Leu Val Gln Ser Gly Ala Glu Val Lys Lys Pro Gly Ser
 1               5                  10                  15

Ser Val Lys Val Ser Cys Lys Ala Ser Gly Asp Thr Phe Arg Ser Tyr
                20                  25                  30

Gly Ile Thr Trp Val Arg Gln Ala Pro Gly Gln Gly Leu Glu Trp Met
            35                  40                  45

Gly Gly Ile Ile Pro Ile Phe Gly Thr Thr Asn Tyr Ala Gln Lys Phe
        50                  55                  60

Gln Gly Arg Val Thr Ile Thr Ala Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Arg Gly Tyr Ser Asn Pro His Trp Leu Asp Pro Trp Gly
            100                 105                 110

Gln Gly Thr Leu Val Thr Val Ser Ser
            115                 120
```

<210> SEQ ID NO 150
<211> LENGTH: 119
<212> TYPE: PRT
<213> ORGANISM: Artificial Sequence
<220> FEATURE:
<223> OTHER INFORMATION: MF5439

<400> SEQUENCE: 150

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Thr Tyr
                20                  25                  30

Gly Ile Leu Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Ile Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Gly Asn Tyr Tyr Glu Phe Val Tyr Trp Gly Gln Gly
            100                 105                 110

Thr Leu Val Thr Val Ser Ser
```

-continued

```
              115

<210> SEQ ID NO 151
<211> LENGTH: 121
<212> TYPE: PRT
<213> ORGANISM: Artificial Sequence
<220> FEATURE:
<223> OTHER INFORMATION: MF5442

<400> SEQUENCE: 151

Glu Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Asn Thr Tyr
            20                  25                  30

Ala Ile Asn Trp Val Arg Gln Ala Pro Gly Gln Gly Leu Glu Trp Val
        35                  40                  45

Gly Arg Ile Ile Pro Ile Phe Asp Thr Ala Asn Tyr Ala Gln Lys Phe
    50                  55                  60

Gln Gly Arg Val Thr Ile Ser Ala Asp Lys Ser Thr Thr Thr Ala Tyr
65                  70                  75                  80

Met Glu Leu Ser Ser Leu Arg Ser Glu Asp Thr Ala Val Phe Tyr Cys
                85                  90                  95

Ala Lys Asp Glu Thr Gly Tyr Ser Ser Ser Asn Phe Gln His Trp Gly
            100                 105                 110

Gln Gly Thr Leu Val Thr Val Ser Ser
        115                 120

<210> SEQ ID NO 152
<211> LENGTH: 125
<212> TYPE: PRT
<213> ORGANISM: Artificial Sequence
<220> FEATURE:
<223> OTHER INFORMATION: MF5553

<400> SEQUENCE: 152

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Ala Ile Asn Trp Val Arg Gln Ala Pro Gly Gln Gly Leu Glu Trp Met
        35                  40                  45

Gly Trp Ile Asn Pro Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Arg Lys Tyr Val Thr Asn Trp Val Phe Ala Glu Asp Phe
            100                 105                 110

Gln His Trp Gly Gln Gly Thr Leu Val Thr Val Ser Ser
        115                 120                 125

<210> SEQ ID NO 153
<211> LENGTH: 122
<212> TYPE: PRT
<213> ORGANISM: Artificial Sequence
<220> FEATURE:
<223> OTHER INFORMATION: MF5557

<400> SEQUENCE: 153
```

```
Gln Val Gln Leu Val Gln Ser Gly Ala Glu Val Lys Arg Pro Gly Ser
1               5                   10                  15

Ser Val Lys Val Ser Cys Lys Ala Ser Gly Gly Thr Phe Asn Thr Tyr
            20                  25                  30

Ser Ile Thr Trp Val Arg Gln Ala Pro Gly Gln Gly Leu Glu Trp Met
        35                  40                  45

Gly Gly Ile Ile Pro Val Phe Gly Thr Ser Lys Tyr Ala Gln Lys Phe
50                  55                  60

Gln Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Ser Phe Ser Ser Ser Gly Trp Phe Asp Pro Trp
            100                 105                 110

Gly Gln Gly Thr Leu Val Thr Val Ser Ser
        115                 120
```

<210> SEQ ID NO 154
<211> LENGTH: 121
<212> TYPE: PRT
<213> ORGANISM: Artificial Sequence
<220> FEATURE:
<223> OTHER INFORMATION: MF5561

<400> SEQUENCE: 154

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Thr Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Arg Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Lys Asp Gln Thr Gly Tyr Ser Ser Thr Leu Phe Asp Tyr Trp Gly
            100                 105                 110

Gln Gly Thr Leu Val Thr Val Ser Ser
        115                 120
```

<210> SEQ ID NO 155
<211> LENGTH: 125
<212> TYPE: PRT
<213> ORGANISM: Artificial Sequence
<220> FEATURE:
<223> OTHER INFORMATION: MF5576

<400> SEQUENCE: 155

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser His
            20                  25                  30

Ala Met Asn Trp Val Arg Gln Ala Pro Gly Gln Gly Leu Glu Trp Met
        35                  40                  45

Gly Trp Ile Asn Pro Asn Thr Gly Asn Pro Thr Tyr Ala Gln Gly Phe
```

50                  55                  60
Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Ile Asp Arg Gly Tyr Met Ser Asn Trp Val Phe Ala Glu Tyr Phe
            100                 105                 110

Pro His Trp Gly Gln Gly Thr Leu Val Thr Val Ser Ser
        115                 120                 125

<210> SEQ ID NO 156
<211> LENGTH: 121
<212> TYPE: PRT
<213> ORGANISM: Artificial Sequence
<220> FEATURE:
<223> OTHER INFORMATION: MF5594

<400> SEQUENCE: 156

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Thr Tyr
             20                  25                  30

Ala Ile Ser Trp Val Arg Gln Ala Pro Gly Gln Gly Leu Glu Trp Met
         35                  40                  45

Gly Trp Ile Ile Pro Ile Phe Asp Thr Gly Asn Tyr Ala Gln Lys Ile
     50                  55                  60

Gln Gly Arg Val Thr Ile Thr Ala Asp Lys Ser Thr Ser Thr Ala Tyr
 65                  70                  75                  80

Met Glu Leu Thr Ser Leu Arg Ser Glu Asp Thr Ala Val Tyr Tyr Cys
                 85                  90                  95

Ala Arg His Asp Tyr Thr Asn Thr Val Asp Ala Phe Asp Ile Trp Gly
            100                 105                 110

Gln Gly Thr Met Val Thr Val Ser Ser
        115                 120

<210> SEQ ID NO 157
<211> LENGTH: 121
<212> TYPE: PRT
<213> ORGANISM: Artificial Sequence
<220> FEATURE:
<223> OTHER INFORMATION: MF5708

<400> SEQUENCE: 157

Gln Val Gln Leu Val Gln Ser Gly Ala Glu Val Lys Lys Pro Gly Ser
 1               5                  10                  15

Ser Val Lys Val Ser Cys Lys Ala Ser Gly Asp Thr Phe Arg Ser Tyr
             20                  25                  30

Gly Ile Thr Trp Val Arg Gln Ala Pro Gly Gln Gly Leu Glu Trp Met
         35                  40                  45

Gly Gly Ile Ile Pro Val Phe Gly Thr Thr Asn Tyr Ala Gln Lys Phe
     50                  55                  60

Gln Gly Arg Val Thr Ile Thr Ala Asp Lys Ser Thr Ser Thr Val Phe
 65                  70                  75                  80

Met Glu Leu Asn Ser Leu Arg Ser Glu Asp Thr Ala Val Tyr Tyr Cys
                 85                  90                  95

Ala Arg Arg Gly Tyr Ser Asn Pro His Trp Leu Asp Pro Trp Gly
            100                 105                 110

Gln Gly Thr Leu Val Thr Val Ser Ser
        115                 120

<210> SEQ ID NO 158
<211> LENGTH: 113
<212> TYPE: PRT
<213> ORGANISM: Artificial Sequence
<220> FEATURE:
<223> OTHER INFORMATION: MF6629

<400> SEQUENCE: 158

Gln Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Glu Thr Arg Tyr Ser Pro Ser Phe
    50                  55                  60

Gln Gly Gln Phe Thr Ile Ser Ala Asp Lys Ser Ile Ser Thr Ala Tyr
65                  70                  75                  80

Leu Gln Trp Ser Ser Leu Arg Ala Ser Asp Thr Ala Met Tyr Tyr Cys
                85                  90                  95

Ala Thr Gly Trp Asp Phe Trp Gly Gln Gly Thr Leu Val Thr Val Ser
            100                 105                 110

Ser

<210> SEQ ID NO 159
<211> LENGTH: 124
<212> TYPE: PRT
<213> ORGANISM: Artificial Sequence
<220> FEATURE:
<223> OTHER INFORMATION: MF6630

<400> SEQUENCE: 159

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Met Val Arg Gly Val Ile Asp Asp Trp Phe Asp
            100                 105                 110

Pro Trp Gly Gln Gly Thr Leu Val Thr Val Ser Ser
        115                 120

<210> SEQ ID NO 160
<211> LENGTH: 121
<212> TYPE: PRT
<213> ORGANISM: Artificial Sequence
<220> FEATURE:
<223> OTHER INFORMATION: MF6637

<400> SEQUENCE: 160

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Asp Tyr
            20                  25                  30

Pro Ile Ser Trp Val Arg Gln Ala Pro Gly Gln Gly Phe Glu Trp Met
        35                  40                  45

Gly Gly Ile Ile Pro Ile Phe Asp Thr Ser Asn Ile Glu Gln Lys Phe
50                      55                  60

Gln Gly Arg Val Thr Leu Thr Ala Asp Lys Ser Ser Thr Val Tyr
65                  70                  75                  80

Met Glu Leu Ser Gly Leu Arg Ser Glu Asp Thr Ala Ile Tyr Tyr Cys
                85                  90                  95

Ala Arg Val Gly Gly Leu Arg Gln Ala Trp Tyr Phe Asp Leu Trp Gly
            100                 105                 110

Arg Gly Thr Leu Val Thr Val Ser Ser
        115                 120

<210> SEQ ID NO 161
<211> LENGTH: 121
<212> TYPE: PRT
<213> ORGANISM: Artificial Sequence
<220> FEATURE:
<223> OTHER INFORMATION: MF6643

<400> SEQUENCE: 161

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Pro Met Asn Trp Val Arg Gln Ala Pro Gly Gln Gly Leu Glu Trp Leu
        35                  40                  45

Gly Trp Ile Asn Thr Asn Thr Gly Thr Pro Thr Tyr Ala His Asp Phe
50                      55                  60

Thr Gly Arg Phe Val Phe Ser Leu Asp Thr Ser Val Ser Thr Ala Tyr
65                  70                  75                  80

Leu Gln Ile Ser Ser Leu Lys Ser Glu Asp Thr Ala Val Tyr Tyr Cys
                85                  90                  95

Ala Arg Gly Gly Trp Glu Leu Leu Phe Asn Tyr Phe Gln Gln Trp Gly
            100                 105                 110

Gln Gly Thr Leu Val Thr Val Ser Ser
        115                 120

<210> SEQ ID NO 162
<211> LENGTH: 116
<212> TYPE: PRT
<213> ORGANISM: Artificial Sequence
<220> FEATURE:
<223> OTHER INFORMATION: MF6645

<400> SEQUENCE: 162

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Asn Arg
            20                  25                  30

Tyr Trp Ser Trp Ile Arg Gln Ser Pro Gly Lys Gly Leu Glu Trp Ile
        35                  40                  45

Gly Tyr Ile Tyr Tyr Ser Gly Asn Thr Asn Tyr Asn Pro Ser Leu Lys

```
                50                  55                  60
Ser Arg Val Thr Ile Ser Val Asp Thr Ser Lys Asn Gln Phe Ser Leu
 65                  70                  75                  80

Lys Val Asn Ser Val Thr Ala Ala Asp Thr Ala Val Tyr Tyr Cys Ala
                    85                  90                  95

Ser Ser Pro Pro Tyr Tyr Met Asp Val Trp Gly Lys Gly Thr Thr Val
                100                 105                 110

Thr Val Ser Ser
            115

<210> SEQ ID NO 163
<211> LENGTH: 119
<212> TYPE: PRT
<213> ORGANISM: Artificial Sequence
<220> FEATURE:
<223> OTHER INFORMATION: MF6646

<400> SEQUENCE: 163

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
                 20                  25                  30

Tyr Met Thr Trp Val Arg Gln Ala Pro Gly Gly Leu Glu Trp Val
             35                  40                  45

Gly Arg Ile Arg Ser Lys Thr Asp Gly Gly Thr Thr Asp Tyr Ala Ala
         50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Ile Phe
                 85                  90                  95

Tyr Cys Thr Thr Gly Phe Asp Trp Tyr Phe Thr Leu Trp Gly Arg Gly
                100                 105                 110

Thr Leu Val Thr Val Ser Ser
            115

<210> SEQ ID NO 164
<211> LENGTH: 125
<212> TYPE: PRT
<213> ORGANISM: Artificial Sequence
<220> FEATURE:
<223> OTHER INFORMATION: MF6648

<400> SEQUENCE: 164

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
                 20                  25                  30

Trp Met Ser Trp Val Arg Gln Val Pro Gly Lys Gly Leu Glu Trp Val
             35                  40                  45

Gly Arg Ile Lys Ser Lys Thr Asp Gly Gly Thr Thr Asp Tyr Ala Val
         50                  55                  60

Ala Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Phe
                 85                  90                  95

Tyr Cys Thr Thr Gly Trp Gly Tyr Ser Gly Tyr Gly Pro Glu Gly Phe
                100                 105                 110
```

```
Asp Ile Trp Gly Gln Gly Thr Thr Val Thr Val Ser Ser
        115                 120                 125
```

<210> SEQ ID NO 165
<211> LENGTH: 122
<212> TYPE: PRT
<213> ORGANISM: Artificial Sequence
<220> FEATURE:
<223> OTHER INFORMATION: MF6655

<400> SEQUENCE: 165

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Ser Ala Gln Asn Phe
    50                  55                  60

Gln Gly Arg Leu Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Gly Gly Thr Gly Thr Thr Asp Trp Tyr Phe Asp Leu Trp
            100                 105                 110

Gly Arg Gly Thr Leu Val Thr Val Ser Ser
        115                 120
```

<210> SEQ ID NO 166
<211> LENGTH: 122
<212> TYPE: PRT
<213> ORGANISM: Artificial Sequence
<220> FEATURE:
<223> OTHER INFORMATION: MF6658

<400> SEQUENCE: 166

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Leu
        35                  40                  45

Gly Gly Ile Ile Pro Ile Phe Gly Thr Ser Asn Ser Ala Gln Asn Phe
    50                  55                  60

Leu Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Ile Tyr Tyr Cys
                85                  90                  95

Ala Arg Val Gly Gly Tyr Thr Ser Ser Ser Trp Phe Phe Asp Leu Trp
            100                 105                 110

Gly Arg Gly Thr Leu Val Thr Val Ser Ser
        115                 120
```

<210> SEQ ID NO 167
<211> LENGTH: 121
<212> TYPE: PRT
<213> ORGANISM: Artificial Sequence
<220> FEATURE:
<223> OTHER INFORMATION: MF6660

```
<400> SEQUENCE: 167

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Val Pro Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asp Gly Gly Asn Ser Asp Trp Tyr Phe Asp Leu Trp Gly
            100                 105                 110

Arg Gly Thr Leu Val Thr Val Ser Ser
        115                 120

<210> SEQ ID NO 168
<211> LENGTH: 123
<212> TYPE: PRT
<213> ORGANISM: Artificial Sequence
<220> FEATURE:
<223> OTHER INFORMATION: MF6675

<400> SEQUENCE: 168

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Pro Ile Ser Trp Val Arg Gln Ala Pro Gly Glu Gly Leu Glu Trp Met
        35                  40                  45

Gly Gly Ile Ile Pro Ile Phe Glu Thr Ala Asn Phe Ala Gln Lys Phe
    50                  55                  60

Gln Gly Arg Val Thr Ile Thr Ala Asp Lys Ser Thr Asn Thr Val Tyr
65                  70                  75                  80

Met Glu Leu Ser Arg Leu Arg Ser Glu Asp Thr Ala Val Tyr Tyr Cys
                85                  90                  95

Val Arg Val Asp Gly Arg Ser Ser Gly Gly Asn Trp His Phe Asp Leu
            100                 105                 110

Trp Gly Arg Gly Thr Leu Val Thr Val Ser Ser
        115                 120

<210> SEQ ID NO 169
<211> LENGTH: 124
<212> TYPE: PRT
<213> ORGANISM: Artificial Sequence
<220> FEATURE:
<223> OTHER INFORMATION: MF6686

<400> SEQUENCE: 169

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Tyr Tyr
            20                  25                  30

Thr Ile Thr Trp Val Arg Gln Ala Pro Gly Gln Gly Phe Glu Trp Met
        35                  40                  45
```

-continued

```
Gly Gly Ile Ile Pro Ile Phe Gly Thr Pro Ser Tyr Ala Gln Lys Phe
        50                  55                  60

Gln Gly Arg Val Thr Ile Thr Ala Asp Lys Tyr Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Tyr Tyr Phe Asp Ser Asn Gly Tyr Pro Pro Phe Asp
            100                 105                 110

Asp Trp Gly Gln Gly Thr Leu Val Thr Val Ser Ser
            115                 120

<210> SEQ ID NO 170
<211> LENGTH: 116
<212> TYPE: PRT
<213> ORGANISM: Artificial Sequence
<220> FEATURE:
<223> OTHER INFORMATION: MF6690

<400> SEQUENCE: 170

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Ala Met Asn Trp Val Arg Gln Ala Pro Gly Gln Gly Leu Glu Trp Met
        35                  40                  45

Gly Trp Ile Asn Thr Ile Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Trp Asp Phe Phe Asp Ser Trp Gly Gln Gly Thr Leu Val
            100                 105                 110

Thr Val Ser Ser
            115

<210> SEQ ID NO 171
<211> LENGTH: 123
<212> TYPE: PRT
<213> ORGANISM: Artificial Sequence
<220> FEATURE:
<223> OTHER INFORMATION: MF6692

<400> SEQUENCE: 171

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Asp Ser Ser Asn
            20                  25                  30

Ala Val Ser Trp Val Arg Gln Ala Pro Gly Gln Gly Phe Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Val Asn
65                  70                  75                  80

Met Glu Leu Arg Ser Leu Arg Ser Glu Asp Thr Ala Val Tyr Tyr Cys
                85                  90                  95

Ala Arg Val Gly Gly Leu Gly Thr Thr Pro His Trp Tyr Phe Asp Leu
            100                 105                 110
```

```
Trp Gly Arg Gly Thr Leu Val Thr Val Ser Ser
        115                 120
```

<210> SEQ ID NO 172
<211> LENGTH: 124
<212> TYPE: PRT
<213> ORGANISM: Artificial Sequence
<220> FEATURE:
<223> OTHER INFORMATION: MF6700

<400> SEQUENCE: 172

```
Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Asn
            20                  25                  30

Ala Ile Ser Trp Val Arg Gln Ala Pro Gly Gln Gly Leu Glu Trp Met
        35                  40                  45

Gly Gly Ile Val Pro Ile Leu Asp Thr Val Asn Tyr Ala Gln Asn Phe
    50                  55                  60

Leu Gly Arg Val Thr Ile Thr Ala Asp Arg Ala Thr Arg Thr Ala Tyr
65                  70                  75                  80

Met Glu Leu Thr Asn Leu Arg Ser Glu Asp Thr Ala Val Tyr Tyr Cys
                85                  90                  95

Ala Ile Pro Ser Tyr Asn Trp Asn Arg Leu Tyr Tyr Tyr Met Asp
            100                 105                 110

Val Trp Gly Lys Gly Thr Thr Val Thr Val Ser Ser
        115                 120
```

<210> SEQ ID NO 173
<211> LENGTH: 125
<212> TYPE: PRT
<213> ORGANISM: Artificial Sequence
<220> FEATURE:
<223> OTHER INFORMATION: MF6706

<400> SEQUENCE: 173

```
Gln Ile Thr Leu Lys Glu Ser Gly Pro Thr Leu Val Arg Pro Thr Gln
1               5                   10                  15

Thr Leu Thr Leu Thr Cys Thr Phe Ser Gly Phe Ser Leu Ser Thr Ser
            20                  25                  30

Ala Val Gly Val Asp Trp Ile Arg Gln Pro Pro Gly Lys Ala Leu Glu
        35                  40                  45

Trp Leu Ala Leu Ile Tyr Trp Ser Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Gln Pro Asn Leu Asp Phe Trp Ser Gly Tyr His Phe
            100                 105                 110

Asp Tyr Trp Gly Gln Gly Thr Leu Val Thr Val Ser Ser
        115                 120                 125
```

<210> SEQ ID NO 174
<211> LENGTH: 124
<212> TYPE: PRT
<213> ORGANISM: Artificial Sequence
<220> FEATURE:
<223> OTHER INFORMATION: MF6714

<400> SEQUENCE: 174

Glu Val Gln Leu Val Gln Ser Gly Ala Glu Val Lys Lys Ser Gly Ser
1               5                   10                  15

Ser Val Lys Val Ser Cys Glu Ala Ser Gly Gly Ser Phe Asn Ser Tyr
            20                  25                  30

Thr Ile Thr Trp Met Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Arg Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Phe Tyr Asp Arg Ser Gly Tyr Pro Pro Phe Asp
            100                 105                 110

Tyr Trp Gly Gln Gly Thr Leu Val Thr Val Ser Ser
        115                 120

<210> SEQ ID NO 175
<211> LENGTH: 116
<212> TYPE: PRT
<213> ORGANISM: Artificial Sequence
<220> FEATURE:
<223> OTHER INFORMATION: MF6721

<400> SEQUENCE: 175

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Lys Gly Trp Gly Ser Gly Trp Gly Gln Gly Thr Leu Val
            100                 105                 110

Thr Val Ser Ser
        115

<210> SEQ ID NO 176
<211> LENGTH: 121
<212> TYPE: PRT
<213> ORGANISM: Artificial Sequence
<220> FEATURE:
<223> OTHER INFORMATION: MF6722

<400> SEQUENCE: 176

Gln Val Gln Leu Val Gln Ser Gly Ala Gly Val Lys Glu Pro Gly Ser
1               5                   10                  15

Ser Val Lys Val Ser Cys Lys Thr Ser Gly Asp Thr Phe Ser Ser Tyr
            20                  25                  30

Ala Ile Ser Trp Leu Arg Gln Ala Pro Gly Gln Gly Leu Glu Trp Met
        35                  40                  45

Gly Gly Ile Ile Pro Ile Phe Asp Thr Ala Asn Ser Asp Gln Lys Phe
            50                  55                  60

Gln Asp Arg Val Thr Ile Thr Ala Asp Arg Ser Thr Asn Thr Val Tyr
65                  70                  75                  80

Met Glu Leu Ser Ser Leu Arg Ser Asp Asp Thr Ala Val Tyr Tyr Cys
                85                  90                  95

Ala Arg Val Gly Gly Tyr Gly Asn Asn Tyr Asn Phe Asp Tyr Trp Gly
                100                 105                 110

Gln Gly Thr Leu Val Thr Val Ser Ser
            115                 120

<210> SEQ ID NO 177
<211> LENGTH: 125
<212> TYPE: PRT
<213> ORGANISM: Artificial Sequence
<220> FEATURE:
<223> OTHER INFORMATION: MF6724

<400> SEQUENCE: 177

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
                20                  25                  30

Trp Met Ser Trp Val Arg Gln Ala Pro Gly Lys Gly Leu Glu Trp Val
            35                  40                  45

Gly Arg Ile Lys Gly Lys Thr Asp Gly Gly Thr Thr Asp Tyr Ala Ser
        50                  55                  60

Pro Val Lys Gly Arg Phe Thr Ile Ser Arg Asp Asp Ser Lys Asn Thr
65                  70                  75                  80

Leu Tyr Leu His Leu Asn Ser Leu Lys Thr Glu Asp Thr Ala Val Tyr
                85                  90                  95

Tyr Cys Thr Thr Asp Pro Ser Gly Ser Tyr Phe Tyr His Tyr Tyr Met
            100                 105                 110

Asp Val Trp Gly Lys Gly Thr Leu Val Thr Val Ser Ser
        115                 120                 125

<210> SEQ ID NO 178
<211> LENGTH: 125
<212> TYPE: PRT
<213> ORGANISM: Artificial Sequence
<220> FEATURE:
<223> OTHER INFORMATION: MF6728

<400> SEQUENCE: 178

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Ala Val Gly Val Gly Trp Ile Arg Gln Pro Pro Gly Lys Ser Leu Glu
            35                  40                  45

Trp Leu Ala Val Ile Tyr Trp Ser Asp Asp Lys Arg Tyr Ser Pro Ser
        50                  55                  60

Leu Lys Ser Arg Leu Thr Ile Thr Lys Asp Thr Ser Lys Asn Gln Val
65                  70                  75                  80

Val Leu Arg Met Thr Asn Met Asp Pro Val Asp Thr Ala Thr Tyr Tyr
                85                  90                  95

Cys Ala His Arg Arg Pro Asn Tyr Asp Ser Trp Ser Gly Tyr Tyr Glu

```
                100             105             110
Asp Tyr Trp Gly Gln Gly Thr Leu Val Thr Val Ser Ser
        115             120             125

<210> SEQ ID NO 179
<211> LENGTH: 121
<212> TYPE: PRT
<213> ORGANISM: Artificial Sequence
<220> FEATURE:
<223> OTHER INFORMATION: MF6729

<400> SEQUENCE: 179

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser His
            20                  25                  30

Val Met Asn Trp Val Arg Gln Ala Pro Gly His Gly Leu Glu Trp Met
        35                  40                  45

Gly Trp Ile Asp Thr Asn Thr Gly Asn Pro Thr Tyr Ala Gln Asp Phe
    50                  55                  60

Thr Gly Arg Phe Val Phe Ser Leu Asp Ser Ser Val Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Gly Gly Trp Gly Leu Leu Arg Glu Tyr Phe Leu Gln Trp Gly
            100                 105                 110

Gln Gly Thr Leu Val Thr Val Ser Ser
        115                 120

<210> SEQ ID NO 180
<211> LENGTH: 119
<212> TYPE: PRT
<213> ORGANISM: Artificial Sequence
<220> FEATURE:
<223> OTHER INFORMATION: MF6826

<400> SEQUENCE: 180

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Gly Met His Trp Val Arg Gln Ala Pro Gly Lys Gly Leu Glu Trp Val
        35                  40                  45

Ala Val Ile Ser Phe Asp Gly Thr Asn Glu Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Lys Ala Glu Asp Thr Ala Val Tyr Tyr Cys
                85                  90                  95

Ala Thr His Thr Gly His Tyr Ser Gly Phe Asp Tyr Trp Gly Gln Gly
            100                 105                 110

Thr Leu Val Thr Val Ser Ser
        115

<210> SEQ ID NO 181
<211> LENGTH: 122
<212> TYPE: PRT
<213> ORGANISM: Artificial Sequence
<220> FEATURE:
```

-continued

<223> OTHER INFORMATION: MF6940

<400> SEQUENCE: 181

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Pro Ile Ser Trp Val Arg Gln Ala Pro Gly Gln Gly Phe Glu Trp Met
        35                  40                  45

Gly Gly Ile Ile Pro Ile Phe Asp Thr Ser Asn Ile Glu Gln Lys Phe
    50                  55                  60

Gln Gly Arg Val Thr Leu Thr Ala Asp Lys Ser Thr Ser Thr Val Tyr
65                  70                  75                  80

Met Glu Leu Ser Gly Leu Arg Ser Glu Asp Thr Ala Ile Tyr Tyr Cys
                85                  90                  95

Ala Arg Val Asp Gly Thr Gly Ile Ser Asn Trp Tyr Phe Asp Leu Trp
            100                 105                 110

Gly Arg Gly Thr Leu Val Thr Val Ser Ser
        115                 120

<210> SEQ ID NO 182
<211> LENGTH: 122
<212> TYPE: PRT
<213> ORGANISM: Artificial Sequence
<220> FEATURE:
<223> OTHER INFORMATION: MF6942

<400> SEQUENCE: 182

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Gly Leu Lys Ala Glu Asp Thr Ala Val Tyr Phe Cys
                85                  90                  95

Thr Arg Gly Tyr Ser Ser Ile Trp His Gly Glu Asn Phe Gln Tyr Trp
            100                 105                 110

Gly Gln Gly Thr Leu Val Thr Val Ser Ser
        115                 120

<210> SEQ ID NO 183
<211> LENGTH: 124
<212> TYPE: PRT
<213> ORGANISM: Artificial Sequence
<220> FEATURE:
<223> OTHER INFORMATION: MF6943

<400> SEQUENCE: 183

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gly Tyr
            20                  25                  30

Ala Ile Asn Trp Val Arg Gln Ala Pro Gly Gln Gly Leu Glu Trp Met

```
                35                  40                  45

Gly Trp Ile Asn Thr Asn Thr Gly Asn Pro Thr Tyr Ala Gln Asp Phe
         50                  55                  60

Thr Gly Arg Phe Val Phe Ser Val Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Met Asp Asn Trp Asn Tyr Glu Gly Tyr Tyr Val Met Asp
            100                 105                 110

Val Trp Gly Lys Gly Thr Thr Val Thr Val Ser Ser
        115                 120

<210> SEQ ID NO 184
<211> LENGTH: 121
<212> TYPE: PRT
<213> ORGANISM: Artificial Sequence
<220> FEATURE:
<223> OTHER INFORMATION: MF6944

<400> SEQUENCE: 184

Glu Val Gln Leu Val Gln Ser Gly Ala Glu Val Lys Lys Pro Gly Ser
 1               5                  10                  15

Ser Val Lys Val Ser Cys Arg Ala Ser Gly Gly Thr Phe Ser Asn Tyr
             20                  25                  30

Ala Ile Ser Trp Val Arg Gln Ala Pro Gly Gln Arg Leu Glu Trp Met
         35                  40                  45

Gly Gly Ile Ile Pro Ile Phe Asp Thr Ala Asn Ser Ala Gln Thr Phe
     50                  55                  60

Gln Asp Arg Val Thr Ile Thr Ala Asp Thr Ser Thr Ser Thr Val Tyr
 65                  70                  75                  80

Met Glu Leu Ser Ser Leu Lys Ser Glu Asp Thr Ala Val Tyr Tyr Cys
                 85                  90                  95

Ala Arg Val Glu Gly Trp Gly Ser Gln Trp Tyr Phe Asp Leu Trp Gly
            100                 105                 110

Arg Gly Thr Leu Val Thr Val Ser Ser
        115                 120

<210> SEQ ID NO 185
<211> LENGTH: 121
<212> TYPE: PRT
<213> ORGANISM: Artificial Sequence
<220> FEATURE:
<223> OTHER INFORMATION: MF6947

<400> SEQUENCE: 185

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Asn Asn Tyr
             20                  25                  30

Pro Ile Ser Trp Val Arg Gln Ala Pro Gly Gln Gly Leu Glu Trp Met
         35                  40                  45

Gly Thr Ile Ile Pro Ile Phe Asp Thr Ser Ser Ala Gln Gln Phe
     50                  55                  60

Gln Gly Arg Val Thr Ile Thr Ala Asp Glu Ser Thr Asn Thr Val Ser
 65                  70                  75                  80

Met Glu Leu Ser Ser Leu Arg Ser Glu Asp Thr Ala Ile Tyr Tyr Cys
                 85                  90                  95
```

```
Ala Arg Val Glu Gly Thr Asp Ser Asn Trp Gly Trp Asp Phe Trp Gly
            100                 105                 110

Gln Gly Thr Leu Val Thr Val Ser Ser
        115                 120

<210> SEQ ID NO 186
<211> LENGTH: 129
<212> TYPE: PRT
<213> ORGANISM: Artificial Sequence
<220> FEATURE:
<223> OTHER INFORMATION: MF6949

<400> SEQUENCE: 186

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Val Asn Trp Val Arg Gln Ala Pro Gly Gln Gly Leu Glu Trp Met
        35                  40                  45

Gly Trp Ile Asn Thr Asp Thr Gly Asn Pro Thr Tyr Ala Gln Gly Phe
    50                  55                  60

Thr Gly Arg Phe Val Phe Ser Leu Asp Thr Ser Val Asn Thr Ala Tyr
65                  70                  75                  80

Leu Gln Ile Asn Ser Leu Lys Pro Glu Asp Thr Ala Val Tyr Tyr Cys
                85                  90                  95

Ala Arg Asp Asp Gly Thr Gly Thr Gly Asp Tyr Val Trp Gly Arg Tyr
            100                 105                 110

Arg Tyr Thr Leu Asp Phe Trp Gly Gln Gly Thr Leu Val Thr Val Ser
        115                 120                 125

Ser

<210> SEQ ID NO 187
<211> LENGTH: 122
<212> TYPE: PRT
<213> ORGANISM: Artificial Sequence
<220> FEATURE:
<223> OTHER INFORMATION: MF7331

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Tyr Lys Leu Tyr Ala Ala Asp Gly Phe Asp Tyr Trp
            100                 105                 110

Gly Gln Gly Thr Leu Val Thr Val Ser Ser
        115                 120

<210> SEQ ID NO 188
<211> LENGTH: 122
```

```
<212> TYPE: PRT
<213> ORGANISM: Artificial Sequence
<220> FEATURE:
<223> OTHER INFORMATION: MF7332

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Met Asp Ser Tyr Pro Phe Tyr Arg Gly Phe Asp Tyr Trp
            100                 105                 110

Gly Gln Gly Thr Leu Val Thr Val Ser Ser
        115                 120

<210> SEQ ID NO 189
<211> LENGTH: 124
<212> TYPE: PRT
<213> ORGANISM: Artificial Sequence
<220> FEATURE:
<223> OTHER INFORMATION: MF7334

<400> SEQUENCE: 189

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asp Asn Thr Met Trp Tyr Ser Arg Pro Tyr Ala Phe Asp
            100                 105                 110

Tyr Trp Gly Gln Gly Thr Leu Val Thr Val Ser Ser
        115                 120

<210> SEQ ID NO 190
<211> LENGTH: 122
<212> TYPE: PRT
<213> ORGANISM: Artificial Sequence
<220> FEATURE:
<223> OTHER INFORMATION: MF7341

<400> SEQUENCE: 190

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
                    20                  25                  30

Gly Ile Ser Trp Val Arg Gln Ala Pro Gly Gln Gly Leu Glu Trp Met
            35                  40                  45

Gly Trp Ile Ser Val Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Pro Tyr Trp Ser Leu Pro Gly Gly Phe Asp Tyr Trp
            100                 105                 110

Gly Gln Gly Thr Leu Val Thr Val Ser Ser
        115                 120

<210> SEQ ID NO 191
<211> LENGTH: 124
<212> TYPE: PRT
<213> ORGANISM: Artificial Sequence
<220> FEATURE:
<223> OTHER INFORMATION: MF7345

<400> SEQUENCE: 191

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Arg Trp Trp Tyr Met Asp Pro Gly Ala Gly Phe Asp
            100                 105                 110

Tyr Trp Gly Gln Gly Thr Leu Val Thr Val Ser Ser
        115                 120

<210> SEQ ID NO 192
<211> LENGTH: 124
<212> TYPE: PRT
<213> ORGANISM: Artificial Sequence
<220> FEATURE:
<223> OTHER INFORMATION: MF7350

<400> SEQUENCE: 192

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Lys Asp Tyr Ser Tyr Ser Gly Thr Gly Ser Ser Ala Phe Asp
            100                 105                 110

Tyr Trp Gly Gln Gly Thr Leu Val Thr Val Ser Ser
        115                 120
```

<210> SEQ ID NO 193
<211> LENGTH: 124
<212> TYPE: PRT
<213> ORGANISM: Artificial Sequence
<220> FEATURE:
<223> OTHER INFORMATION: MF7351

<400> SEQUENCE: 193

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Leu His Gly Ser Tyr Tyr Arg Gly Ser Ala Phe Asp
            100                 105                 110

Tyr Trp Gly Gln Gly Thr Leu Val Thr Val Ser Ser
        115                 120
```

<210> SEQ ID NO 194
<211> LENGTH: 124
<212> TYPE: PRT
<213> ORGANISM: Artificial Sequence
<220> FEATURE:
<223> OTHER INFORMATION: MF7352

<400> SEQUENCE: 194

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Trp His Gly Tyr Tyr Tyr Gly Lys Gly Phe Asp
            100                 105                 110

Tyr Trp Gly Gln Gly Thr Leu Val Thr Val Ser Ser
        115                 120
```

<210> SEQ ID NO 195

<211> LENGTH: 122
<212> TYPE: PRT
<213> ORGANISM: Artificial Sequence
<220> FEATURE:
<223> OTHER INFORMATION: MF7353

<400> SEQUENCE: 195

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Leu Gly Trp Asp Pro Gly Tyr Gly Phe Asp Tyr Trp
            100                 105                 110

Gly Gln Gly Thr Leu Val Thr Val Ser Ser
        115                 120

<210> SEQ ID NO 196
<211> LENGTH: 124
<212> TYPE: PRT
<213> ORGANISM: Artificial Sequence
<220> FEATURE:
<223> OTHER INFORMATION: MF7356

<400> SEQUENCE: 196

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Tyr Gln Gly Met Tyr Tyr Phe Gly Thr Gly Phe Asp
            100                 105                 110

Tyr Trp Gly Gln Gly Thr Leu Val Thr Val Ser Ser
        115                 120

<210> SEQ ID NO 197
<211> LENGTH: 124
<212> TYPE: PRT
<213> ORGANISM: Artificial Sequence
<220> FEATURE:
<223> OTHER INFORMATION: MF7358

<400> SEQUENCE: 197

Gln Val Gln Leu Val Glu Ser Gly Gly Gly Val Val Gln Pro Gly Arg
1               5                   10                  15

-continued

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn His Tyr Tyr Ser Pro Pro Thr Tyr Trp Gly Phe Asp
            100                 105                 110

Tyr Trp Gly Gln Gly Thr Leu Val Thr Val Ser Ser
        115                 120

<210> SEQ ID NO 198
<211> LENGTH: 124
<212> TYPE: PRT
<213> ORGANISM: Artificial Sequence
<220> FEATURE:
<223> OTHER INFORMATION: MF7365

<400> SEQUENCE: 198

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Gln Ser Gln Tyr His Ser Tyr Pro Phe Gly Phe Asp
            100                 105                 110

Tyr Trp Gly Gln Gly Thr Leu Val Thr Val Ser Ser
        115                 120

<210> SEQ ID NO 199
<211> LENGTH: 124
<212> TYPE: PRT
<213> ORGANISM: Artificial Sequence
<220> FEATURE:
<223> OTHER INFORMATION: MF7366

<400> SEQUENCE: 199

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Asp Trp Trp Gln Gly His Trp Tyr Arg Ser Gly Gly Phe Asp
            100                 105                 110

Tyr Trp Gly Gln Gly Thr Leu Val Thr Val Ser Ser
        115                 120

<210> SEQ ID NO 200
<211> LENGTH: 124
<212> TYPE: PRT
<213> ORGANISM: Artificial Sequence
<220> FEATURE:
<223> OTHER INFORMATION: MF7371

<400> SEQUENCE: 200

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Met Asp Tyr Tyr Asp Asp Trp Tyr Ser Ala Phe Asp
            100                 105                 110

Tyr Trp Gly Gln Gly Thr Leu Val Thr Val Ser Ser
        115                 120

<210> SEQ ID NO 201
<211> LENGTH: 124
<212> TYPE: PRT
<213> ORGANISM: Artificial Sequence
<220> FEATURE:
<223> OTHER INFORMATION: MF7372

<400> SEQUENCE: 201

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Gln Gly Ser His Tyr Phe Gly Pro Ala Phe Asp
            100                 105                 110

Tyr Trp Gly Gln Gly Thr Leu Val Thr Val Ser Ser
        115                 120
```

-continued

```
<210> SEQ ID NO 202
<211> LENGTH: 124
<212> TYPE: PRT
<213> ORGANISM: Artificial Sequence
<220> FEATURE:
<223> OTHER INFORMATION: MF7374

<400> SEQUENCE: 202

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Asp Asn Arg Met Tyr Ser Asn Pro Lys Gly Phe Asp
            100                 105                 110

Tyr Trp Gly Gln Gly Thr Leu Val Thr Val Ser Ser
        115                 120

<210> SEQ ID NO 203
<211> LENGTH: 124
<212> TYPE: PRT
<213> ORGANISM: Artificial Sequence
<220> FEATURE:
<223> OTHER INFORMATION: MF7378

<400> SEQUENCE: 203

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Thr Gln Gly Asn Tyr Tyr Arg Ser Arg Gly Phe Asp
            100                 105                 110

Tyr Trp Gly Gln Gly Thr Leu Val Thr Val Ser Ser
        115                 120

<210> SEQ ID NO 204
<211> LENGTH: 124
<212> TYPE: PRT
<213> ORGANISM: Artificial Sequence
<220> FEATURE:
<223> OTHER INFORMATION: MF7382

<400> SEQUENCE: 204

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Leu Gln Gly Ser Asn Tyr His Leu Gly Gly Phe Asp
            100                 105                 110

Tyr Trp Gly Gln Gly Thr Leu Val Thr Val Ser Ser
            115                 120
```

```
<210> SEQ ID NO 205
<211> LENGTH: 124
<212> TYPE: PRT
<213> ORGANISM: Artificial Sequence
<220> FEATURE:
<223> OTHER INFORMATION: MF7383

<400> SEQUENCE: 205

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Asp Met Tyr Gly Gly Trp Gly Ala Trp Gly Phe Asp
            100                 105                 110

Tyr Trp Gly Gln Gly Thr Leu Val Thr Val Ser Ser
            115                 120
```

```
<210> SEQ ID NO 206
<211> LENGTH: 121
<212> TYPE: PRT
<213> ORGANISM: Artificial Sequence
<220> FEATURE:
<223> OTHER INFORMATION: MF7394

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
```

```
                65                  70                  75                  80
Met Glu Leu Arg Ser Leu Arg Ser Asp Asp Thr Ala Val Tyr Tyr Cys
                    85                  90                  95

Ala Arg Asp Tyr Pro Ala Trp Ala Tyr Ser Ala Phe Asp Tyr Trp Gly
                100                 105                 110

Gln Gly Thr Leu Val Thr Val Ser Ser
            115                 120

<210> SEQ ID NO 207
<211> LENGTH: 121
<212> TYPE: PRT
<213> ORGANISM: Artificial Sequence
<220> FEATURE:
<223> OTHER INFORMATION: MF7395

<400> SEQUENCE: 207

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Trp Tyr Tyr Leu Ser Asp Ala Phe Asp Tyr Trp Gly
                100                 105                 110

Gln Gly Thr Leu Val Thr Val Ser Ser
            115                 120

<210> SEQ ID NO 208
<211> LENGTH: 121
<212> TYPE: PRT
<213> ORGANISM: Artificial Sequence
<220> FEATURE:
<223> OTHER INFORMATION: MF7397

<400> SEQUENCE: 208

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Trp Gly Ser Phe Tyr Gly Asp Phe Asp Tyr Trp Gly
                100                 105                 110

Gln Gly Thr Leu Val Thr Val Ser Ser
            115                 120
```

<210> SEQ ID NO 209
<211> LENGTH: 125
<212> TYPE: PRT
<213> ORGANISM: Artificial Sequence
<220> FEATURE:
<223> OTHER INFORMATION: MF5554

<400> SEQUENCE: 209

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser His
            20                  25                  30

Ala Met Asn Trp Val Arg Gln Ala Pro Gly Gln Gly Leu Glu Trp Met
        35                  40                  45

Gly Trp Ile Asn Pro Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Arg Lys Tyr Val Thr Asn Trp Val Phe Ala Glu Asp Phe
            100                 105                 110

Gln His Trp Gly Gln Gly Thr Leu Val Thr Val Ser Ser
        115                 120                 125

<210> SEQ ID NO 210
<211> LENGTH: 125
<212> TYPE: PRT
<213> ORGANISM: Artificial Sequence
<220> FEATURE:
<223> OTHER INFORMATION: MF5576

<400> SEQUENCE: 210

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser His
            20                  25                  30

Ala Met Asn Trp Val Arg Gln Ala Pro Gly Gln Gly Leu Glu Trp Met
        35                  40                  45

Gly Trp Ile Asn Pro Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Ile Asp Arg Gly Tyr Met Ser Asn Trp Val Phe Ala Glu Tyr Phe
            100                 105                 110

Pro His Trp Gly Gln Gly Thr Leu Val Thr Val Ser Ser
        115                 120                 125

<210> SEQ ID NO 211
<211> LENGTH: 125
<212> TYPE: PRT
<213> ORGANISM: Artificial Sequence
<220> FEATURE:
<223> OTHER INFORMATION: MF5578

<400> SEQUENCE: 211

Gln Val Gln Leu Val Gln Ser Gly Ser Glu Leu Lys Lys Pro Gly Ala

-continued

```
                1               5                  10                  15
Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
                35                  40                  45

Gly Trp Ile Asn Thr Asn Thr Gly Asn Pro Thr Tyr Ala Gln Gly Phe
     50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Thr Asp Arg Gly Tyr Ile Ser Ser Trp Val Phe Ala Glu Asp Phe
                100                 105                 110

Gln His Trp Gly Gln Gly Thr Leu Val Thr Val Ser Ser
                115                 120                 125
```

<210> SEQ ID NO 212
<211> LENGTH: 122
<212> TYPE: PRT
<213> ORGANISM: Artificial Sequence
<220> FEATURE:
<223> OTHER INFORMATION: MF7702

<400> SEQUENCE: 212

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
                20                  25                  30

Ala Ile Asn Trp Val Arg Gln Ala Pro Gly Gln Gly Leu Glu Trp Met
                35                  40                  45

Gly Trp Ile Asn Pro Asn Thr Gly Asn Pro Thr Tyr Ala Gln Gly Phe
     50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Arg Asp Arg Lys Tyr Val Thr Asn Trp Val Phe Ala Glu Asp Phe
                100                 105                 110

Gln His Trp Gly Arg Gly Thr Leu Val Thr
                115                 120
```

<210> SEQ ID NO 213
<211> LENGTH: 125
<212> TYPE: PRT
<213> ORGANISM: Artificial Sequence
<220> FEATURE:
<223> OTHER INFORMATION: MF9375

<400> SEQUENCE: 213

```
Gln Val Gln Leu Val Gln Ser Gly Ser Glu Leu Lys Lys Pro Gly Ala
 1               5                  10                  15

Ser Val Lys Val Ser Cys Thr Ala Ser Gly Tyr Thr Phe Thr Ser Tyr
                20                  25                  30

Ala Met Asn Trp Val Arg Gln Ala Pro Gly Gln Arg Leu Glu Trp Met
                35                  40                  45

Ala Cys Val Asn Pro Asn Thr Gly Ser Pro Thr Tyr Ala Gln Gly Ser
     50                  55                  60
```

```
Thr Gly Arg Phe Val Val Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Arg Lys Tyr Val Thr Asn Trp Val Phe Ala Glu Asp Phe
            100                 105                 110

Gln His Trp Gly His Gly Thr Leu Val Thr Val Ser Ser
        115                 120                 125

<210> SEQ ID NO 214
<211> LENGTH: 125
<212> TYPE: PRT
<213> ORGANISM: Artificial Sequence
<220> FEATURE:
<223> OTHER INFORMATION: MF9376

<400> SEQUENCE: 214

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Ala Met Asn Trp Val Arg Gln Ala Pro Gly Gln Gly Leu Glu Trp Met
        35                  40                  45

Gly Trp Met Asn Pro Asn Thr Gly Asn Pro Thr Tyr Ala Gln Gly Ser
    50                  55                  60

Thr Gly Arg Phe Val Val Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Arg Lys Tyr Val Thr Asn Trp Val Phe Ala Glu Asp Phe
            100                 105                 110

Gln His Trp Gly Arg Gly Thr Leu Val Thr Val Ser Ser
        115                 120                 125

<210> SEQ ID NO 215
<211> LENGTH: 127
<212> TYPE: PRT
<213> ORGANISM: Artificial Sequence
<220> FEATURE:
<223> OTHER INFORMATION: TTX specific VH combined with common light
      chain

<400> SEQUENCE: 215

Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr Val Ser Ser
```

<210> SEQ ID NO 216
<211> LENGTH: 255
<212> TYPE: PRT
<213> ORGANISM: Artificial Sequence
<220> FEATURE:
<223> OTHER INFORMATION: CD137 extracellular domain

<400> SEQUENCE: 216

Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys
            20                  25                  30

Pro Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 217
<211> LENGTH: 120
<212> TYPE: PRT
<213> ORGANISM: Artificial Sequence
<220> FEATURE:
<223> OTHER INFORMATION: MF6256

<400> SEQUENCE: 217

Glu Val Gln Leu Val Gln Ser Gly Ala Glu Val Lys Lys Pro Gly Ser
1               5                   10                  15

Ser Met Lys Val Ser Cys Lys Ala Ser Gly Gly Thr Phe Ser Ser Tyr
            20                  25                  30

Val Ile Ser Trp Val Arg Gln Ala Pro Gly Gln Gly Leu Glu Trp Met
        35                  40                  45

```
Gly Met Ile Ile Pro Val Phe Asp Thr Ser Ser Tyr Glu Lys Lys Phe
    50                  55                  60

Gln Gly Arg Ile Thr Ile Ile Ala Asp Lys Ser Thr Ser Thr Val Tyr
65                  70                  75                  80

Leu Glu Leu Ser Ser Leu Arg Ser Glu Asp Ala Ala Val Tyr Tyr Cys
                85                  90                  95

Ala Arg Gly Thr Val Glu Ala Thr Leu Leu Phe Asp Phe Trp Gly Gln
                100                 105                 110

Gly Thr Leu Val Thr Val Ser Ser
            115                 120
```

<210> SEQ ID NO 218
<211> LENGTH: 23
<212> TYPE: PRT
<213> ORGANISM: artificial sequence
<220> FEATURE:
<223> OTHER INFORMATION: signal peptide

<400> SEQUENCE: 218

```
Met Gly Asn Ser Cys Tyr Asn Ile Val Ala Thr Leu Leu Leu Val Leu
1               5                   10                  15

Asn Phe Glu Arg Thr Arg Ser
                20
```

<210> SEQ ID NO 219
<211> LENGTH: 163
<212> TYPE: PRT
<213> ORGANISM: artificial sequence
<220> FEATURE:
<223> OTHER INFORMATION: ECD of huCD137

<400> SEQUENCE: 219

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
                20                  25                  30

Ala Gly Gly Gln Arg Thr Cys Asp Ile Cys Arg Gln Cys Lys Gly Val
                35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
                100                 105                 110

Trp Thr Asn Cys Ser Leu Asp Gly Lys Ser Val Leu Val Asn Gly Thr
                115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln
```

<210> SEQ ID NO 220
<211> LENGTH: 27
<212> TYPE: PRT
<213> ORGANISM: artificial sequence
<220> FEATURE:

<223> OTHER INFORMATION: Predicted TM region

<400> SEQUENCE: 220

Ile Ile Ser Phe Phe Leu Ala Leu Thr Ser Thr Ala Leu Leu Phe Leu
1               5                   10                  15
Leu Phe Phe Leu Thr Leu Arg Phe Ser Val Val
            20                  25

<210> SEQ ID NO 221
<211> LENGTH: 42
<212> TYPE: PRT
<213> ORGANISM: artificial sequence
<220> FEATURE:
<223> OTHER INFORMATION: Intracellular tail

<400> SEQUENCE: 221

Lys Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
            20                  25                  30
Pro Glu Glu Glu Glu Gly Gly Cys Glu Leu
        35                  40

<210> SEQ ID NO 222
<211> LENGTH: 23
<212> TYPE: PRT
<213> ORGANISM: artificial sequence
<220> FEATURE:
<223> OTHER INFORMATION: signal peptide

<400> SEQUENCE: 222

Met Gly Asn Ser Cys Tyr Asn Ile Val Ala Thr Leu Leu Leu Val Leu
1               5                   10                  15
Asn Phe Glu Arg Thr Arg Ser
            20

<210> SEQ ID NO 223
<211> LENGTH: 163
<212> TYPE: PRT
<213> ORGANISM: artificial sequence
<220> FEATURE:
<223> OTHER INFORMATION: ECD of maCD137

<400> SEQUENCE: 223

Leu Gln Asp Leu Cys Ser Asn Cys Pro Ala Gly Thr Phe Cys Asp Asn
1               5                   10                  15
Asn Arg Ser Gln Ile Cys Ser Pro Cys Pro Pro Asn Ser Phe Ser Ser
            20                  25                  30
Ala Gly Gly Gln Arg Thr Cys Asp Ile Cys Arg Gln Cys Lys Gly Val
        35                  40                  45
Phe Lys Thr Arg Lys Glu Cys Ser Ser Thr Ser Asn Ala Glu Cys Asp
    50                  55                  60
Cys Ile Ser Gly Tyr His Cys Leu Gly Ala Glu Cys Ser Met Cys Glu
65                  70                  75                  80
Gln Asp Cys Lys Gln Gly Gln Glu Leu Thr Lys Lys Gly Cys Lys Asp
                85                  90                  95
Cys Cys Phe Gly Thr Phe Asn Asp Gln Lys Arg Gly Ile Cys Arg Pro
            100                 105                 110
Trp Thr Asn Cys Ser Leu Asp Gly Lys Ser Val Leu Val Asn Gly Thr
        115                 120                 125

```
Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160

Ser Pro Gln

<210> SEQ ID NO 224
<211> LENGTH: 26
<212> TYPE: PRT
<213> ORGANISM: artificial sequence
<220> FEATURE:
<223> OTHER INFORMATION: Predicted TM region

<400> SEQUENCE: 224

Ile Ile Phe Phe Leu Ala Leu Thr Ser Thr Val Val Leu Phe Leu Leu
1               5                   10                  15

Phe Phe Leu Val Leu Arg Phe Ser Val Val
            20                  25

<210> SEQ ID NO 225
<211> LENGTH: 42
<212> TYPE: PRT
<213> ORGANISM: artificial sequence
<220> FEATURE:
<223> OTHER INFORMATION: Intracellular tail

<400> SEQUENCE: 225

Lys Arg Ser Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 226
<211> LENGTH: 23
<212> TYPE: PRT
<213> ORGANISM: artificial sequence
<220> FEATURE:
<223> OTHER INFORMATION: signal peptide

<400> SEQUENCE: 226

Met Gly Ser Ser Cys Tyr Asn Met Val Val Thr Val Leu Leu Val Val
1               5                   10                  15

Gly Thr Glu Glu Val Arg Ala
            20

<210> SEQ ID NO 227
<211> LENGTH: 164
<212> TYPE: PRT
<213> ORGANISM: artificial sequence
<220> FEATURE:
<223> OTHER INFORMATION: ECD of raCD137

<400> SEQUENCE: 227

Thr Arg Asn Pro Cys Asp Ser Cys Glu Ala Gly Thr Phe Cys Ser Lys
1               5                   10                  15

Tyr Pro Pro Val Cys Thr Ser Cys Pro Pro Ser Thr Tyr Ser Ser Thr
            20                  25                  30

Gly Gly Gln Pro Asn Cys Asp Ile Cys Arg Val Cys Gln Gly Tyr Phe
        35                  40                  45

Arg Phe Lys Lys Pro Cys Ser Ser Thr His Asn Ala Glu Cys Glu Cys
```

```
                50                  55                  60
Val Glu Gly Phe His Cys Leu Gly Pro Lys Cys Thr Arg Cys Glu Lys
 65                  70                  75                  80

Asp Cys Arg Pro Gly Gln Glu Leu Thr Glu Gln Gly Cys Lys Asn Cys
                 85                  90                  95

Gly Leu Gly Thr Phe Asn Asp Gln Asp Gly Ala Gly Val Cys Arg Pro
                100                 105                 110

Trp Thr Asn Cys Ser Leu Asp Gly Arg Ser Val Leu Lys Asn Gly Thr
            115                 120                 125

Lys Glu Lys Asp Val Val Cys Gly Pro Pro Val Val Ser Leu Ser Pro
    130                 135                 140

Ser Thr Thr Pro Ser Ala Val Thr Thr Pro Glu Arg Glu Ser Gly Glu
145                 150                 155                 160

Arg Pro Leu Gln

<210> SEQ ID NO 228
<211> LENGTH: 23
<212> TYPE: PRT
<213> ORGANISM: artificial sequence
<220> FEATURE:
<223> OTHER INFORMATION: Predicted TM region

<400> SEQUENCE: 228

Val Leu Thr Leu Phe Leu Ala Leu Thr Leu Ala Leu Leu Leu Phe Leu
 1               5                  10                  15

Ile Phe Ile Ile Leu Trp Phe
             20

<210> SEQ ID NO 229
<211> LENGTH: 48
<212> TYPE: PRT
<213> ORGANISM: artificial sequence
<220> FEATURE:
<223> OTHER INFORMATION: Intracellular tail

<400> SEQUENCE: 229

Ser Val Pro Lys Trp Leu Arg Lys Lys Phe Pro His Ile Phe Lys Gln
 1               5                  10                  15

Pro Phe Lys Lys Ala Val Arg Thr Ala Gln Glu Glu Asp Ala Cys Ser
                20                  25                  30

Cys Arg Phe Pro Glu Glu Glu Glu Gly Gly Gly Ser Tyr Glu Leu
            35                  40                  45

<210> SEQ ID NO 230
<211> LENGTH: 18
<212> TYPE: PRT
<213> ORGANISM: artificial sequence
<220> FEATURE:
<223> OTHER INFORMATION: signal peptide

<400> SEQUENCE: 230

Met Arg Ile Phe Ala Val Phe Ile Phe Met Thr Tyr Trp His Leu Leu
 1               5                  10                  15

Asn Ala

<210> SEQ ID NO 231
<211> LENGTH: 220
<212> TYPE: PRT
<213> ORGANISM: artificial sequence
<220> FEATURE:
<223> OTHER INFORMATION: ECD of huPD-L1
```

<400> SEQUENCE: 231

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
        210                 215                 220

<210> SEQ ID NO 232
<211> LENGTH: 21
<212> TYPE: PRT
<213> ORGANISM: artificial sequence
<220> FEATURE:
<223> OTHER INFORMATION: Predicted TM region

<400> SEQUENCE: 232

Thr His Leu Val Ile Leu Gly Ala Ile Leu Leu Cys Leu Gly Val Ala
1               5                   10                  15

Leu Thr Phe Ile Phe
            20

<210> SEQ ID NO 233
<211> LENGTH: 31
<212> TYPE: PRT
<213> ORGANISM: artificial sequence
<220> FEATURE:
<223> OTHER INFORMATION: Intracellular tail

<400> SEQUENCE: 233

Arg Leu Arg Lys Gly Arg Met Met Asp Val Lys Lys Cys Gly Ile Gln
1               5                   10                  15

Asp Thr Asn Ser Lys Lys Gln Ser Asp Thr His Leu Glu Glu Thr
            20                  25                  30

<210> SEQ ID NO 234

```
<211> LENGTH: 18
<212> TYPE: PRT
<213> ORGANISM: artificial sequence
<220> FEATURE:
<223> OTHER INFORMATION: signal peptide

<400> SEQUENCE: 234

Met Arg Ile Phe Ala Val Phe Ile Phe Thr Ile Tyr Trp His Leu Leu
1               5                   10                  15

Asn Ala

<210> SEQ ID NO 235
<211> LENGTH: 220
<212> TYPE: PRT
<213> ORGANISM: artificial sequence
<220> FEATURE:
<223> OTHER INFORMATION: ECD of maPD-L1

<400> SEQUENCE: 235

Phe Thr Val Thr Val Pro Lys Asp Leu Tyr Val Val Glu Tyr Gly Ser
1               5                   10                  15

Asn Met Thr Ile Glu Cys Arg Phe Pro Val Glu Lys Gln Leu Gly Leu
            20                  25                  30

Thr Ser Leu Ile Val Tyr Trp Glu Met Glu Asp Lys Asn Ile Ile Gln
        35                  40                  45

Phe Val His Gly Glu Glu Asp Leu Lys Val Gln His Ser Asn Tyr Arg
    50                  55                  60

Gln Arg Ala Gln Leu Leu Lys Asp Gln Leu Ser Leu Gly Asn Ala Ala
65                  70                  75                  80

Leu Arg Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Leu Asn Val Thr
                165                 170                 175

Ser Thr Leu Arg Ile Asn Thr Thr Ala Asn Glu Ile Phe Tyr Cys Ile
            180                 185                 190

Phe Arg Arg Leu Gly Pro Glu Glu Asn His Thr Ala Glu Leu Val Ile
        195                 200                 205

Pro Glu Leu Pro Leu Ala Leu Pro Pro Asn Glu Arg
    210                 215                 220

<210> SEQ ID NO 236
<211> LENGTH: 21
<212> TYPE: PRT
<213> ORGANISM: artificial sequence
<220> FEATURE:
<223> OTHER INFORMATION: Predicted TM region

<400> SEQUENCE: 236

Thr His Leu Val Ile Leu Gly Ala Ile Phe Leu Leu Leu Gly Val Ala
1               5                   10                  15

Leu Thr Phe Ile Phe
```

```
                        20

<210> SEQ ID NO 237
<211> LENGTH: 31
<212> TYPE: PRT
<213> ORGANISM: artificial sequence
<220> FEATURE:
<223> OTHER INFORMATION: Intracellular tail

<400> SEQUENCE: 237

Tyr Leu Arg Lys Gly Arg Met Met Asp Met Lys Lys Ser Gly Ile Arg
1               5                   10                  15

Val Thr Asn Ser Lys Lys Gln Arg Asp Thr Gln Leu Glu Glu Thr
            20                  25                  30

<210> SEQ ID NO 238
<211> LENGTH: 28
<212> TYPE: PRT
<213> ORGANISM: artificial sequence
<220> FEATURE:
<223> OTHER INFORMATION: signal peptide

<400> SEQUENCE: 238

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly
            20                  25

<210> SEQ ID NO 239
<211> LENGTH: 186
<212> TYPE: PRT
<213> ORGANISM: artificial sequence
<220> FEATURE:
<223> OTHER INFORMATION: ECD

<400> SEQUENCE: 239

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
            180                 185
```

```
<210> SEQ ID NO 240
<211> LENGTH: 21
<212> TYPE: PRT
<213> ORGANISM: artificial sequence
<220> FEATURE:
<223> OTHER INFORMATION: Predicted TM region

<400> SEQUENCE: 240

Val Ala Ala Ile Leu Gly Leu Gly Leu Val Leu Gly Leu Leu Gly Pro
 1               5                  10                  15

Leu Ala Ile Leu Leu
            20

<210> SEQ ID NO 241
<211> LENGTH: 42
<212> TYPE: PRT
<213> ORGANISM: artificial sequence
<220> FEATURE:
<223> OTHER INFORMATION: Intracellular tail

<400> SEQUENCE: 241

Ala Leu Tyr Leu Leu Arg Arg Asp Gln Arg Leu Pro Pro Asp Ala His
 1               5                  10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
            35                  40

<210> SEQ ID NO 242
<211> LENGTH: 19
<212> TYPE: PRT
<213> ORGANISM: artificial sequence
<220> FEATURE:
<223> OTHER INFORMATION: signal peptide

<400> SEQUENCE: 242

Met Tyr Val Trp Val Gln Gln Pro Thr Ala Phe Leu Leu Leu Gly Leu
 1               5                  10                  15

Ser Leu Gly

<210> SEQ ID NO 243
<211> LENGTH: 191
<212> TYPE: PRT
<213> ORGANISM: artificial sequence
<220> FEATURE:
<223> OTHER INFORMATION: ECD

<400> SEQUENCE: 243

Val Thr Val Lys Leu Asn Cys Val Lys Asp Thr Tyr Pro Ser Gly His
 1               5                  10                  15

Lys Cys Cys Arg Glu Cys Gln Pro Gly His Gly Met Val Ser Arg Cys
            20                  25                  30

Asp His Thr Arg Asp Thr Val Cys His Pro Cys Glu Pro Gly Phe Tyr
            35                  40                  45

Asn Glu Ala Val Asn Tyr Asp Thr Cys Lys Gln Cys Thr Gln Cys Asn
        50                  55                  60

His Arg Ser Gly Ser Glu Leu Lys Gln Asn Cys Thr Pro Thr Glu Asp
65                  70                  75                  80

Thr Val Cys Gln Cys Arg Pro Gly Thr Gln Pro Arg Gln Asp Ser Ser
                85                  90                  95
```

His Lys Leu Gly Val Asp Cys Val Pro Cys Pro Gly His Phe Ser
            100                 105                 110

Pro Gly Ser Asn Gln Ala Cys Lys Pro Trp Thr Asn Cys Thr Leu Ser
        115                 120                 125

Gly Lys Gln Ile Arg His Pro Ala Ser Asn Ser Leu Asp Thr Val Cys
    130                 135                 140

Glu Asp Arg Ser Leu Leu Ala Thr Leu Leu Trp Glu Thr Gln Arg Thr
145                 150                 155                 160

Thr Phe Arg Pro Thr Thr Val Pro Ser Thr Val Trp Pro Arg Thr
                165                 170                 175

Ser Gln Leu Pro Ser Thr Pro Leu Val Ala Pro Glu Gly Pro
            180                 185                 190

<210> SEQ ID NO 244
<211> LENGTH: 25
<212> TYPE: PRT
<213> ORGANISM: artificial sequence
<220> FEATURE:
<223> OTHER INFORMATION: Predicted TM region

<400> SEQUENCE: 244

Ala Phe Ala Val Ile Leu Gly Leu Gly Leu Gly Leu Leu Ala Pro Leu
1               5                   10                  15

Thr Val Leu Leu Ala Leu Tyr Leu Leu
            20                  25

<210> SEQ ID NO 245
<211> LENGTH: 36
<212> TYPE: PRT
<213> ORGANISM: artificial sequence
<220> FEATURE:
<223> OTHER INFORMATION: Intracellular tail

<400> SEQUENCE: 245

Arg Lys Ala Trp Arg Ser Pro Asn Thr Pro Lys Pro Cys Trp Gly Asn
1               5                   10                  15

Ser Phe Arg Thr Pro Ile Gln Glu Glu Gln Thr Asp Thr His Phe Thr
            20                  25                  30

Leu Ala Lys Ile
        35

<210> SEQ ID NO 246
<211> LENGTH: 28
<212> TYPE: PRT
<213> ORGANISM: artificial sequence
<220> FEATURE:
<223> OTHER INFORMATION: signal peptide

<400> SEQUENCE: 246

Met Cys Val Gly Ala Arg Arg Leu Gly Arg Gly Pro Cys Ala Ala Leu
1               5                   10                  15

Leu Leu Leu Gly Leu Gly Leu Ser Thr Thr Ala Lys
            20                  25

<210> SEQ ID NO 247
<211> LENGTH: 186
<212> TYPE: PRT
<213> ORGANISM: artificial sequence
<220> FEATURE:
<223> OTHER INFORMATION: ECD

<400> SEQUENCE: 247

-continued

```
Leu His Cys Val Gly Asp Thr Tyr Pro Ser Asn Asp Arg Cys Cys Gln
1               5                   10                  15

Glu Cys Arg Pro Gly Asn Gly Met Val Ser Arg Cys Asn Arg Ser Gln
            20                  25                  30

Asn Thr Val Cys Arg Pro Cys Gly Pro Gly Phe Tyr Asn Asp Val Val
        35                  40                  45

Ser Ala Lys Pro Cys Lys Ala Cys Thr Trp Cys Asn Leu Arg Ser Gly
    50                  55                  60

Ser Glu Arg Lys Gln Pro Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
            115                 120                 125

Pro Ala Ser Asn Ser Ser Asp Ala Ile Cys Glu Asp Arg Asp Pro Pro
        130                 135                 140

Pro Thr Gln Pro Gln Glu Thr Gln Gly Pro Pro Ala Arg Pro Thr Thr
145                 150                 155                 160

Val Gln Pro Thr Glu Ala Trp Pro Arg Thr Ser Gln Arg Pro Ser Thr
                165                 170                 175

Arg Pro Val Glu Val Pro Arg Gly Pro Ala
            180                 185

<210> SEQ ID NO 248
<211> LENGTH: 21
<212> TYPE: PRT
<213> ORGANISM: artificial sequence
<220> FEATURE:
<223> OTHER INFORMATION: Predicted TM region

<400> SEQUENCE: 248

Val Ala Ala Ile Leu Gly Leu Gly Leu Ala Leu Gly Leu Leu Gly Pro
1               5                   10                  15

Leu Ala Met Leu Leu
            20

<210> SEQ ID NO 249
<211> LENGTH: 42
<212> TYPE: PRT
<213> ORGANISM: artificial sequence
<220> FEATURE:
<223> OTHER INFORMATION: Intracellular tail

<400> SEQUENCE: 249

Ala Leu Leu Leu Leu Arg Arg Asp Gln Arg Leu Pro Pro Asp Ala Pro
1               5                   10                  15

Lys Ala Pro Gly Gly Gly Ser Phe Arg Thr Pro Ile Gln Glu Glu Gln
            20                  25                  30

Ala Asp Ala His Ser Ala Leu Ala Lys Ile
            35                  40

<210> SEQ ID NO 250
<211> LENGTH: 7
<212> TYPE: PRT
<213> ORGANISM: artificial sequence
<220> FEATURE:
<223> OTHER INFORMATION: CD137 and PD-L1 binding region Heavy chain CDR1
```

```
<400> SEQUENCE: 250

Thr Thr Gly Val Gly Val Asn
1               5

<210> SEQ ID NO 251
<211> LENGTH: 16
<212> TYPE: PRT
<213> ORGANISM: artificial sequence
<220> FEATURE:
<223> OTHER INFORMATION: CD137 and PD-L1 binding region Heavy chain CDR2

<400> SEQUENCE: 251

Leu Ile Tyr Trp Asn Asp Asp Thr Tyr Tyr Ser Pro Ser Leu Lys Ser
1               5                   10                  15

<210> SEQ ID NO 252
<211> LENGTH: 14
<212> TYPE: PRT
<213> ORGANISM: artificial sequence
<220> FEATURE:
<223> OTHER INFORMATION: CD137 and PD-L1 binding region Heavy chain CDR3

<400> SEQUENCE: 252

Glu Gly Ile Ile Gly Phe Leu Gly Gly Asn Trp Phe Asp Pro
1               5                   10

<210> SEQ ID NO 253
<211> LENGTH: 5
<212> TYPE: PRT
<213> ORGANISM: artificial sequence
<220> FEATURE:
<223> OTHER INFORMATION: CD137 and PD-L1 binding region Heavy chain CDR1

<400> SEQUENCE: 253

Asn Tyr Ala Ile Asn
1               5

<210> SEQ ID NO 254
<211> LENGTH: 17
<212> TYPE: PRT
<213> ORGANISM: artificial sequence
<220> FEATURE:
<223> OTHER INFORMATION: CD137 and PD-L1 binding region Heavy chain CDR2

<400> SEQUENCE: 254

Trp Ile Asn Pro Asn Thr Gly Asn Pro Thr Tyr Ala Gln Gly Phe Thr
1               5                   10                  15

Gly

<210> SEQ ID NO 255
<211> LENGTH: 16
<212> TYPE: PRT
<213> ORGANISM: artificial sequence
<220> FEATURE:
<223> OTHER INFORMATION: CD137 and PD-L1 binding region Heavy chain CDR3

<400> SEQUENCE: 255

Asp Arg Lys Tyr Val Thr Asn Trp Val Phe Ala Glu Asp Phe Gln His
1               5                   10                  15

<210> SEQ ID NO 256
<211> LENGTH: 6
<212> TYPE: PRT
<213> ORGANISM: Artificial Sequence
<220> FEATURE:
<223> OTHER INFORMATION: Common light chain CDR1
```

```
<400> SEQUENCE: 256

Gln Ser Ile Ser Ser Tyr
1               5

<210> SEQ ID NO 257
<211> LENGTH: 9
<212> TYPE: PRT
<213> ORGANISM: Artificial Sequence
<220> FEATURE:
<223> OTHER INFORMATION: Common light chain CDR3

<400> SEQUENCE: 257

Gln Gln Ser Tyr Ser Thr Pro Pro Thr
1               5
```